United States Patent
Sedivy et al.

(10) Patent No.: US 12,246,022 B2
(45) Date of Patent: *Mar. 11, 2025

(54) COMPOSITIONS AND METHODS FOR TREATING, PREVENTING OR REVERSING AGE ASSOCIATED INFLAMMATION AND DISORDERS

(71) Applicant: BROWN UNIVERSITY, Providence, RI (US)

(72) Inventors: John M. Sedivy, Barrington, RI (US); Marco De Cecco, Pawtucket, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,182

(22) Filed: Sep. 19, 2023

(65) Prior Publication Data

US 2024/0197745 A1    Jun. 20, 2024

Related U.S. Application Data

(63) Continuation of application No. 16/934,826, filed on Jul. 21, 2020, now Pat. No. 11,793,814, which is a continuation-in-part of application No. PCT/US2020/015043, filed on Jan. 24, 2020.

(60) Provisional application No. 62/907,251, filed on Sep. 27, 2019, provisional application No. 62/797,109, filed on Jan. 25, 2019.

(51) Int. Cl.
| | |
|---|---|
| A61K 31/52 | (2006.01) |
| A61K 31/513 | (2006.01) |
| A61K 45/06 | (2006.01) |
| A61P 35/00 | (2006.01) |

(52) U.S. Cl.
CPC ............ *A61K 31/52* (2013.01); *A61K 31/513* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,172,896 A | 10/1979 | Uno et al. | |
| 5,358,970 A | 10/1994 | Ruff et al. | |
| 5,427,798 A | 6/1995 | Ludwig et al. | |
| 5,541,231 A | 7/1996 | Ruff et al. | |
| 5,731,000 A | 3/1998 | Ruff et al. | |
| 5,763,493 A | 6/1998 | Ruff et al. | |
| 6,110,973 A | 8/2000 | Young | |
| 6,291,670 B1 | 9/2001 | Ohrui et al. | |
| 6,333,315 B1 | 12/2001 | Ohrui et al. | |
| 6,403,568 B1 | 6/2002 | Ohrui et al. | |
| 7,339,053 B2 | 3/2008 | Kohgo et al. | |
| 7,589,078 B2 | 9/2009 | Cheng et al. | |
| 7,625,877 B2 | 12/2009 | Kohgo et al. | |
| 8,173,623 B2 | 5/2012 | Crawford et al. | |
| 8,193,165 B2 | 6/2012 | Cheng et al. | |
| 8,334,295 B2 | 12/2012 | Guo et al. | |
| 8,354,421 B2 | 1/2013 | He et al. | |
| 8,431,745 B2 | 4/2013 | Crawford et al. | |
| 8,445,669 B2 | 5/2013 | Sato et al. | |
| 8,513,205 B2 | 8/2013 | Anderson et al. | |
| 9,051,288 B2 | 6/2015 | Nagai et al. | |
| 9,126,971 B2 | 9/2015 | Cheng et al. | |
| 9,212,174 B2 | 12/2015 | Iriyama et al. | |
| 9,221,832 B2 | 12/2015 | Hilpert et al. | |
| 9,249,171 B2 | 2/2016 | Ortiz et al. | |
| 9,422,605 B2 | 8/2016 | Dubnau et al. | |
| 9,441,223 B2 | 9/2016 | Dubnau et al. | |
| 9,777,035 B2 | 10/2017 | Girijavallabhan et al. | |
| 9,822,138 B2 | 11/2017 | Vachal et al. | |
| 9,993,547 B2 | 6/2018 | Stenler et al. | |
| 10,059,940 B2 | 8/2018 | Zhong et al. | |
| 10,071,985 B2 | 9/2018 | Graupe et al. | |
| 10,100,307 B2 | 10/2018 | Prochiantz et al. | |
| 10,258,575 B2 | 4/2019 | Li | |
| 10,266,558 B2 | 4/2019 | Ivachtchenko et al. | |
| 10,363,220 B2 | 7/2019 | Li | |
| 10,449,208 B2 | 10/2019 | Da Costa et al. | |
| 10,450,335 B2 | 10/2019 | Fu et al. | |
| 10,479,801 B2 | 11/2019 | Graham et al. | |
| 10,519,159 B2 | 12/2019 | Paparin et al. | |
| 10,537,589 B2 | 1/2020 | Hazuda et al. | |
| 10,654,827 B2 | 5/2020 | Graupe et al. | |
| 11,793,814 B2 | 10/2023 | Sedivy et al. | |
| 2003/0003468 A1 | 1/2003 | Crow | |
| 2004/0229262 A1 | 11/2004 | Franco et al. | |
| 2005/0113324 A1 | 5/2005 | Bondarev et al. | |

(Continued)

FOREIGN PATENT DOCUMENTS

| | | |
|---|---|---|
| WO | WO-2000069876 A1 | 11/2000 |
| WO | WO-2008054808 A2 | 5/2008 |

(Continued)

OTHER PUBLICATIONS

Alexandrova, E., et al., "Sense Transcripts Originated From an Internal Part of the Human Retrotransposon LINE-1 5' UTR," Gene 15(1): 46-53, Elsevier, Netherlands (Dec. 2012).

(Continued)

*Primary Examiner* — Brian J Davis
(74) *Attorney, Agent, or Firm* — Sterne, Kessler, Goldstein & Fox P.L.L.C.

(57) ABSTRACT

Disclosed is a method for preventing, delaying or reversing age-associated inflammation, by administering to a patient in need thereof a therapeutically effective amount of at least one reverse transcriptase inhibitor (RTI).

20 Claims, 47 Drawing Sheets

Specification includes a Sequence Listing.

(56) References Cited

U.S. PATENT DOCUMENTS

| | | |
|---|---|---|
| 2006/0020042 A1 | 1/2006 | McDONALD et al. |
| 2006/0160087 A1 | 7/2006 | Mcgrath et al. |
| 2010/0048726 A1 | 2/2010 | McDONALD et al. |
| 2011/0150997 A1 | 6/2011 | Shah et al. |
| 2014/0113952 A1 | 4/2014 | Dubnau et al. |
| 2015/0018297 A1 | 1/2015 | Jo et al. |
| 2015/0038446 A1 | 2/2015 | Ambati et al. |
| 2015/0104511 A1 | 4/2015 | Malhotra et al. |
| 2016/0130260 A1 | 5/2016 | Ortiz et al. |
| 2016/0339019 A1 | 11/2016 | Laberge et al. |
| 2017/0224680 A2 | 8/2017 | Laberge et al. |
| 2017/0335320 A1 | 11/2017 | Prochiantz et al. |
| 2018/0002366 A1 | 1/2018 | Girijavallabhan et al. |
| 2018/0050000 A1 | 2/2018 | Mckearn et al. |
| 2018/0065999 A1 | 3/2018 | Vachal et al. |
| 2018/0153859 A1 | 6/2018 | Didsbury et al. |
| 2018/0185372 A1 | 7/2018 | Schinazi et al. |
| 2018/0230464 A1 | 8/2018 | Zhong |
| 2018/0305688 A1 | 10/2018 | Zhong |
| 2018/0362562 A1 | 12/2018 | Raheem et al. |
| 2019/0022115 A1 | 1/2019 | Girijavallabhan et al. |
| 2019/0038659 A1 | 2/2019 | Nath et al. |
| 2019/0055273 A1 | 2/2019 | Beigelman et al. |
| 2019/0083478 A1 | 3/2019 | Houston et al. |
| 2019/0084963 A1 | 3/2019 | Shi |
| 2019/0177326 A1 | 6/2019 | Alexandre et al. |
| 2019/0183912 A1 | 6/2019 | Da Costa et al. |
| 2019/0185508 A1 | 6/2019 | Alexandre et al. |
| 2019/0262365 A1 | 8/2019 | Paparin et al. |
| 2019/0315769 A1 | 10/2019 | Graham et al. |
| 2019/0321380 A1 | 10/2019 | De et al. |
| 2019/0388336 A1 | 12/2019 | Barrett et al. |
| 2019/0388590 A1 | 12/2019 | Barrett et al. |
| 2020/0010834 A1 | 1/2020 | Novick et al. |
| 2020/0010868 A1 | 1/2020 | Duan et al. |
| 2020/0038389 A1 | 2/2020 | Bauer et al. |
| 2020/0101098 A1 | 4/2020 | Hazuda et al. |
| 2020/0138845 A1 | 5/2020 | Scott |
| 2020/0171020 A1 | 6/2020 | Balan et al. |

FOREIGN PATENT DOCUMENTS

| | | |
|---|---|---|
| WO | WO-2009153009 A1 | 12/2009 |
| WO | WO-2012068636 A1 | 5/2012 |
| WO | WO-2013057469 A1 | 4/2013 |
| WO | WO-2014184553 A1 | 11/2014 |
| WO | WO-2016005327 A1 | 1/2016 |
| WO | WO-2016138425 A1 | 9/2016 |
| WO | WO-2016149561 A1 | 9/2016 |
| WO | WO-2017050803 A1 | 3/2017 |
| WO | WO-2017138022 A1 | 8/2017 |
| WO | WO-2018102358 A1 | 6/2018 |
| WO | WO-2018136920 A1 | 7/2018 |
| WO | WO-2018191093 A1 | 10/2018 |
| WO | WO-2018203235 A1 | 11/2018 |
| WO | WO-2019009793 A1 | 1/2019 |
| WO | WO-2019133712 A1 | 7/2019 |
| WO | WO-2019140365 A1 | 7/2019 |
| WO | WO-2019171285 A1 | 9/2019 |
| WO | WO-2019246422 A1 | 12/2019 |
| WO | WO-2020007070 A1 | 1/2020 |
| WO | WO-2020014041 A1 | 1/2020 |
| WO | WO-2020018352 A1 | 1/2020 |
| WO | WO-2020018399 A1 | 1/2020 |
| WO | WO-2020031131 A1 | 2/2020 |
| WO | WO-2020044257 A1 | 3/2020 |
| WO | WO-2020053811 A1 | 3/2020 |
| WO | WO-2020058844 A1 | 3/2020 |
| WO | WO-2020081622 A1 | 4/2020 |
| WO | WO-2020092621 A1 | 5/2020 |
| WO | WO-2020128525 A1 | 6/2020 |
| WO | WO-2020131649 A1 | 6/2020 |
| WO | WO-2020185676 A1 | 9/2020 |
| WO | WO-2021041317 A1 | 3/2021 |

OTHER PUBLICATIONS

An, W., et al., "Characterization of a Synthetic Human LINE-1 Retrotransposon ORFeus-Hs," Mobile DNA 2, BioMed Central Ltd., London (Feb. 2011).

Athanikar, J., et al., "A YY1-Binding Site Is Required for Accurate Human Line-1 Transcription Initiation," Nucleic Acids Research 32(13): 3846-3855, Oxford University Press, London (Jul. 2004).

Baker, D.J., et al., "Clearance of P16ink4a-positive Senescent Cells Delays Ageing-associated Disorders," Nature 479(7372):232-236, Nature Publishing Group, United Kingdom (Nov. 2011).

Baker, D.J., et al., "Naturally Occurring P16(Ink4a)-positive Cells Shorten Healthy Lifespan," Nature 530(7589):184-189, Nature Publishing Group, United Kingdom (Feb. 2016).

Benjamini, Y. and Hochberg, Y., "Controlling the False Discovery Rate: A Practical and Powerful Approach to Multiple Testing," Journal of the Royal Statistical Society. Series B (Methodological) 57(1):289-300, Wiley, United States (1995).

Bingham, A.L., et al., "Over One Hundred Solvates of Sulfathiazole," Chemical Communications 7:603-604, Royal Society of Chemistry, United States (2001).

Bowen, L. N., et al., "HIV-associated motor neuron disease: HERV-K activation and response to antiretroviral therapy," Neurology 87(17):1756-1762, American Academy of Neurology, United States (published online Sep. 2016, published in print Oct. 2016).

Brown, J. P., et al., "Bypass of Senescence After Disruption of P21cipl/wafl Gene in Normal Diploid Human Fibroblasts," Science 277(5327): 831-834, American Association for the Advancement of Science, United States (Aug. 1997).

Brydon, E., "Cshl neuroscientists show 'jumping genes' may contribute to aging-related brain defects," 7 pages, Cold Spring Harbor Laboratory, United States (Apr. 2013).

Bundo, M., et al., "Increased L1 Retrotransposition in the Neuronal Genome in Schizophrenia," Neuron 81(2):306-313, Cell Press, United States (Jan. 2014).

Bussian, T.J., et al., "Clearance of Senescent Glial Cells Prevents Tau-dependent Pathology and Cognitive Decline," Nature 562(7728):578-582, Nature Publishing Group, United Kingdom (Oct. 2018).

Caira, M.R., et al., "Preparation and Crystal Characterization of a Polymorph, a Monohydrate, and an Ethyl Acetate Solvate of the Antifungal Fluconazole," Journal of Pharmaceutical Sciences 93(3):601-611, American Pharmaceutical Assn, United States (Mar. 2004).

Chang, J., et al., "Clearance of Senescent Cells by ABT263 Rejuvenates Aged Hematopoietic Stem Cells in Mice," Nature Medicine 22:78-83, Nature Research, United States (Jan. 2016).

Childs, B G., et al., "Cellular Senescence in Aging and Age-related Disease: From Mechanisms to Therapy," Nature Medicine 21(12):1424-1435, Nature Publishing Company, United States (Dec. 2015).

Childs, B G., et al., "Senescent Intimal Foam Cells Are Deleterious at All Stages of Atherosclerosis," Science 354(6311):472-477, American Association for the Advancement of Science, United States (Oct. 2016).

Chinta, S., et al., "Cellular Senescence Is Induced by the Environmental Neurotoxin Paraquat and Contributes to Neuropathology Linked to Parkinson's Disease," Cell Reports 22(4):930-940, Cell Press, United States (Jan. 2018).

Chu, S. C., et al., "Inhibitory effects of flavonoids on Moloney murine leukemia virus reverse transcriptase activity," Journal of Natural Products 55(2):179-183, American Chemical Society, United States (Feb. 1992).

Chung, H.Y., et al., "Molecular inflammation: underpinnings of aging and age-related diseases," Ageing Research Reviews 8(1):18-30, Elsevier Science, United Kingdom (Jan. 2009).

Coppe, J.P., et al., "The Senescence-associated Secretory Phenotype: the Dark Side of Tumor Suppression," Annual Review of Pathology 5:99-118, Annual Reviews, United States (2010).

Coufal, N. G., et al., "L1 Retrotransposition in Human Neural Progenitor Cells," Nature 460(7259):1127-1131, Nature Publishing Group, United Kingdom (Aug. 2009).

(56) References Cited

OTHER PUBLICATIONS

Criscione, S.W., et al., "Transcriptional Landscape of Repetitive Elements in Normal and Cancer Human Cells," BMC Genomics 15:583, BioMed Central, United Kingdom (Jul. 2014).

Dai, L., et al., "Effect of reverse transcriptase inhibitors on LINE-1 and Ty1 reverse transcriptase activities and on LINE-1 retrotransposition," BMC Biochem 12:18, 11 pages, BioMed Central Ltd., United Kingdom (May 2011).

De Cecco, M., et al., "Genomes of replicatively senescent cells undergo global epigenetic changes leading to gene silencing and activation of transposable elements," Aging Cell 12(2):247-256, Wiley-Blackwell Publishing Ltd., United Kingdom (published online Jan. 2013, published in print Apr. 2013).

De Cecco, M., et al., "Transposable elements become active and mobile in the genomes of aging mammalian somatic tissues," Aging 5(12):867-883, Impact Journals LLC, United States (Dec. 2013).

De Koning, A.P.J., et al., "Repetitive Elements May Comprise Over Two-thirds of the Human Genome," PLos Genetics 7(12):e1002384, Public Library of Science, United States (Dec. 2011).

Demaria, M., et al., "An Essential Role for Senescent Cells in Optimal Wound Healing through Secretion of PDGF-AA," Developmental Cell 31(6): 722-733, Cell Press, United States (Dec. 2014).

Demaria, M., et al., "Cellular Senescence Promotes Adverse Effects of Chemotherapy and Cancer Relapse," Cancer Discovery 7(2):165-176, American Association for Cancer Research, United States (Feb. 2017).

Denli, A.M., et al., "Primate-specific ORF0 Contributes to Retrotransposon-mediated Diversity," Cell 163(3):583-593, Cell Press, United States (Oct. 2015).

Dhanwani, R., et al., "Cytosolic Sensing of Immuno-stimulatory DNA, the Enemy Within," Current Opinion in Immunology 50:82-87, Elsevier, United Kingdom (Feb. 2018).

Diagnostic and Statistical Manual of Mental Disorders, Fifth Edition, pp. 602-614, American Psychiatric Association Publishing, Washington, DC (2013).

Dou, Z., et al., "Cytoplasmic Chromatin Triggers Inflammation in Senescence and Cancer," Nature 550(7676):402-406, Nature Publishing Group, United Kingdom (Oct. 2017).

Else, J., et al., "Pharmacokinetics of Lamivudine and Lamivudine-triphosphate After Administration of 300 Milligrams and 150 Milligrams Once Daily to Healthy Volunteers: Results of the ENCORE 2 Study," Antimicrobial Agents and Chemotherapy 56(3):1427-1433, American Society for Microbiology, United States (Mar. 2012).

Engel, P., "These Staggering Maps Show How Much The World's Population Is Aging," Business Insider (May 2014).

Erwin, J.A., et al., "Mobile DNA Elements in the Generation of Diversity and Complexity in the Brain," Nature Reviews. Neuroscience 15(8):497-506, Nature Publishing Group, United Kingdom (Aug. 2014).

Farr, J.N., et al., "Targeting Cellular Senescence Prevents Age-related Bone Loss in Mice," Nature Medicine 23(9):1072-1079, Nature Publishing Company, United States (Sep. 2017).

Fikes, B. J., "HIV drugs may help Alzheimer's, says study proposing an undiscovered root cause," MedicalXpress.com, 5 pages, The San Diego Union-Tribune, United States (Nov. 2018).

Fowler, B. J., et al., "Nucleoside reverse transcriptase inhibitors possess intrinsic anti-inflammatory activity," Science 346(6212):1000-1003, American Association for the Advancement of Science, United States (Nov. 2014).

Franceschi, C. and Campisi, J., "Chronic Inflammation (Inflammaging) and Its Potential Contribution to Age-associated Diseases," The Journals of Gerontology. Series A, Biological Sciences and Medical Sciences 69 Suppl 1:S4-S9, Gerontological Society of America, United States (Jun. 2014).

Frasca, D. and Blomberg, B., "Inflammaging Decreases Adaptive and Innate Immune Responses in Mice and Humans," Biogerontology 17(1):7-19, Kluwer Academic, Netherlands (Feb. 2016).

Fumagalli, M., et al., "Stable Cellular Senescence Is Associated With Persistent DDR Activation," PloS One 9(10):e110969, Public Library of Science, United States (Oct. 2014).

Gautier, G., et al., "A Type I Interferon Autocrine-paracrine Loop Is Involved in Toll-like Receptor-induced Interleukin-12p70 Secretion by Dendritic Cells," The Journal of Experimental Medicine 201(9):1435-1446, Rockefeller University Press, United States (May 2005).

Giri Repbase., 31 pages, accessed at [URL:http://www.girinst.org/repbase/update/browse.php] on Apr. 22, 2021.

Gorbunova, V., et al., "Human Genomics. Sleeping dogs of the genome," Science 346(6214):1187-1188, American Association for the Advancement of Science, United States (Dec. 2014).

Hampel, H., et al., "Advances in the development of biomarkers for Alzheimer's disease: from CSF total tau and Abeta(1-42) proteins to phosphorylated tau protein," Brain Research Bulletin 61(3):243-253, Elsevier Inc., United States (Aug. 2003).

Han, J. S., "Non-long terminal repeat (non-LTR) retrotransposons: mechanisms, recent developments, and unanswered questions," Mobile DNA 1(1):15, 12 pages, BioMed Central Ltd., United Kingdom (May 2010).

Hancks, D.C. and Kazazian, H.H., Jr., "Active Human Retrotransposons: Variation and Disease," Current Opinion in Genetics & Development 22(3):191-203, Elsevier, United Kingdom (Jun. 2012).

Herbig, U., et al., "Cellular Senescence in Aging Primates," Science 311(5765):1257, American Association for the Advancement of Science, United States (Mar. 2006).

Herbig, U., et al., "Telomere Shortening Triggers Senescence of Human Cells Through a Pathway Involving Atm, P53, and P21(Cip1), but Not P16(Ink4a)," Molecular Cell 14(4):501-513, Cell Press, United States (May 2004).

Huang, C.R.L., et al., "Active Transposition in Genomes," Annual Review of Genetics 46:651-475, Annual Reviews, United States (2012).

International Search Report and Written Opinion for International Application No. PCT/US2020/015043, Commissioner for Patents, Virginia, mailed on Jul. 7, 2020.

Ishak, C.A., et al., "An RB-EZH2 Complex Mediates Silencing of Repetitive DNA Sequences," Molecular Cell 64(6):1074-1087, Cell Press, United States (Dec. 2016).

Itahana, K., et al., "Methods to Detect Biomarkers of Cellular Senescence: the Senescence-associated Beta-galactosidase Assay," Methods in Molecular Biology 371:21-31, Humana Press, United States (2007).

Ivanov, A., et al., "Lysosome-mediated Processing of Chromatin in Senescence," The Journal of Cell Biology 202(1):129-143, Rockefeller University Press, United States (Jul. 2013).

Jurk, D., et al., "Chronic Inflammation Induces Telomere Dysfunction and Accelerates Ageing in Mice," Nature Communications 2:4172, Nature Pub. Group, United Kingdom (Jun. 2014).

Kamentsky, L., et al., "Improved Structure, Function and Compatibility for CellProfiler: Modular High-Throughput Image Analysis Software," Bioinformatics 27(8):1179-1180, Oxford University Press, United Kingdom (Apr. 2011).

Katoh, K. and Standley, D.M., "MAFFT Multiple Sequence Alignment Software Version 7: Improvements in Performance and Usability," Molecular Biology and Evolution 30(4):772-780, Oxford University Press, United States (Apr. 2013).

Kent, J., "UCSC In-Silico PCR," Dec. 2013, 1 page, accessed on [URL:https://genome.ucsc.edu/cgi-bin/hgPcr].

Kim, D., et al., "HISAT: A Fast Spliced Aligner With Low Memory Requirements," Nature Methods 12(4):357-360, Nature Pub. Group, United States (Apr. 2015).

Kreiling, J.A., et al., "Age-associated Increase in Heterochromatic Marks in Murine and Primate Tissues," Aging Cell 10(2):292-304, Wiley-Blackwell, United Kingdom (Apr. 2011).

Kreiling, J.A., et al., "Contribution of Retrotransposable Elements to Aging," In book: Human Retrotransposons in Health and Disease, pp. 297-321, Springer, Cham (Jan. 2017).

Langmead, B., "Aligning Short Sequencing Reads With Bowtie," Current Protocols in Bioinformatics Chapter 11:Unit 11.7, John Wiley & Sons, United States (Dec. 2010).

(56) References Cited

OTHER PUBLICATIONS

Le, O.N.L., et al., "Ionizing Radiation-induced Long-term Expression of Senescence Markers in Mice Is Independent of P53 and Immune Status," Aging Cell 9(3):398-409, Wiley-Blackwell, United Kingdom (Jun. 2010).
Lee, M-H., and Chun, J., "Mosaic APP Gene Recombination in Alzheimer's Disease-What's Next?," Journal of Experimental Neuroscience 13: 1179069519849669, Rockefeller University Press, United States (May 2019).
Lee, M-H., et al., "Somatic APP gene recombination in Alzheimer's disease and normal neurons," Nature 563(7733):639-645, Nature Publishing Group, United Kingdom (Nov. 2018).
Cognitive Vitality Reports, "LINE1 inhibition (with nucleoside reverse transcriptase inhibitors)," Alzheimer's Drug Discovery Foundation, Jul. 31, 2020.
Levin, J., Conference Report, "Single Doses as Low as 0.5 mg of the Novel NRTTI MK-8591 Suppress HIV for At Least Seven Days," 9th IAS Conference on HIV Science; Paris, France; Jul. 23-26, 2017, accessed at [https://www.natap.org/2017/IAS/IAS_36.htm] on May 21, 2021, 6 pages.
Li, Q., et al., "FOXA1 Mediates P16(INK4a) Activation During Cellular Senescence," The EMBO Journal 32(6):858-873, Wiley Blackwell, United Kingdom (Mar. 2013).
Li, W. et al., "The EMBL-EBI Bioinformatics Web and Programmatic Tools Framework," Nucleic Acids Research 43:W580-W584, Oxford University Press, United Kingdom (Jul. 2015).
Liao, Y., et al., "FeatureCounts: An Efficient General Purpose Program for Assigning Sequence Reads to Genomic Features," Bioinformatics 30(7):923-930, Oxford University Press, Oxford (Apr. 2014).
Lopez-Otin, C., et al., "The Hallmarks of Aging," Cell 153(6):1194-1217, Cell Press, United States (Jun. 2013).
Martinez-Santibanez, G., et al., "Imaging White Adipose Tissue With Confocal Microscopy," Methods in Enzymology 537:17-30, Academic Press, United States (2014).
Mattson, M.P., "Perspective: Does Brown Fat Protect Against Diseases of Aging?," Ageing Research Reviews 9(1):69-76, Elsevier Science, United Kingdom (Jan. 2010).
Meter, M.V., et al., "SIRT6 Represses LINE1 Retrotransposons by Ribosylating KAP1 but This Repression Fails With Stress and Age," Nature Communications 5:5011, Nature Pub. Group, United Kingdom (Sep. 2014).
Michaud, K., et al., "Pharmacologic Inhibition of Cyclin-dependent Kinases 4 and 6 Arrests the Growth of Glioblastoma Multiforme Intracranial Xenografts," Cancer Research 70(8):3228-3238, American Association for Cancer Research, United States (Apr. 2010).
Moles, J-P., et al., "Cytosolic RNA:DNA Duplexes Generated by Endogenous Reverse Transcriptase Activity as Autonomous Inducers of Skin Inflammation in Psoriasis," PLoS One 12(1):e0169879, Public Library of Science, United States (Jan. 2017).
Montoya-Durango, D.E., et al., "Epigenetic Control of Mammalian Line-1 Retrotransposon by Retinoblastoma Proteins," Mutation Research 665(1-2):20-28, Elsevier, Netherlands (Jun. 2009).
Zhang, X., et al., "New Understanding of the Relevant Role of LINE-1 Retrotransposition in Human Disease and Immune Modulation," Frontiers in Cell and Developmental Biology, 8:657, doi:10.3389/fcell.2020.00657 (Aug. 2020).
NCT01767701, "Raltegravir (Isentress) Pilot Study in Relapsing Multiple Sclerosis (INSPIRE)," first posted online Jan. 14, 2013, accessed at https://clinicaltrials.gov/ct2/show/NCT01767701, accessed on May 20, 2021, 8 pages.
NCT02363452, "Reverse Transcriptase Inhibitors in AGS (RTIs in AGS)," first posted online Feb. 16, 2015, accessed at https://clinicaltrials.gov/ct2/show/NCT02363452, accessed on May 20, 2021, 9 pages.
NCT02437110, "Herv-K Suppression Using Antiretroviral Therapy in Volunteers With Amyotrophic Lateral Sclerosis (ALS)," first posted online May 7, 2015, accessed at https://clinicaltrials.gov/ct2/show/NCT02437110, accessed on May 20, 2021, 10 pages.

Olovnikov, I.A., et al., "Key Role of the Internal Region of the 5'-UTR Segment in the Transcription Acitivity of the Human L1 Retrotransposon," Molecular Biology 41(3):453-458, Pleiades Publishing, Inc. (May-Jun. 2007).
Pawelec, G., et al., "Inflammation, Ageing and Chronic Disease," Current Opinion in Immunology 29:23-28, Elsevier, United Kingdom (Aug. 2014).
Penzkofer, T., et al., "L1Base: From Functional Annotation to Prediction of Active Line-1 Elements," Nucleic Acids Research 33(Database Issue): D498-D500, Information Retrieval ltd., United Kingdom (Jan. 2005).
Rangwala, S.H., et al., "Many LINE1 Elements Contribute to the Transcriptome of Human Somatic Cells," Genome Biology 10: R100, BioMed Central, United Kingdom (2009).
Reich, M., et al., "GenePattern 2.0," Nature Genetics 38(5):500-501, Nature Publishing Group, United States (May 2006).
Robinson, M.D., et al., "edgeR: A Bioconductor Package for Differential Expression Analysis of Digital Gene Expression Data," Bioinformatics 26(1):139-140, Oxford University Press, United Kingdom (Jan. 2010).
Rodic, N., et al., "Long Interspersed Element-1 Protein Expression Is a Hallmark of Many Human Cancers," The American Journal of Pathology 184(5):1280-1286, Elsevier, United States (May 2014).
Safrin, S., "Antiviral Agents (Chapter 49). In: Basic and Clinical Pharmacology," 14th Edition. Katzung BG, Masters SB, Trevor AJ (Editors). McGraw-Hill Education. (2018).
Salama, R., et al., "Cellular Senescence and Its Effector Programs," Genes & Development 28(2):99-114, Cold Spring Harbor Laboratory Press, United States (Jan. 2014).
Saleh, A., et al., "Transposable Elements, Inflammation, and Neurological Disease," Frontiers in Neurology 10: 894, Frontiers Research Foundation, Switzerland (Aug. 2019).
Sanjana, N.E., et al., "Improved Vectors and Genome-wide Libraries for CRISPR Screening," Nature Methods 11(8):783-784, Nature Pub. Group, United States (Aug. 2014).
Schafer, M.J., et al., "Cellular Senescence Mediates Fibrotic Pulmonary Disease," Nature Communications 8:14532, Nature Pub. Group, United Kingdom (Feb. 2017).
Schoenmaker, M., et al., "Evidence of genetic enrichment for exceptional survival using a family approach: the Leiden Longevity Study," European Journal of Human Genetics: EJHG 14(1):79-84, Nature Publishing Group, United Kingdom (Jan. 2006).
Schorl, C. and Sedivy, J.M., "Analysis of Cell Cycle Phases and Progression in Cultured Mammalian Cells," Methods 41(2):143-150, Academic Press, United States (Feb. 2007).
Sedivy, J. M., et al., "Death by transposition—the enemy within?" Bioessays 35(12):1035-1043, John Wiley and Sons Inc., United States (published online Oct. 2013, published in print Dec. 2013).
Shalem, O., et al., "Genome-Scale CRISPR-Cas9 Knockout Screening In Human Cells," Science, 343(6166):84-87, American Association for the Advancement of Science, United States (Jan. 2014).
Simon, M., et al., "Inhibition of retrotransposition improves health and extends lifespan of SIRT6 knockout mice," BioRXiv.org, accessed at URL:[https://www.biorxiv.org/content/10.1101/460808v1.full], 53 pages, Cold Spring Harbor Laboratory, United States (Nov. 2018).
Singh, T. and Newman, A.B., "Inflammatory Markers in Population Studies of Aging," Ageing Research Reviews 10(3):319-329, Elsevier Science, United Kingdom (Jul. 2011).
Skowron, G., and Ogden, R., eds., "Reverse transcriptase inhibitors in HIV/AIDS Therapy," pp. 1-527, Humana Press Inc., United States (2006).
Sonnier, L., et al., "Progressive loss of dopaminergic neurons in the ventral midbrain of adult mice heterozygote for Engrailed1," The Journal of Neuroscience 27(5):1063-1071, Society for Neuroscience, United States (Jan. 2007).
Stetson, D.B., et al., "Trex1 Prevents Cell-intrinsic Initiation of Autoimmunity," Cell 134(4):587-598, Cell Press, United States (Aug. 2008).
Stoddart, C.A., et al., "Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque," Antimicrobial Agents

(56) References Cited

OTHER PUBLICATIONS and Chemotherapy 59(7): 4190-4198, American Society for Microbiology, United States (Jul. 2015).
Suarez, N.A., et al., "LINE-1 Retrotransposons in Healthy and Diseased Human Brain," Developmental Neurobiology 78(5): 434-455, Wiley Subscription Services, United States (May 2018).
Subramanian, A., et al., "Gene Set Enrichment Analysis: a Knowledge-based Approach for Interpreting Genome-wide Expression Profiles," Proceedings of the National Academy of Sciences 102(43):15545-15550, The National Academy of Sciences, United States (Oct. 2005).
Sun, X., et al., "Transcription Factor Profiling Reveals Molecular Choreography and Key Regulators of Human Retrotransposon Expression," Proceedings of the National Academy of Sciences of the United States of America 115(24):E5526-E5535, National Academy of Sciences, United States (Jun. 2018).
Takahashi, A., et al., "Downregulation of Cytoplasmic Dnases Is Implicated in Cytoplasmic DNA Accumulation and SASP in Senescent Cells," Nature Communications 9:1249, Nature Research, United Kingdom (Mar. 2018).
Tam, O. H., et al., "Postmortem Cortex Samples Identify Distinct Molecular Subtypes of ALS: Retrotransposon Activation, Oxidative Stress, and Activated Glia," Cell Reports 29(5):1164-1177, Cell Press, United States (Oct. 2019).
Tchkonia, T., et al., "Fat Tissue, Aging, and Cellular Senescence," Aging Cell 9(5): 667-684, Wiley-Blackwell, United Kingdom (Oct. 2010).
Thomas, C.A., et al., "Modeling of TREX1-Dependent Autoimmune Disease using Human Stem Cells Highlights L1 Accumulation as a Source of Neuroinflammation," Cell Stem Cell 21(3):319-331, Cell Press, United States (Sep. 2017).
Toti, L., et al., "Gastric dysregulation induced by microinjection of 6-OHDA in the substantia nigra pars compacta of rats is determined by alterations in the brain-gut axis," American Journal of Physiology-Gastrointestinal and Liver Physiology 307(10):G1013-G1023, American Physiological Society, United States (published online Oct. 2014, published in print Nov. 2014).
University of Texas Health Science Center at San Antonio, "First-in-human trial of senolytic drugs encouraging: Small pilot study points to feasibility of larger trials in age-related diseases," ScienceDaily. com, accessed at URL:[www.sciencedaily.com/releases/2019/01/190107112944.htm] on May 20, 2021, 3 pages (Jan. 2019).
Van Tonder, E.C., et al., "Preparation and Physicochemical Characterization of 5 Niclosamide Solvates and 1 Hemisolvate," AAPS PharmSciTech 5(1):E12, American Association of Pharmaceutical Scientists, United States (Feb. 2004).
Volkman, H.E. and Stetson D.B., "The Enemy Within: Endogenous Retroelements and Autoimmune Disease," Nature Immunology 15(5): 415-422, Nature America Inc., United States (May 2014).
Waaijer, M.E., et al., "The Number of p16INK4a Positive Cells in Human Skin Reflects Biological Age," Aging Cell 11(4):722-725, Wiley-Blackwell, United Kingdom (Aug. 2012).
Waterhouse, A.M., et al., " Jalview Version 2—A Multiple Sequence Alignment Editor and Analysis Workbench," Bioinformatics 25(9):1189-1191, Oxford University Press, United Kingdom (May 2009).
West, A.P., et al., "Mitochondrial DNA in Innate Immune Responses and Inflammatory Pathology," Nature Reviews. Immunology 17(6):363-375, Nature Pub. Group, United Kingdom (Jun. 2017).
West, A.P., et al., "Mitochondrial DNA Stress Primes the Antiviral Innate Immune Response," Nature 520:553-557, Nature Publishing Group, United Kingdom (Apr. 2015).
Westarp, M. E., et al., "Antiretroviral therapy in sporadic adult amyotrophic lateral sclerosis," NeuroReport 4(6):819-822, Rapid Communications of Oxford Ltd., United Kingdom (Jun. 1993).
Wikipedia., "Senotherapy," 5 pages, accessed at [URL:https://en.wikipedia.org/wiki/Senotherapy] on Apr. 23, 2021.
Xie, Y., et al., "Characterization of L1 Retrotransposition With High-throughput Dual-luciferase Assays," Nucleic Acids Research 39(3):e16, Oxford University Press, United Kingdom (Feb. 2011).
Xu, M., et al., "Senolytics Improve Physical Function and Increase Lifespan in Old Age," Nature Medicine 24(8): 1246-1256, Nature Publishing Company, United States (Aug. 2018).
Ye, J., et al., "Primer-BLAST: a Tool to Design Target-specific Primers for Polymerase Chain Reaction," BMC Bioinformatics 13:134 (Jun. 2012).
Zhao, B., et al., "Somatic LINE-1 Retrotransposition in Cortical Neurons and Non-brain Tissues of Rett Patients and Healthy Individuals," Plos Genetics 15(4):e1008043, Public Library of Science, United States (Apr. 2019).
Zhu, Y., et al., "The Achilles' Heel of Senescent Cells: From Transcriptome to Senolytic Drugs," Aging Cell 14(4):644-658, Wiley-Blackwell, United Kingdom (Aug. 2015).
Li, W., et al., "Activation of Transposable Elements During Aging and Neuronal Decline in *Drosophila*," Nature Neuroscience, 16(5):529-531, Springer Nature (May 2013).
Brydon, E., "CSHL neuroscientists show 'jumping genes' may contribute to aging-related brain defects," CSHL Stories and Media, https://www.cshl.edu/cshl-neuroscientists-show-jumping-genes-may-contribute-to-aging-related-brain-defects/ (Apr. 7, 2013).
Fikes, B. J., "HIV drugs may help Alzheimer's, say study proposing an undiscovered root cause," The San Diego Union-Tribune (Nov. 23, 2018).
Achuthan, V., et al., "Physiological $Mg^{2+}$ Conditions Significantly Alter the Inhibition of HIV-1 and HIV-2 Reverse Transcriptases by Nucleoside and Non-Nucleoside Inhibitors in Vitro," Biochemistry 56(1):33-46, American Chemical Society, United States (Jan. 2017).
Alexandre, F., et al., "Synthesis and Antiviral Evaluation of Carbocyclic Nucleoside Analogs of Nucleoside Reverse Transcriptase Translocation Inhibitor MK-8591 (4'-Ethynyl-2-fluoro-2'-deoxyadenosine)," J. Med. Chem. 61(20):9218-9228, American Chemical Society, United States (Oct. 2018).
Beutner, G., et al., "Follow the Silyl Cation: Insights into the Vorbrüggen Reaction," Org. Process Res. Dev. 23(9):2050-2056, American Chemical Society, United States (Aug. 2019).
Boojamra, C., et al., "Design, synthesis, and anti-HIV activity of 4'-modified carbocyclic nucleoside phosphonate reverse transcriptase inhibitors," Bioorg. Med. Chem. 17(4):1739-1746, Elsevier, Netherlands (Feb. 2009).
Coufal, N., et al., "Ataxia telangiectasia mutated (ATM) modulates long interspersed element-1 (L1) retrotransposition in human neural stem cells," Proc. Natl. Acad. Sci. U.S.A. 108(51):20382-20387, National Academy of Sciences, United States (Dec. 2011).
Cutinho, P., et al., "Design of metronidazole derivatives and flavonoids as potential non-nucleoside reverse transcriptase inhibitors using combined ligand-and structure-based approaches," J. Biomol. Struct. Dyn. 38(6):1626-1648, Taylor & Francis, United Kingdom (Apr. 2020).
Douville, R., et al., "Identification of active loci of a human endogenous retrovirus in neurons of patients with amyotrophic lateral sclerosis," Ann. Neurol. 69(1):141-151, Wiley, United States (Jan. 2011).
Driver, C., and Vogrig, D., "Apparent retardation of aging in Drosophila melanogaster by inhibitors of reverse transcriptase," Ann. N.Y. Acad. Sci. 717:189-197, Wiley-Blackwell, United States (Jun. 1994).
Fukuyama, K., et al., "Synthesis of EFdA via a diastereoselective aldol reaction of a protected 3-keto furanose," Org. Lett. 17(4):828-831, American Chemical Society, United States (Feb. 2017).
Gallagher, W., et al., "A Claisen approach to 4'-Ed4T," Org. Lett. 17(1):14-17, American Chemical Society, United States (Jan. 2015).
Gallagher, W., et al., "Selective opening of nucleoside derived acetals to form highly functionalized vinyl ethers," Tetrahedron Lett. 61(15):151750, Elsevier, Netherlands (Feb. 2020).
Geser, F., et al., "Amyotrophic lateral sclerosis, frontotemporal dementia and beyond: the TDP-43 diseases," J. Neurol. 256(8):1205-1214, Springer Science+Business Media, Germany (Aug. 2009).
Haraguchi, K., et al., "Synthesis of a highly active new anti-HIV agent 2',3'-didehydro-3'-deoxy-4'-ethynylthymidine," Bioorg. Med. Chem. Lett. 13(21):3775-3777, Elsevier, Netherlands (Nov. 2003).

(56) References Cited

OTHER PUBLICATIONS

Haraguchi, K., et al., "An alternative method suitable for a large scale synthesis of 4'-ethynyl-2',3'-didehydro-3'-deoxythymidine," Nucleic Acids Symp. Ser. (Oxf). 48:43-44, Oxford University Press, United Kingdom (2004).
Haraguchi, K., et al., "Synthesis and anti-HIV activity of 4'-cyano-2',3'-didehydro-3'-deoxythymidine," Nucleotides Nucleic Acids 23(4):647-654, Taylor & Francis, United Kingdom (2004).
Haraguchi, K., et al., "A new approach to the synthesis of 4'-carbon-substituted nucleosides: development of a highly active anti-HIV agent 2', 3'-didehydro-3'-deoxy-4'-ethynylthymidine," Nucleotides Nucleic Acids 24(5-7):343-347, Taylor & Francis, United Kingdom (Apr. 2005).
Haraguchi, K., et al., "Nucleophilic substitution at the 4'-position of nucleosides: new access to a promising anti-HIV agent 2',3'-didehydro-3'-deoxy-4'-ethynylthymidine," J. Org. Chem. 71(12):4433-4438, American Chemical Society, United States (Jun. 2006).
Haraguchi, K., et al., "An alternative synthetic method for 4'-C-ethynylstavudine by means of nucleophilic substitution of 4'-benzoyloxythymine nucleoside," Nucleotides Nucleic Acids 26(6-7):835-839, Taylor & Francis, United Kingdom (Dec. 2007).
Haraguchi, K., et al., "From the chemistry of epoxy-sugar nucleosides to the discovery of anti-HIV agent 4'-ethynylstavudine-Festinavir," Curr. Pharm. Des. 19(10):1880-1897, Bentham Science Publishers, United Arab Emirates (2013).
Hattori, S., et al., "Potent activity of a nucleoside reverse transcriptase inhibitor, 4'-ethynyl-2-fluoro-2'-deoxyadenosine, against human immunodeficiency virus type 1 infection in a model using human peripheral blood mononuclear cell-transplanted NOD/SCID Janus kinase 3 knockout mice," Antimicrob. Agents Chemother. 53(9):3887-3893, American Society for Microbiology, United States (Sep. 2009).
Huffman, M., et al., "Design of an in vitro biocatalytic cascade for the manufacture of islatravir," Science 368(6488)1255-1259, American Association for the Advancement of Science, United States (Apr. 2020).
Isono, Y., et al., "Synthesis of 1-benzyl-3-(3,5-dimethylbenzyl)uracil derivatives with potential anti-HIV activity," Antivir. Chem. Chemother. 22(2):57-65, International Medical Press, United Kingdom (Oct. 2011).
Jeong, B., et al., "The prevalence of human endogenous retroviruses in cerebrospinal fluids from patients with sporadic Creutzfeldt-Jakob disease," J. Clin. Virol. 47(2):136-142, Elsevier, Netherlands (Feb. 2010).
Joshi, P., et al., "Inhibition of Heat Shock Protein 90 Prevents HIV Rebound," J. Biol. Chem. 291(19):10332-10346, American Society for Biochemistry and Molecular Biology, United States (May 2016).
Kageyama, M., et al., "Concise synthesis of the anti-HIV nucleoside EFdA," Biosci. Biotechnol. Biochem. 76(6):1219-1225, Japan Society for Bioscience, Biotechnology, and Agrochemistry, Japan (Jun. 2012).
Kageyama, M., et al., "Enantioselective total synthesis of the potent anti-HIV nucleoside EFdA," Org. Lett. 13(19)-5264-5266, American Chemical Society, United States (Oct. 2011).
Kamata, M., et al., "Synthesis of nucleotide analogues, EFdA, EdA and EdAP, and the effect of EdAP on hepatitis B virus replication," Biosci. Biotechnol. Biochem. 84(2):217-227, Japan Society for Bioscience, Biotechnology, and Agrochemistry, Japan (Feb. 2020).
Kawamoto, A., et al., "2'-deoxy-4'-C-ethynyl-2-halo-adenosines active against drug-resistant human immunodeficiency virus type 1 variants," Int. J. Biochem. Cell Biol. 40(11):2410-2420, Elsevier, Netherlands (Apr. 2008).
Kirby, K., et al., "Effects of substitutions at the 4' and 2 positions on the bioactivity of 4'-ethynyl-2-fluoro-2'-deoxyadenosine," Antimicrob. Agents Chemother. 57(12):6254-6264, American Society for Microbiology, United States (Dec. 2013).
Kirby, K., et al., "The sugar ring conformation of 4'-ethynyl-2-fluoro-2'-deoxyadenosine and its recognition by the polymerase active site of HIV reverse transcriptase," Cell. Mol. Biol. 57(1):40-46, American Society for Microbiology, United States (Feb. 2011).

Kovarova, M., et al., "HIV pre-exposure prophylaxis for women and infants prevents vaginal and oral HIV transmission in a preclinical model of HIV infection," J. Antimicrob. Chemother. 71(11):3185-3194, Oxford University Press, United Kingdom (Nov. 2016).
Kubota, Y., et al., "Synthesis and anti-HIV-1 evaluation of phosphonates which mimic the 5'-monophosphate of 4'-branched 2',3'-didehydro-2',3'-dideoxy nucleosides," Bioorg. Med. Chem. 18(20):7186-7192, Elsevier, Netherlands (Oct. 2010).
Kumamoto, H., et al., "Synthesis of carbocyclic analogues of 4'-ethynyl-and 4'-cyano-d4T," Nucleic Acids Symp. Ser. (Oxf). (48):41-42, Oxford University Press, United Kingdom (2004).
Kumamoto, H., et al., "Synthesis of (+/−)-4'-ethynyl and 4'-cyano carbocyclic analogues of stavudine (d4T)," Nucleosides Nucleotides Nucleic Acids, 24(2):73-83, Taylor & Francis, United Kingdom (2005).
Kumamoto, H., et al., "Synthesis and anti-human immunodeficiency virus activity of 4'-branched (+/−)-4'-thiostavudines," J. Med. Chem. 49(26):7861-7867, American Chemical Society, United States (Dec. 2006).
Kumamoto, H., et al., "Synthesis and antiviral evaluation of (+/−)-4'-ethynyl-5'-difluorocarbocyclic-d4T analogue," Nucleic Acids Symp. Ser. (Oxf). (52):609-610, Oxford University Press, United Kingdom (2008).
Kumamoto, H., et al., "Synthesis of (±)-4'-ethynyl-5',5'-difluoro-2',3'-dehydro-3'-deoxy-carbocyclic thymidine: a difluoromethylidene analogue of promising anti-HIV agent Ed4T," Tetrahedron Lett. 65(36):7630-7636, Elsevier, Netherlands (Sep. 2009).
MacKenzie, I., and Rademakers, R., "The role of transactive response DNA-binding protein-43 in amyotrophic lateral sclerosis and frontotemporal dementia," Curr. Opin. Neurol. 21(6):693-700, Lippincott Williams & Wilkins, United States (Dec. 2008).
Maddaford, A., et al., "Stereoselective Synthesis of rac-4'-Ethynyl-2'-deoxy-and 4'-Ethynyl-2',3'-dideoxy-2',3'-didehydronucleoside Analogues," Synthesis 9:1378-1384, Georg Thieme Verlag Stuttgart, Germany (2007).
Maidji, E., et al., "Cellular HIV Reservoirs and Viral Rebound from the Lymphoid Compartments of 4'-Ethynyl-2-Fluoro-2'-Deoxyadenosine (EFdA)-Suppressed Humanized Mice," Viruses 11(3):256, MDPI, Switzerland (Mar. 2019).
Markowitz, M., et al., "Once-Weekly Oral Dosing of MK-8591 Protects Male Rhesus Macaques From Intrarectal Challenge With SHIV109CP3," J. Infect. Dis. 221(9):1398-1406, Oxford University Press, United Kingdom (Apr. 2020).
Matsuzawa, T., et al., "EFdA, a reverse transcriptase inhibitor, potently blocks HIV-1 ex vivo infection of Langerhans cells within epithelium," J. Invest. Dermatol. 134(4):1158-1161, Elsevier, Netherlands (Apr. 2014).
McLaughlin, M., et al., "Enantioselective Synthesis of 4'-Ethynyl-2-fluoro-2'-deoxyadenosine (EFdA) via Enzymatic Desymmetrization," Org. Lett. 19(4):926-929, American Chemical Society, United States (Feb. 2017).
Michailidis, E., et al., "4'-Ethynyl-2-fluoro-2'-deoxyadenosine (EFdA) inhibits HIV-1 reverse transcriptase with multiple mechanisms," J. Biol. Chem. 289(35):24533-48, American Society for Biochemistry and Molecular Biology, United States (Aug. 2014).
Michailidis, E., et al., "Hypersusceptibility mechanism of Tenofovir-resistant HIV to EFdA," Retrovirology 10:65, BioMed Central Ltd., United Kingdom (Jun. 2013).
Michailidis, E., et al., "Mechanism of inhibition of HIV-1 reverse transcriptase by 4'-Ethynyl-2-fluoro-2'-deoxyadenosine triphosphate, a translocation-defective reverse transcriptase inhibitor," J. Biol. Chem. 284(51)35681-35691, American Society for Biochemistry and Molecular Biology, United States (Dec. 2009).
Muftuoglu, Y., et al., "Probing the molecular mechanism of action of the HIV-1 reverse transcriptase inhibitor 40-ethynyl-2-fluoro-2'-deoxyadenosine (EFdA) using pre-steady-state kinetics," Antiviral Res. 106:1-4, Elsevier, Netherlands (Jun. 2014).
Muotri, A., et al., "L1 retrotransposition in neurons is modulated by MeCP2," Nature 468(7322):443-446, Nature Publishing Group, United Kingdom (Nov. 2010).
Murphey-Corb, M., et al., "Response of simian immunodeficiency virus to the novel nucleoside reverse transcriptase inhibitor 4'-ethynyl-

(56) References Cited

OTHER PUBLICATIONS 2-fluoro-2'-deoxyadenosine in vitro and in vivo," Antimicrob. Agents Chemother. 56(9):4707-4712, American Society for Microbiology, United States (Sep. 2012).

Nakata, H., et al., "Activity against human immunodeficiency virus type 1, intracellular metabolism, and effects on human DNA polymerases of 4'-ethynyl-2-fluoro-2'-deoxyadenosine," Antimicrob. Agents Chemother. 51(8):2701-2708, American Society for Microbiology, United States (Aug. 2007).

Nawrat, C. C., et al., "Nine-Step Stereoselective Synthesis of Islatravir from Deoxyribose," Org. Lett. 22(6):2167-2172, American Chemical Society, United States (Mar. 2020).

Ni, G., et al., "Review of α-nucleosides: from discovery, synthesis to properties and potential applications," RSC Adv. 9(25):14302-14320, Royal Society of Chemistry, United Kingdom (May 2019).

Nomura, M., et al., "Nucleosides and nucleotides. 185. Synthesis and biological activities of 4'alpha-C-branched-chain sugar pyrimidine nucleosides," J. Med. Chem. 42(15):2901-2908, American Chemical Society, United States (Jul. 1999).

Ohrui, H., et al., "2'-deoxy-4'-C-ethynyl-2-fluoroadenosine: a nucleoside reverse transcriptase inhibitor with highly potent activity against wide spectrum of HIV-1 strains, favorable toxic profiles, and stability in plasma," Nucleosides Nucleotides Nucleic Acids 26(10-12):1543-1546, Taylor & Francis, United Kingdom (2007).

Ohrui, H., "Chapter 16: 4'-C-Ethynyl-2'-Deoxynucleosides," in *Biochemistry, Biotechnology, and Medicine*, Herdewijn, P., ed., pp. 425-431, Wiley-VCH, Germany (2008).

Ohrui, H., "A Proposal of the Structure of Modified Nucleosides Expected to be Highly Anti-Viral Active and Lowly Toxic," Nucleic Acids Symp. Ser. (Oxf) 52:631-632, Oxford University Press, United Kingdom (2008).

Ohrui, H., "Creation of Low Toxic Reverse-transcriptase Inhibitory Nucleosides that Prevent the Emergence of Drug-resistant HIV Variants," J. Syn. Org. Chem. Jpn. 64(7):716-723, J- Stage, Japan (2006).

Ohrui, H., "Development of modified nucleosides that have supremely high anti-HIV activity and low toxicity and prevent the emergence of resistant HIV mutants," Proc. Jpn. Acad. Ser. B. Phys. Biol. Sci. 87(3):53-65, Japan Academy, Japan (2011).

Oliveira, M., et al., "M184I/V substitutions and E138K/M184I/V double substitutions in HIV reverse transcriptase do not significantly affect the antiviral activity of EFdA," J. Antimicrob. Chemother. 72(11):3008-3011, Oxford University Press, United Kingdom (Nov. 2017).

O'Reilly, E., and Ryan, J., "Biocatalytic cascades go viral: An investigational drug targeting the HIV virus is synthesized with nine enzymes," Biocatalysis 336(6470):1199-1200, American Association for the Advancement of Science, United States (Dec. 2019).

Ortiz, A., et al., "Scalable Synthesis of the Potent HIV Inhibitor BMS-986001 by Non-Enzymatic Dynamic Kinetic Asymmetric Transformation (DYKAT)," Angew. Chem. Int. Ed. Engl. 54(24):7185-7188, Wiley-VCH, Germany (Jun. 2015).

Paintsil, E., et al., "Intracellular metabolism and persistence of the anti-human immunodeficiency virus activity of 2',3'-didehydro-3'-deoxy-4'-ethynylthymidine, a novel thymidine analog," Antimicrob. Agents Chemother. 51(11):3870-3879, American Society for Microbiology, United States (Nov. 2007).

Parang, K., et al., "Comparative Antiviral Activity of Remdesivir and Anti-HIV Nucleoside Analogs Against Human Coronavirus 229E (HCoV-229E)," Molecules 25(10):2343, MDPI, Switzerland (May 2020).

Patel, N., et al., "Synthesis of Islatravir Enabled by a Catalytic, Enantioselective Alkynylation of a Ketone," Org. Lett. 22(12):4659-4664, American Chemical Society, United States (Jun. 2020).

Rai, M., et al., "Emerging reverse transcriptase inhibitors for HIV-1 infection," Expert Opin. Emerg. Drugs 23(2):149-157, Informa, United Kingdom (Jun. 2018).

Rana, A., et al., "Advances in Long-Acting Agents for the Treatment of HIV Infection," Drugs 80(6):535-545, Springer Nature, Germany (Apr. 2020).

Salie, Z. L., et al., "Structural basis of HIV inhibition by translocation-defective RT inhibitor 4'-ethynyl-2-fluoro-2'-deoxyadenosine (EFdA)," Proc. Natl. Acad. Sci. U.S.A. 113(33):9274-9279, National Academy of Sciences, United States (Aug. 2016).

Sohl, C., et al., "Mechanism of interaction of human mitochondrial DNA polymerase γ with the novel nucleoside reverse transcriptase inhibitor 4'-ethynyl-2-fluoro-2'-deoxyadenosine indicates a low potential for host toxicity," Antimicrob. Agents Chemother. 56(3):1630-1634, American Society for Microbiology, United States (Mar. 2012).

Takamatsu, Y., et al., "4'-modified nucleoside analogs: potent inhibitors active against entecavir-resistant hepatitis B virus," Hepatology 62(4):1024-1036, Wiley, United States (Oct. 2015).

Takamatsu, Y., et al., "The High Genetic Barrier of EFdA/MK-8591 Stems from Strong Interactions with the Active Site of Drug-Resistant HIV-1 Reverse Transcriptase," Cell Chem. Biol. 25(10):1268-1278, Cell Press, United States (Oct. 2018).

Takeuchi, T., et al., "Design, Synthesis, and Biological Evaluation of EdAP, a 4'-Ethynyl-2'-Deoxyadenosine 5'-Monophosphate Analog, as a Potent Influenza a Inhibitor," Molecules 24(14):2603, MDPI, Switzerland (Jul. 2019).

Tan, H., et al., "Retrotransposon activation contributes to fragile X premutation rCGG-mediated neurodegeneration," Hum. Mol. Genet. 21(1):57-65, Oxford University Press, United Kingdom (Jan. 2012).

Tanaka, H., et al., "4'-Ethynylstavudine (4'-Ed4T) has potent anti-HIV-1 activity with reduced toxicity and shows a unique activity profile against drug-resistant mutants," Antivir. Chem. Chemother. 16(4):217-221, International Medical Press, United Kingdom (2005).

Tanaka, H., et al., "Synthetic use of epoxy-sugar nucleosides," Nucleosides Nucleotides Nucleic Acids 26(6-7):547-554, Taylor & Francis, United Kingdom (2007).

Wu, V., et al., "MK-8591 (4'-Ethynyl-2-Fluoro-2'-Deoxyadenosine) Exhibits Potent Activity against HIV-2 Isolates and Drug-Resistant HIV-2 Mutants in Culture," Antimicrob. Agents Chemother. 61(8):e00744-00717, American Society for Microbiology, United States (Jul. 2017).

Yang, G., et al., "Impact of novel human immunodeficiency virus type 1 reverse transcriptase mutations P119S and T165A on 4'-ethynylthymidine analog resistance profile," Antimicrob. Agents Chemother. 53(11):4640-4646, American Society for Microbiology, United States (Nov. 2009).

Yasutake, Y., et al., "Structural features in common of HBV and HIV-1 resistance against chirally-distinct nucleoside analogues entecavir and lamivudine," Sci. Rep. 10(1):3021, Nature Portfolio, Germany (Feb. 2020).

Zhang, W., et al., "Development of a vaginal delivery film containing EFdA, a novel anti-HIV nucleoside reverse transcriptase inhibitor," Int. J. Pharm. 461(1-2):203-213, Elsevier, Netherlands (Jan. 2014).

Zhang, W., et al., "In vitro transport characteristics of EFdA, a novel nucleoside reverse transcriptase inhibitor using Caco-2 and MDCKII cell monolayers," Eur. J. Pharmacol. 732:86-95, Elsevier, Netherlands (Jun. 2014).

Zhang, W., et al., "Preformulation studies of EFdA, a novel nucleoside reverse transcriptase inhibitor for HIV prevention," Drug Dev. Ind. Pharm. 40(8):1101-1111, Marcel Dekker, United States (Aug. 2014).

Zhang, W., et al., "Vaginal Microbicide Film Combinations of Two Reverse Transcriptase Inhibitors, EFdA and CSIC, for the Prevention of HIV-1 Sexual Transmission," Pharm. Res. 32(9):2960-2972, Springer Science+Business Media, Germany (Sep. 2015).

Asahchop, E., et al., "Antiviral Drug Resistance and the Need for Development of New HIV-1 Reverse Transcriptase Inhibitors," Antimicrobial Agents and Chemotherapy 56(10):5000-5008, American Society for Microbiology, United States (Oct. 2012).

Kinney, J.W., et al., "Inflammation as a central mechanism in Alzheimer's disease," Alzheimer's & Dementia: Translational Research & Clinical Interventions 4(1):575-590, Alzheimer's Association, United States (2018).

Akiyama, H., "Inflammation and Alzheimer's disease," Neurobiology of Aging 21(3):383-421, Elsevier, The Netherlands (May-Jun. 2000).

(56) References Cited

OTHER PUBLICATIONS

Griffin, W.S.T., et al., "Inflammation and neurodegenerative diseases," Am J Clin Nutr 83(suppl):470S-474S, American Society for Nutrition, United States (Feb. 2006).

Markowitz, M., et al., "EFdA (4'-ethynyl-2-fluoro-2'-deoxyadenosine, MK-8591): A Novel HIV-1 Reverse Transcriptase Translocation Inhibitor," Curr Opin HIV AIDS 13(4):294-299, Wolters Kluwer Health, Inc., United States (Jul. 2018).

Bollati, V., et al., "DNA methylation in repetitive elements and Alzheimer disease," Brain Behav Immun 25(6):1078-1083, Elsevier, Netherlands (Aug. 2011).

Esposito, F., et al., "HIV-1 Reverse Transcriptase Still Remains a New Drug Target: Structure, Function, Classical Inhibitors, and New Inhibitors with Innovative Mechanisms of Actions," Mol Biol Int 2012:586401, Hindawi, United Kingdom (Jun. 2012).

Iijima, K., et al., "Viral protein R of human immunodeficiency virus type-1 induces retrotransposition of long interspersed element-1," Retrovirology 10:83, BioMed Central, United Kingdom (Aug. 2013).

Jones, R.B., et al., "Nucleoside analogue reverse transcriptase inhibitors differentially inhibit human LINE-1 retrotransposition," PLoS One 3(2):e1547, PLoS, United States (Feb. 2008).

Kharkevich, D.A., "Doses and Concentrations" in *Pharmacology*, 10th Ed., pp. 73-74, GEOTAR-Media, Moscow, Russia (2010).

Savage, A.L., et al., "Retrotransposons in the development and progression of amyotrophic lateral sclerosis," J Neurol Neurosurg Psychiatry 90(3):284-293, BMJ, United Kingdom (Mar. 2019).

English language translation of Office Action for Russian Patent Application No. 2021119040/04(040073), received Aug. 3, 2023, 10 pages.

Meyzer, G., et al., "Reverse-Transcriptase Inhibitors in the Aicardi-Goutières Syndrome," New England Journal of Medicine 379:2275-2277, Massachusetts Medical Society, United States (Dec. 2018).

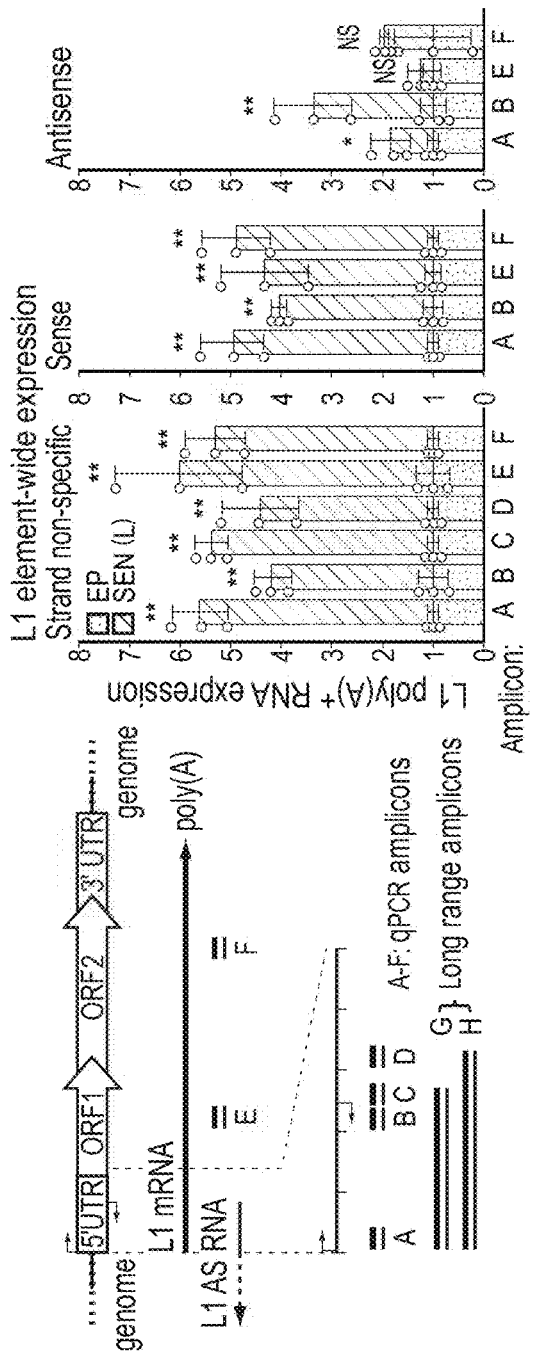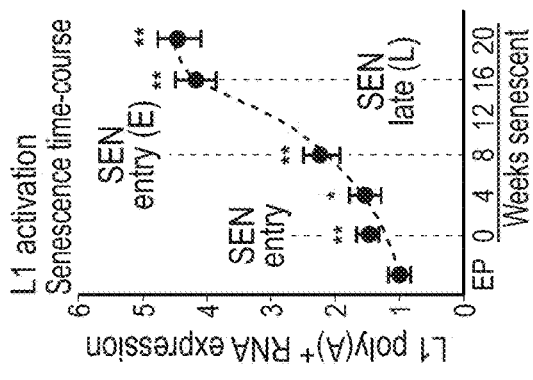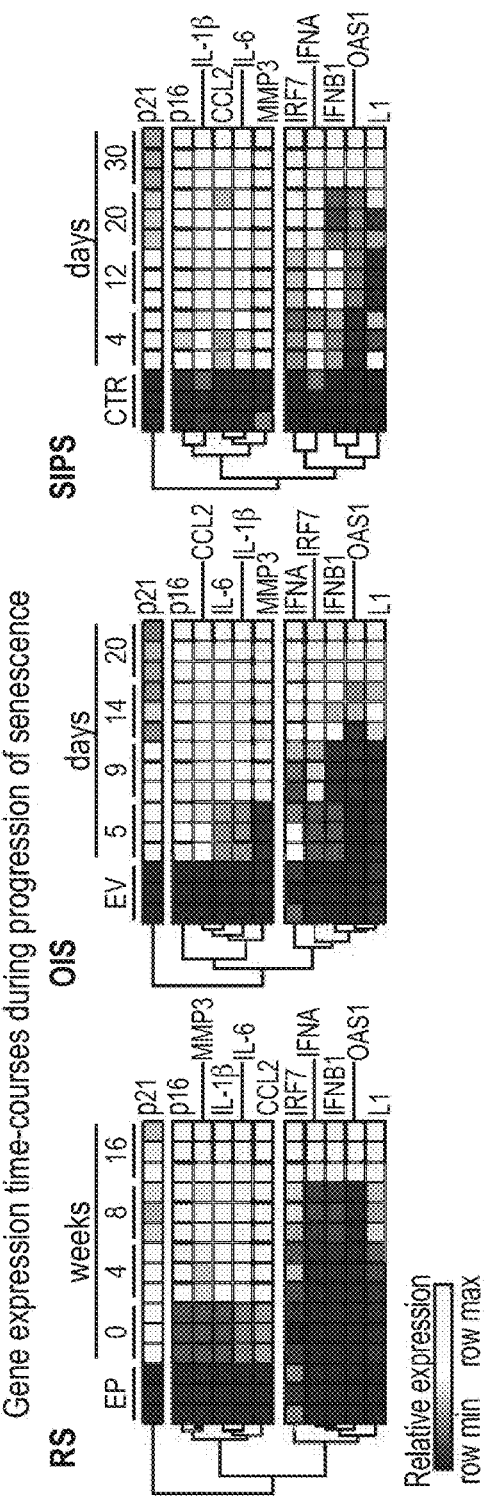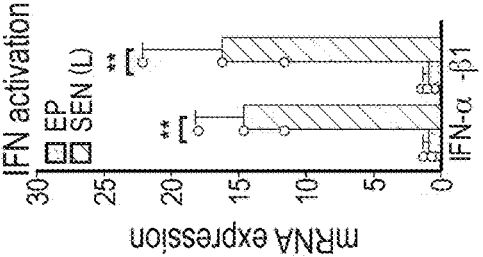

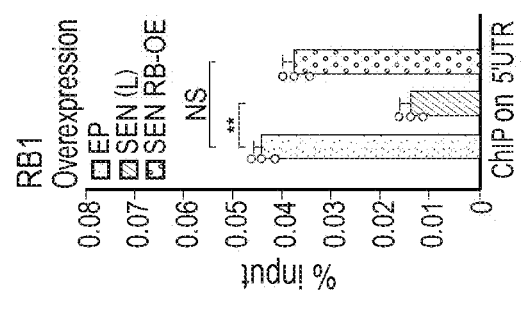
FIG. 2C
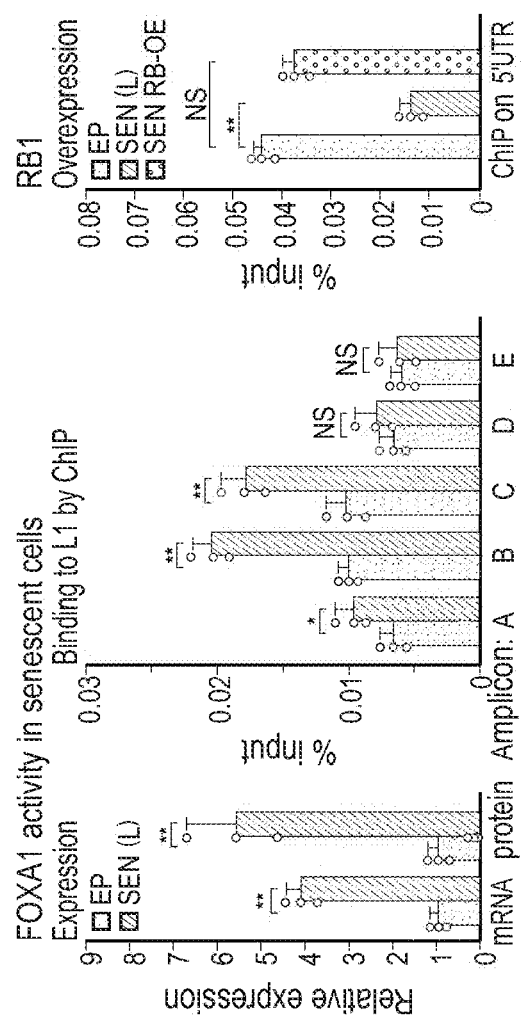
FIG. 2B
FIG. 2A
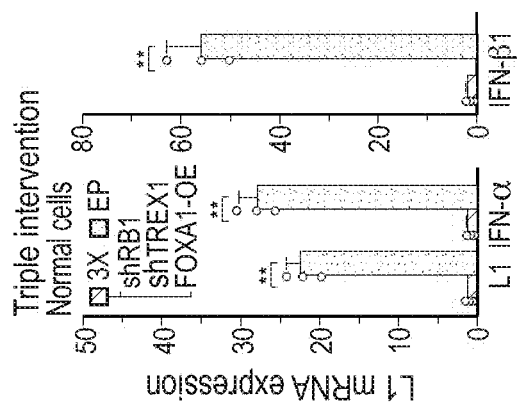
FIG. 2F
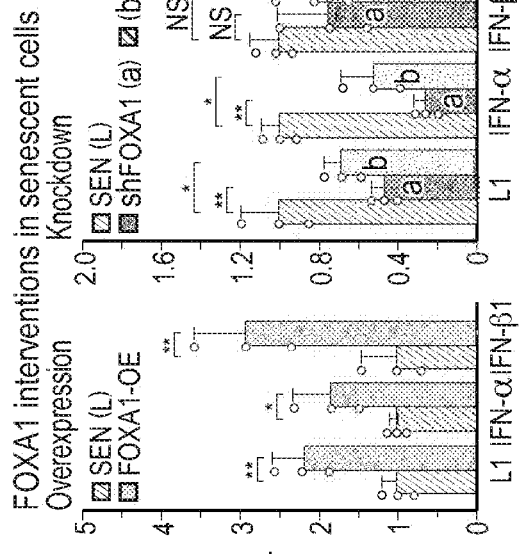
FIG. 2E
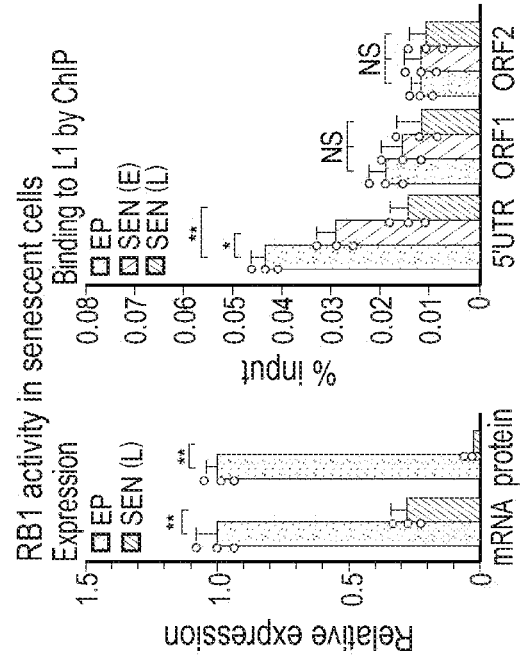
FIG. 2D

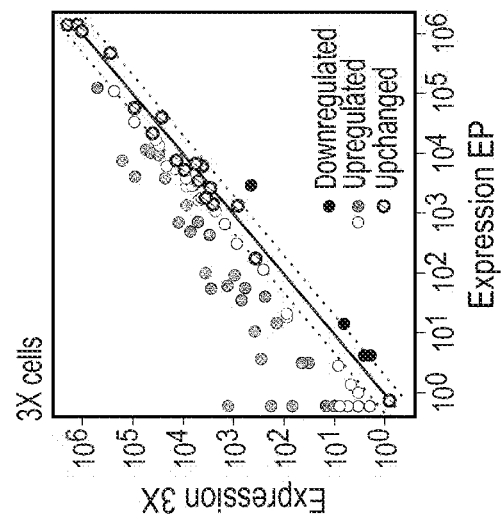
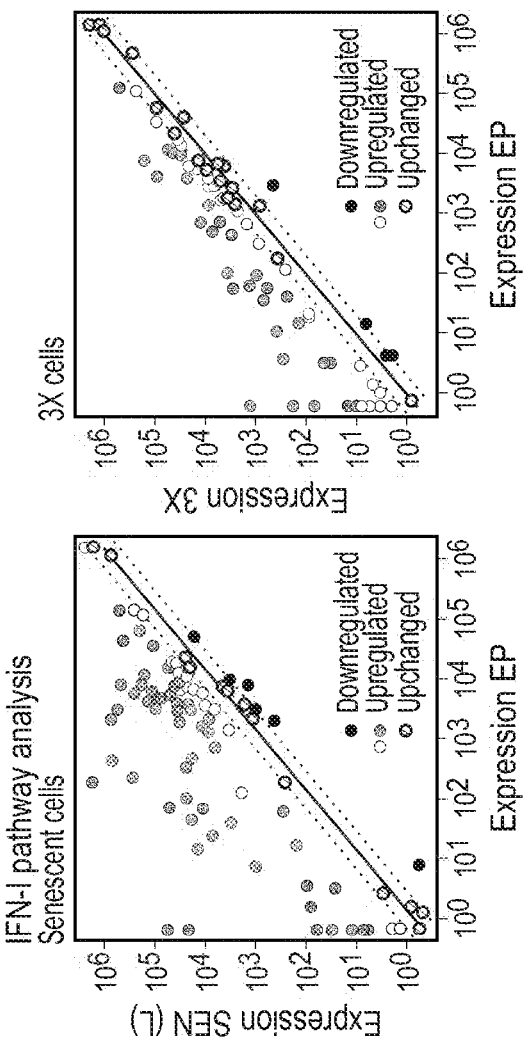
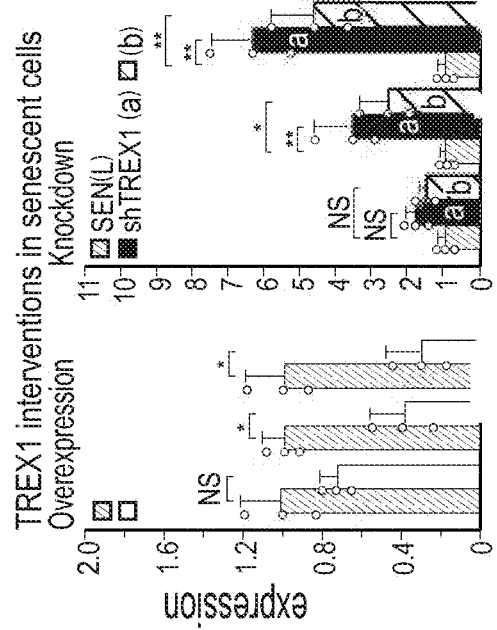
FIG. 2G
FIG. 2H

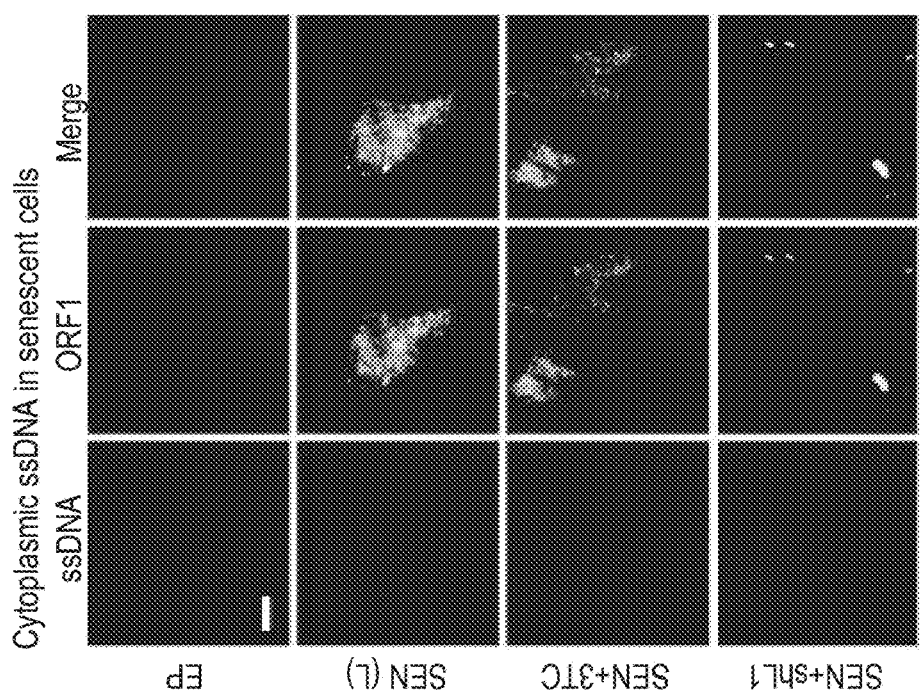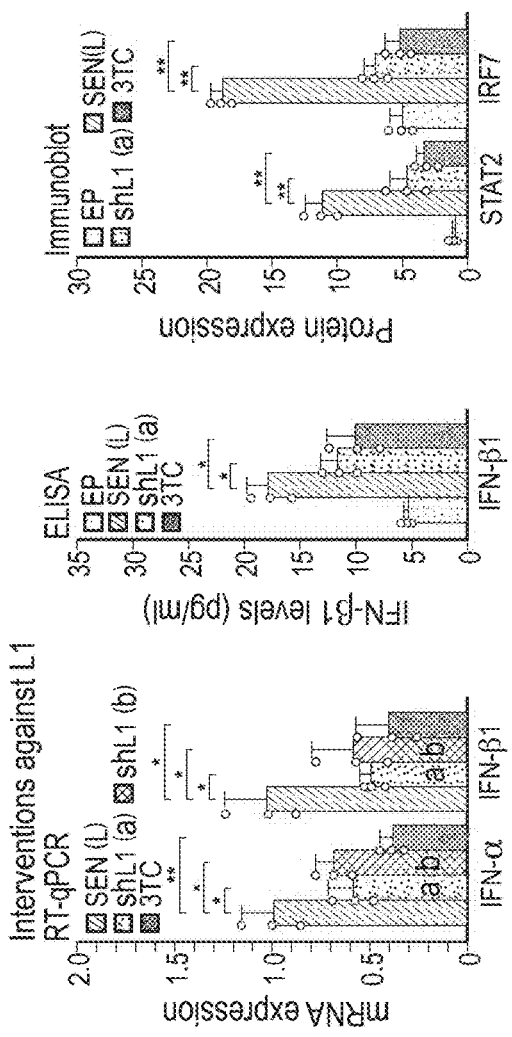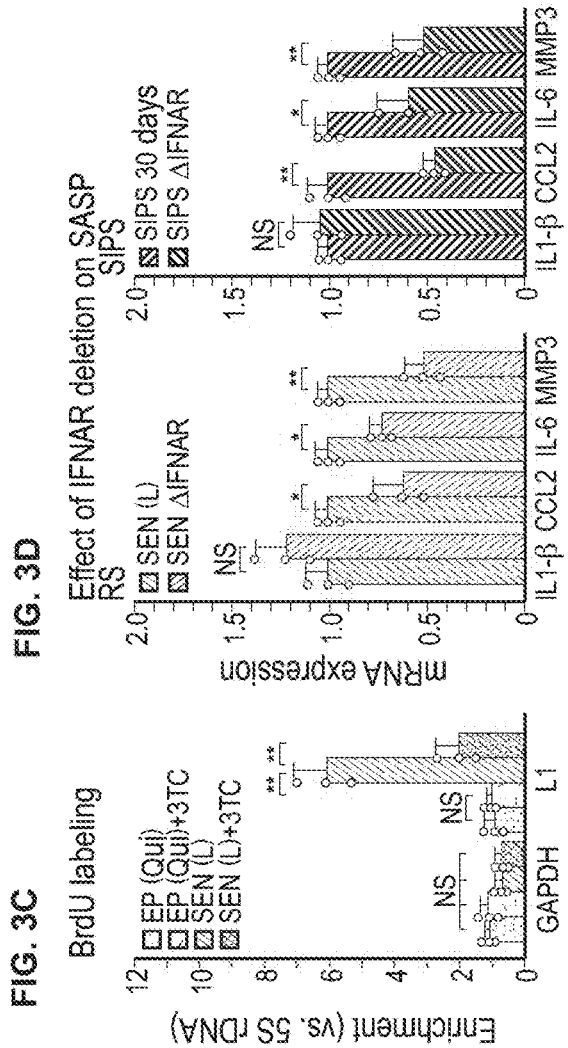
FIG. 3A
FIG. 3B
FIG. 3C
FIG. 3D

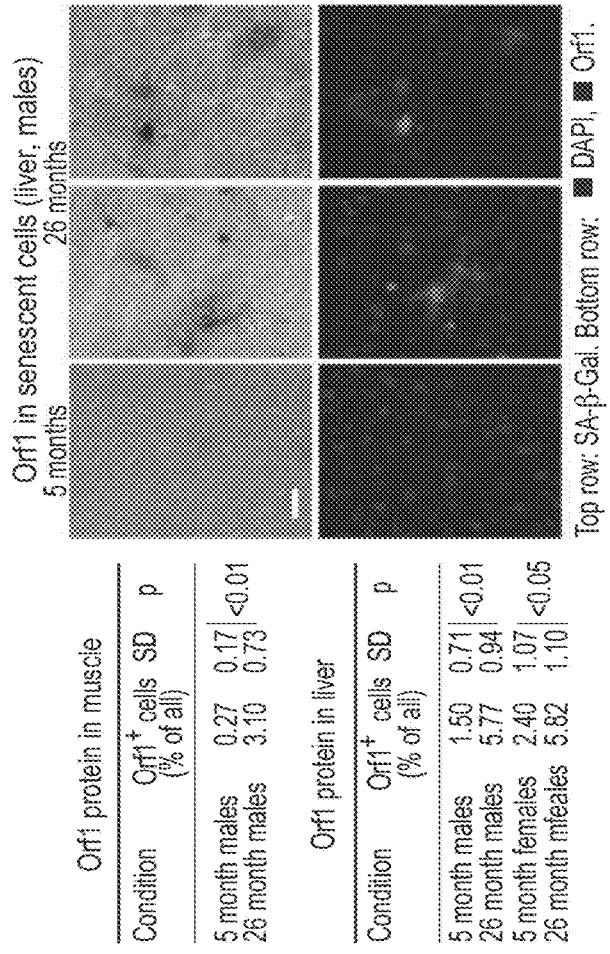
FIG. 4A
FIG. 4B
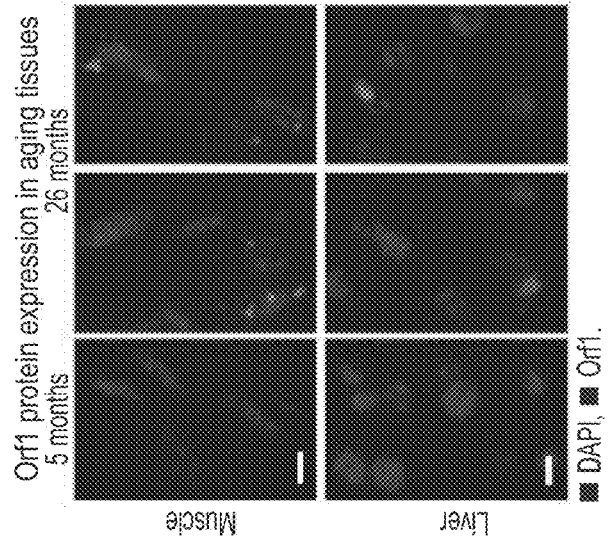
FIG. 4C
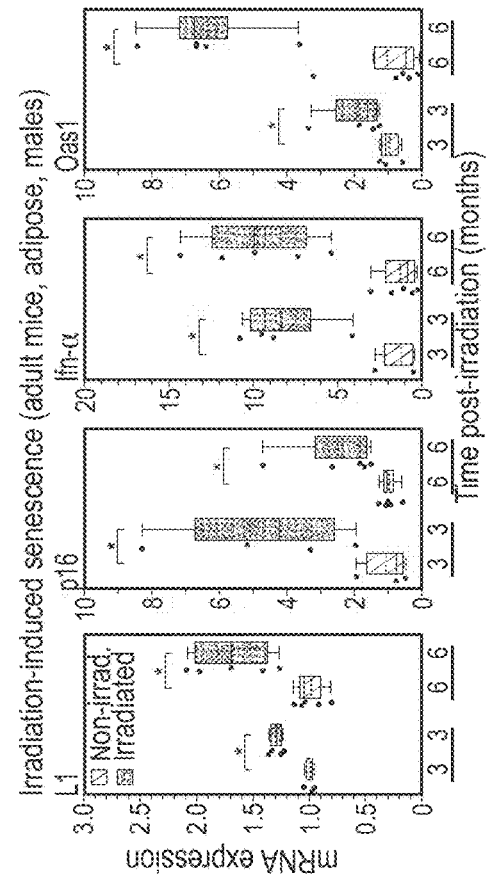
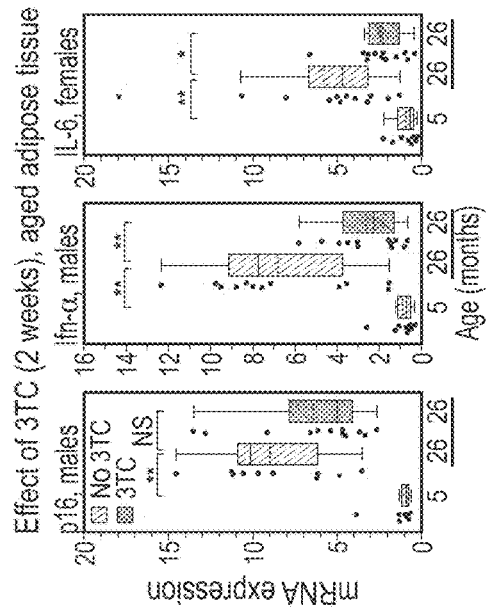
FIG. 4D

ROLE OF CELLULAR SENESCENCE IN AGE-ASSOCIATED INFLAMMATION
CELLULAR SENESCENCE
UPREGULATION OF RTEs
(in particular LINE-1)
ACCUMULATION OF CYTOPLASMIC L1 cDNA
INDUCTION OF IFN-I
(via cGAS/STING etc.)
Crosstalk to Immune System, Reinforcement of SASP
Promotion of Age-Associated, "Sterile" Inflammation
FIG. 5

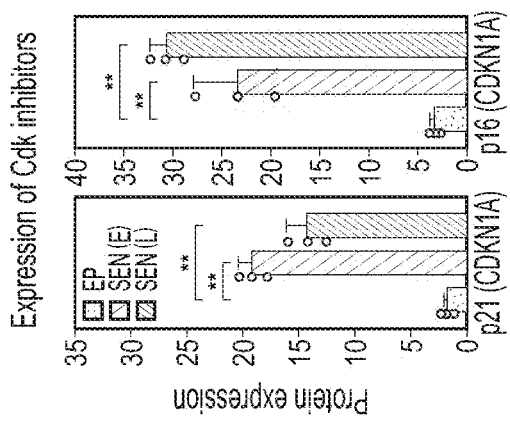
FIG. 6A
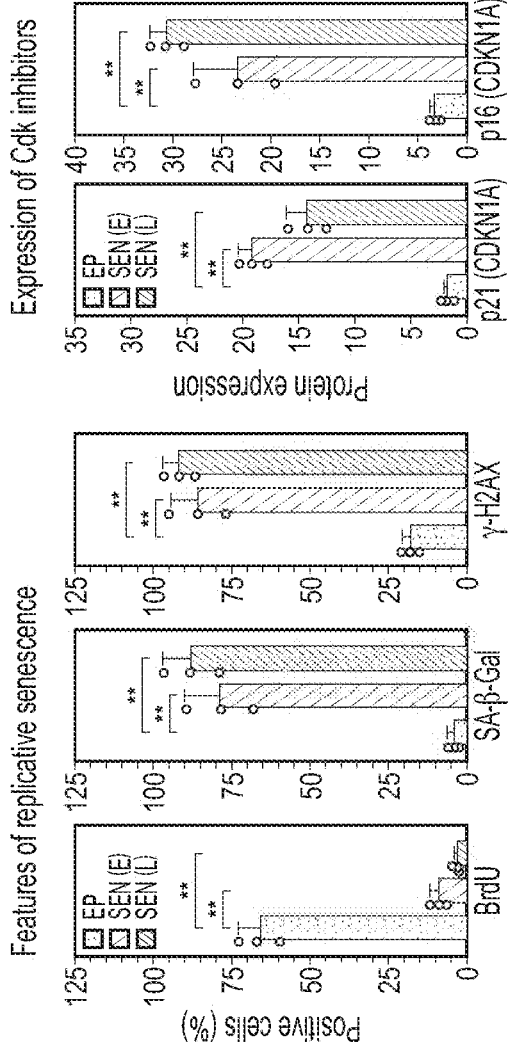
FIG. 6B
FIG. 6C
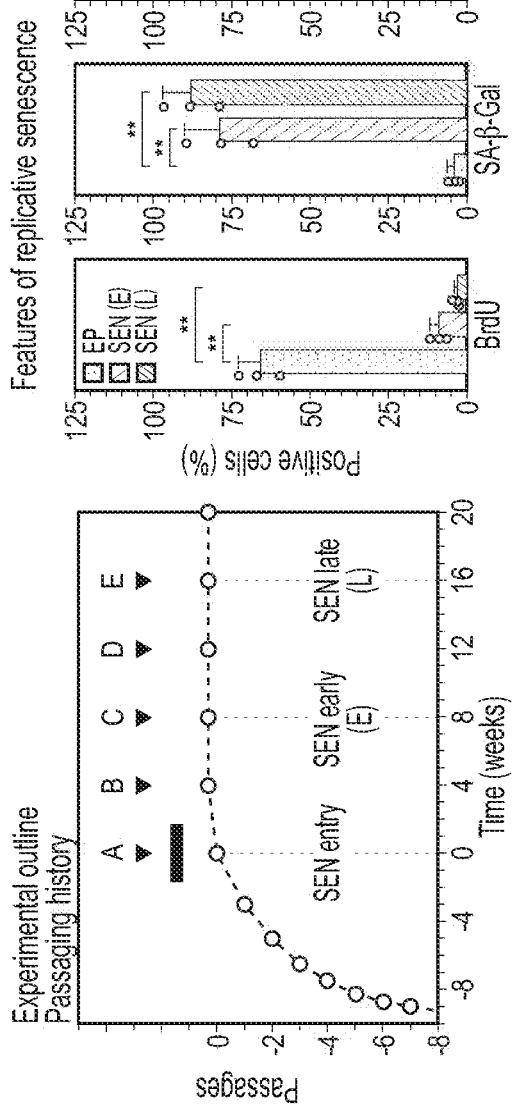
FIG. 6D
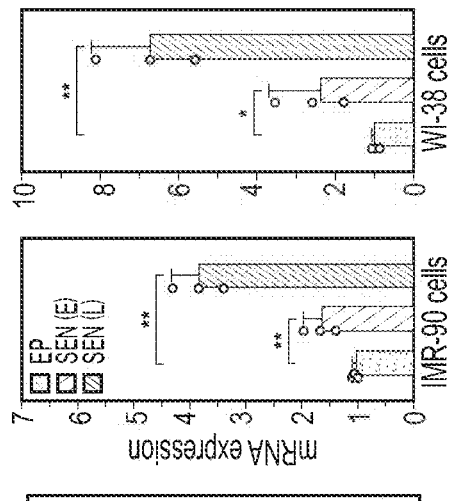
FIG. 6E
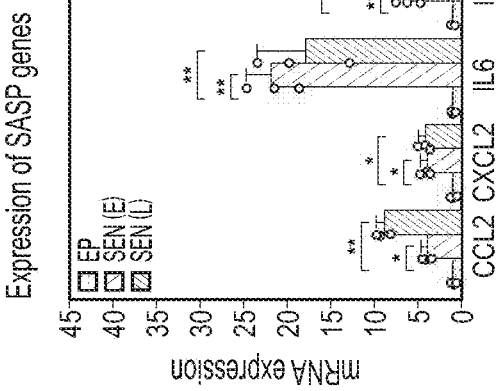

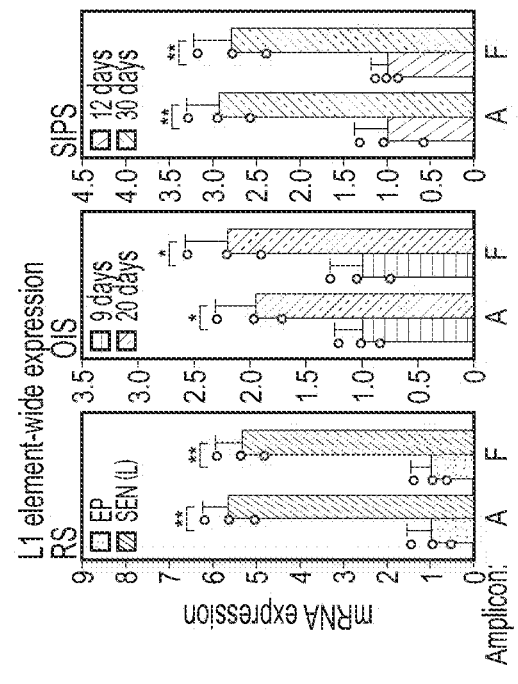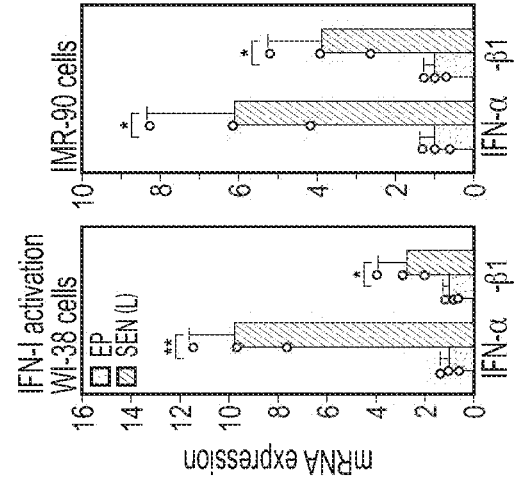

| Summary of 5'RACE data | |
|---|---|
| Sequenced clones | 50 |
| Start: < −40 bp | 4 |
| −25 bp to +25 bp | 28 |
| +25 bp to +180 bp | 6 |
| > +180 bp | 12 |

| Family | Count | % |
|---|---|---|
| L1HS | 8 | 16 |
| L1PA2 | 9 | 18 |
| L1PA3 | 11 | 22 |
| L1PA4 | 7 | 14 |
| L1PA5 | 8 | 18 |
| L1PA7 | 2 | 4 |
| L1P1 | 5 | 10 |

GSEA analysis of all KEGG pathways
Upregulated from early passage to early senescence (EP_SEN-E_UP)

| Pathway name | Size | NES | NOM p-val | FDR p-val |
|---|---|---|---|---|
| ASTHMA | 28 | 1.7864 | <1.00E-03 | <1.00E-02 |
| GRAFT_VERSUS_HOST_DISEASE | 35 | 1.7654 | <1.00E-03 | <1.00E-02 |
| CELL_ADHESION_MOLECULES_CAMS | 127 | 1.7538 | <1.00E-03 | <1.00E-02 |
| OLFACTORY_TRANSDUCTION | 367 | 1.7468 | <1.00E-03 | <1.00E-02 |
| TYPE_I_DIABETES_MELLITUS | 41 | 1.7140 | <1.00E-03 | <1.00E-02 |
| LYSOSOME | 119 | 1.6878 | <1.00E-03 | <1.00E-02 |
| COMPLEMENT_AND_COAG_CASCADES | 67 | 1.6854 | <1.00E-03 | <1.00E-02 |
| ECM_RECEPTOR_INTERACTION | 84 | 1.5487 | <1.00E-03 | <1.00E-02 |
| LEISHMANIA_INFECTION | 68 | 1.6559 | 1.79E-03 | <1.51E-02 |
| CUSTOM_SASP | 85 | 1.6517 | 1.80E-03 | <1.51E-02 |
| PRION_DISEASES | 34 | 1.6397 | 1.84E-03 | <1.51E-02 |
| CYTOKINE_CYTOKINE_RECEPTOR_INTERACT. | 254 | 1.5705 | 1.62E-03 | <1.51E-02 |
| TOLL_LIKE_RECEPTOR_SIGNALING_PATHWAY | 99 | 1.4920 | 1.73E-03 | <1.51E-02 |
| AUTOIMMUNE_THYROID_DISEASE | 48 | 1.5336 | 3.77E-03 | <2.66E-02 |
| ENDOCYTOSIS | 174 | 1.4427 | 5.21E-03 | <3.49E-02 |

Upregulated from early passage to late senescence (EP_SEN-L_UP)

| Pathway name | Size | NES | NOM p-val | FDR p-val |
|---|---|---|---|---|
| OLFACTORY_TRANSDUCTION | 367 | 1.9816 | <1.00E-03 | <5.00E-03 |
| TYPE_I_DIABETES_MELLITUS | 41 | 1.7551 | <1.00E-03 | <5.00E-03 |
| GRAFT_VERSUS_HOST_DISEASE | 35 | 1.7098 | <1.00E-03 | <5.00E-03 |
| CELL_ADHESION_MOLECULES_CAMS | 127 | 1.6868 | <1.00E-03 | <5.00E-03 |
| RETINOL_METABOLISM | 56 | 1.6689 | <1.00E-03 | <5.00E-03 |
| CUSTOM_SASP | 85 | 1.6282 | <1.00E-03 | <5.00E-03 |
| LEISHMANIA_INFECTION | 68 | 1.6260 | <1.00E-03 | <5.00E-03 |
| CUSTOM_IFN-I | 50 | 1.6246 | <1.00E-03 | <5.00E-03 |
| COMPLEMENT_AND_COAG_CASCADES | 67 | 1.6008 | <1.00E-03 | <5.00E-03 |
| TOLL_LIKE_RECEPTOR_SIGNALING_PATHWAY | 99 | 1.5759 | <1.00E-03 | <5.00E-03 |
| NEUROACTIVE_LIGAND_RECEPTOR_INTERACT. | 270 | 1.5340 | <1.00E-03 | <5.00E-03 |
| CYTOKINE_CYTOKINE_RECEPTOR_INTERACT. | 254 | 1.5008 | <1.00E-03 | <5.00E-03 |
| HEMATOPOIETIC_CELL_LINEAGE | 85 | 1.5269 | 1.07E-03 | 5.32E-03 |
| DRUG_METABOLISM_CYTOCHROME_P450 | 63 | 1.5343 | 1.12E-03 | 5.32E-03 |
| ANTIGEN_PROCESSING_AND_PRESENTATION | 73 | 1.6286 | 1.08E-03 | 5.32E-03 |
| XEBOBIOTIC_METAB_BY_CYTOCHROME_P450 | 62 | 1.5245 | 3.36E-03 | 1.51E-02 |
| CYTOSOLIC_DNA_SENSING_PATHWAY | 52 | 1.5816 | 3.42E-03 | 1.51E-02 |
| VIRAL_MYOCARDITIS | 68 | 1.4405 | 4.39E-03 | 1.96E-02 |
| ASCORBATE_AND_ALDARATE_METABOLISM | 21 | 1.5205 | 6.20E-03 | 2.86E-02 |
| NATURAL_KILLER_CELL_MEDIATED_CYTOTOX. | 123 | 1.3730 | 7.22E-03 | 3.25E-02 |
| STEROID_HORMONE_BIOSYNTHESIS | 49 | 1.5533 | 7.94E-03 | 3.62E-02 |
| CALCIUM_SIGNALING_PATHWAY | 173 | 1.3406 | 9.14E-03 | 3.97E-02 |
| LINOLEIC_ACID_METABOLISM | 29 | 1.4904 | 1.00E-02 | 4.21E-02 |
| AUTOIMMUNE_THYROID_DISEASE | 48 | 1.5072 | 1.04E-02 | 4.21E-02 |
| ECM_RECEPTOR_INTERACTION | 84 | 1.4313 | 1.09E-02 | 4.53E-02 |

Upregulated from early senescence to late senescence (SEN-E_SEN-L_UP)

| Pathway name | Size | NES | NOM p-val | FDR p-val |
|---|---|---|---|---|
| OLFACTORY_TRANSDUCTION | 367 | 1.6009 | <1.00E-03 | <5.00E-02 |
| CUSTOM_IFN-I | 50 | 1.4722 | <1.00E-03 | <5.00E-02 |
| NEUROACTIVE_LIGAND_RECEPTOR_INTERACT. | 270 | 1.3253 | <1.00E-03 | <5.00E-02 |

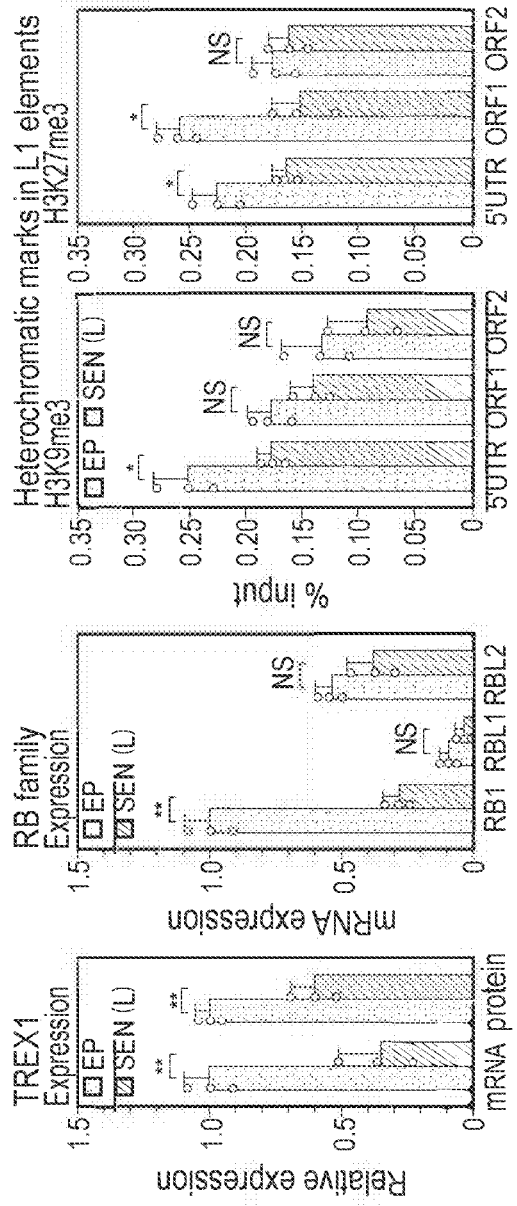
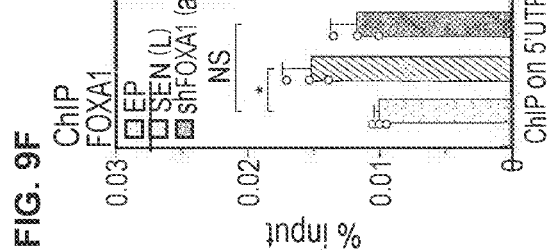
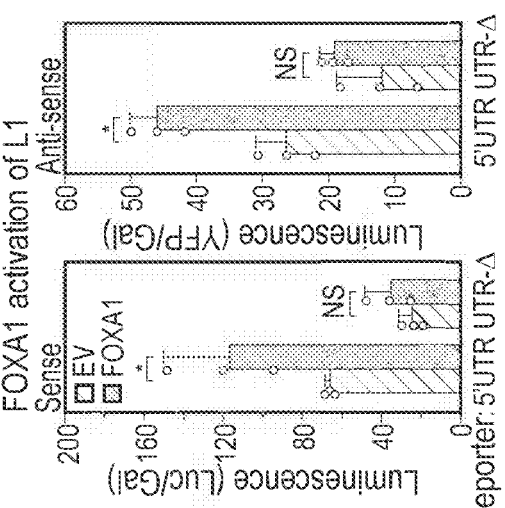
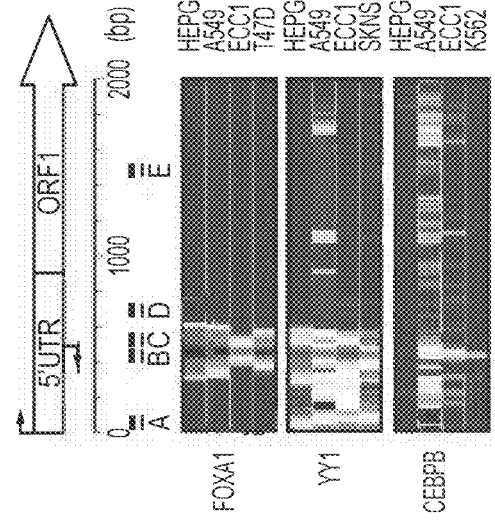

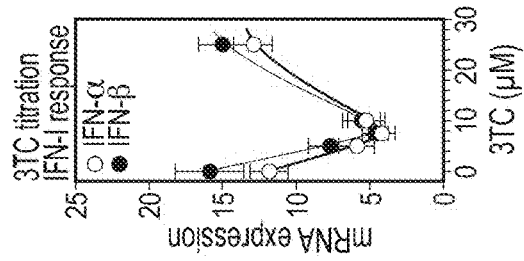
FIG. 10A
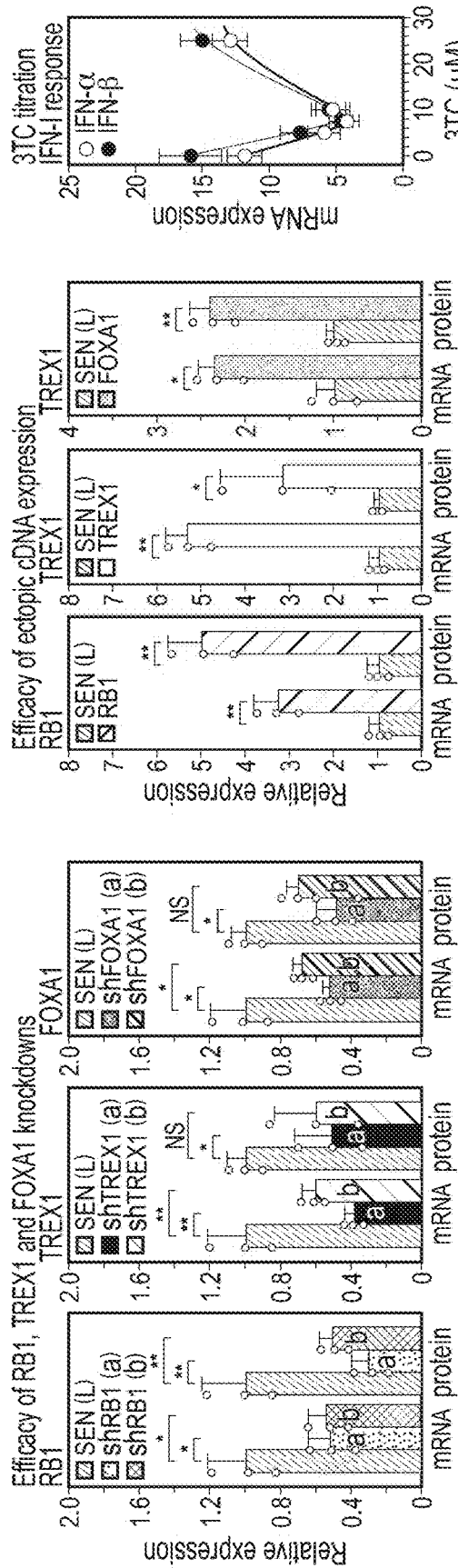
FIG. 10B
FIG. 10C
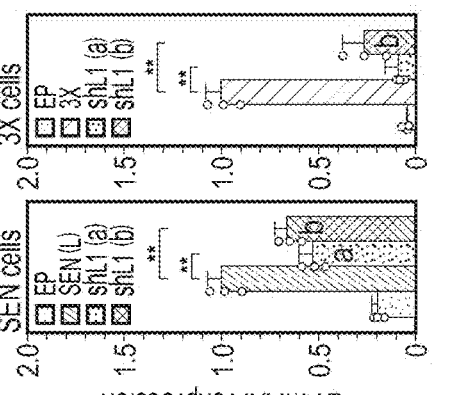
FIG. 10F
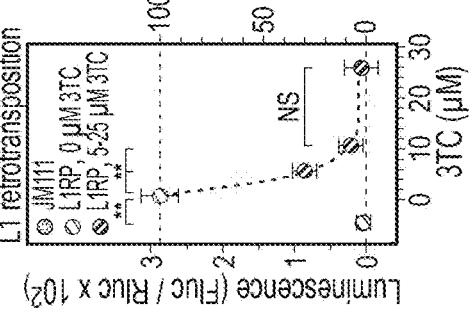
FIG. 10E
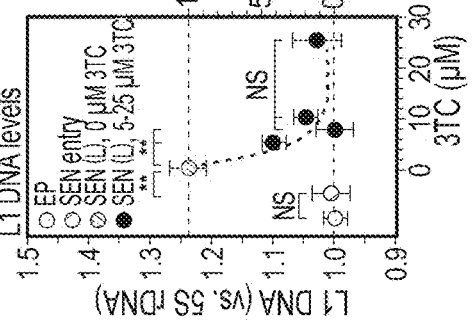
FIG. 10D
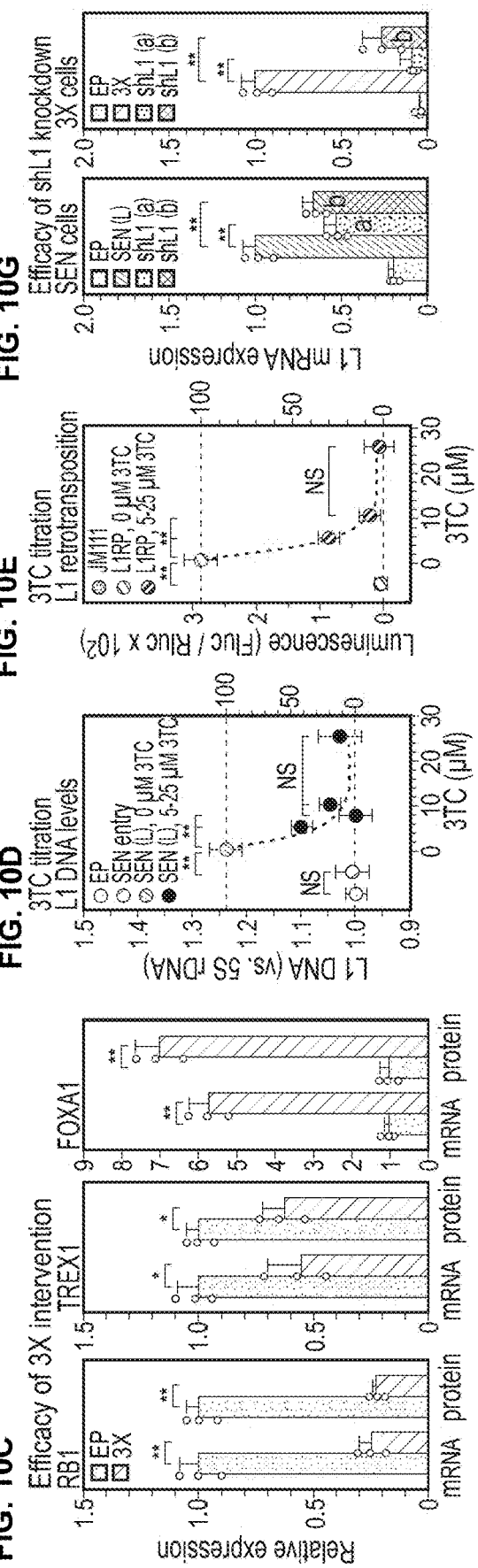
FIG. 10G

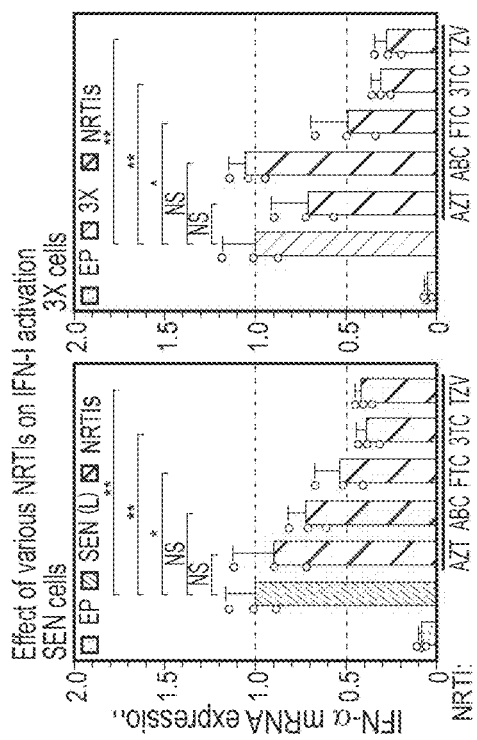
FIG. 10H
FIG. 10I
FIG. 10J
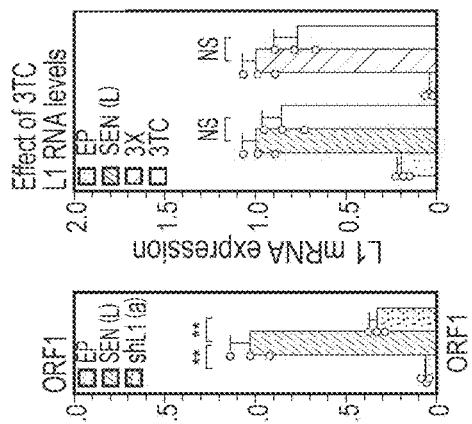
FIG. 10K
FIG. 10L
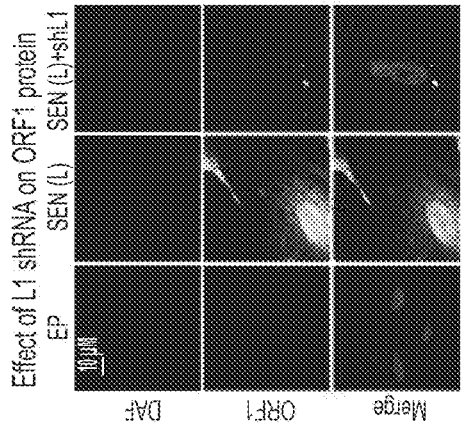
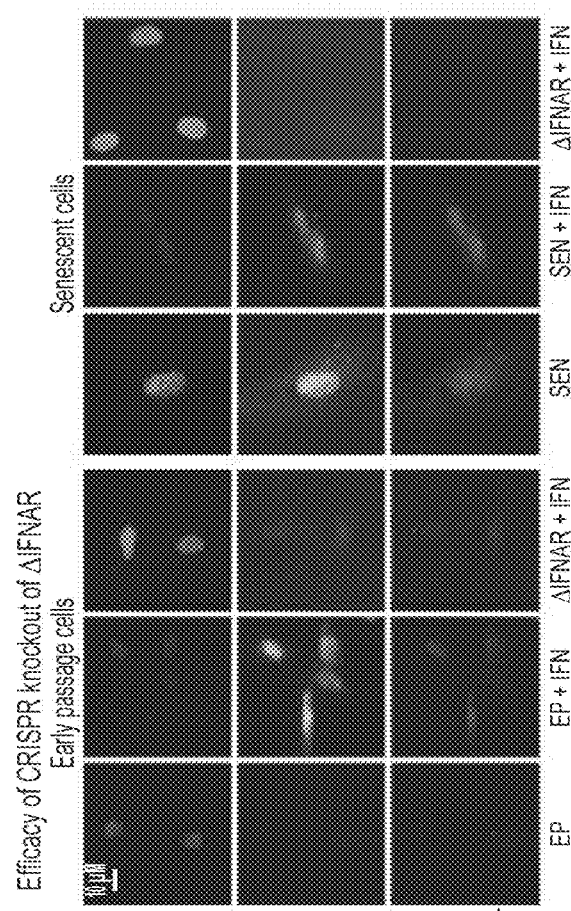
FIG. 10M
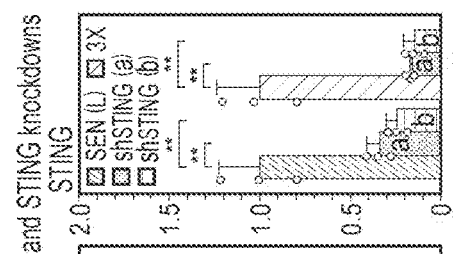
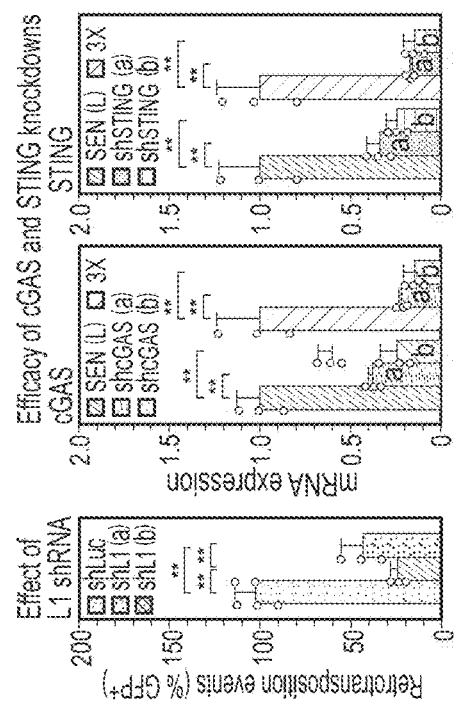

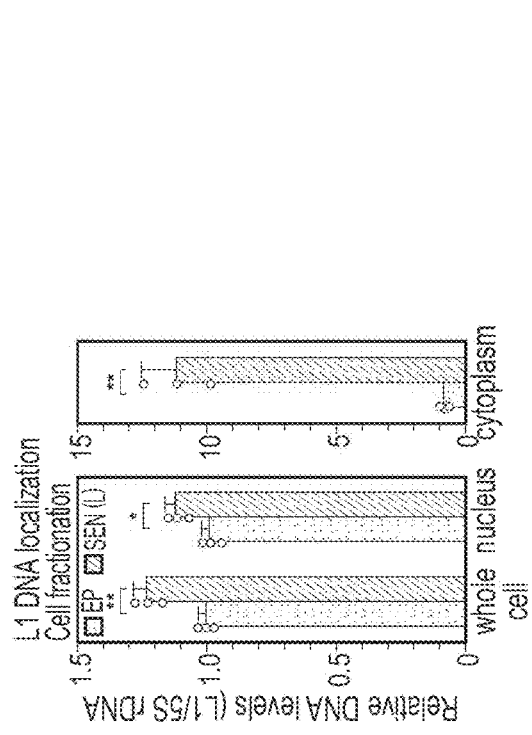
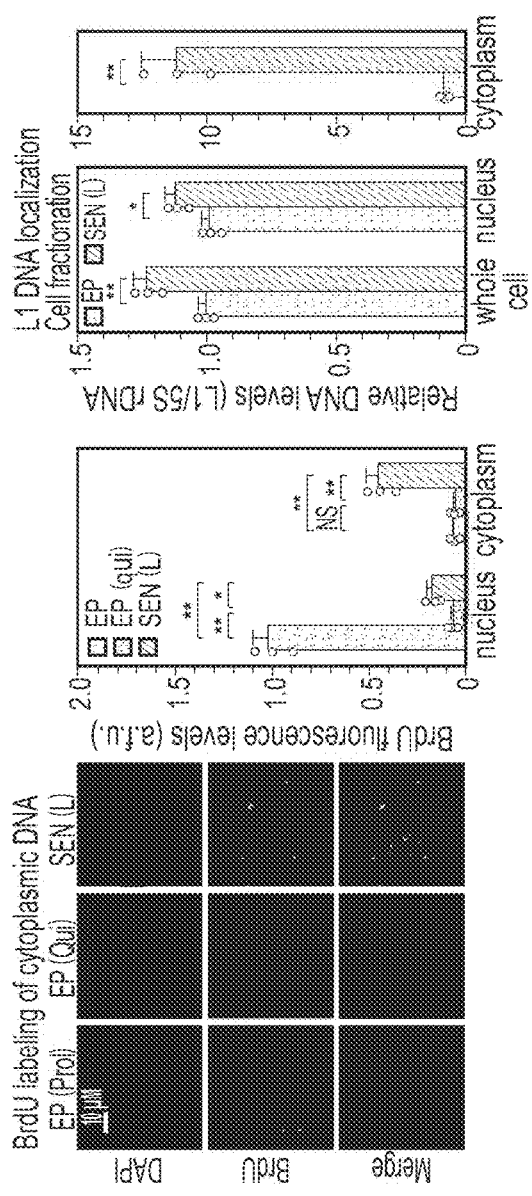
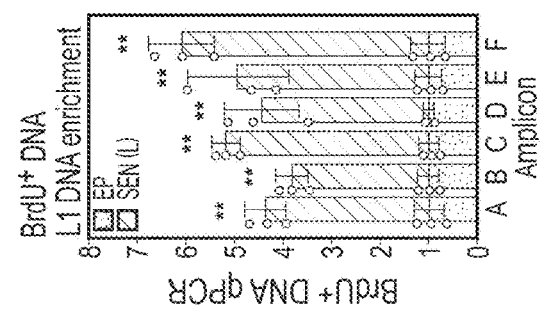
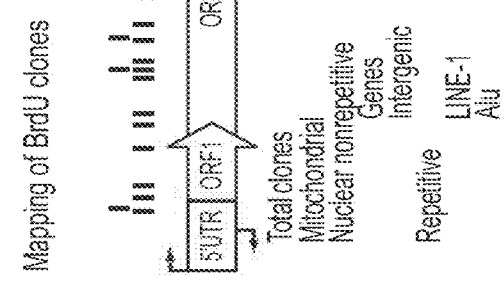
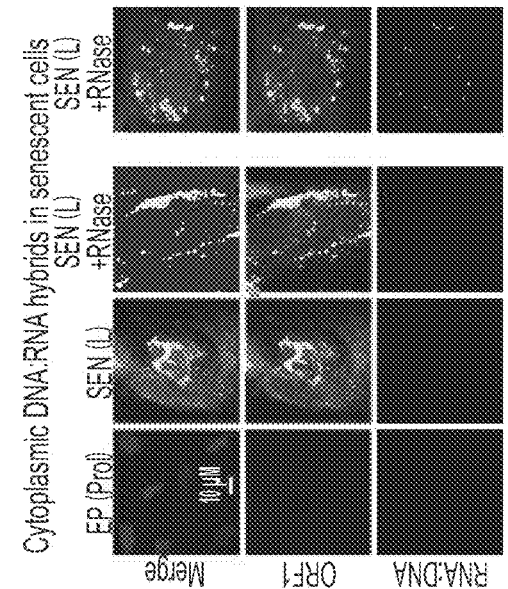

FIG. 12A
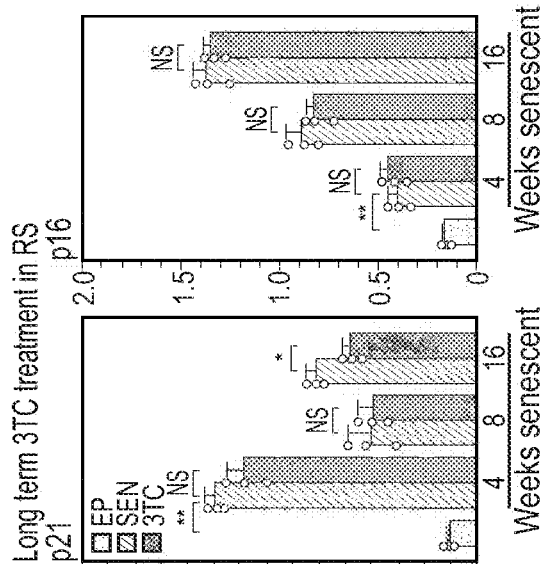
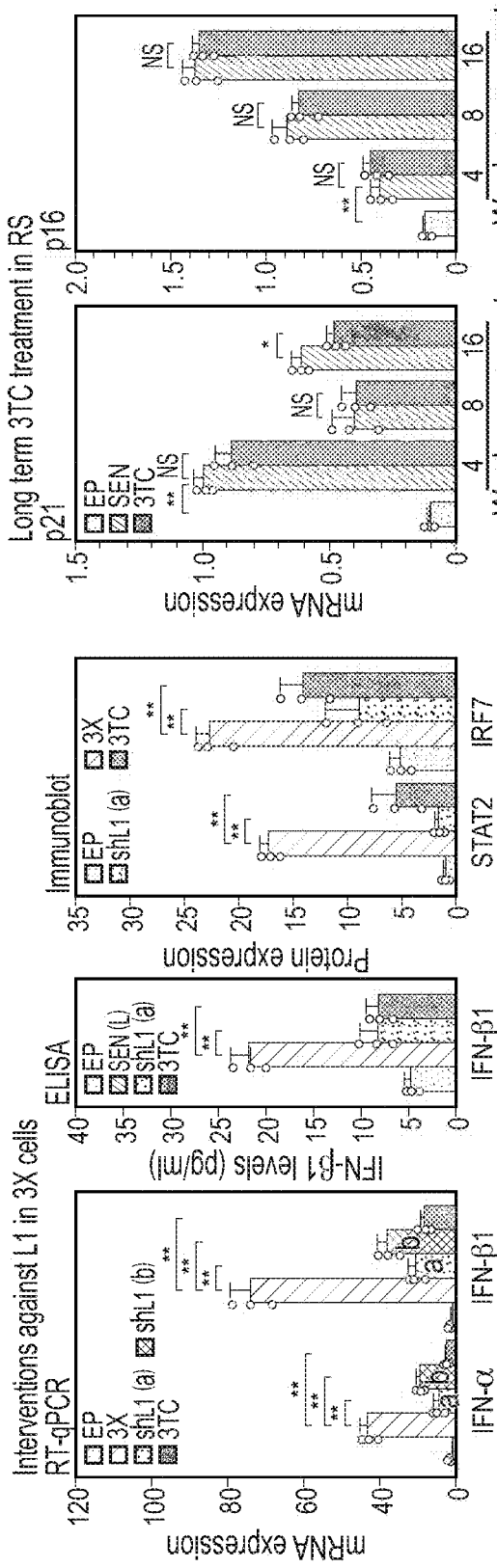
FIG. 12B
FIG. 12C
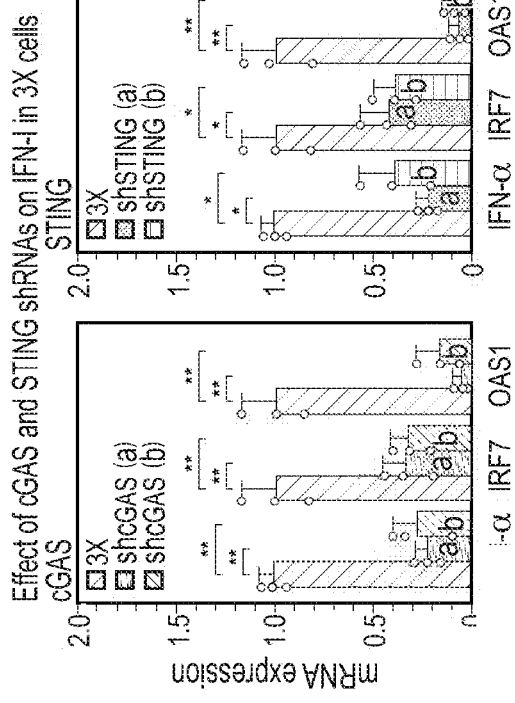
FIG. 12D
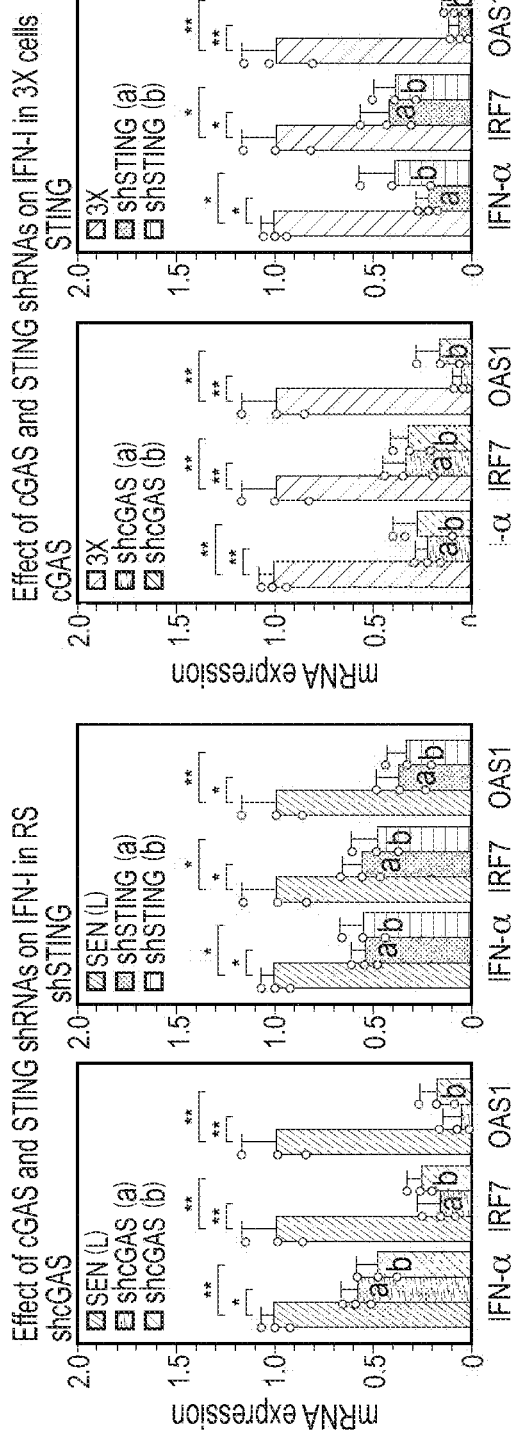

FIG. 12E
FIG. 12F
FIG. 12G
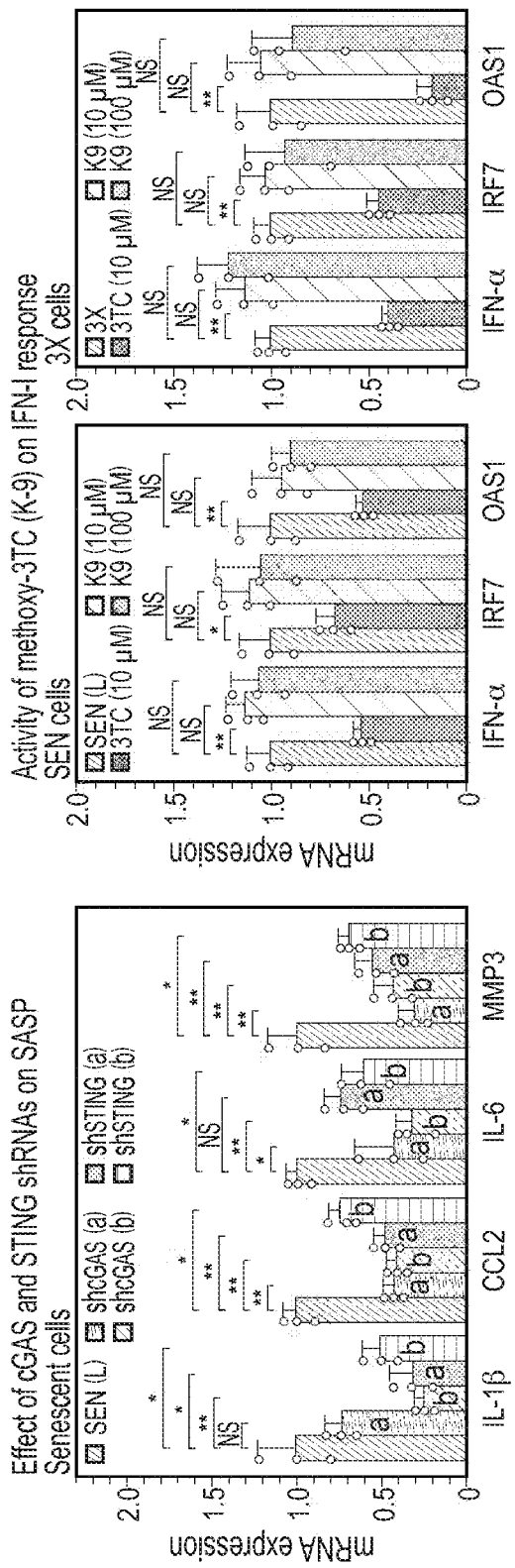
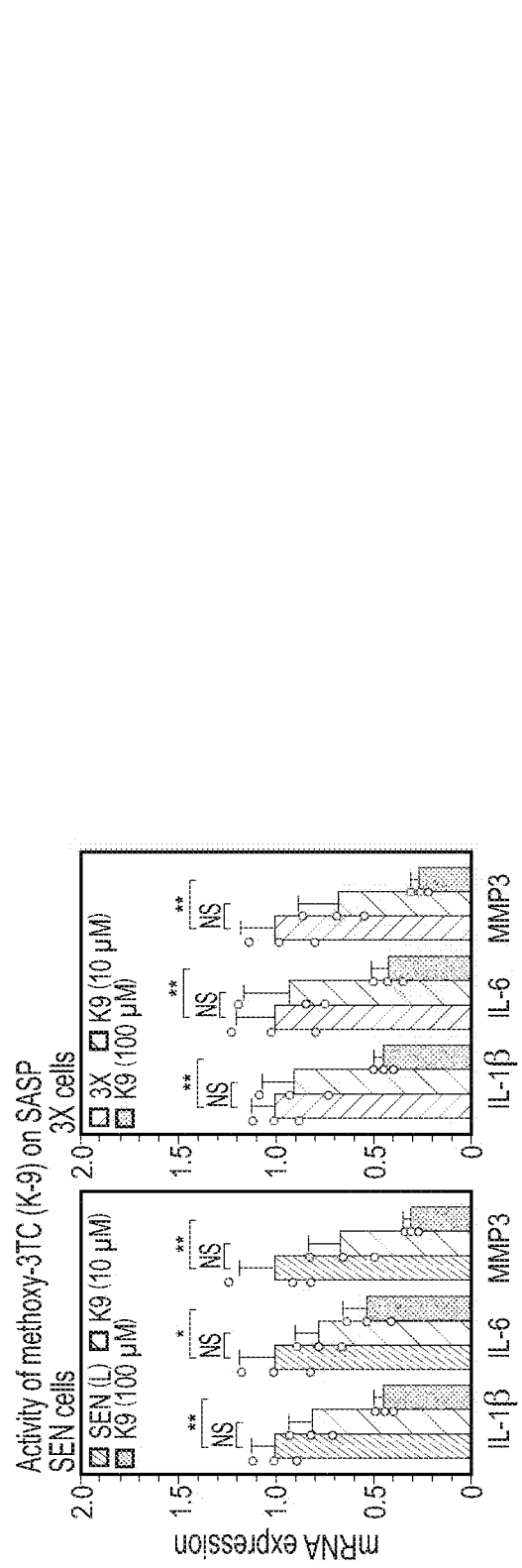

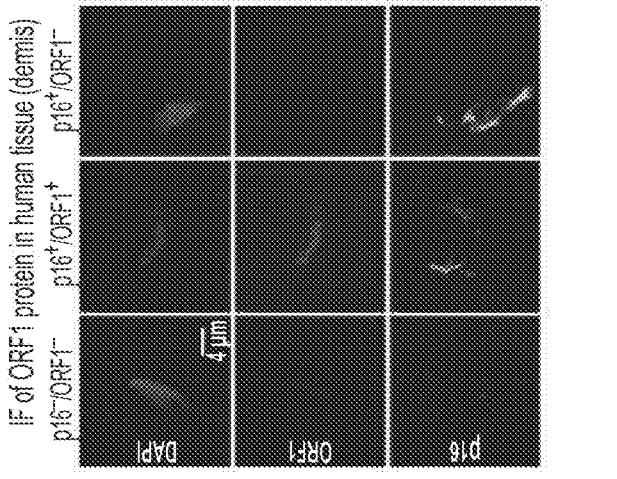
FIG. 13A
FIG. 13B
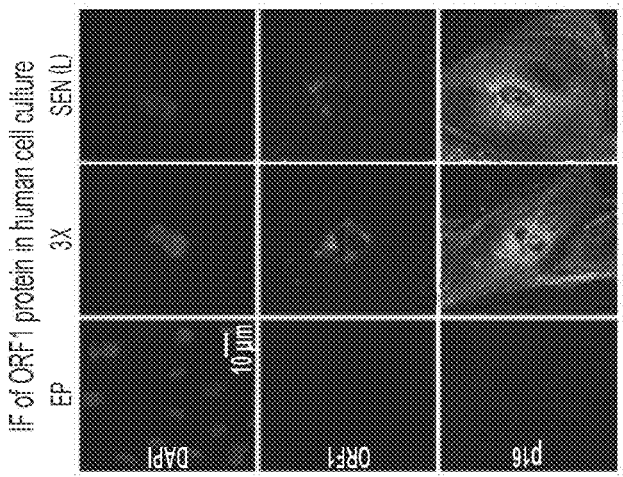
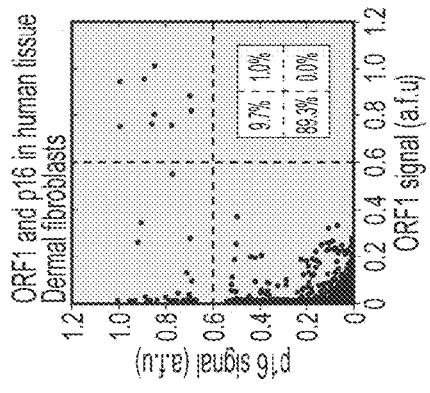
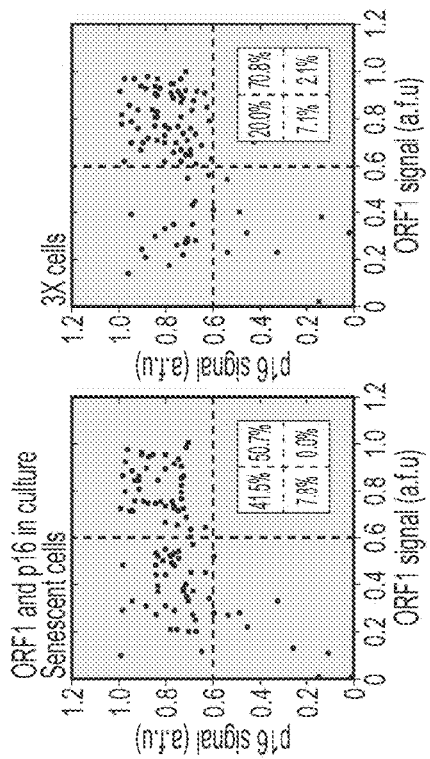
FIG. 13C
FIG. 13D

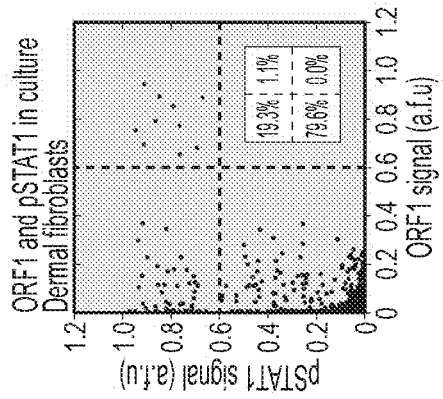

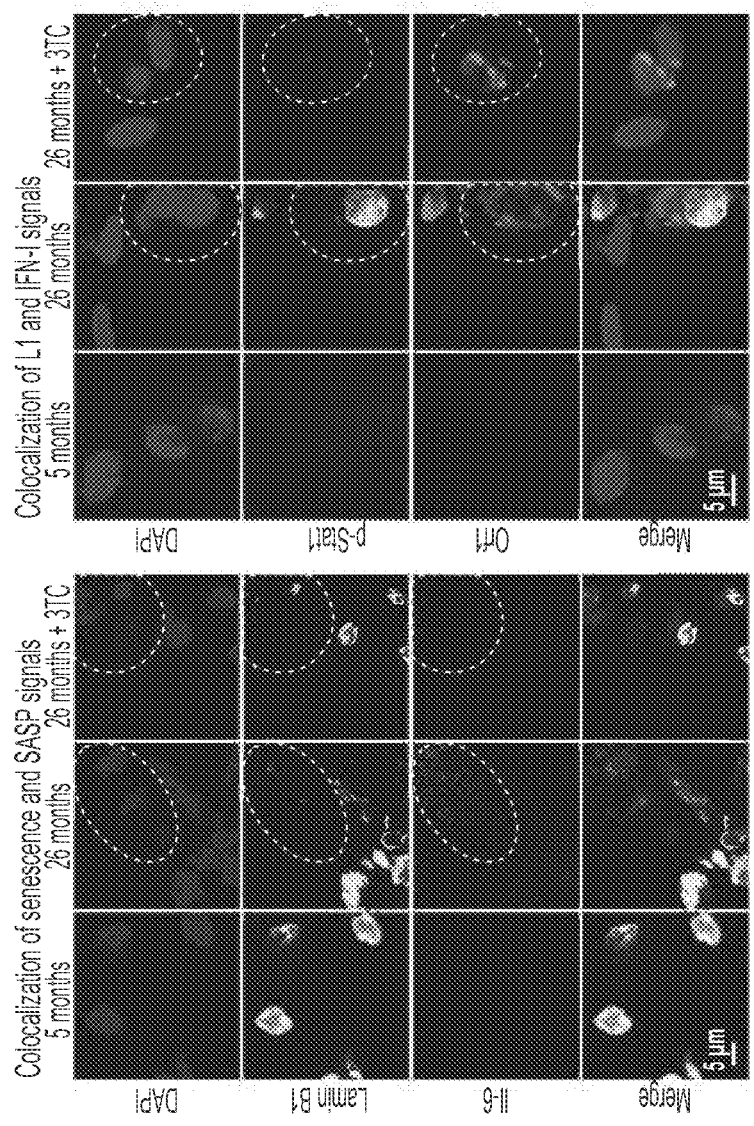

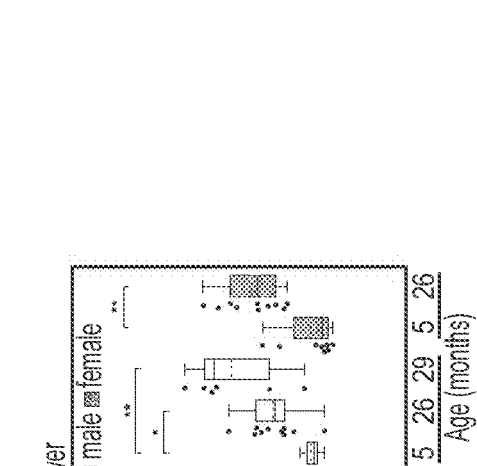
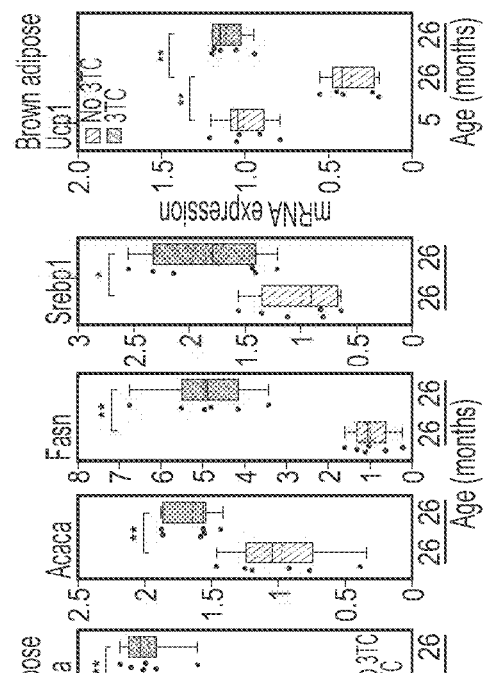
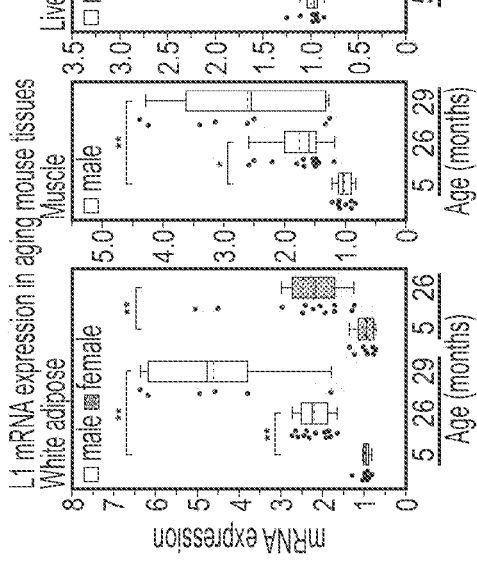
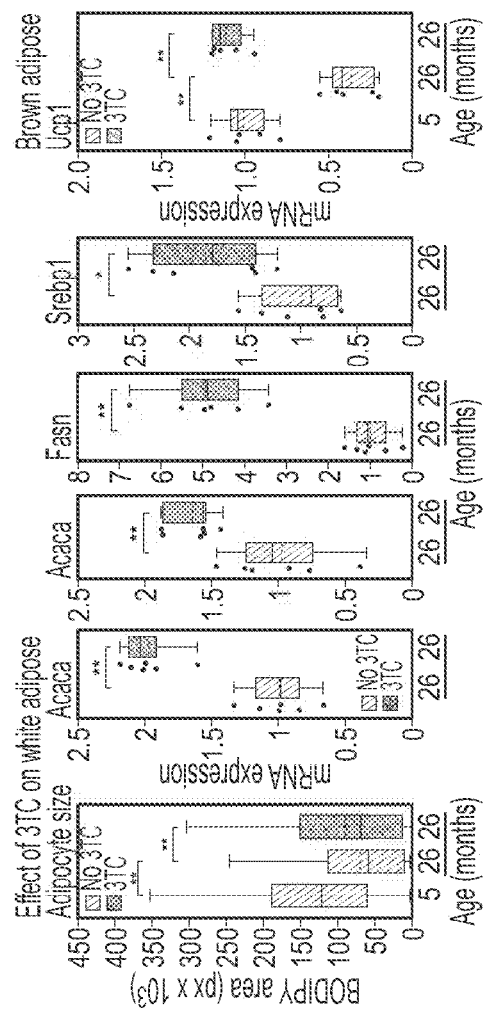
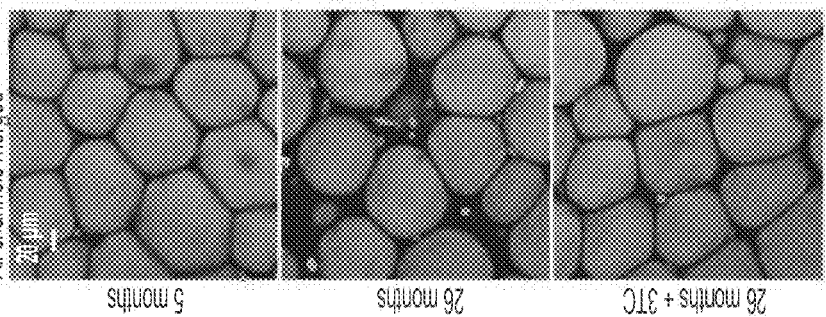

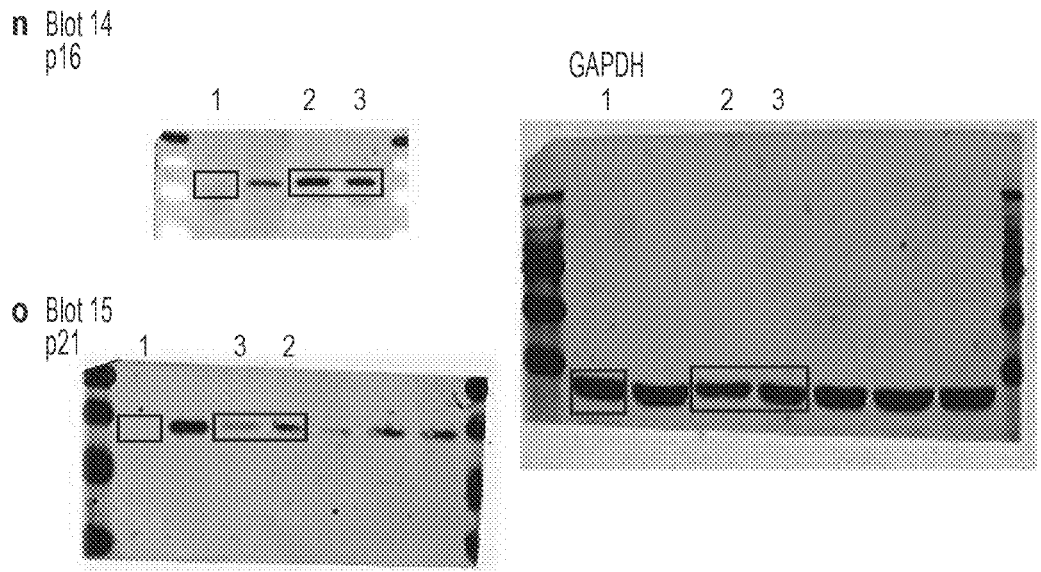

a, Blot 1 - RB1: 1. EP; 2. SEN (L); 3. OE – SEN; 4. SEN (E)
b, Blot 2 - TREX1: 1. EP; 2. SEN (E); 3. SEN (L)
c, Blot 3 - FOXA1: 1. EP; 2. Arrest; 3. SEN (E); 4. SEN (L)
d, Blot 4 - RB1: 1. EP; 2. 3X
e, Blot 5 - TREX1: 1. EP; 2. 3X
f, Blot 6 - FOXA1: 1. EP; 2. 3X
g, Blot 7 - RB1: 1. SEN (L); 2. shRB1(b); 3. shRB1(a); 4. OE-RB1
h, Blot 8 - TREX1: 1. SEN (L); 2. shTREX1 (b); 3. shTREX1 (a); 4. OE-TREX1
I, Blot 9 - FOXA1: 1. shFOXA1 (a); 2. shFOXA1 (b); 3. SEN (L); 4. OE-FOXA1
j, Blot 10 - STAT2: 1. 3X; 2. shL1; 3. NRTI; 4. ΔIFNAR; 5. EP
k, Blot 11 - IRF7: 1. EP; 2. shL1; 3. 3X; 4. shL1; 5. ΔIFNAR
l, Blot 12 - STAT2: 1. SEN (L); 2. ΔIFNAR; 3. shL1; 4. NRTI
m, Blot 13 - IRF7; 5. SEN (L); 6. ΔIFNAR; 7. shL1; 8. NRTI
n, Blot 14 – p16 (CDKN2A): 1. EP; 2. SEN (E); 3. SEN (L)
o, Blot 15 – p21 (CDKN1A): 1. EP; 2. SEN (E); 3. SEN (L)

FIG. 16E

FIG. 17A L1 copy number
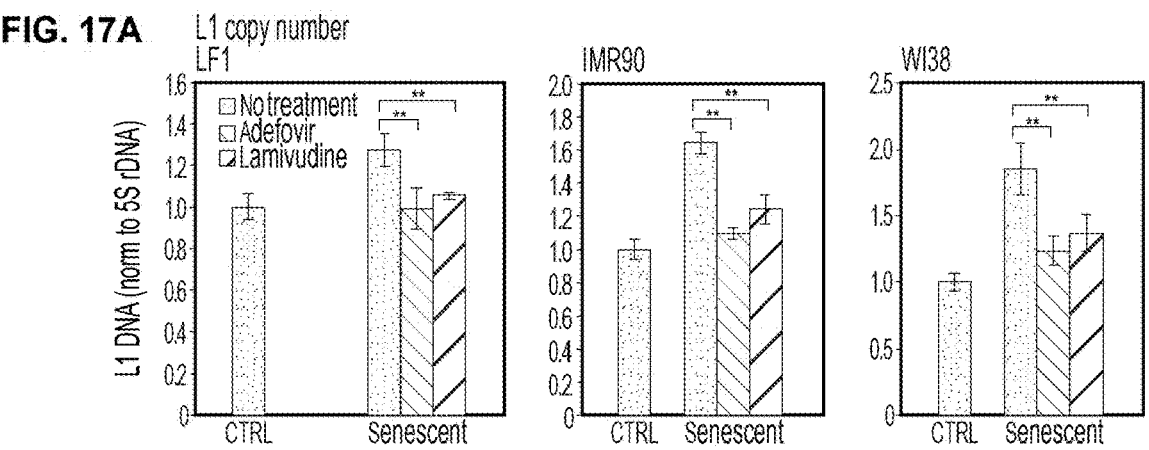
FIG. 17B Type-I Interferons
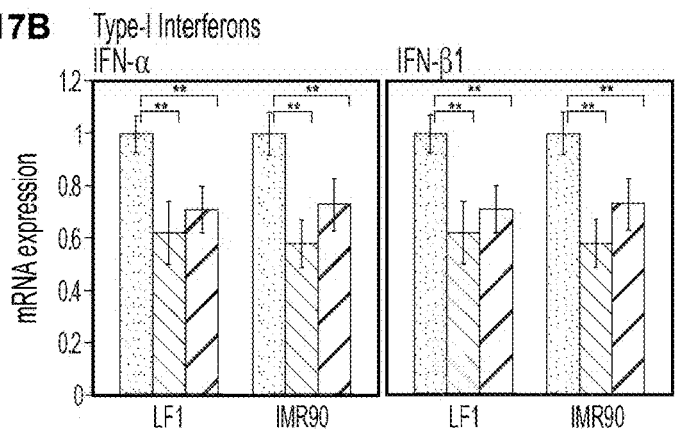
FIG. 17C SASP gene expression
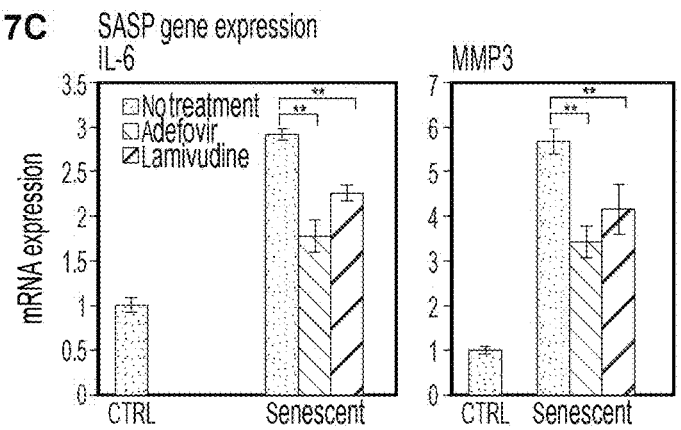
FIG. 17D Type-I Interferons
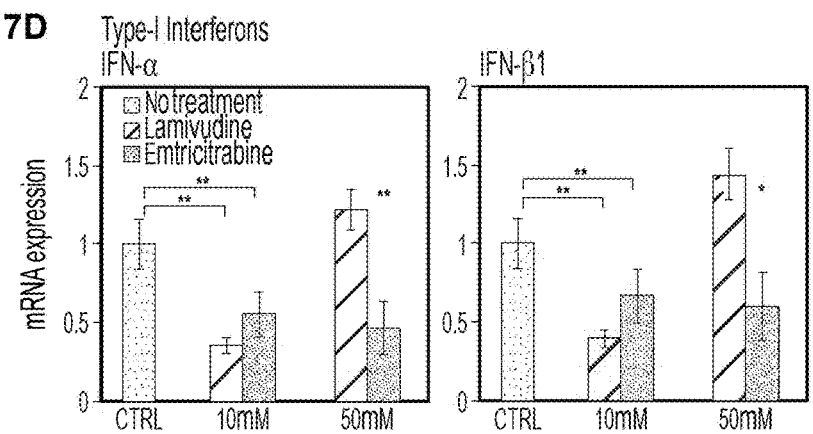

SEQUENCE LISTING

```
Sequence total quantity: 114
SEQ ID NO: 1                    moltype = DNA   length = 20
FEATURE                         Location/Qualifiers
source                          1..20
                                mol_type = other DNA
                                note = Synthetic primer
                                organism = synthetic construct
SEQUENCE: 1
aaagtttctt atggccgggc                                                    20

SEQ ID NO: 2                    moltype = DNA   length = 20
FEATURE                         Location/Qualifiers
source                          1..20
                                mol_type = other DNA
                                note = Synthetic primer
                                organism = synthetic construct
SEQUENCE: 2
gctgaacttg tggccgttta                                                    20

SEQ ID NO: 3                    moltype = DNA   length = 21
FEATURE                         Location/Qualifiers
source                          1..21
                                mol_type = other DNA
                                note = Synthetic oligonucleotide
                                organism = synthetic construct
SEQUENCE: 3
aagacacatg cacacgtatg t                                                  21

SEQ ID NO: 4                    moltype = DNA   length = 21
FEATURE                         Location/Qualifiers
source                          1..21
                                mol_type = other DNA
                                note = Synthetic oligonucleotide
                                organism = synthetic construct
SEQUENCE: 4
aacaggagcg atgagtctgt a                                                  21

SEQ ID NO: 5                    moltype = DNA   length = 20
FEATURE                         Location/Qualifiers
source                          1..20
                                mol_type = other DNA
                                note = Synthetic oligonucleotide
                                organism = synthetic construct
SEQUENCE: 5
gtgtatatca gcctcgtgtt                                                    20

SEQ ID NO: 6                    moltype = DNA   length = 20
FEATURE                         Location/Qualifiers
source                          1..20
                                mol_type = other DNA
                                note = Synthetic primer
                                organism = synthetic construct
SEQUENCE: 6
gccaagatgg ccgaatagga                                                    20

SEQ ID NO: 7                    moltype = DNA   length = 20
FEATURE                         Location/Qualifiers
source                          1..20
                                mol_type = other DNA
                                note = Synthetic primer
                                organism = synthetic construct
SEQUENCE: 7
aaatcacccg tcttctgcgt                                                    20

SEQ ID NO: 8                    moltype = DNA   length = 20
FEATURE                         Location/Qualifiers
source                          1..20
                                mol_type = other DNA
                                note = Synthetic primer
                                organism = synthetic construct
SEQUENCE: 8
cgagatcaaa ctgcaaggcg                                                    20

SEQ ID NO: 9                    moltype = DNA   length = 20
FEATURE                         Location/Qualifiers
source                          1..20
                                mol_type = other DNA
                                note = Synthetic primer
```

```
                       organism = synthetic construct
SEQUENCE: 9
ccggccgctt tgtttaccta                                                    20

SEQ ID NO: 10          moltype = DNA   length = 19
FEATURE                Location/Qualifiers
source                 1..19
                       mol_type = other DNA
                       note = Synthetic primer
                       organism = synthetic construct
SEQUENCE: 10
taaacaaagc ggccgggaa                                                     19

SEQ ID NO: 11          moltype = DNA   length = 20
FEATURE                Location/Qualifiers
source                 1..20
                       mol_type = other DNA
                       note = Synthetic primer
                       organism = synthetic construct
SEQUENCE: 11
agaggtggag cctacagagg                                                    20

SEQ ID NO: 12          moltype = DNA   length = 20
FEATURE                Location/Qualifiers
source                 1..20
                       mol_type = other DNA
                       note = Synthetic primer
                       organism = synthetic construct
SEQUENCE: 12
agagagcagt ggttctccca                                                    20

SEQ ID NO: 13          moltype = DNA   length = 20
FEATURE                Location/Qualifiers
source                 1..20
                       mol_type = other DNA
                       note = Synthetic primer
                       organism = synthetic construct
SEQUENCE: 13
cagtctgccc gttctcagat                                                    20

SEQ ID NO: 14          moltype = DNA   length = 20
FEATURE                Location/Qualifiers
source                 1..20
                       mol_type = other DNA
                       note = Synthetic primer
                       organism = synthetic construct
SEQUENCE: 14
acctgaaagt gacggggaga                                                    20

SEQ ID NO: 15          moltype = DNA   length = 20
FEATURE                Location/Qualifiers
source                 1..20
                       mol_type = other DNA
                       note = Synthetic primer
                       organism = synthetic construct
SEQUENCE: 15
cctgccttgc tagattgggg                                                    20

SEQ ID NO: 16          moltype = DNA   length = 23
FEATURE                Location/Qualifiers
source                 1..23
                       mol_type = other DNA
                       note = Synthetic primer
                       organism = synthetic construct
SEQUENCE: 16
caaacaccgc atattctcac tca                                                23

SEQ ID NO: 17          moltype = DNA   length = 23
FEATURE                Location/Qualifiers
source                 1..23
                       mol_type = other DNA
                       note = Synthetic primer
                       organism = synthetic construct
SEQUENCE: 17
cttcctgtgt ccatgtgatc tca                                                23

SEQ ID NO: 18          moltype = DNA   length = 15
FEATURE                Location/Qualifiers
source                 1..15
```

```
                          mol_type = other DNA
                          note = Synthetic probe
                          organism = synthetic construct
SEQUENCE: 18
aggtgggaat tgaac                                                    15

SEQ ID NO: 19             moltype = DNA   length = 23
FEATURE                   Location/Qualifiers
source                    1..23
                          mol_type = other DNA
                          note = Synthetic primer
                          organism = synthetic construct
SEQUENCE: 19
ctcgtctgat ctcggaagct aag                                           23

SEQ ID NO: 20             moltype = DNA   length = 20
FEATURE                   Location/Qualifiers
source                    1..20
                          mol_type = other DNA
                          note = Synthetic primer
                          organism = synthetic construct
SEQUENCE: 20
gcggtctccc atccaagtac                                               20

SEQ ID NO: 21             moltype = DNA   length = 14
FEATURE                   Location/Qualifiers
source                    1..14
                          mol_type = other DNA
                          note = Synthetic probe
                          organism = synthetic construct
SEQUENCE: 21
agggtcgggc ctgg                                                     14

SEQ ID NO: 22             moltype = DNA   length = 20
FEATURE                   Location/Qualifiers
source                    1..20
                          mol_type = other DNA
                          note = Synthetic primer
                          organism = synthetic construct
SEQUENCE: 22
ttgaggtcaa tgaagggtc                                                20

SEQ ID NO: 23             moltype = DNA   length = 20
FEATURE                   Location/Qualifiers
source                    1..20
                          mol_type = other DNA
                          note = Synthetic primer
                          organism = synthetic construct
SEQUENCE: 23
gaaggtgaag gtcggagtca                                               20

SEQ ID NO: 24             moltype = DNA   length = 21
FEATURE                   Location/Qualifiers
source                    1..21
                          mol_type = other DNA
                          note = Synthetic primer
                          organism = synthetic construct
SEQUENCE: 24
ccaggagtga gtggaagaca g                                             21

SEQ ID NO: 25             moltype = DNA   length = 20
FEATURE                   Location/Qualifiers
source                    1..20
                          mol_type = other DNA
                          note = Synthetic primer
                          organism = synthetic construct
SEQUENCE: 25
ctagttgcct cccaaaagca                                               20

SEQ ID NO: 26             moltype = DNA   length = 20
FEATURE                   Location/Qualifiers
source                    1..20
                          mol_type = other DNA
                          note = Synthetic primer
                          organism = synthetic construct
SEQUENCE: 26
ttgatggcaa ccagttccag                                               20

SEQ ID NO: 27             moltype = DNA   length = 20
```

```
FEATURE                 Location/Qualifiers
source                  1..20
                        mol_type = other DNA
                        note = Synthetic primer
                        organism = synthetic construct
SEQUENCE: 27
tcatcccaag cagcagatga                                                        20

SEQ ID NO: 28           moltype = DNA  length = 20
FEATURE                 Location/Qualifiers
source                  1..20
                        mol_type = other DNA
                        note = Synthetic primer
                        organism = synthetic construct
SEQUENCE: 28
tgttcccaag cagcagatga                                                        20

SEQ ID NO: 29           moltype = DNA  length = 20
FEATURE                 Location/Qualifiers
source                  1..20
                        mol_type = other DNA
                        note = Synthetic primer
                        organism = synthetic construct
SEQUENCE: 29
acgccgcatt gaccatctat                                                        20

SEQ ID NO: 30           moltype = DNA  length = 20
FEATURE                 Location/Qualifiers
source                  1..20
                        mol_type = other DNA
                        note = Synthetic primer
                        organism = synthetic construct
SEQUENCE: 30
gtctcattcc agccagtgct                                                        20

SEQ ID NO: 31           moltype = DNA  length = 20
FEATURE                 Location/Qualifiers
source                  1..20
                        mol_type = other DNA
                        note = Synthetic primer
                        organism = synthetic construct
SEQUENCE: 31
actctcacct cccatgttgc                                                        20

SEQ ID NO: 32           moltype = DNA  length = 20
FEATURE                 Location/Qualifiers
source                  1..20
                        mol_type = other DNA
                        note = Synthetic primer
                        organism = synthetic construct
SEQUENCE: 32
atccgtgcac tcctgttctg                                                        20

SEQ ID NO: 33           moltype = DNA  length = 20
FEATURE                 Location/Qualifiers
source                  1..20
                        mol_type = other DNA
                        note = Synthetic primer
                        organism = synthetic construct
SEQUENCE: 33
ccaagaagcg ctctgctgta                                                        20

SEQ ID NO: 34           moltype = DNA  length = 21
FEATURE                 Location/Qualifiers
source                  1..21
                        mol_type = other DNA
                        note = Synthetic primer
                        organism = synthetic construct
SEQUENCE: 34
gcagggggatt ctgcatcact a                                                     21

SEQ ID NO: 35           moltype = DNA  length = 19
FEATURE                 Location/Qualifiers
source                  1..19
                        mol_type = other DNA
                        note = Synthetic primer
                        organism = synthetic construct
SEQUENCE: 35
agtcgcccac ccctcagat                                                         19
```

| | | |
|---|---|---|
| SEQ ID NO: 36<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 36<br>ttccctccag cgtgtagctt | | 20 |
| SEQ ID NO: 37<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 37<br>tccccttcgg atcttaacac | | 20 |
| SEQ ID NO: 38<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 38<br>cgaaaaagat gagggtctgc | | 20 |
| SEQ ID NO: 39<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 39<br>ggaagaccgg ccagctagag | | 20 |
| SEQ ID NO: 40<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 40<br>tgaaggagta gtgggggtcc | | 20 |
| SEQ ID NO: 41<br>FEATURE<br>source | moltype = DNA  length = 24<br>Location/Qualifiers<br>1..24<br>mol_type = other DNA<br>note = Synthetic primer<br>organism = synthetic construct | |
| SEQUENCE: 41<br>agccttccaa ctctggagta atgt | | 24 |
| SEQ ID NO: 42<br>FEATURE<br>source | moltype = DNA  length = 20<br>Location/Qualifiers<br>1..20<br>mol_type = other DNA<br>note = Synthetic primer<br>organism = synthetic construct | |
| SEQUENCE: 42<br>ccgatgatct cccctgacaa | | 20 |
| SEQ ID NO: 43<br>FEATURE<br>source | moltype = DNA  length = 24<br>Location/Qualifiers<br>1..24<br>mol_type = other DNA<br>note = Synthetic primer<br>organism = synthetic construct | |
| SEQUENCE: 43<br>cccaccttac atacaggatt gtga | | 24 |
| SEQ ID NO: 44<br>FEATURE<br>source | moltype = DNA  length = 23<br>Location/Qualifiers<br>1..23<br>mol_type = other DNA<br>note = Synthetic primer<br>organism = synthetic construct | |

-continued

```
SEQUENCE: 44
cccagacttt cagagctttc tca                                              23

SEQ ID NO: 45           moltype = DNA  length = 22
FEATURE                 Location/Qualifiers
source                  1..22
                        mol_type = other DNA
                        note = Synthetic primer
                        organism = synthetic construct
SEQUENCE: 45
cactggcaga aaacaacctg aa                                               22

SEQ ID NO: 46           moltype = DNA  length = 22
FEATURE                 Location/Qualifiers
source                  1..22
                        mol_type = other DNA
                        note = Synthetic primer
                        organism = synthetic construct
SEQUENCE: 46
accaggcaag tctcctcatt ga                                               22

SEQ ID NO: 47           moltype = DNA  length = 24
FEATURE                 Location/Qualifiers
source                  1..24
                        mol_type = other DNA
                        note = Synthetic primer
                        organism = synthetic construct
SEQUENCE: 47
gtttttgaag agggctgaga attc                                             24

SEQ ID NO: 48           moltype = DNA  length = 24
FEATURE                 Location/Qualifiers
source                  1..24
                        mol_type = other DNA
                        note = Synthetic primer
                        organism = synthetic construct
SEQUENCE: 48
ccctacaaca gacccacaca atac                                             24

SEQ ID NO: 49           moltype = DNA  length = 20
FEATURE                 Location/Qualifiers
source                  1..20
                        mol_type = other DNA
                        note = Synthetic primer
                        organism = synthetic construct
SEQUENCE: 49
aagaccattg tggccaagga                                                  20

SEQ ID NO: 50           moltype = DNA  length = 19
FEATURE                 Location/Qualifiers
source                  1..19
                        mol_type = other DNA
                        note = Synthetic primer
                        organism = synthetic construct
SEQUENCE: 50
ttcggagttt gggtttgct                                                   19

SEQ ID NO: 51           moltype = DNA  length = 22
FEATURE                 Location/Qualifiers
source                  1..22
                        mol_type = other DNA
                        note = Synthetic primer
                        organism = synthetic construct
SEQUENCE: 51
agaatgggca gaaagcttgt ct                                               22

SEQ ID NO: 52           moltype = DNA  length = 22
FEATURE                 Location/Qualifiers
source                  1..22
                        mol_type = other DNA
                        note = Synthetic primer
                        organism = synthetic construct
SEQUENCE: 52
ccttctggtc agttggattt gc                                               22

SEQ ID NO: 53           moltype = DNA  length = 22
FEATURE                 Location/Qualifiers
source                  1..22
                        mol_type = other DNA
```

```
                        note = Synthetic primer
                        organism = synthetic construct
SEQUENCE: 53
cgccagtgaa atgatggctt at                                                    22

SEQ ID NO: 54           moltype = DNA  length = 22
FEATURE                 Location/Qualifiers
source                  1..22
                        mol_type = other DNA
                        note = Synthetic primer
                        organism = synthetic construct
SEQUENCE: 54
ctggaaggag cacttcatct gt                                                    22

SEQ ID NO: 55           moltype = DNA  length = 20
FEATURE                 Location/Qualifiers
source                  1..20
                        mol_type = other DNA
                        note = Synthetic primer
                        organism = synthetic construct
SEQUENCE: 55
caactgaggc cccctttcaa                                                       20

SEQ ID NO: 56           moltype = DNA  length = 20
FEATURE                 Location/Qualifiers
source                  1..20
                        mol_type = other DNA
                        note = Synthetic primer
                        organism = synthetic construct
SEQUENCE: 56
cgcccgttgt agatgaaggt                                                       20

SEQ ID NO: 57           moltype = DNA  length = 20
FEATURE                 Location/Qualifiers
source                  1..20
                        mol_type = other DNA
                        note = Synthetic primer
                        organism = synthetic construct
SEQUENCE: 57
ggctggaaaa ccaacttccg                                                       20

SEQ ID NO: 58           moltype = DNA  length = 20
FEATURE                 Location/Qualifiers
source                  1..20
                        mol_type = other DNA
                        note = Synthetic primer
                        organism = synthetic construct
SEQUENCE: 58
gttatcccgc agcatcacga                                                       20

SEQ ID NO: 59           moltype = DNA  length = 20
FEATURE                 Location/Qualifiers
source                  1..20
                        mol_type = other DNA
                        note = Synthetic primer
                        organism = synthetic construct
SEQUENCE: 59
tggagaccca aagggttgga                                                       20

SEQ ID NO: 60           moltype = DNA  length = 20
FEATURE                 Location/Qualifiers
source                  1..20
                        mol_type = other DNA
                        note = Synthetic primer
                        organism = synthetic construct
SEQUENCE: 60
aggaagcagg aggtctcacc                                                       20

SEQ ID NO: 61           moltype = DNA  length = 22
FEATURE                 Location/Qualifiers
source                  1..22
                        mol_type = other DNA
                        note = Synthetic primer
                        organism = synthetic construct
SEQUENCE: 61
acgtgctgtg aaaacaaaga ag                                                    22

SEQ ID NO: 62           moltype = DNA  length = 21
FEATURE                 Location/Qualifiers
```

```
                        -continued source                  1..21
                        mol_type = other DNA
                        note = Synthetic primer
                        organism = synthetic construct
SEQUENCE: 62
gtcccactga ctgtcttgag g                                              21

SEQ ID NO: 63           moltype = DNA   length = 20
FEATURE                 Location/Qualifiers
source                  1..20
                        mol_type = other DNA
                        note = Synthetic primer
                        organism = synthetic construct
SEQUENCE: 63
atatctgcgg ctgatcctgc                                                20

SEQ ID NO: 64           moltype = DNA   length = 20
FEATURE                 Location/Qualifiers
source                  1..20
                        mol_type = other DNA
                        note = Synthetic primer
                        organism = synthetic construct
SEQUENCE: 64
ggtctgctgg ggcagtttat                                                20

SEQ ID NO: 65           moltype = DNA   length = 22
FEATURE                 Location/Qualifiers
source                  1..22
                        mol_type = other DNA
                        note = Synthetic primer
                        organism = synthetic construct
SEQUENCE: 65
gagactctca gggtcgaaaa cg                                             22

SEQ ID NO: 66           moltype = DNA   length = 19
FEATURE                 Location/Qualifiers
source                  1..19
                        mol_type = other DNA
                        note = Synthetic primer
                        organism = synthetic construct
SEQUENCE: 66
ttcctgtggg cggattagg                                                 19

SEQ ID NO: 67           moltype = DNA   length = 20
FEATURE                 Location/Qualifiers
source                  1..20
                        mol_type = other DNA
                        note = Synthetic primer
                        organism = synthetic construct
SEQUENCE: 67
cggaaggtcc ctcagacatc                                                20

SEQ ID NO: 68           moltype = DNA   length = 20
FEATURE                 Location/Qualifiers
source                  1..20
                        mol_type = other DNA
                        note = Synthetic primer
                        organism = synthetic construct
SEQUENCE: 68
ccctgtagga ccttcggtga                                                20

SEQ ID NO: 69           moltype = DNA   length = 18
FEATURE                 Location/Qualifiers
source                  1..18
                        mol_type = other DNA
                        note = Synthetic primer
                        organism = synthetic construct
SEQUENCE: 69
cggccgcatc ttcttgtg                                                  18

SEQ ID NO: 70           moltype = DNA   length = 18
FEATURE                 Location/Qualifiers
source                  1..18
                        mol_type = other DNA
                        note = Synthetic primer
                        organism = synthetic construct
SEQUENCE: 70
gtgaccaggc gcccaata                                                  18
```

| | | |
|---|---|---|
| SEQ ID NO: 71 | moltype = DNA length = 21 | |
| FEATURE | Location/Qualifiers | |
| source | 1..21<br>mol_type = other DNA<br>note = Synthetic primer<br>organism = synthetic construct | |
| SEQUENCE: 71 | | |
| ccaccaccct gctctgtact a | | 21 |
| | | |
| SEQ ID NO: 72 | moltype = DNA length = 20 | |
| FEATURE | Location/Qualifiers | |
| source | 1..20<br>mol_type = other DNA<br>note = Synthetic primer<br>organism = synthetic construct | |
| SEQUENCE: 72 | | |
| cctctccatg gtgcacttcc | | 20 |
| | | |
| SEQ ID NO: 73 | moltype = DNA length = 20 | |
| FEATURE | Location/Qualifiers | |
| source | 1..20<br>mol_type = other DNA<br>note = Synthetic primer<br>organism = synthetic construct | |
| SEQUENCE: 73 | | |
| cgtgacctttt gtgagcaacg | | 20 |
| | | |
| SEQ ID NO: 74 | moltype = DNA length = 20 | |
| FEATURE | Location/Qualifiers | |
| source | 1..20<br>mol_type = other DNA<br>note = Synthetic primer<br>organism = synthetic construct | |
| SEQUENCE: 74 | | |
| ctgctccata ctcgctctgg | | 20 |
| | | |
| SEQ ID NO: 75 | moltype = DNA length = 18 | |
| FEATURE | Location/Qualifiers | |
| source | 1..18<br>mol_type = other DNA<br>note = Synthetic primer<br>organism = synthetic construct | |
| SEQUENCE: 75 | | |
| tctgatgcag caggtggg | | 18 |
| | | |
| SEQ ID NO: 76 | moltype = DNA length = 24 | |
| FEATURE | Location/Qualifiers | |
| source | 1..24<br>mol_type = other DNA<br>note = Synthetic primer<br>organism = synthetic construct | |
| SEQUENCE: 76 | | |
| agggctctcc agacttctgc tctg | | 24 |
| | | |
| SEQ ID NO: 77 | moltype = DNA length = 18 | |
| FEATURE | Location/Qualifiers | |
| source | 1..18<br>mol_type = other DNA<br>note = Synthetic primer<br>organism = synthetic construct | |
| SEQUENCE: 77 | | |
| ctcctgagcg cagccttg | | 18 |
| | | |
| SEQ ID NO: 78 | moltype = DNA length = 20 | |
| FEATURE | Location/Qualifiers | |
| source | 1..20<br>mol_type = other DNA<br>note = Synthetic primer<br>organism = synthetic construct | |
| SEQUENCE: 78 | | |
| gttcttactg ctggggccat | | 20 |
| | | |
| SEQ ID NO: 79 | moltype = DNA length = 20 | |
| FEATURE | Location/Qualifiers | |
| source | 1..20<br>mol_type = other DNA<br>note = Synthetic primer<br>organism = synthetic construct | |
| SEQUENCE: 79 | | |

```
tctgctttat ggggcttcgg                                                            20

SEQ ID NO: 80          moltype = DNA   length = 20
FEATURE                Location/Qualifiers
source                 1..20
                       mol_type = other DNA
                       note = Synthetic primer
                       organism = synthetic construct
SEQUENCE: 80
tcgactccca tactcccagg                                                            20

SEQ ID NO: 81          moltype = DNA   length = 20
FEATURE                Location/Qualifiers
source                 1..20
                       mol_type = other DNA
                       note = Synthetic primer
                       organism = synthetic construct
SEQUENCE: 81
ctgccttgca agaagagagc                                                            20

SEQ ID NO: 82          moltype = DNA   length = 20
FEATURE                Location/Qualifiers
source                 1..20
                       mol_type = other DNA
                       note = Synthetic primer
                       organism = synthetic construct
SEQUENCE: 82
agtgctgcgt tctgatgatg                                                            20

SEQ ID NO: 83          moltype = DNA   length = 16
FEATURE                Location/Qualifiers
source                 1..16
                       mol_type = other DNA
                       note = Synthetic primer
                       organism = synthetic construct
SEQUENCE: 83
ccagggccgt gtgcat                                                                16

SEQ ID NO: 84          moltype = DNA   length = 20
FEATURE                Location/Qualifiers
source                 1..20
                       mol_type = other DNA
                       note = Synthetic primer
                       organism = synthetic construct
SEQUENCE: 84
tacgtgaacg ttgcccatca                                                            20

SEQ ID NO: 85          moltype = DNA   length = 20
FEATURE                Location/Qualifiers
source                 1..20
                       mol_type = other DNA
                       note = Synthetic primer
                       organism = synthetic construct
SEQUENCE: 85
gactcaaggg tggatgctgt                                                            20

SEQ ID NO: 86          moltype = DNA   length = 20
FEATURE                Location/Qualifiers
source                 1..20
                       mol_type = other DNA
                       note = Synthetic primer
                       organism = synthetic construct
SEQUENCE: 86
ccaactgcga agatccactg                                                            20

SEQ ID NO: 87          moltype = DNA   length = 23
FEATURE                Location/Qualifiers
source                 1..23
                       mol_type = other DNA
                       note = Synthetic primer
                       organism = synthetic construct
SEQUENCE: 87
cggagaggag acttcacaga gga                                                        23

SEQ ID NO: 88          moltype = DNA   length = 23
FEATURE                Location/Qualifiers
source                 1..23
                       mol_type = other DNA
                       note = Synthetic primer
```

```
                              -continued
                        organism = synthetic construct
SEQUENCE: 88
tttccacgat ttcccagaga aca                                           23

SEQ ID NO: 89           moltype = DNA   length = 20
FEATURE                 Location/Qualifiers
source                  1..20
                        mol_type = other DNA
                        note = Synthetic primer
                        organism = synthetic construct
SEQUENCE: 89
ggaagggcaa catgaccagg                                               20

SEQ ID NO: 90           moltype = DNA   length = 20
FEATURE                 Location/Qualifiers
source                  1..20
                        mol_type = other DNA
                        note = Synthetic primer
                        organism = synthetic construct
SEQUENCE: 90
agctgctctt ggtcggaaag                                               20

SEQ ID NO: 91           moltype = DNA   length = 21
FEATURE                 Location/Qualifiers
source                  1..21
                        mol_type = other DNA
                        note = Synthetic primer
                        organism = synthetic construct
SEQUENCE: 91
ctggctgcat ccattatgtc a                                             21

SEQ ID NO: 92           moltype = DNA   length = 20
FEATURE                 Location/Qualifiers
source                  1..20
                        mol_type = other DNA
                        note = Synthetic primer
                        organism = synthetic construct
SEQUENCE: 92
tggtagactg cccgtgtgaa                                               20

SEQ ID NO: 93           moltype = DNA   length = 20
FEATURE                 Location/Qualifiers
source                  1..20
                        mol_type = other DNA
                        note = Synthetic primer
                        organism = synthetic construct
SEQUENCE: 93
ctgcgtggct atgattatgg                                               20

SEQ ID NO: 94           moltype = DNA   length = 20
FEATURE                 Location/Qualifiers
source                  1..20
                        mol_type = other DNA
                        note = Synthetic primer
                        organism = synthetic construct
SEQUENCE: 94
aggttgctgt cgtctgtagt                                               20

SEQ ID NO: 95           moltype = DNA   length = 21
FEATURE                 Location/Qualifiers
source                  1..21
                        mol_type = other DNA
                        note = Synthetic primer
                        organism = synthetic construct
SEQUENCE: 95
actttccctt aacgtgggcc t                                             21

SEQ ID NO: 96           moltype = DNA   length = 20
FEATURE                 Location/Qualifiers
source                  1..20
                        mol_type = other DNA
                        note = Synthetic primer
                        organism = synthetic construct
SEQUENCE: 96
catctcggcc agtgtctgtt                                               20

SEQ ID NO: 97           moltype = DNA   length = 20
FEATURE                 Location/Qualifiers
source                  1..20
```

```
                              mol_type = other DNA
                              note = Synthetic primer
                              organism = synthetic construct
SEQUENCE: 97
ttcgggtcgc tggatctcta                                                    20

SEQ ID NO: 98                 moltype = DNA  length = 20
FEATURE                       Location/Qualifiers
source                        1..20
                              mol_type = other DNA
                              note = Synthetic primer
                              organism = synthetic construct
SEQUENCE: 98
tcaaggagaa accaccacgg                                                    20

SEQ ID NO: 99                 moltype = DNA  length = 22
FEATURE                       Location/Qualifiers
source                        1..22
                              mol_type = other DNA
                              note = Synthetic primer
                              organism = synthetic construct
SEQUENCE: 99
agaagcgagc actgcaaggt tg                                                 22

SEQ ID NO: 100                moltype = DNA  length = 22
FEATURE                       Location/Qualifiers
source                        1..22
                              mol_type = other DNA
                              note = Synthetic primer
                              organism = synthetic construct
SEQUENCE: 100
ggaagatgga ctccacctgg tt                                                 22

SEQ ID NO: 101                moltype = DNA  length = 20
FEATURE                       Location/Qualifiers
source                        1..20
                              mol_type = other DNA
                              note = Synthetic primer
                              organism = synthetic construct
SEQUENCE: 101
ttcgctgatg cactgcctat                                                    20

SEQ ID NO: 102                moltype = DNA  length = 20
FEATURE                       Location/Qualifiers
source                        1..20
                              mol_type = other DNA
                              note = Synthetic primer
                              organism = synthetic construct
SEQUENCE: 102
ggaatgcgag tggtcttcca                                                    20

SEQ ID NO: 103                moltype = DNA  length = 20
FEATURE                       Location/Qualifiers
source                        1..20
                              mol_type = other DNA
                              note = Synthetic primer
                              organism = synthetic construct
SEQUENCE: 103
atctgtctcc caggtctgct                                                    20

SEQ ID NO: 104                moltype = DNA  length = 20
FEATURE                       Location/Qualifiers
source                        1..20
                              mol_type = other DNA
                              note = Synthetic primer
                              organism = synthetic construct
SEQUENCE: 104
tcctccgttt acctttcgcc                                                    20

SEQ ID NO: 105                moltype = DNA  length = 20
FEATURE                       Location/Qualifiers
source                        1..20
                              mol_type = other DNA
                              note = Synthetic primer
                              organism = synthetic construct
SEQUENCE: 105
gcttcggtga agtagctgga                                                    20

SEQ ID NO: 106                moltype = DNA  length = 20
```

```
FEATURE                 Location/Qualifiers
source                  1..20
                        mol_type = other DNA
                        note = Synthetic primer
                        organism = synthetic construct
SEQUENCE: 106
ttcgttagag tcacgccgag                                                   20

SEQ ID NO: 107          moltype = DNA   length = 20
FEATURE                 Location/Qualifiers
source                  1..20
                        mol_type = other DNA
                        note = Synthetic primer
                        organism = synthetic construct
SEQUENCE: 107
agccaaatgg atggacctgg                                                   20

SEQ ID NO: 108          moltype = DNA   length = 20
FEATURE                 Location/Qualifiers
source                  1..20
                        mol_type = other DNA
                        note = Synthetic primer
                        organism = synthetic construct
SEQUENCE: 108
aaggaggggc atagtgtcca                                                   20

SEQ ID NO: 109          moltype = DNA   length = 19
FEATURE                 Location/Qualifiers
source                  1..19
                        mol_type = other DNA
                        note = Synthetic primer
                        organism = synthetic construct
SEQUENCE: 109
atccggacca gaggacagg                                                    19

SEQ ID NO: 110          moltype = DNA   length = 16
FEATURE                 Location/Qualifiers
source                  1..16
                        mol_type = other DNA
                        note = Synthetic primer
                        organism = synthetic construct
SEQUENCE: 110
atggcgaccg ctgctg                                                       16

SEQ ID NO: 111          moltype = DNA   length = 20
FEATURE                 Location/Qualifiers
source                  1..20
                        mol_type = other DNA
                        note = Synthetic primer
                        organism = synthetic construct
SEQUENCE: 111
agagaaccgg acccaatcca                                                   20

SEQ ID NO: 112          moltype = DNA   length = 20
FEATURE                 Location/Qualifiers
source                  1..20
                        mol_type = other DNA
                        note = Synthetic primer
                        organism = synthetic construct
SEQUENCE: 112
gcttgtgccc ctactcagac                                                   20

SEQ ID NO: 113          moltype = DNA   length = 20
FEATURE                 Location/Qualifiers
source                  1..20
                        mol_type = other DNA
                        note = Synthetic primer
                        organism = synthetic construct
SEQUENCE: 113
tccccacggg atcctaagac                                                   20
```

```
SEQ ID NO: 114           moltype = DNA   length = 20
FEATURE                  Location/Qualifiers
source                   1..20
                         mol_type = other DNA
                         note = Synthetic primer
                         organism = synthetic construct
SEQUENCE: 114
ctctgcaggc aagctctctt                                                      20
```

COMPOSITIONS AND METHODS FOR TREATING, PREVENTING OR REVERSING AGE ASSOCIATED INFLAMMATION AND DISORDERS

REFERENCE TO SEQUENCE LISTING SUBMITTED ELECTRONICALLY

The content of the electronically submitted sequence listing (Name: 4572_0070005_Seglisting_ST26; Size: 121,863 bytes; and Date of Creation: Sep. 19, 2023) filed with the application is incorporated herein by reference in its entirety.

FIELD OF THE INVENTION

The invention is in the field of medicinal chemistry. In particular, the invention relates to a method for treating, preventing and/or reversing a pathophysiological L1-associated process, e.g., age-associated inflammation, by administering a reverse transcriptase inhibitor (RTI) to a patient in need thereof. The pathophysiological L1-associated process may be in a patient having Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, Rett Syndrome, schizophrenia, autism spectrum disorder (ADS) and/or pulmonary fibrosis, or in a patient in need of wound healing or tissue regeneration.

STATEMENT REGARDING FEDERALLY SPONSORED RESEARCH OR DEVELOPMENT

This invention was developed with the following funding: Glenn/AFAR Postdoctoral Fellowship, NIH P20 GM119943 COBRE pilot award; NIH F31 AG043189; NIH T32 AG041688; NIH F31 AG050365; Biotechnology and Sport Medicine Fellowships, School of Pharmacy, University of Bologna, Bologna, Italy; NIH R37 AG016667, RO1 AG024353, P01 AG051449, Glenn-AFAR Breakthroughs in Gerontology Award; NIH RO1 AG050582, P20 GM109035; NIH R37 AG016694, P01 AG051449.

BACKGROUND OF THE INVENTION

The number of people living to be 60 years or older is increasing worldwide. Between 2012 and 2050, the proportion of the number of people aged 60 years and over is expected to increase from 809 million to 2 billion (or 11% to 22% of the population).[1] Among the leading causes of death in the elderly are several chronic conditions including heart disease, cancer, diabetes, Alzheimer's disease, and infection. Importantly, many of these age-related diseases and aging itself are closely associated with low-level chronic inflammation.[2,3,4] Systemic chronic inflammation can accelerate aging.[5] Indeed, many Inflammatory markers are significant predictors of mortality in older humans.[6]

Despite this common link between aging, inflammation, and chronic diseases, limited progress has been made to understand the mechanisms that control age-related inflammation, and the causal relationship of these regulators to chronic degenerative diseases is not completely understood. A better understanding of the role of these regulators in age-related inflammation should lead to new strategies for extending the health of the older population.

As such, there is a need in the art for better treatment and prevention of age-related inflammation and age-related disorders.

BRIEF SUMMARY OF THE INVENTION

The present invention provides a better understanding of the mechanisms underlying age-related inflammation and its role in the aging, and other pathophysiological processes related to LINE-1 (L1) retrotransposons, as well as compositions and methods for treating, preventing and/or reducing age-associated inflammation and other disorders.

Retrotransposable elements (RTEs) are deleterious at multiple levels, and failure of host surveillance systems can thus have negative consequences. However, the contribution of RTE activity to aging and age-associated diseases was not known. The present invention is based on several empirical observations including that, during cellular senescence, LINE-1 (L1) elements become transcriptionally upregulated and activate a type-I interferon (IFN-I) response. The IFN-I response is a novel phenotype of late senescence and contributes to the maintenance of the senescence associated secretory phenotype (SASP). The IFN-I response is triggered by cytoplasmic L1 cDNA and is antagonized by reverse transcriptase inhibitors (RTIs) that inhibit the L1 reverse transcriptase (RT). Treatment of aged mice with the RTI lamivudine downregulated IFN-I activation and age-associated inflammation in several tissues. As such, RTE activation is an important component of sterile inflammation that is a hallmark of aging, and L1 RT is a relevant target for the treatment of age-associated disorders.

The present invention provides a method for treating, preventing and/or reversing a pathophysiological L1-associated process such as age-associated inflammation in a patient in need thereof by administering a therapeutically-effective amount of at least one reverse transcriptase inhibitor (RTI) to the patient.

In a comparative assessment of several RTI drugs in a dose-response assay of the inhibition of L1 activity, three RTI drugs, islatravir, censavudine and elvucitabine, displayed unexpected ability to inhibit mouse and human L1 activity. In particular, islatravir was a surprisingly potent inhibitor of human L1. The present invention further provides a method for treating, preventing and/or reversing pathophysiological L1-associated processes such as age-associated inflammation in a patient in need thereof by administering a therapeutically-effective amount of islatravir and/or censavudine and/or elvucitabine to the patient.

Without wishing to be bound by any particular theory, the pathophysiological L1-associated process, e.g., age-associated inflammation, is associated with an upregulation of L1, an accumulation of cytoplasmic L1 cDNA, an activation of an IFN-I response, and/or a reinforcement of a SASP pro-inflammatory state. The RTI drug is administered in an amount sufficient to prevent or reverse at least one of the upregulation of L1, the accumulation of cytoplasmic L1 cDNA, the activation of the IFN-I response, and/or the SASP pro-inflammatory state.

The pathophysiological L1-associated processes, that can be prevented, treated, or reversed with the methods of the present invention is in a patient having a disease or disorder including, but not limited to: Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, Rett Syndrome, schizophrenia, autism spectrum disorder (ADS) and/or pulmonary fibrosis, or in a patient in need of wound healing or tissue regeneration. In one embodiment, the age-associated inflammation is in a patient having Alzheimer's disease. In an alternate embodiment, the age-associated inflammation is in a patient having ALS.

Also provided is a method for delaying or reversing the progression of the underlying pathology of disease disorder caused by age-associated inflammation, comprising administering to a patient in need thereof a therapeutically effective amount of at least one RTI. In some embodiments, the patient has Alzheimer's disease or ALS and experiences a decrease in one or more symptoms of Alzheimer's disease or ALS compared to before the first administration of the RTI to the patient. In some embodiments, the one or more symptoms of Alzheimer's disease comprise memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory.

In some embodiments, the decrease in the one or more symptoms of Alzheimer's disease is evaluated according to the DSM-5.[7] In some embodiments, the decrease of symptoms is determined using the cognitive subscale of the Alzheimer's Disease Assessment Scale (ADAS-cog). In some embodiments, the decrease of symptoms is determined using the Clinician's Interview-Based Impression of Change (CIBIC-plus). In some embodiments, the decrease of symptoms is determined using the Activities of Daily Living (ADL) scale. In some embodiments, the decrease of symptoms is for 1-36 months.

In some embodiments, any change in the underlying pathology is identified by detection of a biomarker before and after the RTI administration. In some embodiments, the biomarker is β-amyloid or Tau protein. In some embodiments, the biomarker is detected by PET imaging. In some embodiments, the underlying pathology is identified by measurement of β-amyloid or Tau protein in the cerebrospinal fluid. In some embodiments, the underlying pathology is identified by measurement of brain volume before and after the RTI administration. In some embodiments, the underlying pathology is reversed or delayed for at 1-36 months.

In some embodiments, the at least one RTI is a nucleoside reverse transcriptase inhibitor (NRTI). In some embodiments, the at least one NRTI is selected from: abacavir (ZIAGEN™), abacavir/lamivudine (Epzicom), abacavir/lamivudine/zidovudine (TRIZIVIR™) adefovir, alovudine, amdoxovir, apricitabine, ATRIPLA®, BARACLUDE®, BIKTARVY®, censavudine, COVIRACIL™, DAPD/DXG, D-D4FC, dexelvucitabine, didanosine (VIDEX™), didanosine extended-release (Videx EC), dOTC, EFdA (islatravir), emtricitabine (EMTRIVA™) emtricitabine/tenofovir alafenamide (DESCOVY®), emtricitabine/tenofovir disoproxil fumarate (TRUVADA®), elvucitabine, fosalvudine, lamivudine/zidovudine (COMBIVIR™), EVIPLERA™, GENVOYA®, HMD™, KIVEXA™, lamivudine (EPIVIR™), LODENOSINE™, ODEFSEY®, PREVEON®, racivir, stampidine, stavudine (ZERIT™), STRIBILD®, TENOFOVIR™, tenofovir disoproxil fumarate (VIREAD™), TRIUMEQ®, Trizivir, VEMLIDY®, Telbivudine and/or zidovudine (RETROVIR™). In some embodiments, the at least one NRTI is censavudine. In some embodiments, the at least one NRTI is elvucitabine. In some embodiments, the at least one NRTI is EFdA (islatravir).

In some embodiments, the at least one RTI is a non-nucleoside reverse transcriptase inhibitor (NNRTI). In some embodiments, the at least one NNRTI is selected from: Delavirdine (DLV), Efavirenz (EFV), Etravirine (TMC125), Nevirapine (NVP), and/or Rilpivirine.

In some embodiments, the patient has Alzheimer's disease and the method further comprises administering at least one second therapeutic agent useful for the treatment of the symptoms of Alzheimer's disease. In some embodiments, the at least one second therapeutic agent is selected from: donepezil, galantamine, memantine, and/or rivastigmine. In some embodiments, the at least one second therapeutic agent is an antibody that binds to β-amyloid or Tau protein. In some embodiments, the antibody binds to β-amyloid and is bapineuzumab. In some embodiments, the antibody binds to Tau protein and is ABBV-8E12. In some embodiments, the at least one second therapeutic agent is a vaccine against β-amyloid or Tau protein. In some embodiments, the at least one second therapeutic agent is an agent that reduces or alters the brain content of β-amyloid or Tau. In some embodiments, the second therapeutic agent reduces or alters the brain content of β-amyloid and is a β-secretase 1 (BACE) inhibitor. In some embodiments, the BACE inhibitor is selected from: CTS-21166, lanabecestat (AZD3293), LY2886721, and verubecestat (MK-8931). In some embodiments, the second agent reduces or alters the brain content of Tau and is nicotinamide, or MPTOG211. In some embodiments, the at least one second therapeutic agent is an Interferon-gamma antibody. In some embodiments, the at least one second therapeutic agent is a JAK/STAT pathway inhibitor.

In some embodiments, the patient has ALS and the method further comprises administering at least one second therapeutic agent useful for the treatment of the symptoms of ALS. In some embodiments, the at least one second agent useful for the treatment of ALS is edaravone and/or riluzole. In other embodiments, the at least one second agent is an integrase inhibitor. In some embodiments, the integrase inhibitor is selected from: aurintricarboxylic acid, derivatives of aurintricarboxylic acid, BMS-538158, caffeic acid phenethyl ester, derivatives of caffeic acid phenethyl ester, curcumin, derivatives of curcumin, chicoric acid, derivatives of chicoric acid, 3,5-dicaffeoylquinic acid, derivatives of 3,5-dicaffeoylquinic acid, GSK364735C, L-870812, and L-25 870810, MK-0518, quercetin, derivatives of quercetin, raltegravir, S-1360, tyrphostin, derivatives of tyrphostin, and/or zintevir (AR-177).

In some embodiments, the patient is evaluated for one or more symptoms or disease pathology for 1-36 months after the first administration to the patient of the RTI.

In some embodiments, the RTI inhibits L1 reverse transcriptase activity in a cell of the patient.

Also provided is a method for preventing the onset of Alzheimer's disease in a patient suspected of having mild cognitive impairment or preclinical Alzheimer's disease, comprising administering a therapeutically effective amount of at least one RTI to a patient in need thereof.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

FIGS. 1A-1E show the activation of L1, IFN-I and SASP in senescent cells. Gene expression was assessed by RT-qPCR. Poly(A)-purified RNA was used in all L1 assays. FIG. 1A is a line graph showing the time course of L1 activation. P values were calculated relative to EP, early passage control. FIG. 1B is a schematic of L1 RT-PCR strategy. For primer specificity, see FIGS. 6F-H; for primer design, see Methods. Primers for amplicon F were used in (a) and (e). FIG. 1C is three bar graphs showing strand-specific L1 transcription was assessed using amplicons A-F. Transcription from the 5'UTR antisense promoter was also detected. SEN (L), late senescence (16 weeks). FIG. 1D is a bar graph showing induction of IFN-α and IFN-β1 mRNA levels. FIG. 1E is three images showing the temporal induction of genes associated with DNA damage (p21, also known as CDKN1A), SASP (IL-1p6, CCL2, IL-6, MMP3), and the IFN-I response (IRF7, IFN-α, IFN-β1, OAS1). Row clustering was calculated as 1-Pearson correlation. RS, replicative senescence; OIS, oncogene induced senescence (elicited by Ha-RAS infection); SIPS, stress induced premature senescence (gamma irradiation). Controls: EP, early passage; EV, empty vector infected; CTR, non-irradiated. (FIGS. 1A, 1C-E), n=3 independent biological samples, repeated in two independent experiments. (FIGS. 1A, 1C, 1D) Data are mean±s.d. *P<0.05, **P<0.01, unpaired two-sided t-tests.

FIGS. 2A-H show the regulation of L1 activation and IFN-I induction. FIG. 2A is two bar graphs showing expression and ChIP of RB1 and FIG. 2B is two bar graphs showing FOXA1 expression was measured by RT-qPCR and immunoblotting (left panels). Binding to L1 elements was assessed with ChIP-qPCR (right panels). For primer specificity, see FIG. 6B RB1: 5'UTR, ORF1 and ORF2, primers for amplicons A, E and F, respectively. FOXA1: primers for amplicons A-E. qPCR was normalized to input chromatin. SEN (E), early senescence (8 weeks). For gel source, data see FIG. 16. FIG. 2C is a bar graph, and FIGS. 2D-F are each two bar graphs showing RB1, FOXA1 or TREX1 were overexpressed (OE) or ablated with shRNAs and the effects on expression of L1, IFN-α and IFN-β1 were determined by RT-qPCR of poly(A)-purified RNA. In all cases, lentiviral vectors were used to deliver the interventions directly into senescent cells at 12 weeks (point D, FIG. 6A), and cells were harvested for analysis four weeks later (point E, 16 weeks). Controls were uninfected senescent cells harvested at the same time (point E, 16 weeks). Two distinct shRNAs (a, b) were used for each gene. Primers for amplicon F were used for L1. FIG. 2F is two bar graphs showing RB1 was overexpressed as above and its binding to the 5'UTR was assessed by ChIP-qPCR (amplicon A). FIG. 2G is two bar graphs showing activation of L1, IFN-α and IFN-β1 expression after the triple (3×) intervention using shRB1 (a), shTREX1 (a) and FOXA1-OE in early passage cells. Lentiviral infections were performed sequentially with drug selections at each step (shRB1, puromycin→shTREX1, hygromycin→FOXA1-OE, blasticidin). FIG. 2H is two line graphs showing expression of IFN-I pathway genes determined with the RT2 Profiler PCR array (Qiagen). Normalized mean expression is shown for all 84 genes in the array. Red symbols: significantly upregulated genes. Dashed lines demarcate the ±2-fold range. (FIGS. 2A, 2B, 2H), n=3 independent biological samples, repeated in 2 independent experiments. (FIGS. 2C-G), n=3 independent experiments. (FIGS. 2A-G) Data are mean±s.d. *P≤0.05, **P≤0.01, unpaired two-sided t-tests.

FIGS. 3A-F show that the ablation of L1 relieves IFN-I activation and blunts the SASP response. FIG. 3A is twelve images showing cells were examined by immunofluorescence (IF) microscopy using antibodies to single-stranded DNA (ssDNA) or L1 ORF1 protein. Note the bright ssDNA puncta in senescent cells that colocalized with prominent puncta of ORF1. The experiment was independently repeated 3 times with similar results. Scale bar=10 µm. FIG. 3B is three bar graphs showing senescent cells were treated with L1 shRNAs (using lentiviral vectors as described in FIGS. 2C, 2E, 2F) or with 3TC (7.5 µM) between 12 and 16 weeks of senescence. Effects on the IFN-I response were determined by RT-qPCR, ELISA or immunoblotting. For gel source data, see FIG. 16. FIG. 3C is a bar graph showing cells were labeled with BrdU for 2 weeks (with or without 7.5 µM 3TC), labeled DNA was immunoprecipitated, and its L1 sequence content was quantified using a TaqMan multiplex qPCR assay16 (FIG. 1B, amplicon F). EP (qui), early passage quiescent cells. FIG. 3D is two bar graphs showing Left panel, RS cells: IFNAR1 and IFNAR2 genes were mutagenized using the CRISPR/Cas9 system delivered with lentivirus vectors directly into senescent cells. As with shRNA interventions, cells were infected at 12 weeks and harvested at 16 weeks of senescence (see FIGS. 1D-F, see Methods). Right panel, SIPS cells: CRISPR/Cas9 intervention was performed in early passage cells and a validated clone was irradiated to induce SIPS. FIG. 3E is two bar graphs showing OIS and SIPS were induced as in FIG. 1D and cells were harvested 20 days (OIS) or 30 days (SIPS) later. 3TC (7.5 µM) was present throughout. IFN-I gene expression (IFN-α, IRF7, OAS1) was measured by RT-qPCR. FIG. 3F is four bar graphs showing cells were serially passaged into replicative senescence (RS) with 3TC (10 µM) present throughout, and the temporal induction of SASP response genes (IL-1β, CCL2, IL-6, MMP3) was assessed. (FIGS. 3B-D, F), n=3 independent experiments. (FIG. 3E) n=3 independent biological samples, repeated in 2 independent experiments. (FIGS. 3B-F) Data are mean±s.d. *P≤0.05, **P≤0.01. (FIGS. 3B, D-F) unpaired two-sided t-tests, (c) 1-way ANOVA with Tukey's multiple comparisons test.

FIGS. 4A-F show that L1s are activated with age in murine tissues and the IFN-I proinflammatory response is relieved by RTI treatment. FIG. 4A is six images and a table showing presence of L1 Orf1 protein in tissues was examined by IF microscopy. Quantification of ORF1 expressing cells is shown in the right panel; three animals and at least 200 cells per animal were scored for each condition. Scale bar=4 µm. FIG. 4B is six images and a table showing activation of L1 in senescent cells was examined by co-staining for SA-β-Gal activity and Orf1 protein by IF (male liver, 5 and 26 months). Scale bar=4 µm. The experiment was repeated three times independently with similar results. FIG. 4C is three box plots showing mice were administered 3TC (2 mg/ml) in drinking water at the indicated ages for two weeks and sacrificed after treatment. Expression of p16, an IFN-I response gene (IFN-α), and a marker of a proinflammatory state (Il-6) were assessed by RT-qPCR. See FIG. 14 for additional tissues and genes. The box plots show the range of the data (whiskers), 25th and 75 percentiles (box), means (dashed line), and medians (solid line). Each point represents one animal. 5 months, n=8; 26 months, n=12; 29 months, n=6. FIG. 4D is four box plots showing six-month-old were non-lethally irradiated and expression of L1, p16 and representative IFN-I response genes (Ifn-α, Oas1) were assessed by RT-qPCR at the indicated times post-irradiation. Graphical presentation is as in (c); non-irradiated, n=3 animals at 3 months, n=5 animals at 6 months; irradiated, n=4 animals at 3 months, n=5 animals at 6 months. FIG. 4E is four box plots and two images showing macrophage infiltration into white adipose tissue and kidney was scored as F4/80 positive cells (% of total nuclei). n=5 animals group (adipose); n=8 (kidney). Skeletal muscle fiber diameter was measured (see Methods for details) and plotted as an aggregate box plot. n=5 animals per group, 500 fibers total. Glomerulosclerosis was scored in periodic acid-Shiff (PAS)-stained sections (see Methods for details) as the sum of all glomeruli with a score of 3 or 4 divided by the total. n=7 animals per group, 40 glomeruli per animal. Graphical presentation is as in (c). 3TC treatment was 2 weeks for white adipose and 6 months (20-26 months) for other tissues. Dashed circle demarcates a single glomerulus. Scale bar=50 µm. FIG. 4F is a schematic showing breakdown of L1 surveillance mechanisms leads to chronic activation of the IFN-I response. ISD: interferon-stimulatory DNA pathway. *P≤0.05, P≤0.01, unpaired two-sided t-tests (FIGS. 4A, 4D, 4E) or 1-way ANOVA with Tukey's multiple comparisons test (FIGS. 4C, 4E** white adipose).

FIG. 5 is a flow chart outlining the molecular pathway of cellular senescence leading to age-associated, "sterile" inflammation.

FIGS. 6A-K show the establishment of senescent cultures and analysis of L1 and IFN-I activation. FIG. 6A is a line graph showing the passaging regimen to obtain long-term replicatively senescent cells (details in Methods). Point A was designated as zero for time in senescence. Confirmation of the senescent status of cultures. A representative experiment is shown; other experiments were monitored in the same manner and generated data that met these benchmarks. EP, early passage control; SEN (E), early senescence (8 weeks); SEN (L), late senescence (16 weeks FIG. 6B is three bar graphs showing cells were labeled with BrdU for 6 hours. BrdU incorporation[8] and senescence-associated β-galactosidase (SA-β-Gal) activity[9] were determined as indicated. DNA damage foci were visualized using γ-H2AX antibodies and immunofluorescence microscopy (IF).[10] FIG. 6C is two bar graphs showing expression of p21 (CDKN1A) and p16 (CDKN2A) proteins was determined by immunoblotting. GAPDH was the loading control. For gel source data, see FIG. 16. FIG. 6D is a bar graph showing expression of genes characteristic of the SASP was determined by RT-qPCR. FIG. 6E is two bar graphs showing L1 activation during senescence of IMR-90 and WI-38 strains of fibroblasts was assessed by RT-qPCR using poly(A) purified RNA and primers for amplicon F (FIG. 1B). FIG. 6F is a graph showing long-range RT-PCR was performed with primers A-forward and C-reverse (amplicon G) and primers A-forward and D-reverse (amplicon H) (FIG. 1B, Table 1) and the cDNAs were cloned and sequenced. Several attempts using the same protocol on early passage proliferating cells did not yield any L1 clones. Sequences were mapped to the unmasked reference genome demanding 100% identify. 658 clones could be thus mapped, 51 additional clones contained at least 1 mismatch and thus likely represent elements that are polymorphic in the cell line, and 58 were cloning artifacts. Among the 658 mappable clones 224 unique elements were represented (Table 3). Intact elements are the subset of full-length elements annotated with no ORF inactivating mutations. Size of the features corresponds to the number of times the element was represented among the 658 clones. FIG. 6G is a table showing the summary of long-range PCR data presented in FIG. 6F and Table 3. FIG. 6H is a table showing apparent genomic copy numbers of elements detected with our amplicons (see FIG. 1b for locations of amplicons and Methods for primer design strategy). Predicted: in silico PCR (see Methods for details). Observed: qPCR was performed on 1 ng of genomic DNA and normalized to a known single copy locus. FIG. 6I is a two bar graphs showing activation of IFN-α and IFN-β1 genes during senescence of WI-38 and IMR-90 cells was determined by RT-qPCR. FIG. 6J is two bar graphs showing confirmation of the senescent status of cells in OIS (20 days, FIG. 6E) and SIPS (30 days, FIG. 6E) by SA-β-Gal activity. EV, empty vector control; CTR, non-irradiated cells. FIG. 6K is three bar graphs showing confirmation of full length L1 mRNA expression in all forms of senescence using RT-qPCR with primers for amplicons A and F on poly(A)-purified RNA. Late onset activation is shown by comparing days 9 and 20 for OIS and days 12 and 30 for SIPS. (FIGS. 6B-E, 6I-K), n=3 independent biological samples, repeated in 2 independent experiments. Data are mean±s.d. *P≤0.05, **P≤0.01, unpaired two-sided t-tests.

FIGS. 7A-B show the mapping of transcriptional start sites in L1 elements activated during cellular senescence. 5'RACE was performed with primers C and D (FIG. 1A, Table 1) on late senescent cells (16 weeks, point D in FIG. 6A), the products were cloned, and individual clones were Sanger sequenced (see Methods for details). FIG. 7A is a series of images showing a multiple sequence alignment of the 50 mappable clones against the L1HS consensus was generated with MAFFT software. The L1HS consensus is shown on top. Blue color shading of the aligned clones shows their degree of identity with the consensus. The green vertical line marks the start (position 1) of the L1 HS consensus. Red vertical lines mark short gaps (1-4 nucleotides) opened in the L1HS consensus by individual clones. The consensus of the 50 clones is shown at the bottom and was generated with Jalview. The initiation of L1 transcription is known to be imprecise, with the majority of start sites occurring +/−50 bp of the consensus start site, and a subset as far down as +180 bp.[11] FIG. 7B is a table showing the summary of the mapping data and classification of clones to families of L1 elements. The relative start sites were calculated relative to the L1 HS consensus start site. RepEnrich software[12] was used to assign the clones to L1 families.

FIGS. 8A-G show the evolution of transcriptomic changes during progression of cellular senescence. RNA-seq was performed on early proliferating LF1 cells (EP) and cultures at 8 weeks (SEN-E) and 16 weeks (SEN-L) in senescence (points C and D, respectively, in Extended Data FIG. 6A). Data were analyzed using a 3-way comparison: EP versus SEN-E, EP versus SEN-L and SEN-E versus SEN-L (see Methods for details). FIG. 8A is a series of six images showing area-proportional generalized Venn diagrams depicting the intersections of the three comparisons for the following datasets. i-ii, significantly upregulated and downregulated genes (row 2× in panel b). iii-iv, significant KEGG pathways identified by GSEA. Note the considerable evolution the transcriptome in late senescence, exemplified by large changes (especially upregulated) in differentially expressed genes as well as pathways. v-vi, significantly changing genes in the IFN-1 and SASP gene sets (see Table 4 for annotation of gene sets). Note that the majority of changes in SASP genes occur early, whereas a large component of IFN-1 changes is specific for late senescence. FIG.

8B is a table showing the summary of significantly changing genes using a fixed FDR (<0.05) and variable fold-change cutoffs (2×, 1.75× and 1.5×). FIG. 8C is an image showing GSEA analysis of KEGG pathways. Heatmap representation shows significantly upregulated pathways in red (also see panel e) and downregulated pathways in blue. Non-significant comparisons are shown in black; vertical annotations refer to Venn diagrams in (a, iii-iv). Note that the SASP gene set is upregulated early whereas the IFN-1 gene set is upregulated late. FIG. 8D is an image showing heatmaps of significantly changing genes in the IFN-1 and SASP gene sets. Vertical annotations refer to Venn diagrams in (a, v-vi). FIG. 8E is three tables showing the list of significantly upregulated KEGG pathways identified using GSEA (see Table 5 for a list of all pathways). NES, normalized enrichment scores. IFN-1 and SASP gene sets are highlighted in yellow. Note the significant upregulation of IFN-1 between early and late senescence. Red type identifies KEGG pathways indicative of cytosolic DNA sensing and a type I interferon response at late times. FIG. 8F is three images and FIG. 8G is three images showing GSEA profiles of the IFN-1 and SASP genesets for all comparisons; FDR is highlighted in yellow. Note that the upregulation of IFN-1 is significant for EP_SEN-L and SEN-E_SEN-L but not for EP_SEN-E, and that the upregulation of SASP is significant for EP_SEN-E and EP_SEN-L but not SEN-E_SEN-L. n=3 independent biological samples. Differential expression data were analyzed for significance using the GSEA GenePattern interface and the outputs were corrected for multiple comparisons by adjusting the nominal p values using the Benjamini-Hochberg method (see Methods for details).

FIGS. 9A-K show the characterization of L1 effectors and the IFN-1 response. FIG. 9A is a bar graph showing expression of TREX1 was determined by RT-qPCR and immunoblotting. For gel source data, see FIG. 16. FIG. 9B is a bar graph showing expression of RB family genes were compared by RT-qPCR. Primer pairs for all genes were verified to be of equivalent efficiency. FIG. 9C is two bar graphs showing enrichment of H3K9me3 and H3K27me3 on L1 elements was examined by ChIP-qPCR (PCR primers illustrated in FIG. 1B were used: 5'UTR, amplicon A; ORF1, amplicon E; ORF2, amplicon F). FIG. 9D is an image showing ChIP-seq data from ENCODE were investigated for transcription factors that bind to the L1 consensus sequence. The log 2 fold change enrichment relative to input controls is shown for the indicated cell-lines. The binding of YY1 to the L1 promoter has been documented[13] and was used as a positive control. CEBPB was used as a negative control. A schematic illustrating L1 coordinates and relevant features is shown above. Amplicons A-E are the same as shown in FIG. 1B. FIG. 9E is two bar graphs showing transcriptional activity of the intact L1 5'UTR or a UTR lacking the FOXA1 binding site (UTR-A) was determined using sense and antisense reporters cotransfected into early passage LF1 cells either with a FOXA1 expression plasmid or empty vector (EV). FIG. 9F is a bar graph showing FOXA1 was knocked down in senescent cells with shFOXA1 (a) (see also FIG. 2E and FIG. 10A) and binding to the L1 5'UTR (amplicon B) was determined by ChIP-qPCR. FIG. 9G is three bar graphs showing knockdown of RB1, TREX1 and ectopic expression of FOXA1 were performed in early passage cells in all single (1×), double (2×) and triple (3×) combinations and assessed by RT-qPCR using poly(A)-purified RNA for activation of L1, IFN-α and IFN-β1 expression (primers for amplicon F). Three controls are shown: cells infected with irrelevant shRNA (shGFP), expression construct (LacZ), or uninfected early passage cells (EP). FIG. 9H is two bar graphs showing L1 5'UTR occupancy of RB1 and FOXA1 in 3× cells was determined by ChIP-qPCR performed as in FIGS. 2A, 2B. Primers for amplicons A and B were used for RB1 and FOXA1, respectively. For comparison, single interventions in early passage cells with shRB1 (a) or FOXA1 cDNA expression (EP FOXA1-OE) are also shown. FIG. 9I is a bar graph showing confirmation of full length L1 mRNA expression in 3× cells using RT-qPCR with primers for amplicons A and F on poly(A)-purified RNA. CTR, cells infected with irrelevant shRNA (shGFP). FIG. 9J is an image of a heat map representation showing all biological replicates for the 67 genes significantly changing expression in SEN and/or 3× cells (FIG. 2H, Table 6). Column clustering was calculated as 1-Pearson correlation. Rows have been grouped into functional subsets of the IFN-1 response. FIG. 9K is a Venn diagram showing the overlap between the 67 significantly changing genes. (FIGS. 9A-F, 9H) n=3 independent biological samples, repeated in two independent experiments. (FIGS. 9G, 9I), n=3 independent experiments. (FIGS. 9A-1) Data are mean±s.d. *P≤0.05, **P≤0.01, unpaired two-sided t-tests.

FIGS. 10A-M show the efficacy of genetic and pharmacological interventions. FIG. 10A is three bar graphs showing knockdowns with two distinct shRNAs (a, b) or FIG. 10B is three bar graphs showing ectopic cDNA expression were performed in senescent cells as described in FIGS. 2D, 2E, 2G (also see Methods). The effectiveness of these manipulations on their targets was assessed by RT-qPCR and immunoblotting. For gel source data see FIG. 16. FIG. 10C is three bar graphs showing RB1, TREX1 and FOXA1 mRNA and protein expression after the triple (3×) intervention (FIG. 2F). FIG. 10D is a line graph showing the effect of 3TC treatment on the relative abundance of L1HS sequences in senescent cells was determined by multiplex TaqMan qPCR on total DNA (primer set 6, Table 1). SEN entry, 0 weeks in senescence (FIG. 1A; point A in FIG. 6A). 3TC was administered continuously from SEN entry until harvest 16 weeks later. FIG. 10E is a line graph showing the dual luciferase L1 reporter system[14] was used to determine the effect of 3TC dosing on retrotransposition. L1 reporters were introduced into early passage cells using lentivirus vectors (see Methods for details) and cells were treated with 3TC for 4 days prior to harvest and assay. JM111, a defective reporter carrying mutations in ORF1 (absence of 3TC); L1RP, a retrotransposition competent reporter. FIG. 10F is a line graph showing the effect of 3TC dosing on the IFN-I response. The experiment above (d) was processed by RT-qPCR to determine the expression of IFN-α and IFN-β1. FIG. 10G is two bar graphs showing knockdowns of L1 were performed with two distinct shRNAs (a, b) in senescent cells (as in FIGS. 2D, 2E, 2G) or 3× cells (as in FIG. 2G). The effectiveness on L1 expression was assessed by RT-qPCR using poly(A)-purified RNA and primers F. FIG. 10H is nine images and a bar graph showing cells in the experiment in (g) were examined for levels of ORF1 protein by immunofluorescence (IF). Image analysis was performed with CellProfiler software (see Methods for details). >200 cells were examined for each condition (a.f.u., arbitrary fluorescence units). FIG. 10I is a bar graph showing the L1 shRNA treatment in the experiment in (g) was substituted with 3TC treatment (10 μM) for the same period of time. FIG. 10J is two bar graphs showing five different RTIs (or combinations) were tested for effects on the IFN-I response. AZT (Zidovudine, 15 μM), ABC (Abacavir, 15 μM), FTC (Emtricitabine, 10 μM), 3TC (aka Lamivudine or Epivir, 10 μM), TZV (Trizivir, a combination of 15 μM AZT, 15 μM ABC and 7.5 µM 3TC). Cells were treated for 4 weeks between 12 and 16 weeks in senescence (FIG. 1A; points D and E in FIG. 1A). 3× cells (FIG. 2F) were treated with 3TC for 48 hours after the completion of the last drug selection. IFN-α expression was determined by RT-qPCR. FIG. 10K is a bar graph showing a native L1 reporter (pLD143)[15] was co-transfected with shRNA plasmid vectors into HeLa cells (see Methods for details). Retrotransposition was scored as GFP-positive cells, and shL1 knockdowns were normalized to a shLuc negative control. The absolute average retrotransposition frequency (percentage of GFP-positive cells) was 4.1, which matches the published values for the reporter used (pLD143)53. FIG. 10L is two bar graphs showing knockdowns of cGAS and STING were performed in senescent or 3× cells as with the other shRNAs (FIG. 2D, 2E, 2G and FIG. 10A, 10G above). FIG. 10M is 18 images showing downregulation of interferon signaling after CRISPR-mediated inactivation of IFNAR1 and IFNAR2 genes was verified by the absence of IRF9 nuclear translocation and STAT2 phosphorylation in response to interferon stimulation. Cells were infected with lentivirus vectors expressing Cas9 and gRNAs to both IFNAR1 and IFNAR2 (ΔIFNAR, see Methods). After the infection cells were re-seeded on coverslips, treated with interferon for 2 hours, and examined by IF microscopy. The experiment was repeated 3 times with similar results. (FIGS. 10A-I, L) n=3 independent experiments. (FIG. 10K) n=3 independent biological samples, repeated in 2 independent experiments. (FIGS. 10A-I) Data are mean±s.d. *P≤0.05, **P≤0.01, unpaired two-sided t-tests.

FIGS. 11A-H show the characterization of cytoplasmic DNA in senescent cells. FIG. 11A is nine images and a bar graph showing quiescent and senescent cells were treated with BrdU as in FIG. 3A and the cellular localization of BrdU incorporation was visualized by IF microscopy. Proliferating cells, EP(Prol), are shown as a positive control for nuclear BrdU incorporation. The signals were quantified using CellProfiler software (right panel, see Methods). >200 cells were examined for each condition (a.f.u., arbitrary fluorescence units).

FIG. 11B is two bar graphs showing senescent (and EP control) cells (neither labeled with BrdU) were fractionated into nuclear and cytoplasmic fractions, and the representation of L1 sequences in these compartments (as well as whole cells) was assessed with qPCR as in FIG. 3A (TaqMan multiplex qPCR assay16, amplicon F, FIG. 1B). Note that the Y axis units differ by 10-fold between the left and right panels. FIG. 11C is twelve images showing cells Ge4s were examined by IF microscopy for the presence of ORF1 protein, RNA-DNA hybrids, and single-stranded DNA (ssDNA). See Methods and Table 2 for antibodies. The RNA-DNA signal in senescent cells largely colocalized with the ORF1 signal and was lost after RNase A treatment. The ssDNA signal also colocalized with the ORF1 signal and was exposed by RNase treatment. The experiment was repeated three times with similar results. FIG. 11D is an image showing the pulled-down BrdU-containing DNA (FIG. 3C, panel (a) above, see Methods) was cloned and Sanger sequenced. Of the 96 total clones examined, 37 mapped to L1. Red boxes represent the relative positions of these clones on the L1 consensus sequence. FIG. 11E is a bar graph showing senescent cells labeled with BrdU (FIG. 3C, panel (a) above) were immunoprecipitated with anti-BrdU antibodies, and the representation of L1 sequences in the pulled-down DNA was assessed using qPCR with primers spanning the entirety of L1 elements (FIG. 1B, 1C). FIG. 11F is a bar graph showing senescent cells were treated with L1 shRNA (using lentiviral vectors as described in FIG. 10G) between 12 and 16 weeks of senescence, and expression of SASP genes was determined. FIG. 11G is three bar graphs showing transcription throughout murine L1 elements was assessed in a strand-specific manner using the same strategy as was applied to human L1 elements (FIG. 1B, 1C). The amplicons (designated W-Z to distinguish them from the human-specific primers) correspond to the 5'UTR (W), Orf1 (X), Orf2 (Y) and 3'UTR (Z). Also see Methods and Table 1 for primer sequences (primer sets 37, 48-50). Poly(A) RNA was prepared from male white adipose tissue. A total of 12 animals were assessed (3 pools of 4 animals each) in three independent experiments. FIG. 11H is a bar graph showing expression of the three currently active families of murine L1 elements. Primers were designed to distinguishing 5'UTR polymorphisms of the MdA, MdN and Tf families (see Methods, Table 1 primer sets 51-53). RT-qPCR was performed as in (f) above (non-strand-specific). (FIGS. 11A, 11B, 11E) n=3 independent biological samples, repeated in two independent experiments. (FIG. 11F), n=3 independent experiments. (FIGS. 11A, 11E-H) Data are mean±s.d. *P≤0.05, **P≤0.01. (FIG. 11A) 1-way ANOVA with Tukey's multiple comparisons test, (FIGS. 11B, 11E-H) unpaired two-sided t-tests.

FIGS. 12A-G show the effects of ablating L1 activation, the cytoplasmic DNA sensing pathway, or interferon signaling on expression of the IFN-I and SASP responses. FIG. 12A is three bar graphs showing 3× cells were treated with L1 shRNA or with 3TC for 48 hours as described in FIGS. 10G, 10I. Effects on the IFN-I response were determined by RT-qPCR, ELISA or immunoblotting. For gel source data, see FIG. 16. FIG. 12B is two bar graphs showing cells were serially passaged into replicative senescence (RS) with 3TC (10 µM) present throughout as in FIG. 3F, and expression of Cdk inhibitors p21 and p16 was assessed by RT-qPCR. FIG. 12C is two bar graphs showing senescent cells were treated with shRNAs against cGAS or STING between 12 and 16 weeks of senescence (as described in FIG. 10L), and expression of IFN-I response genes (IFN-α, IRF7, OAS1) was determined. FIG. 12D is two bar graphs showing cGAS and STING knockdowns were performed with shRNAs in 3× cells (as in panel (c) above), and expression of IFN-I genes was examined by RT-qPCR. FIG. 12E is a bar graph showing cGAS and STING were knocked down in senescent cells with shRNAs (as in panel (c) above) and expression of SASP response genes (IL-1p6, CCL2, IL-6, MMP3) was assayed by RT-qPCR. FIG. 12F is two bar graphs and FIG. 12G is two bar graphs showing the activity of K-9 was compared with 3TC in senescent and 3× cells. Senescent cultures were treated between 12 and 16 weeks (as in FIG. 3B) and 3× cultures for 48 hrs (as in panel (a) above). Effects on the expression of IFN-I genes (IFN-α, IRF7, OAS1) and SASP genes (IL-1p6, IL-6, MMP3) was assessed by RT-qPCR. (FIGS. 12A-G), n=3 independent experiments. (FIGS. 12A-G) Data are mean±s.d. *P≤0.05, **P≤0.01, unpaired two-sided t-tests.

FIGS. 13A-H show the assessment of p16, L1 ORF1 and pSTAT1 expression in senescent cells and skin specimens from aged humans. FIG. 13A is nine images showing immunofluorescence (IF) detection of p16 and ORF1 in early passage, 3× and senescent cells.

FIG. 13B is 18 images showing representative images of combinatorial ORF1 and p16 or ORF1p and pSTAT1 staining in human dermis. The experiments shown in panels (a, b) was repeated three times independently with similar results. FIG. 13C is two graphs showing cells were plated on cover slips, stained and quantified as described in the Methods. 200 cells in multiple fields were scored for each condition. a.f.u., arbitrary fluorescence units. Insets show the % of cells found in each quadrant. FIG. 13D is a graph and FIG. 13E is a graph showing abundance of ORF1 and p16 or pSTAT1 cells in human skin. Skin biopsies were cryosectioned and stained as described in the Methods. 200 dermal fibroblast cells in multiple fields were scored for each subject. Aggregated data for four subjects (800 cells) are shown. FIG. 13F is a table showing data in (c) and (d) were recalculated to show the relative abundance of p16+ cells among all cells, and ORF1+ cells in the p16+ pool of cells. FIG. 13G is a table showing data in (e) were recalculated as in (f). FIG. 13H is a table showing characteristics of the human subjects used in the analysis of dermal fibroblasts. These specimens were collected as part of the ongoing Leiden Longevity Study.[16] The specimens used here were chosen randomly from left over material. The TIF assay[17] relies on a two-parameter (color) visualization of telomeres (using a FISH probe) and immunofluorescent detection of DNA damage foci (using antibody to 53BP1). Because of limiting material, it was not possible to combine detection of p16 with TIFs in a three-color experiment.

FIGS. 14A-D are each a series of eight box plots showing mice at the indicated ages were treated with 3TC continuously for two weeks (see also FIGS. 4C, 4E, 15D-F, and Methods). For all conditions the expression of L1 mRNA, p16, three representative IFN-I response genes (Ifn-α, Irf7, Oas1) and three representative SASP genes (Il-6, Mmp3, Pai1) were assessed by RT-qPCR. In no instance was expression at 5 months+3TC significantly different from the no drug control; therefore, these data are not shown in the figure (for all collected data, see Table 7). The box plots show the range of the data (whiskers), 25th and 75 percentiles (box), means (dashed line), and medians (solid line). Each point represents one animal. FIG. 14A, Visceral white adipose, male mice. 5 months, n=8 animals; 26 months, n=12 animals; 26 months+3TC, n=12 animals. FIG. 14B, Visceral white adipose, female mice. 5 months, n=8 animals; 26 months, n=12 animals; 26 months+3TC, n=12 animals. FIG. 14C, Liver, male mice. 5 months, n=8 animals; 26 months, n=10 animals; 26 months+3TC, n=10 animals. FIG. 14D, Mice at the age of 26 months were treated with K-9 or 3TC in drinking water for two weeks and analyzed by RT-qPCR as above. NT, not treated. Visceral white adipose, male mice, n=7 animals for each group. Data are mean±s.d. *P ≤ 0.05, **P≤0.01, 1-way ANOVA with Tukey's multiple comparisons test.

FIGS. 15A-G show the combinatorial assessment of senescence, IFN-I, SASP and L1 markers and effects of 3TC on age-associated phenotypes in mouse tissues. FIG. 15A and FIG. 15B are each twelve images showing whole-mount IF was performed on white adipose of 5 months and 26 months old (with and without 2 weeks of 3TC treatment) male mice. In (a), loss of Lamin B1 (senescence marker) was colocalized with IL-6 (SASP marker). In (b), pStat1 (IFN-1 marker) was colocalized with Orf1 (L1 marker). FIG. 15C is a table showing quantification of the experiments shown in (a) and (b). Four animals and at least 200 cells per animal were scored for each condition. FIG. 15D is three images showing neutral lipids were stained with BODIPY to visualize mature adipocytes in whole-mount preparations, and macrophages were detected by IF using the F4/80 antibody. FIG. 15E is five box plots showing the effects of 2 weeks of 3TC treatment on adipogenesis were assessed by measuring mean adipocyte size (left panel), and by RT-qPCR to determine the expression of key adipogenic genes (right panels; Acaca, acetyl-CoA carboxylase 1; Cebpa, CCAAT/enhancer-binding protein alpha; Fasn, fatty acid synthase; Srebp1, sterol regulatory element-binding protein 1). The box plots show the range of the data (whiskers), 25th and 75 percentiles (box), means (dashed line), and medians (solid line). Adipocyte size (BODIPY-stained area) was calculated using CellProfiler; aggregated data for 5 animals and 500 total cells are shown. For RT-qPCR data, each point represents one animal; n=6 animals. FIG. 15F is a box plot showing expression of the Ucp1 gene (thermogenin) in brown adipose tissue was determined by RT-qPCR and is represented as in (e). n=5 animals. FIG. 15G is three box plots showing expression of L1 mRNA was determined by RT-qPCR and is represented as in (e). 5 months, n=8 animals; 26 months, n=12 animals; 29 months, n=6 animals. (FIGS. 15E-G) Data are mean±s.d. *P:≤ 0.05, **P≤0.01. (FIGS. 15C, 15E left panel, FIGS. 15F, 15G) 1-way ANOVA with Tukey's multiple comparisons test, (FIG. 15E right panels) unpaired two-sided t-tests.

FIGS. 16A-E show scans of raw immunoblots. FIG. 16A: Panel a, shows Blot 1-RB1: 1. EP; 2. SEN (L); 3. OE-SEN; 4. SEN (E); Panel b, shows Blot 2-TREX1: 1. EP; 2. SEN (E); 3. SEN (L); and Panel c, shows Blot 3-FOXA1: 1. EP; 2. Arrest; 3. SEN (E); 4. SEN (L). FIG. 16B: Panel d, shows Blot 4-RB1: 1. EP; 2. 3×; Panel e, shows Blot 5-TREX1: 1. EP; 2. 3×; and Panel f, shows Blot 6-FOXA1: 1. EP; 2. 3×. FIG. 16C: Panel g, shows Blot 7-RB1: 1. SEN (L); 2. shRB1(b); 3. shRB1(a); 4. OE-RB1; Panel h, shows Blot 8-TREX1: 1. SEN (L); 2. shTREX1 (b); 3. shTREX1 (a); 4. OE-TREX1; and Panel i, shows Blot 9-FOXA1: 1. shFOXA1 (a); 2. shFOXA1 (b); 3. SEN (L); 4. OE-FOXA1. FIG. 16D: Panel j, shows Blot 10-STAT2: 1. 3×; 2. shL1; 3. NRTI; 4. ΔIFNAR; 5. EP; Panel k, shows Blot 11-IRF7: 1. EP; 2. shL1; 3. 3×; 4. shL1; 5. ΔIFNAR; Panel I, shows Blot 12-STAT2: 1. SEN (L); 2. ΔIFNAR; 3. shL1; 4. NRTI; and Panel m, shows Blot 13-IRF7: 5. SEN (L); 6. ΔIFNAR; 7. shL1; 8. NRTI.

FIG. 16E shows: Panel n, shows Blot 14-p16 (CDKN2A): 1. EP; 2. SEN (E); 3. SEN (L); and Panel o, shows Blot 15-p21 (CDKN1A): 1. EP; 2. SEN (E); 3. SEN (L).

FIGS. 17A-D show the effects of Adefovir and Lamivudine on senescence-induced increases in L1 sequence abundance, interferon gene expression, and SASP gene expression. FIG. 17A is three bar graphs depicting the effects of 5 μM Adefovir and Lamivudine on L1 sequence abundance (copy number) in three different human fibroblast cell lines: LF1, IMR90, W138 using qPCR assays. FIG. 17B is two bar graphs depicting the effects of 5 μM Adefovir and Lamivudine on interferon gene expression of two interferon genes (IFN-α and IFN-#61) in two cell lines (LF1 and IMR90). FIG. 17C is two bar graphs depicting the effects of 5 μM Adefovir and Lamivudine on two SASP genes (IL-6 and MMP3) in the LF1 cell line. FIG. 17D is two bar graphs depicting the effects of higher doses of Adefovir and Lamivudine (10 μM and 50 μM) on interferon gene expression (IFN-α and IFN-β1) in the LF1 cell line.

DETAILED DESCRIPTION OF THE INVENTION

Figures 3E, 3F:
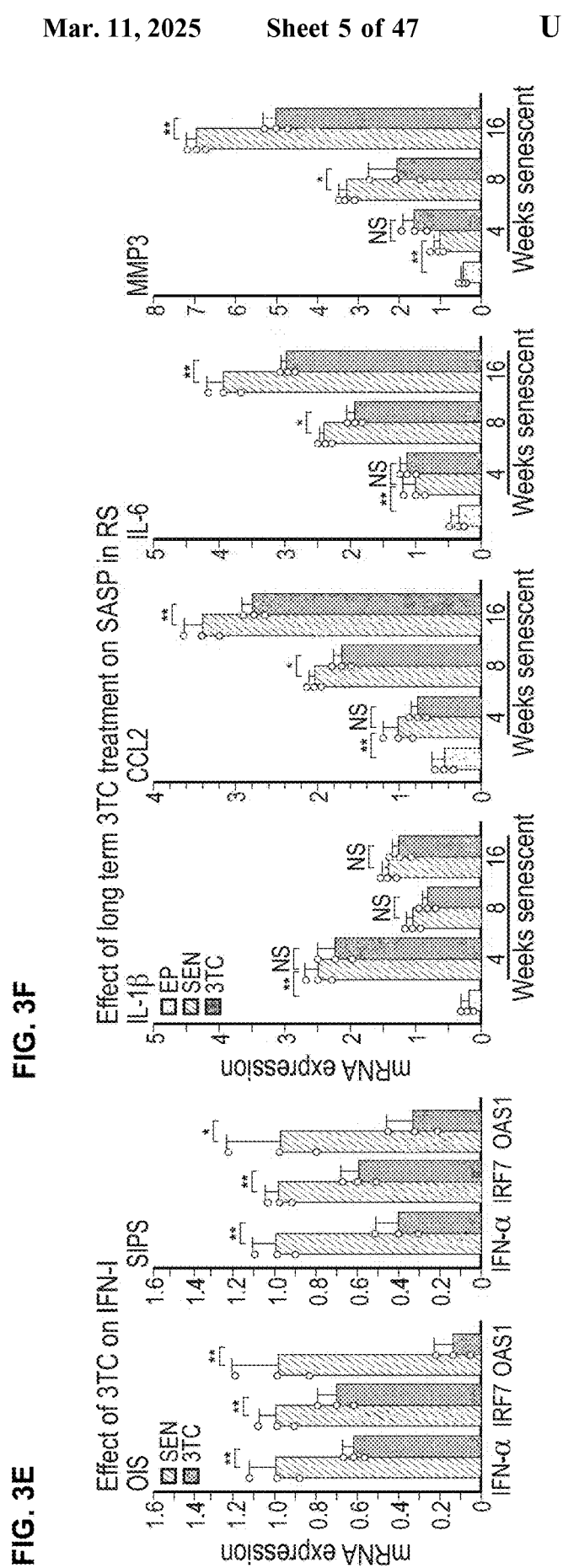

It is to be appreciated that certain aspects, modes, embodiments, variations and features of the invention are described below in various levels of detail in order to provide a substantial understanding of the present invention.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art.

Definitions

The definitions of certain terms as used in this specification and the appended claims are provided below. Unless defined otherwise, all technical and scientific terms used herein generally have the same meaning as commonly understood by one of ordinary skill in the art to which this invention belongs.

As used in this specification and the appended claims, the singular forms "a," "an" and "the" include plural referents unless the content clearly dictates otherwise. For example, reference to "a cell" includes a combination of two or more cells, and the like.

The term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

The terms "effective amount" and "therapeutically-effective amount" include an amount sufficient to prevent or ameliorate a manifestation of disease or medical condition, such as an age-associated disorder. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the subject, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

As used herein, the term "long-term" administration means that the therapeutic agent or drug is administered for a period of at least 12 weeks. This includes that the therapeutic agent or drug is administered such that it is effective over, or a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

As used herein, the term "age-related inflammation" (or "age-associated inflammation") is an inflammation, typically a chronic, particularly a chronic systemic inflammation which occurs with increasing age. Such inflammation may be observed above the age of 30, 35 or 40 but typically is seen in subjects aged 45, 50, 55 or 60 or more. In many cases this may be a low-level inflammation.

As used herein, the term "chronic inflammation" means an inflammation (e.g., an inflammatory condition) that is of persistent or prolonged duration in the body of a subject. Generally speaking, this means an inflammatory response or condition of duration of 20, 25 or 30 days or more or 1 month or more, more particular of at least 2 or 3 months or more. Chronic inflammation leads to a progressive shift in the type of cells present at the site of inflammation. Chronic inflammation may be a factor in the development of a number of diseases or disorders, including particularly degenerative diseases, or diseases or conditions associated with loss of youthful function or aging.

As used herein, the term "systemic inflammation" is inflammation which is not confined to a particular tissue or site or location in the body. The inflammation may be generalized throughout the body. Systemic inflammation typically involves the endothelium and other organ systems.

As used herein, the term "low-level inflammation" (which term is used herein as synonymous with "low-grade inflammation") is characterized by a 2- to threefold increase in the systemic concentrations of cytokines such as TNFα, IL-6, and CRP, e.g., as measured in the plasma or serum. The increase may be relative to, or as compared with, normal concentrations or reference concentrations, for example concentrations as determined in a particular reference cohort or population of subjects, e.g., young subjects (e.g., young adults) or healthy subjects, for example subjects who are not suffering from any disease or condition, including any inflammatory disease, or who do not have inflammation. The increase may also be relative to the level of concentration in a subject prior to development of the inflammation. Low-level inflammation may be observed in the absence of overt signs or symptoms of disease. Thus, low-level inflammation may be sub-clinical inflammation. Alternatively, a subject with low-level inflammation may not have a clinically diagnosed condition or disease but may exhibit certain signs or symptoms of an inflammatory response or inflammatory condition. In other words, there may be signs or symptoms of the effect of inflammation in the body, but this may not yet have progressed to an overt or recognized disease.

As used herein, the term "cancer inflammation" is inflammation that occurs in the context of cancer and may alternatively be defined as "cancer-associated inflammation". Inflammation has been identified as a hallmark of cancer and may be necessary for tumorigenesis and maintenance of the cancer state. Cancer symptoms are associated with inflammation. Thus, a subject with cancer may have or exhibit inflammation, which can be a low-level or peripheral inflammation as discussed above, and in particular a chronic or systemic inflammation as discussed above.

As used herein the term "pathophysiological L1-associated process" refers to a disordered physiological process relating to aberrant LINE-1 (L1) retrotransposition activity. See, e.g., Suarez et al., Dev Neurobiol 78:434-455 (2018); Saleh et al, (2019) Front. Neurol. 10:894. doi: 10.3389/fneur.2019.00894. Zhao et al., PLoS Genet 15(4): e1008043. https://doi.org/i0.1371/journal.pgen.1008043; Bundo et al., Neuron 81:306-313 (2014).

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropyl methyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropyl methyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, micro-emulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art.[18]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, l-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, l-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Role of Cellular Senescence in Aging and Age-Associated Diseases

FIG. 5 provides a flow chart outlining the molecular pathway of cellular senescence leading to age-associate, sterile inflammation, which are described in further detail below.

Upregulation of Retrotransposable Elements (RTEs)

RTEs have been known to be activated transcriptionally in senescent cells[19] and in some mouse tissues.[20] Three regulators have been previously shown to be involved with regulation of L1: FOXA1, RB, TREX1. FOXA1 was reported to be upregulated in senescent cells[21] and to bind to the L1 promoter.[22] RB has been reported to represses L1 elements.[23] The complete loss of TREX1 (germline deletion) has been reported to lead to an autoimmune disease (Aicardi-Gutierrez syndrome, AGS), which is associated with L1 activation.[24]

Although these three regulators had been reported to have a role in the regulation of L1, the data in the present disclosure provides the first demonstration that the misregulation of the combination of these three factors is sufficient to allow activation of endogenous L1 elements in normal cells. See, Example 2. Moreover, the present disclosure provides the first description of late senescence as a discrete temporal, and hitherto unknown, stage of senescence, and one that is characterized by the upregulation of L1 elements and triggering on an IFN-1 response. See, Example 1.

Accumulation of Cytoplasmic L1 cDNA

The existence of cytoplasmic L1 cDNA has been known. One source has been shown to be from mitochondria.[25] The nuclei has been reported to "leak" chromosomal DNA into the cytoplasm in senescent cells.[26] These were subsequently termed "cytoplasmic chromatin fragments" (CCF)[27] and later described in senescent cells.[28] However, none of these reports mention RTEs and L1s as components of CCF.

The data in the present disclosure not only show that L1 DNA sequences are found in the cytoplasm in senescent cells, but also that they are enriched relative to nuclear DNA sequences. See, Example 3. As such, the previously-reported simple extrusion of bulk chromosomal DNA from the nucleus into the cytoplasm cannot explain the enrichment of L1 sequences observed herein.

Although it had been previously reported L1 DNA was enriched in TREX1 null cells (AGS)[29] and that the L1 cDNA accumulating in TREX1 knockout cells was cytoplasmic in localization,[30] AGS in a rare autoimmune disease that is not age-associated. In contrast, the data in the present disclosure generalizes the presence of cytoplasmic L1 DNA to cellular senescence, one of the major driver of aging and aging-associated diseases.

Induction of IFN-I and Crosstalk to Immune System, Reinforcement of SASP

Cytoplasmic DNA (and CCF in particular) has been previously reported to be recognized by the cGAS/STING sensor pathway, which consequently promotes an inflammatory state.[31] In the context of cellular senescence, this pro-inflammatory state is known as the senescence-associated secretory phenotype (SASP). These reports showed that SASP was at least in part dependent on CCF, since knockdown of cGAS/STING pathway components reduced SASP. The IFN-I response was also reported to be a part of this pro-inflammatory cascade.[32] As noted above, none of these previous reports implicated L1 elements in the promotion of SASP by CCF.

The data in the present disclosure establish that, not only does L1 DNA comprise a significant proportion of CCF that is enriched in cytoplasmic DNA relative to nuclear sequences, but it is also functionally relevant for the promotion of SASP. In particular, the data in the present disclosure show that decreasing the amount of cytoplasmic L1 DNA, either by shRNA to L1 or by blocking L1 reverse transcription with RTI drugs, reduced both the IFN-I response and SASP in senescent cells. Importantly, the data in the present disclosure represent the first evidence that RTI treatment can effectively reverse both IFN-I and the proinflammatory SASP after they are fully established in senescent cells. See, Examples 3 and 4.

All prior work relevant to therapy has been limited to interfering with the cGAS/STING sensor pathway, for example showing that shRNAs against components of the cGAS/STING pathway downregulated the IFN-I response and SASP.[33,34] Although one could envision using small molecular inhibitors of the cGAS/STING pathway to down-regulate SASP, such treatments would result in increased sensitivity to viral, bacterial and other pathogen infections.

The approach of the present invention of targeting the synthesis of L1 DNA with RTI drugs goes to the root of the problem because it targets the prime causative agent (L1 DNA itself), as opposed to downstream processing events, such as the cGAS/STING sensor pathway, or even further downstream interferon or immune signaling components. It has been appreciated in the present invention that all of these downstream components have essential cellular functions, and hence targeting them would compromise, in some aspect, normal physiological processes. On the other hand, the L1 DNA is a unique "non-self" component, whose pharmacological targeting would only be compromised by "off-target" effects.

In recent years, it has become clear that cellular senescence is one of the major drivers of organismal aging and aging-associated diseases.[35] Hence, there is considerable interest in "seno-therapies" to block the deleterious effects of senescent cells.[36] The major effort has been directed at "senolytic" drugs that selectively kill (and hence remove) senescent cells from tissues. "Senomorphics" have been classified as small molecules that suppress senescent phenotypes without cell killing. We prefer to refer to such drugs as "senostatic" drugs to emphasize that their main effect is to halt, or block the harmful effects of senescent cells, in particular the SASP.

The data of the present disclosure demonstrate that, in human cells and mouse models, RTIs are senostatic drugs that reverse the SASP of senescent cells and hence alleviate the age-associated proinflammatory state. The data of the present disclosure also describe which specific RTIs, and which doses, are particularly effective in reversing SASP. The broad efficacy of RTIs as senostatic drugs that can treat multiple age-associated conditions has not been previously described in the art.

Promotion of Age-Associated, "Sterile" Inflammation

Sterile inflammation, also known as inflammaging, is a hallmark of aging and a contributing factor to many age-related diseases.[37,38] The data of the present disclosure indicate that activation of L1 elements (and possibly other RTEs) promotes inflammaging, and that the L1 RT is a relevant target for the treatment of age-associated inflammation and disorders.

The data of the present disclosure provide specific examples, in aged mice, of which age-associated pathologies can be reversed, or at least downregulated, by administration of RTIs. For example, the NRTI Lamivudine (aka 3TC or Epivir) was shown to reverse or downregulate:

Panel of IFN-I and SASP markers, measured by RT-qPCR in multiple tissues;
  Infiltration of macrophages into white adipose and kidney tissues measured by IF microscopy;
  Muscle atrophy measured by muscle fiber diameter;
  Kidney glomerulosclerosis measured by pathological evaluation of PAS-stained sections;
  Adipocyte atrophy measured microscopically by cell size and by RT-qPCR analysis of key adipogenic genes; and
  Thermogenesis measured by RT-qPCR analysis of Ucp1 expression.

Accordingly, the present invention provides that RTIs can be used as "senostatic" drugs that are able to halt, or block the harmful effects of senescent cells, in particular the SASP, and prevent or reverse age-related inflammation and disorders.

Nucleoside Reverse Transcriptase Inhibitors (NRTIs)

NRTIs are active inhibitors of reverse transcriptase found in retroviruses such as the human immunodeficiency virus (HIV). The different nucleoside reverse transcriptase inhibitors may be activated differently but they have the same mechanism of action. NRTIs are activated generally by phosphorylation to the triphosphate form by cellular enzymes. It then competes with cellular triphosphates, which are substrates for proviral DNA by viral reverse transcriptase. NRTIs were the first type of drugs available for the treatment of human immunodeficiency virus (HIV infection) and acquired immune deficiency syndrome (AIDS).

Table 8 provides a list of common approved NRTI drugs or NRTI combination drugs used for the treatment of HIV infection and AIDS. As described above, according to the methods of the present invention, NRTIs can be used as "senostatic" drugs that are able to halt, or block the harmful effects of senescent cells, in particular the SASP, and prevent or reverse age-related inflammation and disorders.

NRTI drugs that can be used in the methods of the present invention include, but are not limited to: Amdoxovir, Apricitabine (ATC), ATRIPLA® (efavirenz/emtricitabine/tenofovir disoproxil), BARACLUDE® (entecavir; ETV), BIKTARVY® (bictegravir/emtricitabine/tenofovir alafenamide), Censavudine (INN; BMS-986001; OBP-601; festinavir), COMBIVIR™ (zidovudine/lamivudine), COVIRACIL™ (emtricitabine; FTC), DAPD/DXG (active metabolite of DAPD-2,6-diaminopurine dioxolane), DESCOVY® (emtricitabine/tenofovir alafenamide), D-D4FC (Dexelvucitabine; Reverset; INCB-8721; DPC 817), dOTC (2'-Deoxy-3'-Oxa-4'-Thiocytidine; BCH-10652), Elvucitabine, EMTRIVA™ (emtricitabine), EPIVIR™ (lamivudine; 3TC), EFdA (4'-Ethynyl-2-fluoro-2'-deoxyadenosine; MK-8591), EVIPLERA™ (rilpivirine/emtricitabine/tenofovir disoproxil), GENVOYA® (elvitegravir/cobicistat/emtricitabine/tenofovir alafenamide), HMD™ (zalcitabine; ddC), KIVEXA™ (abacavir/lamivudine), LODENOSINE™ (F-ddA), ODEFSEY® (rilpivirine/tenofovir alafenamide/emtricitabine), PREVEON® (adefovir dipivoxil), Racivir (RCV; (+/−)-Emtricitabine), RETROVIR™ (zidovudine; ZDV; azidothymidine; AZT), Stampidine, STRIBILD® (Elvitegravir/cobicistat/emtricitabine/tenofovir disoproxil), TENOFOVIR™ (TDF, bis-POC PMPA), TRIUMEQ® (dolutegravir/abacavir/lamivudine), TRIZIVIR™ (abacavir/lamivudine/zidovudine), TRUVADA® (emtricitabine/tenofovir disoproxil), VEMLIDY® (tenofovir alafenamide; TAF), VIDEX™ (didanosinel ddl), VIREAD™ (tenofovir disoproxil), ZIAGEN™ (abacavir; 159U89), and ZERIT™ (stavudine; d4T).

At the doses used for HIV/AIDS therapy, these drugs can cause a wide range of side effects. Common Side Effects of NRTIs include, interalia, mitochondrial toxicity (associated with inhibition of mitochondrial polymerase), neuropathy, pancreatitis, hepatic steatosis and lactic acidosis, myelosuppression, symptomatic myopathy, and cardiomyopathy.[39] Although the NRTIs can be used at the dosage approved for HIV/AIDS treatment, lower dosages can be used for the prevention or treatment of age-related inflammation and disorders in order to avoid the side effects associated with the higher doses. In one embodiment, the dosage used for the prevention or treatment of age-related inflammation and disorders is half (50%) of the dosage approved for HIV/AIDS treatment (see Table 9). In an alternate embodiment, the dosage used is 75% of the dosage approved for HIV/AIDS treatment. In yet another alternate embodiment, the dosage used is 25% of the dosage approved for HIV/AIDS treatment. In other alternate embodiments, the dosage used is 90%, 80%, 70%, 60%, 40%, 30%, 20%, or 10% of the dosage approved for HIV/AIDS treatment. In yet other alternate embodiments, the dosage used is 0.1 to 99.5%, 10 to 90%, 20 to 80%, 25 to 75%, 30 to 70%, 40 to 60% or 45 to 55% of the dosage approved for HIV/AIDS treatment.

In some embodiments, the subject undergoes long term administration of one or more RTI drugs, as defined herein. In one embodiment, the subject is treated for a period of at least 12 weeks. In many cases, long-term administration is for at least 4, 5, 6, 7, 8, 9 months or more, or for at least 1, 2, 3, 5, 7 or 10 years, or more.

Age-Associated Disorders

Given that cellular senescence is one of the major drivers of organismal aging and aging-associated diseases,[40] the methods of the present invention can be used to prevent or treat disorders or diseases that have been associated with cellular senescence, in particular in which the presence of senescent cells is likely to have a deleterious effect, by the administration of one or more senostatic RTI drugs.

Disorders or diseases that have been associated with cellular senescence include, but are not limited to, Alzheimer's disease,[41] amyotrophic lateral sclerosis (ALS), atherosclerosis,[42] Huntington's disease, vision loss, hearing loss, peripheral degenerative diseases, cardiovascular dysfunction,[43] atherosclerosis, frontotemporal dementia (FTD), multiple sclerosis (MS), Aicardi Goutiere's syndrome, progressive supra nuclear palsy (PSP), chemotherapy-induced adverse effects (e.g., bone marrow suppression, cardiotoxicity, cancer recurrence, blood clots, fatigue),44 hematopoietic stem cell function,[45] osteoarthritis,[46] osteoporosis,[47] osteoporosis, Parkinson's disease,[48] physical function,[49] pulmonary fibrosis,[50] skin aging, wound healing, and/or tissue regeneration.[51]

Methods of Treating, Preventing and/or Reversing Age-Associated Inflammation and Other Diseases or Disorders with RTIs Provided is a method for treating, preventing and/or reversing a pathophysiological L1-associated process, e.g., age-associated inflammation, in a patient in need thereof by administering a reverse transcriptase inhibitor (RTI) to a patient in need thereof. In some embodiments, the age-associated inflammation may be in a patient having Alzheimer's disease, amyotrophic lateral sclerosis, Parkinson's disease, Huntington's disease, vision loss, hearing loss, peripheral degenerative diseases, and cardiovascular dysfunction. In some embodiments, the disclosure provides a method for treating, preventing and/or reversing Alzheimer's disease, amyotrophic lateral sclerosis (ALS), frontotemporal dementia (FTD), progressive supra nuclear palsy (PSP), dementia with Lewy bodies (DLB), multi systems atrophy (MSA), corticobasal degeneration (CDB), mild cognitive impairment (MCI), Parkinson's disease, Huntington's disease, Rett Syndrome, schizophrenia, autism spectrum disorder (ADS), vision loss, hearing loss, peripheral degenerative diseases, cardiovascular dysfunction, and autoimmune disease.

In one embodiment is provided a method for delaying or reversing the progression of the underlying pathology of an age-associated inflammatory disorder, comprising administering to a patient in need thereof a therapeutically effective amount of at least one reverse transcriptase inhibitor (RTI). In some embodiments, the patient experiences a decrease in one or more symptoms of Alzheimer's disease compared to before the first administration of the RTI to the patient.

In another embodiment, provided is a method for preventing the onset of an age-associated inflammatory disorder in a patient suspected of having mild cognitive impairment, comprising administering at least one RTI to a patient in need thereof.

In some embodiments, the NRTI is abacavir, lamivudine, zidovudine, emtricitabine, tenofovir disoproxil fumarate, tenofovir alafenamide, didanosine, stavudine, apricitabine, alovudine, dexelvucitabine, amdoxovir, fosalvudine or elvucitabine. In other embodiments, the RTI is abacavir (Ziagen), abacavir/lamivudine (Epzicom), abacavir/lamivudine/zidovudine (Trizivir), lamivudine/zidovudine (Combivir), lamivudine (Epivir), zidovudine (Retrovir), emtricitabine/tenofovir disoproxil fumarate (Truvada), emtricitabine (Emtriva), tenofovir disoproxil fumarate (Viread), emtricitabine/tenofovir alafenamide (Descovy), didanosine (Videx), didanosine extended-release (Videx EC), or stavudine (Zerit). In another embodiment, the NRTI is censavudine.

In some embodiments, the at least one RTI is a non-nucleoside reverse transcriptase inhibitor (NNRTI). In some embodiments, the at least one NRTI is Efavirenz (EFV), Nevirapine (NVP), Delavirdine (DLV), Etravirine or Rilvipirine.

In a further embodiment, the RTI inhibits L1 reverse transcriptase activity in a cell, e.g., a brain cell, of the patient.

Where the RTI is an FDA approved drug, the RTI may be administered in therapeutically effective amounts that are approved for therapeutic use. In other embodiments, the amounts effective can be determined with no more than routine experimentation. For example, amounts effective may range from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. In other embodiments, the dosage is 1 mg-500 mg. In some embodiments, the dosage is 10, 20, 30, 40, 50, 60, 70, 80, 90, 100, 110, 120, 130, 140, or 150 mg. These doses may be unitary or divided and may be administered one or more times per day. The above dosages are exemplary of the average case, but there can be individual instances in which higher or lower dosages are merited, and such are within the scope of this disclosure. In practice, the physician determines therapeutically effective amounts and the actual dosing regimen that is most suitable for an individual subject, which can vary with the age, weight, and response of the particular subject.

The RTI may be administered once, twice or three times per day for 1 day to the end of life, or for 1 day to 1, 2, 3, 4, 5, 6, 7, 8, 9, or 10 or more years, or until the RTI causes unacceptable side effects or is no longer useful.

The patient is monitored for changes in the symptoms of the age-associated inflammatory disease. In one embodiment, there is a reduction in the symptoms. In another embodiment, the symptoms remain about the same and there is no evidence of progression. In connection with Alzheimer's disease, such symptoms include memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory. Methods for monitoring and quantifying any change of these symptoms can be carried out by routine methods or by routine experimentation.

In one embodiment, symptoms of mild cognitive impairment and any change in the symptoms of Alzheimer's disease is determined using the criteria set forth in DSM-5. In another embodiment, symptoms of mild cognitive impairment and the any change in the symptoms of Alzheimer's disease is determined using the Clinician's Interview-Based Impression of Change (CIBIC-plus). In another embodiment, symptoms of mild cognitive impairment and any change in symptoms is determined using the Clinician's Interview-Based Impression of Change (CIBIC-plus).

Any change in symptoms may be monitored for 1-36 months or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In another embodiment, the patient is monitored for a change in the underlying pathology of Alzheimer's disease. In one embodiment, there is a reduction in the underlying pathology. In another embodiment, the underlying pathology remains about the same and there is no evidence of progression.

In some embodiments, any change in the underlying pathology is identified by detection of a biomarker before and after the RTI administration. In one embodiment, the biomarker is β-amyloid or Tau protein. In another embodiment, the biomarker is detected by PET imaging. In another embodiment, the underlying pathology is identified by measurement of brain volume before and after the RTI administration.

In some embodiments, the decrease of the underlying pathology is reversed or delayed for at 1-36 months, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of the RTI.

In some embodiments, the patient is also administered at least one second therapeutic agent useful for the treatment of the symptoms of an age-associated inflammatory disorder. In one embodiment, the patient is administered at least one second therapeutic agent useful for the treatment of Alzheimer's disease. In some embodiments, the at least one second therapeutic agent is donepezil, galantamine, rivastigmine, or memantine. In another embodiment, the at least one second therapeutic agent is an antibody that binds to β-amyloid or Tau protein. In another embodiment, the antibody binds to β-amyloid and is bapineuzumab. In another embodiment, the antibody binds to Tau protein and is ABBV-8E12. In another embodiment, the at least one second therapeutic agent is a vaccine against β-amyloid or Tau protein. In another embodiment, the at least one second therapeutic agent is an agent that reduces or alters the brain content of β-amyloid or Tau. In another embodiment, the second therapeutic agent reduces or alters the brain content of β-amyloid and is a β-secretase 1 (BACE) inhibitor. In another embodiment, the BACE inhibitor is CTS-21166, verubecestat (MK-8931), lanabecestat (AZD3293) or LY2886721. In another embodiment, the second agent reduces or alters the brain content of β-amyloid or Tau alters the brain content of Tau and is nicotinamide, or MPTOG211.

The at least one RTI and at least one second therapeutic agent may be administered separately or together as part of a unitary pharmaceutical composition.

When the age-associated inflammatory disorder is ALS, the patient may be administered at least one second agent useful for the treatment of the symptoms of ALS. In some embodiments, the at least one second agent is an integrase inhibitor. In some embodiments, the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.[52]

The patient may be monitored for improvement of the symptoms of ALS. Such symptoms include one or more of the following: difficulty walking or doing normal daily activities, tripping and falling, weakness of the legs, feet or ankles, hand weakness or clumsiness, slurred speech or trouble swallowing, muscle cramps, twitching in the arms, shoulders or tongue, inappropriate crying, cognitive changes, and behavior changes.

Any change in symptoms may be monitored for 1-36 months or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In some embodiments, the decrease of the underlying pathology is reversed or delayed for at 1-36 months, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of the RTI.

Salts, Pharmaceutical Compositions, and Kits

The methods of the present disclosure can be accomplished by administering an at least one RTI as the neat compound or as a pharmaceutical composition. Administration of a pharmaceutical composition, or neat compound of an RTI, can be performed before or after the clinical diagnosis of a disorder associated with age-associated inflammation. Typically, the pharmaceutical compositions are sterile, and contain no toxic, carcinogenic, or mutagenic compounds that would cause an adverse reaction when administered.

Further provided are kits comprising at least one RTI and, optionally, at least one second therapeutic agent useful for the treatment or prevention of a disorder associated with age-associated inflammation, packaged separately or together, and an insert having instructions for using these active agents. In one embodiment, the at least one RTI is packaged alone together with instructions to administered together with the at least one second therapeutic agent. The at least one RTI and the at least one second therapeutic agent can be administered simultaneously or sequentially to achieve the desired effect. In addition, the RTI and the at least one second therapeutic agent can be administered from a single composition or two separate compositions.

Examples of the at least one second therapeutic agents useful for the treatment of Alzheimer's disease that may be in the kit include donepezil, galantamine, rivastigmine and memantine. Other optional therapeutic agents that may be in the kit include an antibody that binds to β-amyloid or Tau protein. In one embodiment, the antibody binds to β-amyloid and is bapineuzumab. In another embodiment, the antibody binds to Tau and is ABBV-8E12.

In another embodiment, the kit may contain least one second therapeutic agent that is a vaccine against β-amyloid or Tau protein.

In another embodiment, the kit may contain at least one second therapeutic agent that reduces or alters the brain content of β-amyloid or Tau protein. In some embodiments, the second therapeutic agent that alters or reduces the brain content of β-amyloid is a β-secretase 1 (BACE) inhibitor. In some embodiment, the BACE inhibitor is CTS-21166, verubecestat (MK-8931), lanabecestat (AZD3293) or LY2886721, each of which have been in clinical trials for the treatment of Alzheimer's disease.

In another embodiment, the kit may contain a second agent that reduces or alters the brain content of Tau and is nicotinamide, or MPTOG211.

In some embodiments, the patient has ALS and the kit further comprises at least one second agent useful for the treatment of ALS. In other embodiments, the RTI is packaged alone together with instructions to administer at least one second therapeutic agent for the treatment of ALS. In some embodiments, the at least one second therapeutic agent for the treatment of ALS is edaravone or riluzole.

In some embodiments, the at least one second agent is an integrase inhibitor. In some embodiments, the integrase inhibitor is raltegravir, curcumin, derivatives of curcumin, chicoric acid, derivatives of chicoric acid, 3,5-dicaffeoylquinic acid, derivatives of 3,5dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.[53]

The second therapeutic agent is administered in an amount to provide its desired therapeutic effect. The effective dosage range for each optional therapeutic agent is known in the art, and the optional therapeutic agent is administered to an individual in need thereof within such established ranges.

The present disclosure encompasses the preparation and use of salts of RTIs. As used herein, a "pharmaceutically acceptable salt" refers to salts or zwitterionic forms of the RTIs. Salts of RTIs can be prepared during the final isolation and purification of the compounds or separately by reacting the compound with a suitable acid. The pharmaceutically acceptable salts of RTIs can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of RTIs include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2 naphthalenesulfonate, oxalate, pamoate, pectinate, persulfate, 3 phenylproprionate, picrate, pivalate, propionate, trichloroacetate, trifluoroacetate, phosphate, glutamate, bicarbonate, para-toluenesulfonate, undecanoate, lactate, citrate, tartrate, gluconate, methanesulfonate, ethanedisulfonate, benzene sulfonate, and p toluenesulfonate salts. In addition, available amino groups present in the RTIs can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to RTIs appearing herein is intended to include the RTIs as well as pharmaceutically acceptable salts, hydrates, or solvates thereof.

The present disclosure encompasses the preparation and use of solvates of RTIs. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. RTIs can be present as solvated forms with a pharmaceutically acceptable solvent, such as water, methanol, and ethanol, and it is intended that the disclosure includes both solvated and unsolvated forms of RTIs. One type of solvate is a hydrate. A "hydrate" relates to a particular subgroup of solvates where the solvent molecule is water. Solvates typically can function as pharmacological equivalents. Preparation of solvates is known in the art. See, e.g., Caira et al. (2004),[54] which describes the preparation of solvates of fluconazole with ethyl acetate and with water. Similar preparation of solvates, hemisolvates, hydrates, and the like are described by Van Tonder et al. (2004)[55] and Bingham et al. (2001).[56] A typical, non-limiting, process of preparing a solvate would involve dissolving the at least one RTI or at least one second therapeutic agent in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

The at least one RTI and at least one second therapeutic agent typically are administered in admixture with a pharmaceutical carrier to give a pharmaceutical composition selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of the at least one RTI and at least one second therapeutic agent.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the at least one RTI and/or at least one second therapeutic agent is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of the at least one RTI and at least one second therapeutic agent. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of the at least one RTI and at least one second therapeutic agent.

When a therapeutically effective amount of the at least one RTI and at least one second therapeutic agent is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

The at least one RTI and at least one second therapeutic agent can be readily combined with pharmaceutically acceptable carriers well-known in the art. Standard pharmaceutical carriers are described in Remington's Pharmaceutical Sciences.[57] Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the at least one RTI and/or the at least one second therapeutic agent to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The at least one RTI and at least one second therapeutic agent can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the at least one RTI and at least one second therapeutic agent can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The at least one RTI and at least one second therapeutic agent also can be formulated in rectal compositions, such as suppositories or retention enemas, e.g., containing conventional suppository bases. In addition to the formulations described previously, the at least one RTI and at least one second therapeutic agent also can be formulated as a depot preparation. Such long-acting formulations can be administered by implantation (for example, subcutaneously or intramuscularly) or by intramuscular injection. Thus, for example, the at least one RTI and at least one second therapeutic agent can be formulated with suitable polymeric or hydrophobic materials (for example, as an emulsion in an acceptable oil) or ion exchange resins.

In particular, the at least one RTI and at least one second therapeutic agent can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The at least one RTI and at least one second therapeutic agent also can be injected parenterally, for example, intravenously, intramuscularly, subcutaneously, or intracoronarily. For parenteral administration, the at least one RTI and at least one second therapeutic agent are typically used in the form of a sterile aqueous solution which can contain other substances, for example, salts or monosaccharides, such as mannitol or glucose, to make the solution isotonic with blood.

Islatravir

In some embodiments, provided is a method for treating, preventing and/or reversing Alzheimer's disease, amyotrophic lateral sclerosis (ALS), frontotemporal dementia (FTD), progressive supra nuclear palsy (PSP), dementia with Lewy bodies (DLB), multi systems atrophy (MSA), corticobasal degeneration (CDB), mild cognitive impairment (MCI), Parkinson's disease, Huntington's disease, vision loss, hearing loss, peripheral degenerative diseases, cardiovascular dysfunction, and autoimmune disease by administering to a patient in need thereof a therapeutically effective amount of islatravir (also known as EDdA, MK-8591 or 2'-deoxy-4'-ethynyl-2-fluoroadenosine). Islatravir and its method of synthesis is described in U.S. Pat. No. 7,625,877. The chemical structure of islatravir is:

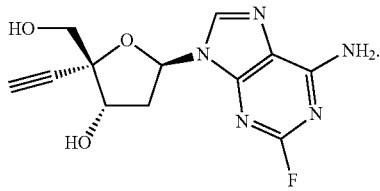 [SMILES: C#C[C@]1(CO)O[C@@H](n2cnc3c(N)nc(F)nc32)C[C@@H]1O]

In some embodiments, islatravir is administered daily in an amount that ranges from about 0.1 mg to about 20 mg, e.g., about 0.2 mg to about 15 mg, e.g., about 1 mg to about 10 mg, e.g. 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 1 mg, 2 mg, 3 mg, 4 mg, 5 mg, 6 mg, 7 mg, 8 mg, 9 mg, or 10 mg. In some embodiments, islatravir is administered daily in an amount of 0.25, 0.5 or 0.75 mg.

In some embodiments, islatravir is administered monthly in an amount from 50-150 mg, e.g., 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, or 150 mg.

In some embodiments, islatravir is administered by continuous release from an implant. In some embodiments, the implant comprises 30 to 80 mg islatravir. In some embodiments, the implant comprises 30 mg, 35 mg, 40 mg, 45 mg, 50 mg, 51 mg, 52 mg, 54 mg, 55 mg, 56 mg, 57 mg, 58 mg, 59 mg, 60 mg, 61 mg, 62 mg, 63 mg, 64 mg, 65 mg, 70 mg, 75 mg, or 80 mg. In some embodiments, islatravir is administered by continuous release from an implant containing 54 or 62 mg islatravir.

In some embodiments, islatravir is administered to a patient is (a) not infected with the HIV virus, (b) is not suspected of being infected with the HIV virus, and/or (c) is not being treated to prevent infection with the HIV virus.

In one embodiment is provided a method for delaying or reversing the progression of the underlying pathology of Alzheimer's disease, comprising administering to a patient in need thereof a therapeutically effective amount of islatravir. In some embodiments, the patient experiences a decrease in one or more symptoms of Alzheimer's disease compared to before the first administration of islatravir to the patient.

In another embodiment, provided is a method for preventing the onset of Alzheimer's disease in a patient suspected of having mild cognitive impairment, comprising administering islatravir to a patient in need thereof.

In some embodiments, the patient is monitored for changes in the symptoms of the disorder after the first administration of islatravir. In one embodiment, there is a reduction in the symptoms. In another embodiment, the symptoms remain about the same and there is no evidence of progression of the disorder. In connection with Alzheimer's disease, such symptoms include memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory. Methods for monitoring and quantifying any change of these symptoms can be carried out by routine methods or by routine experimentation.

In one embodiment, symptoms of mild cognitive impairment and any change in the symptoms of Alzheimer's disease is determined using the criteria set forth in the Diagnostic and Statistical Manual of Mental Disorders, Fifth Edition (DSM-5). In another embodiment, symptoms of mild cognitive impairment and the any change in the symptoms of Alzheimer's disease is determined using the Clinician's Interview-Based Impression of Change (CIBIC-plus). In another embodiment, symptoms of mild cognitive impairment and any change in symptoms is determined using the Clinician's Interview-Based Impression of Change (CIBIC-plus).

Any change in symptoms may be monitored for 1-36 months or more, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In another embodiment, the patient is monitored for a change in the underlying pathology of Alzheimer's disease. In one embodiment, there is a reduction in the underlying pathology. In another embodiment, the underlying pathology remains about the same and there is no evidence of progression.

In some embodiments, any change in the underlying pathology is identified by detection of a biomarker before and after islatravir administration. In one embodiment, the biomarker is β-amyloid or Tau protein. In another embodiment, the biomarker is detected by PET imaging. In another embodiment, the underlying pathology is identified by measurement of brain volume before and after islatravir administration.

In some embodiments, the decrease of the underlying pathology is reversed or delayed for 1-36 months, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of islatravir.

In some embodiments, the patient is also administered at least one second therapeutic agent useful for the treatment of the symptoms of Alzheimer's disease, ALS, FTD, PSP, DLB, MSA, CDB, MCI, Parkinson's disease, Huntington's disease, vision loss, hearing loss, peripheral degenerative diseases, cardiovascular dysfunction, or autoimmune disease. In one embodiment, the patient is administered at least one second therapeutic agent useful for the treatment of Alzheimer's disease. In some embodiments, the at least one second therapeutic agent is donepezil, galantamine, rivastigmine, or memantine. In another embodiment, the at least one second therapeutic agent is an antibody that binds to β-amyloid or Tau protein. In another embodiment, the antibody binds to β-amyloid and is bapineuzumab. In another embodiment, the antibody binds to Tau protein and is ABBV-8E12. In another embodiment, the at least one second therapeutic agent is a vaccine against β-amyloid or Tau protein. In another embodiment, the at least one second therapeutic agent is an agent that reduces or alters the brain content of β-amyloid or Tau. In another embodiment, the second therapeutic agent reduces or alters the brain content of β-amyloid and is a β-secretase 1 (BACE) inhibitor. In another embodiment, the BACE inhibitor is CTS-21166, verubecestat (MK-8931), lanabecestat (AZD3293) or LY2886721. In another embodiment, the second agent reduces or alters the brain content of β-amyloid or Tau alters the brain content of Tau and is nicotinamide, or MPTOG211.

Islatravir and at least one second therapeutic agent may be administered separately or together as part of a unitary pharmaceutical composition.

When the age-associated disorder is ALS, the patient may be administered at least one second agent useful for the treatment of the symptoms of ALS. In some embodiments, the at least one second agent is an integrase inhibitor. In some embodiments, the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C. See, U.S. Patent Appln. Pub. 2018/0050000.

The patient may be monitored for improvement of the symptoms of ALS. Such symptoms include difficulty walking or doing normal daily activities, tripping and falling, weakness of the legs, feet or ankles, hand weakness or clumsiness, slurred speech or trouble swallowing, muscle cramps, twitching in the arms, shoulders or tongue, inappropriate crying, cognitive changes, and behavior changes.

Any change in symptoms may be monitored for 1-36 months or more, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. In some embodiments, the decrease of the underlying pathology is reversed or delayed for at 1-36 months, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after the first administration of islatravir.

In some embodiments, the second therapeutic agent is a nucleoside reverse transcriptase inhibitor (NRTI). In some embodiments, the NRTI is abacavir, lamivudine, zidovudine, emtricitabine, tenofovir disoproxil fumarate, tenofovir alafenamide, didanosine, stavudine, apricitabine, alovudine, dexelvucitabine, amdoxovir, fosalvudine or elvucitabine. In other embodiments, the RTI is abacavir (Ziagen), abacavir/lamivudine (Epzicom), abacavir/lamivudine/zidovudine (Trizivir), lamivudine/zidovudine (Combivir), lamivudine (Epivir), zidovudine (Retrovir), emtricitabine/tenofovir disoproxil fumarate (Truvada), emtricitabine (Emtriva), tenofovir disoproxil fumarate (Viread), emtricitabine/tenofovir alafenamide (Descovy), didanosine (Videx), didanosine extended-release (Videx EC), or stavudine (Zerit). In another embodiment, the NRTI is censavudine.

In some embodiments, second therapeutic agent is a non-nucleoside reverse transcriptase inhibitor (NNRTI). In some embodiments, the at least one NNRTI is Efavirenz (EFV), Nevirapine (NVP), Delavirdine (DLV), Etravirine or Rilpivirine.

In a further embodiment, the second therapeutic agent inhibits L1 reverse transcriptase activity in a cell, e.g., a brain cell, of the patient.

Where the reverse transcriptase inhibitor (RTI) is an FDA approved drug, the RTI may be administered in therapeutically effective amounts that are approved for therapeutic use. In other embodiments, the amounts effective can be determined with no more than routine experimentation. For example, amounts effective may range from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. In other embodiments, the dosage is 1 mg-500 mg. In some embodiments, the dosage is 10, 20, 30, 40, 50, 60, 70, 80, 90, 100, 110, 120, 130, 140, or 150 mg. These doses may be unitary or divided and may be administered one or more times per day. The above dosages are exemplary of the average case, but there can be individual instances in which higher or lower dosages are merited, and such are within the scope of this disclosure. In practice, the physician determines therapeutically effective amounts and the actual dosing regimen that is most suitable for an individual subject, which can vary with the age, weight, and response of the particular subject.

The RTI may be administered once, twice or three times per day for 1 day to the end of life, or for 1 day to 1, 2, 3, 4, 5, 6, 7, 8, 9, or 10 or more years, or until the RTI causes unacceptable side effects or is no longer useful.

In some embodiments, islatravir is formulated as part of an implant as disclosed in US 2019/0388590. In some embodiments, the implant comprises a biocompatible, nonerodible polymer and islatravir, wherein the implant is implanted sub-dermally and islatravir is continually released in vivo at a rate resulting in a plasma concentration between 0.02 ng/mL and 300.0 ng/mL. In some embodiments, islatravir plasma concentration is between 0.02 ng/mL and 30.0 ng/mL. In some embodiments, islatravir plasma concentration is between 0.02 ng/mL and 8.0 ng/mL.

In some embodiments, the biocompatible, nonerodible polymer is selected from the group consisting of ethylenevinylacetate copolymer (EVA), poly(urethane), silicone, crosslinked poly(vinyl alcohol), poly(hydroxyethylmethacrylate), acyl substituted cellulose acetates, partially hydrolyzed alkylene-vinyl acetate copolymers, completely hydrolyzed alkylene-vinyl acetate copolymers, unplasticized polyvinyl chloride, crosslinked homopolymers of polyvinylacetate, crosslinked copolymers of polyvinyl acetate, crosslinked polyesters of acrylic acid, crosslinked polyesters of methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole),poly(esters), poly(ethylene terephthalate), polyphosphazenes, chlorosulphonated polylefins, and combinations thereof. In some embodiments, the biocompatible, nonerodible polymer is ethylene vinyl acetate copolymer.

In some embodiments, the biocompatible, nonerodible polymer is selected from the group consisting ethylene vinylacetate copolymer (9% vinyl acetate), ethylene vinyl acetate copolymer(15% vinyl acetate), ethylene vinyl acetate copolymer (28% vinylacetate), and ethylene vinyl acetate copolymer (33% vinyl acetate). In some embodiments, the biocompatible, nonerodible polymer is ethylene vinyl acetate copolymer (9% vinylacetate). In some embodiments, the biocompatible, nonerodible polymer is ethylene vinyl acetate copolymer (15% vinylacetate).

In some embodiments, the biocompatible, nonerodible polymer is poly(urethane).

In some embodiments, the implant further comprises a diffusional barrier selected from the group consisting of ethylenevinylacetate copolymer (EVA), poly(urethane), silicone, crosslinkedpoly(vinyl alcohol), poly(hydroxy ethylmethacrylate), acyl substituted cellulose acetates, partially hydrolyzed alkylene-vinyl acetate copolymers, completely hydrolyzed alkylene-vinyl acetate copolymers, unplasticized polyvinyl chloride, crosslinked homopolymers of polyvinylacetate, crosslinked copolymers of polyvinyl acetate, crosslinked polyesters of acrylic acid, crosslinked polyesters of methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(esters), poly(ethyleneterephthalate), polyphosphazenes, chlorosulphonated polylefins, and combinations thereof. In some embodiments, the diffusional barrier is ethylene vinyl acetate copolymer. In some embodiments, the diffusional barrier is poly(urethane).

In some embodiments, islatravir is dispersed or dissolved in the biocompatible nonerodible polymer.

In some embodiments, islatravir is present in the biocompatible, nonerodible polymer between 0.10% to 80% by weight of drug loading. In some embodiments, islatravir is present at in the biocompatible, nonerodible polymer between 30% to 65% by weight of drug loading. In some embodiments, islatravir is present in the biocompatible, nonerodible polymer between 40% to 50% by weight of drug loading.

In some embodiments, the implant further comprises between 1% and 20% by weight of a radiopaque material. The radiopaque component will cause the implant to be X-ray visible. The radiopaque component can be any such element known in the art, such as barium sulphate, titanium dioxide, bismuth oxide, tantalum, tungsten or platinum. In a specific embodiment, the radiopaque component is barium sulphate.

In some embodiments, radiopaque material is about 1% to 30% by weight. In another embodiment, the radiopaque material is about 1% to 20% by weight. In another embodiment, the radiopaque material is about 4% to 25% by weight. In further embodiment, the radiopaque material is about 6% to 20% by weight. In another embodiment, the radiopaque material is about 4% to 15% by weight. In another embodiment, the radiopaque material is about 8% to 15% by weight.

In some embodiments, islatravir is released at therapeutic concentrations for a duration from between three months and thirty-six months. In some embodiments, islatravir is released at prophylactic concentrations for a duration from between three months and thirty-six months.

Some embodiments of the technology described herein can be defined according to any of the following numbered paragraphs:

1. A method for treating, preventing and/or reversing age-associated inflammation in a patient in need thereof comprising administering a therapeutically effective amount of a reverse transcriptase inhibitor (RTI) to the patient in need thereof, wherein the RTI comprises censavudine or elvucitabine.
2. The method of paragraph 1, wherein the age-associated inflammation is in a patient having Alzheimer's disease, amyotrophic lateral sclerosis (ALS), Parkinson's disease, Huntington's disease, vision loss, hearing loss, peripheral degenerative diseases, or cardiovascular dysfunction, frontotemporal dementia (FTD), multiple sclerosis (MS), Aicardi Goutiere's syndrome, progressive supra nuclear palsy (PSP), osteoarthritis, skin aging, atherosclerosis, chemotherapy-induced adverse effects, hematopoietic stem cell function, osteoporosis, physical function, and/or pulmonary fibrosis, or in a patient in need of wound healing or tissue regeneration.
3. The method of paragraph 1, wherein the age-associated inflammation is in a patient having Alzheimer's disease.
4. The method of paragraph 1, wherein the age-associated inflammation is in a patient having ALS.
5. A method for delaying or reversing the progression of the underlying pathology of a disorder caused by age-associated inflammation, comprising administering to a patient in need thereof a therapeutically effective amount of a reverse transcriptase inhibitor (RTI), wherein the RTI comprises censavudine or elvucitabine.
6. The method of paragraph 5, wherein the patient has Alzheimer's disease or ALS and experiences a decrease in one or more symptoms of Alzheimer's disease or ALS compared to before the first administration to the patient.
7. The method of paragraph 6, wherein the patient has Alzheimer's disease and the one or more symptoms comprise memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory.

8. The method of paragraph 6, wherein the patient has Alzheimer's disease and the decrease in the one or more symptoms are evaluated according to the DSM-5.

9. The method of paragraph 6, wherein the patient has Alzheimer's disease and the decrease of symptoms is determined using the cognitive subscale of the Alzheimer's Disease Assessment Scale (ADAS-cog).

10. The method of paragraph 6, wherein the patient has Alzheimer's disease and the decrease of symptoms is determined using the Clinician's Interview-Based Impression of Change (CIBIC-plus).

11. The method of paragraph 6, wherein the patient has Alzheimer's disease and the decrease of symptoms is determined using the Activities of Daily Living Scale (ADL).

12. The method of any one of paragraphs 6-11, wherein the decrease of symptoms is for 1-36 months.

13. The method of any one of paragraphs 6-11, wherein any change in the underlying pathology is identified by detection of a biomarker before and after the RTI administration.

14. The method of paragraph 13, wherein the biomarker is β-amyloid or Tau protein.

15. The method of paragraphs 13 or 14, wherein the biomarker is detected by PET imaging.

16. The method of paragraphs 13 or 14, wherein the biomarker is detected by measurement in the cerebrospinal fluid.

17. The method of any one of paragraphs 6-11, wherein the underlying pathology is identified by measurement of brain volume before and after the RTI administration.

18. The method of any one of paragraphs 6-17, wherein the decrease of the underlying pathology is reversed or delayed for 1-36 months.

19. A method for preventing the onset of Alzheimer's disease in a patient suspected of having mild cognitive impairment, comprising administering to a patient in need thereof a therapeutically effective amount of a reverse transcriptase inhibitor (RTI), wherein the RTI comprises censavudine or elvucitabine.

20. The method of any one of paragraphs 1-19, wherein the patient has Alzheimer's disease or mild cognitive impairment, and further comprising administering at least one second therapeutic agent useful for the treatment of the symptoms of Alzheimer's disease.

21. The method of paragraph 20, wherein the at least one second therapeutic agent is donepezil, galantamine, rivastigmine, or memantine.

22. The method of paragraph 20, wherein the at least one second therapeutic agent is an antibody that binds to β-amyloid or Tau protein.

23. The method of paragraph 22, wherein the antibody is binds to β-amyloid and is bapineuzumab.

24. The method of paragraph 22, wherein the antibody binds to Tau protein and is ABBV-8E12.

25. The method of paragraph 20, wherein the at least one second therapeutic agent is a vaccine against β-amyloid or Tau protein.

26. The method of paragraph 20, wherein the at least one second therapeutic agent is an agent that reduces or alters the brain content of β-amyloid or Tau.

27. The method of paragraph 26, wherein the second therapeutic agent reduces or alters the brain content of β-amyloid and is a β-secretase 1 (BACE) inhibitor.

28. The method of paragraph 27, wherein the BACE inhibitor is CTS-21166, verubecestat (MK-8931), lanabecestat (AZD3293) or LY2886721.

29. The method of paragraph 26, wherein the second agent reduces or alters the brain content of Tau and is nicotinamide, or MPTOG211.

30. The method of any one of paragraphs 1, 2, or 4, wherein the patient has ALS, and further comprising administering at least one second agent useful for the treatment of ALS.

31. The method of paragraph 30, wherein the drug useful for the treatment of ALS is edaravone or riluzole.

32. The method of paragraph 30, wherein the at least one second agent is an integrase inhibitor.

33. The method of paragraph 32, wherein the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.

34. The method of any one of paragraphs 1-33, wherein the patient is evaluated for one or more symptoms or disease pathology 1-36 months after the first administration to the patient of the RTI.

35. The method of any one of paragraphs 1-34, wherein the RTI inhibits L1 reverse transcriptase activity in a cell of the patient.

36. The method of any one of paragraphs 1-35, wherein the RTI is elvucitabine.

37. The method of any one of paragraphs 1-35, wherein the RTI is censavudine.

38. The method of any one of paragraphs 1-35 further comprising administering at least one second therapeutic agent to the patient.

39. The method of paragraph 38, wherein the patient has Alzheimer's disease and the at least one second therapeutic agent is useful for the treatment of the symptoms of Alzheimer's disease.

40. The method of paragraph 38, wherein the patient has amyotrophic lateral sclerosis (ALS) and the at least one second therapeutic agent is useful for the treatment of ALS.

41. A method for treating, preventing, delaying the progression of the underlying pathology, and/or reversing the underlying pathology of a disease, condition, or disorder in patient in need thereof, the method comprising administering a therapeutically effective amount of islatravir, censavudine, or elvucitabine to the patient, wherein the disease, condition, or disorder is Alzheimer's disease, amyotrophic lateral sclerosis (ALS), atherosclerosis, autism spectrum disorder (ADS), autoimmune disease, cardiovascular dysfunction, chemotherapy-induced adverse effects, dementia with lewy Bodies (DLB), frontotemporal dementia (FTD), hearing loss, hematopoietic stem cell function, Huntington's disease, mild cognitive impairment (MCI), multi systems atrophy (MSA), corticobasal degeneration (CDB), multiple sclerosis (MS), osteoarthritis, osteoporosis, Parkinson's disease, peripheral degenerative disease, physical function, progressive supra nuclear palsy (PSP), pulmonary fibrosis, Rett Syndrome, schizophrenia, skin aging, vision loss, or in a patient in need of wound healing or tissue regeneration, or in a patient in need of wound healing or tissue regeneration.

42. The method of paragraph 41 for treating or preventing the disease, condition, or disorder in the subject in need thereof.

43. The method of paragraph 41 for delaying the progression of the underlying pathology or reversing the underlying pathology of the disease, condition, or disorder in the subject in need thereof.

44. The method of any one of paragraphs 41-43, wherein the disease, condition, or disorder is Alzheimer's disease, ALS, FTD, PSP, or Rett Syndrome.

45. The method of paragraph 44, wherein the disease, condition, or disorder is Alzheimer's disease or ALS, and the patient experiences a decrease in one or more symptoms of Alzheimer's disease or ALS after administration of islatravir, censavudine, or elvucitabine to the patient.

46. The method of paragraph 45, wherein the disease, condition, or disorder is Alzheimer's disease, and the one or more symptoms comprise memory loss, misplacing items, forgetting the names of places or objects, repeating questions, being less flexible, confusion, disorientation, obsessive behavior, compulsive behavior, delusions, aphasia, disturbed sleep, mood swings, depression, anxiety, frustration, agitation, difficulty in performing spatial tasks, agnosia, difficulty with ambulation, weight loss, loss of speech, loss of short term memory or loss of long term memory.

47. The method of paragraph 45, wherein the disease, condition, or disorder is Alzheimer's disease, and the decrease in the one or more symptoms are evaluated according to the DSM-5.

48. The method of paragraph 45, wherein the disease, condition, or disorder is Alzheimer's disease, and the decrease of symptoms is determined using the cognitive subscale of the Alzheimer's disease Assessment Scale (ADAS-cog).

49. The method of paragraph 45, wherein disease, condition, or disorder is Alzheimer's disease, and the decrease of symptoms is determined using the Clinician's Interview-Based Impression of Change (CIBIC-plus).

50. The method of paragraph 45, wherein the disease, condition, or disorder is Alzheimer's disease and the decrease of symptoms is determined using the Activities of Daily Living Scale (ADL).

51. The method of any one of paragraphs 45-50, wherein the decrease of symptoms is for 1-36 months.

52. The method of paragraph 43, wherein the underlying pathology is identified by detection of a biomarker before and after administration of islatravir, censavudine, or elvucitabine to the patient.

53. The method of paragraph 52, wherein the biomarker is β-amyloid or Tau protein.

54. The method of paragraph 52 or 53, wherein the biomarker is detected by PET imaging.

55. The method of paragraph 52 or 53, wherein the biomarker is detected by measurement in the cerebrospinal fluid.

56. The method of any one of paragraphs 52-55, wherein the underlying pathology is identified by measurement of brain volume before and after islatravir, censavudine, or elvucitabine administration.

57. The method of paragraph 43, the underlying pathology is delayed or reversed for 1-36 months.

58. The method of paragraph 41, wherein disease, condition, or disorder is an autoimmune disease.

59. The method of paragraph 58, wherein the autoimmune disease is Aicardi Goutiere's Syndrome (AGS), lupus, or rheumatoid arthritis.

60. The method of any one of paragraph 41-59, further comprising administering a therapeutically effective amount of at least one second therapeutic agent useful for treating or preventing the disease, condition, or disorder.

61. The method of paragraph 60, wherein the at least one second therapeutic agent is a nucleoside reverse transcriptase inhibitor (NRTI).

62. The method of paragraph 61, wherein the at least one NRTI is abacavir (Ziagen), abacavir/lamivudine (Epzicom), abacavir/lamivudine/zidovudine (Trizivir), lamivudine/zidovudine (Combivir), lamivudine (Epivir), zidovudine (Retrovir), emtricitabine/tenofovir disoproxil fumarate (Truvada), emtricitabine (Emtriva), tenofovir disoproxil fumarate (Viread), emtricitabine/tenofovir alafenamide (Descovy), didanosine (Videx), didanosine extended-release (Videx EC), stavudine (Zerit), apricitabine, alovudine, dexelvucitabine, amdoxovir, fosalvudine or elvucitabine.

63. The method of paragraph 60, wherein the at least one second therapeutic agent is a non-nucleoside reverse transcriptase inhibitor (NNRTI).

64. The method of paragraph 63, wherein the NNRTI is Efavirenz (EFV), Nevirapine (NVP), Delavirdine (DLV), Etravirine or Rilpivirine.

65. The method of paragraph 60, wherein the disease, condition, or disorder is Alzheimer's disease or mild cognitive impairment, and the at least one second therapeutic agent is useful for the treatment of the symptoms of Alzheimer's disease.

66. The method of paragraph 65, wherein the at least one second therapeutic agent is donepezil, galantamine, rivastigmine, or memantine.

67. The method of paragraph 65, wherein the at least one second therapeutic agent is an antibody that binds to β-amyloid or Tau protein.

68. The method of paragraph 67, wherein the antibody binds to β-amyloid and is bapineuzumab.

69. The method of paragraph 67, wherein the antibody binds to Tau protein and is ABBV-8E12.

70. The method of paragraph 60, wherein the at least one second therapeutic agent is a vaccine against β-amyloid or Tau protein.

71. The method of paragraph 60, wherein the at least one second therapeutic agent is an agent that reduces or alters the brain content of β-amyloid or Tau.

72. The method of paragraph 71 wherein the second therapeutic agent reduces or alters the brain content of β-amyloid is a β-secretase 1 (BACE) inhibitor.

73. The method of paragraph 72, wherein the BACE inhibitor is CTS-21166, verubecestat (MK-8931), lanabecestat (AZD3293) or LY2886721.

74. The method of paragraph 71, wherein the second agent reduces or alters the brain content of Tau is nicotinamide, or MPTOG211.

75. The method of paragraph 60, wherein the patient has ALS, and further comprises administering at least one second therapeutic agent useful for the treatment of ALS.

76. The method of paragraph 75, wherein the second therapeutic agent is edaravone or riluzole.

77. The method of paragraph 75, wherein the at least one second therapeutic agent is an integrase inhibitor.

78. The method of paragraph 77, wherein the integrase inhibitor is raltegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-25 870810, MK-0518, BMS-538158, or GSK364735C.

79. The method of any one of paragraphs 41-78, wherein the patient is evaluated for one or more symptoms or disease pathology 1-36 months after the first administration to the patient of islatravir, censavudine, or elvucitabine.

80. The method of any one of paragraphs 41-79, wherein the patient is (a) not infected with the HIV virus, (b) is not suspected of being infected with the HIV virus, and/or (c) is not being treated to prevent infection with the HIV virus.

81. The method of any one of paragraphs 41-80 comprising administering a therapeutically effective amount of islatravir to the patient in need thereof.

82. The method of paragraph 81, wherein islatravir is administered daily.

83. The method of paragraph 82, wherein islatravir is administered daily in an amount about 0.1 mg to about 10 mg.

84. The method of paragraph 81, wherein islatravir is administered monthly.

85. The method of paragraph 84, wherein islatravir is administered monthly in an amounts of about 60 or about 120 mg.

86. The method of paragraph 81, wherein islatravir is administered from an implant that contains 54 or 62 mg of islatravir.

87. The method of any one of paragraphs 41-80 comprising administering a therapeutically effective amount of censavudine to the patient in need thereof.

88. The method of any one of paragraphs 41-80 comprising administering a therapeutically effective amount of elvucitabine to the patient in need thereof.

EXAMPLES

The invention now being generally described, it will be more readily understood by reference to the following examples which are included merely for purposes of illustration of certain aspects and embodiments of the present invention and are not intended to limit the invention.
Methods
Cell Culture Several different strains of normal human fibroblasts were employed in this study. LF1 cells were derived from embryonic lung tissue as described.[58] These cells have been in continuous use in our laboratory since their isolation in 1996. For this study original samples frozen in 1996 and in continuous storage in our laboratory were recovered and used. IMR-90 and WI-38 cells were obtained from the ATCC. None of these cell lines are listed in the International Cell Line Authentication Committee (ICLAC) database. These normal fibroblast cell lines were cultured using physiological oxygen conditions (92.5% $N_2$, 5% $CO_2$, 2.5% $O_2$), in Ham's F-10 nutrient mixture (Thermo Scientific) with 15% fetal bovine serum (FBS, Hyclone). Medium was additionally supplemented with L-glutamine (2 mM), penicillin and streptomycin.[59] Cell cultures were periodically tested for *mycoplasma* contamination with MycoAlert® *Mycoplasma* Detection Kit (Lonza).

To obtain replicatively senescent (RS) cells, LF1 cultures were serially propagated until proliferation ceased. At each passage, after reaching 80% confluence cells were trypsinized and diluted 1:4. Hence each passage is equivalent to approximately two population doublings. In early passage cultures, the time between passages is constant at approximately 3 days. As cultures approached senescence the time between passages gradually increased. An interval of 2-3 weeks indicated that the culture was in its penultimate passage. At this point, after reaching 80% confluence, the cells were replated at 1:2 dilution, and this time was designated as the last passage (point A in FIG. 2A). Some cell growth typically does occur in the next 2-3 weeks, but the cultures do not reach 80%. Under this experimental regimen, the majority of the cells in the culture enter senescence within a 3-4 weeks window centered roughly around the time of last passage (grey bar in FIG. 2A). At point B (4 weeks), the cultures were trypsinized and replated as described[60] to eliminate a small fraction of persisting contact-inhibited cells. Cultures were again replated at point C (8 weeks).

Oncogene-induced senescence (OIS) was elicited by infecting proliferating LF1 cells with pLenti CMV RasV12 Neo (Addgene plasmid #22259). Generation of lentiviral particles and the infection procedure are described below. At the end of the infection, cells were reseeded at 15-20% confluency and selected with G418 (250 µg/ml) maintained continuously until the end of the experiment Medium was changed every 3 days until the cultures were harvested at the indicated time points. Stress-induced premature senescence (SIPS) was elicited by X-ray irradiation with 20 Gy given at a rate of 87 cGy/min in one fraction using a cesium-137 gamma source (Nordion Gammacell 40). Cells were 15-20% confluent at the time of irradiation. Medium was changed immediately after irradiation, and at 3-day intervals thereafter. 293T cells (Clontech) were used to package lentivirus vectors and were cultured at 37° C. in DMEM with 10% FBS under normoxic conditions (air supplemented with 5% CO2).
Reverse Transcriptase Inhibitors (RTIs)

All RTIs (lamivudine, 3TC; zidovudine, AZT; abacavir, ABC; emtricitabine, FTC) used in this study were USP grade and obtained from Aurobindo Pharma, Hyderabad, India. For Trizivir (TZV), its constituents (ABC, AZT and 3TC) were combined in the appropriate amounts.
Mouse Husbandry C57BL/6J mice of both sexes were obtained from the NIA Aged Rodent Colonies[61] at 5 and 18 months of age. The 5-month old animals were sacrificed after a short (1 week) acclimatization period, a variety of tissues were harvested, snap frozen in LN2 and stored at −80° C. The 18-month old animals were housed until they reached a desired age. Mice were housed in a specific pathogen-free AAALAC-certified barrier facility. Cages, bedding (Sani-chip hardwood bedding) and food (Purina Lab Chow 5010) were sterilized by autoclaving. Food and water (also sterilized) were provided ad libitum. A light-dark cycle of 12 hours was used (7 AM On, 7 PM Off). Temperature was maintained at 70° F., and humidity at 50%. All animals were observed daily and weighed once per week. In a pilot experiment, three cohorts of 10 animals each were treated with 3TC dissolved in drinking water (1.5 mg/ml, 2.0 mg/ml, 2.5 mg/ml) continuously from 18 months until sacrifice at 24 months. The fourth (control) cohort was provided with the same water without drug. No significant differences in behavior, weight, or survival were observed between the 4 cohorts during the entire experiment. Once during the experiment (at 20 months of age) the animals were subjected to a single tail bleed of approximately 70 µL. The collected plasma was shipped to the University of North Carolina CFAR Clinical Pharmacology and Analytical Chemistry Core for analysis of 3TC. For the 2 mg/mL cohort the concentration of 3TC in plasma averaged 7.2 µM. This dose of drug was chosen for further experiments to mimic the human HIV therapeutic dose (300 mg per day, 5-8 µM in plasma).[62] For the experiments presented in this communication animals were aged in house until they reached 26 months of age. They were then assigned randomly to two cohorts by a technician that was blinded to the appearance or other characteristics of the animals. One cohort was treated for 2 weeks with 2 mg/mL of 3TC in drinking water, and the other (control) cohort with same water without drug, administered in the same manner. At the end of the treatment period all animals were sacrificed and harvested for tissues as described above. All the animals in both cohorts were all included in all subsequent analyses. The experiment was performed on separate occasions with male and female animals. Non-lethal total body irradiation (6 Gy) was performed as described[63] and tissue specimens were kept on dry ice.

PCR

The ABI ViiA 7 instrument (Applied Biosystems) was used for all experiments. qPCR of DNA was performed using the TaqMan system (Applied Biosystems) as described by Coufal et al. (2009).[64] 100 µg of purified genomic DNA was used with the indicated primers (see Table 1). Reverse transcription qPCR (RT-qPCR) of RNA was performed using the SYBR Green system (Applied Biosystems). Polyadenylated RNA was used in all experiments assessing transcription of L1 elements, and total RNA was used for all other genes. Total RNA was harvested using the Trizol reagent (Invitrogen). Poly(A) RNA was isolated from total RNA using the NEBNext Poly(A) mRNA Magnetic Isolation Module (New England Biolabs). 1 µg of total RNA, or 10 ng of poly(A) RNA, were reverse-transcribed into cDNA in 50 µL reactions using the TaqMan kit (Applied Biosystems). To assess strand-specific transcription, the random primers in the RT reaction were substituted with a strand-specific primer to the target RNA. 1 µL of each RT reaction was used in subsequent qPCR reactions. GAPDH was used as the normalization control in experiments with human cells. The arithmetic mean of Gapdh and two additional controls (Hsp90 and GusB) was used for normalization of RT-qPCR experiments with murine tissues, with the exception of liver that was normalized to Hsp90 and GusB. For measuring L1 transcription, poly(A) RNA samples were exhaustively digested with RNase-free DNase (Qiagen) prior to the synthesis of cDNA6. Effectiveness of the DNase digestion was assessed using controls that omitted the RT enzyme.

Design of PCR Primers

Primer sets 1 to 5 (Table 1, amplicons A to E in FIG. 1B) to human L1 were designed to preferentially amplify elements of the human-specific L1 HS and evolutionarily recent primate-specific L1 PA(2-6) subfamilies, as follows. First, the consensus sequences of L1HS and L1PA2 through L1PA6 elements were obtained from Repbase (Genetic Information Research Institute[65]). Second, a consensus sequence of these six sequences was generated with the Clustal Omega multiple sequence alignment tool.[66,67] Primer design was then done on the overall consensus with Primer3 and BLAST using the NCBI Primer-BLAST tool.[68,69] L1 primer pairs were evaluated for their targets using the In-Silico PCR[70] tool against the latest genome assembly (hg38) with a minimum perfect match on 3' end of each primer equal to 15. Primers to ORF2 (primer set 6, amplicon F in FIG. 1B) were developed by Coufal et al. (2009) to preferentially target L1 HS. Primers to assess transcription of active murine L1 elements (primer set 37, Table 1) were designed on the combined consensus sequence of the L1MdA and L1Tf families obtained from Repbase and validated as described above. L1 primer pairs, spanning the full length these elements (primer sets 48-50), were designed using the same strategy. Primer pairs specific to the three active families of murine L1 elements (primer sets 51-53) were designed exploiting polymorphisms in the 5'UTR region. RT-qPCR analysis of L1 transcription was performed on poly(A) purified RNA using the SYBR Green method. For all other (non-L1) genes, whenever possible, primers are separated by at least one intron in the genomic DNA sequence (as indicated in Table 1). Primers to the human IFN alpha family were designed against a consensus sequence of all the human IFN alpha gene sequences (IFNA1, IFNA2, IFNA4, IFNA5, IFNA6, IFNA7, IFNA8, IFNA10, IFNA13, IFNA14, IFNA16, IFNA17, IFNA21) generated with the Clustal Omega multiple sequence alignment tool. All primers against murine targets were designed as described above and are listed in Table 1. Sequences of primers corresponding to a consensus of all the murine IFN alpha family genes, as well as to the IFNB1 gene, were obtained from the publication by Gautier et al.[71] For quantifying relative L1 genomic copy number (human cells), the TaqMan multiplex method developed by Coufal et al. (2009)[72] was used. These primers are listed as set #6 and set #7 (with their corresponding VIC and 6FAM probes) in Table 1.

Chromatin Immunoprecipitation

All ChIP experiments were performed using the Chromatrap spin column ChIP kit (Porvair). Briefly, 2×10$^6$ cells were crosslinked in their culture dishes with 1% formaldehyde (10 min, room temperature), quenched with glycine, washed twice with ice-cold PBS (containing protease inhibitors), and finally scraped into a microfuge tube. Cell pellets were resuspended in 0.4 mL of hypotonic buffer and incubated for 10 min on ice. Nuclei were spun down, resuspended in 0.3 mL lysis buffer, and sonicated using a Bioruptor UCD-200 instrument (Diagenode) set to pulse on high (30 sec followed by 30 sec. rest) for a total time of 10 min The extracts were centrifuged in a microfuge (top speed, 5 min, 4° C.) to remove debris, the supernatants were transferred to new tubes, and stored at −80° C. An amount of extract containing 2 µg of DNA was combined with 4 µg of antibody and loaded on a Chromatrap solid phase Protein A matrix. Immunocomplexes were allowed to form overnight at 4° C. with mild agitation, following which the samples were washed and eluted according to the manufacturer's protocol. Rabbit IgG and 1% input were used as controls. 1 µL of immunoprecipitated DNA was used in each qPCR reaction.

BrdU Pull-Down

To obtain quiescent cells, proliferating cells were grown to 50% confluence, serum supplementation of the medium was changed to 0.1% FBS, and incubation was continued until harvest. Quiescent and senescent cells were continuously labeled for two weeks with BrdU (BrdU Labeling Reagent, Thermo Fisher) according to the manufacturer's protocol for labeling of culture cells. Cell were harvested and counted: $5 \times 10^5$ cells were processed per condition. Genomic DNA was purified via Phenol:Chloroform extraction, RNase A treated and subsequently sheared using a Bioruptor UCD-200 instrument (pulse on Low, 30 sec on and 30 sec off, 10 min total). DNA tubes were incubated in a heat block (100° C.) for exactly one minute and then flash frozen in liquid nitrogen. Tubes were let thaw at room temperature and 1 µg of purified anti-BrdU antibody (BD Pharmingen, Cat. #555627) was added per tube together with magnetic protein A/G beads and ChIP Dilution Buffer. Immuno-slurries were incubated overnight at 4° C. with constant rotation. Immuno-captured BrdU labeled DNA was purified according to the *Magna* ChIP™ A/G Chromatin Immunoprecipitation Kit (Millipore Sigma). Unbound DNA was kept as input. 1 µL of immunoprecipitated DNA was used in each qPCR reaction. Alternatively, to enrich for single-stranded BrdU-labeled DNA the heat-mediated denaturation was omitted and samples were processed for BrdU pull-down as above. The DNA second strand was then generated by adding a mixture of random primers (Thermo Fisher), second strand synthesis reaction buffer, dNTPs and DNA Pol I (New England Biolabs). The reaction was incubated for 4 hrs at 16° C. and subsequently purified by phenol-chloroform extraction. Following the second strand synthesis, the dsDNA was end-repaired with the End-It DNA End-Repair Kit (Epicenter, Cat. #ER0720). Blunt-ended fragments were cloned using the Zero Blunt TOPO PCR Cloning Kit (Thermo Fisher), and then used to transform One Shot TOP10 chemically competent *E. coli* (Thermo Fisher, Cat. #C404010). Individual colonies were picked and subjected to Sanger sequencing using a T7 promoter primer at Beckman Coulter Genomics.

RNA-Seq

Figure 6F:
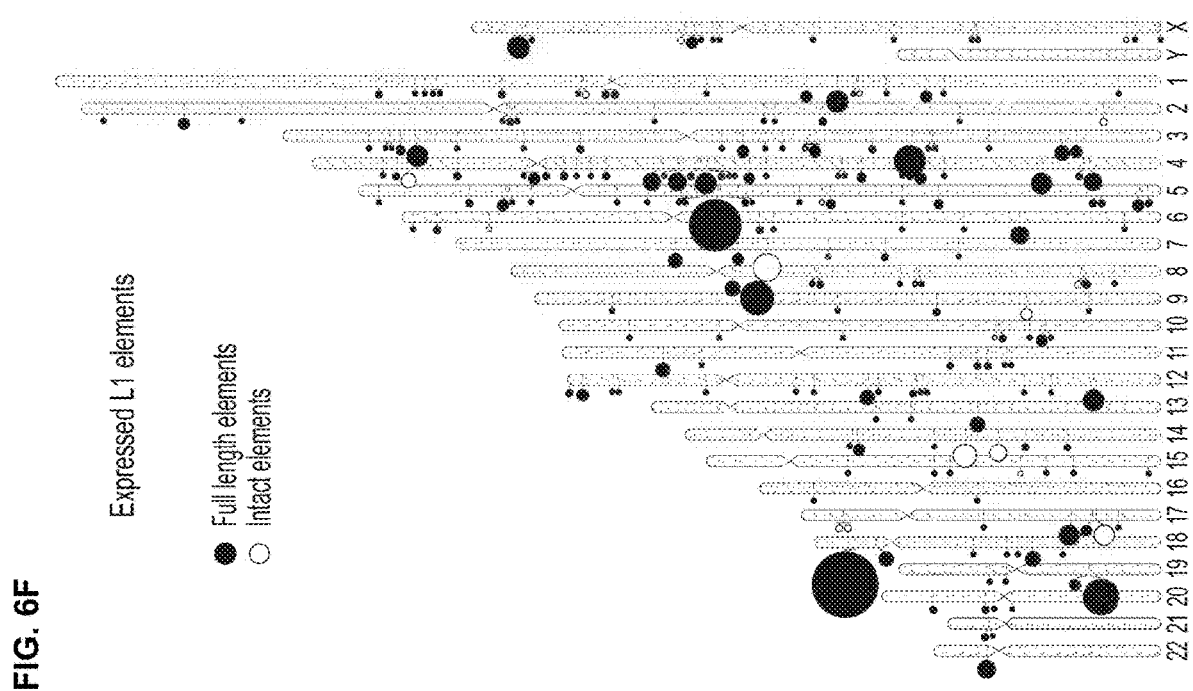
Figure 7A:
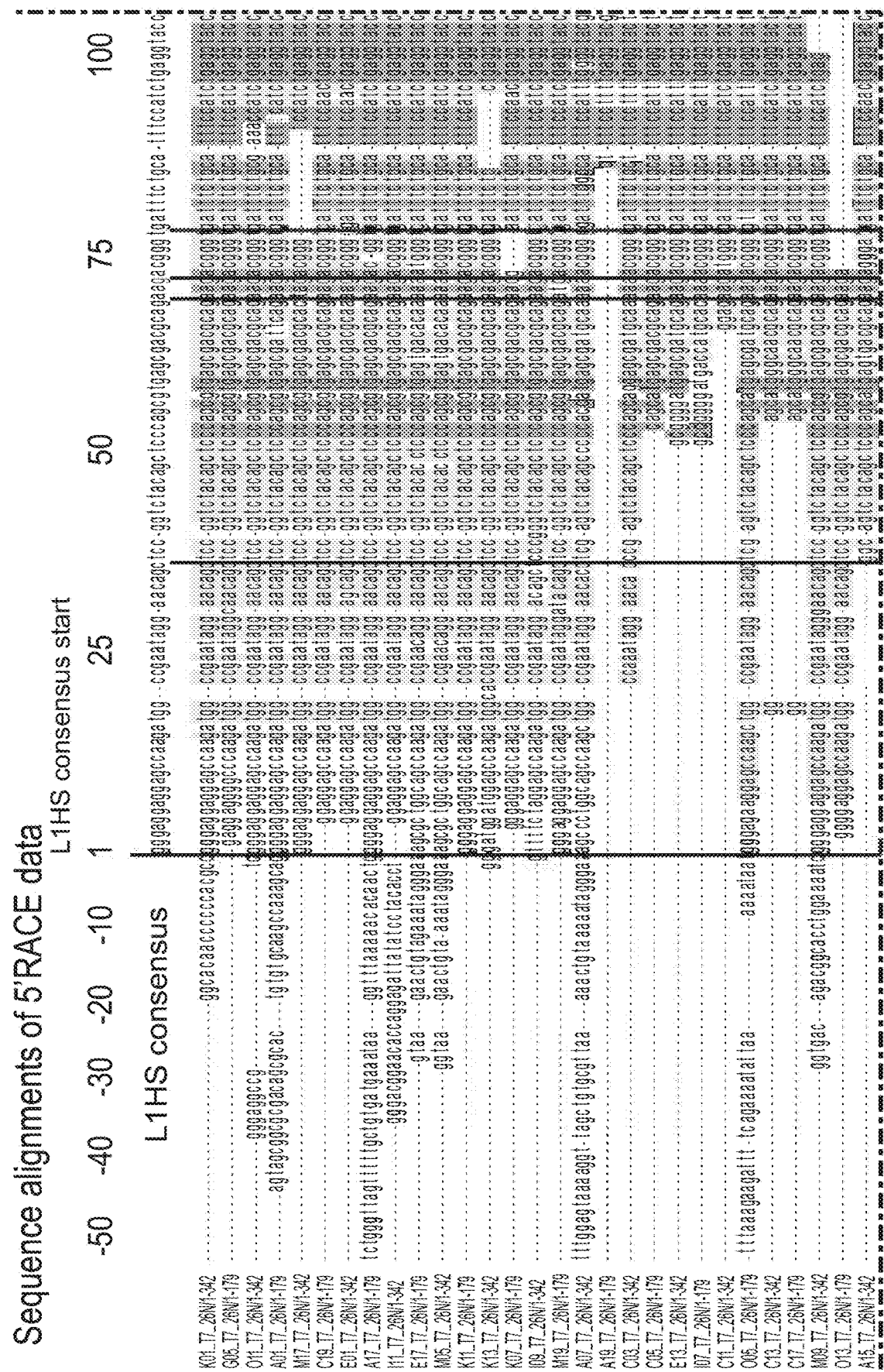
Figure 7A:
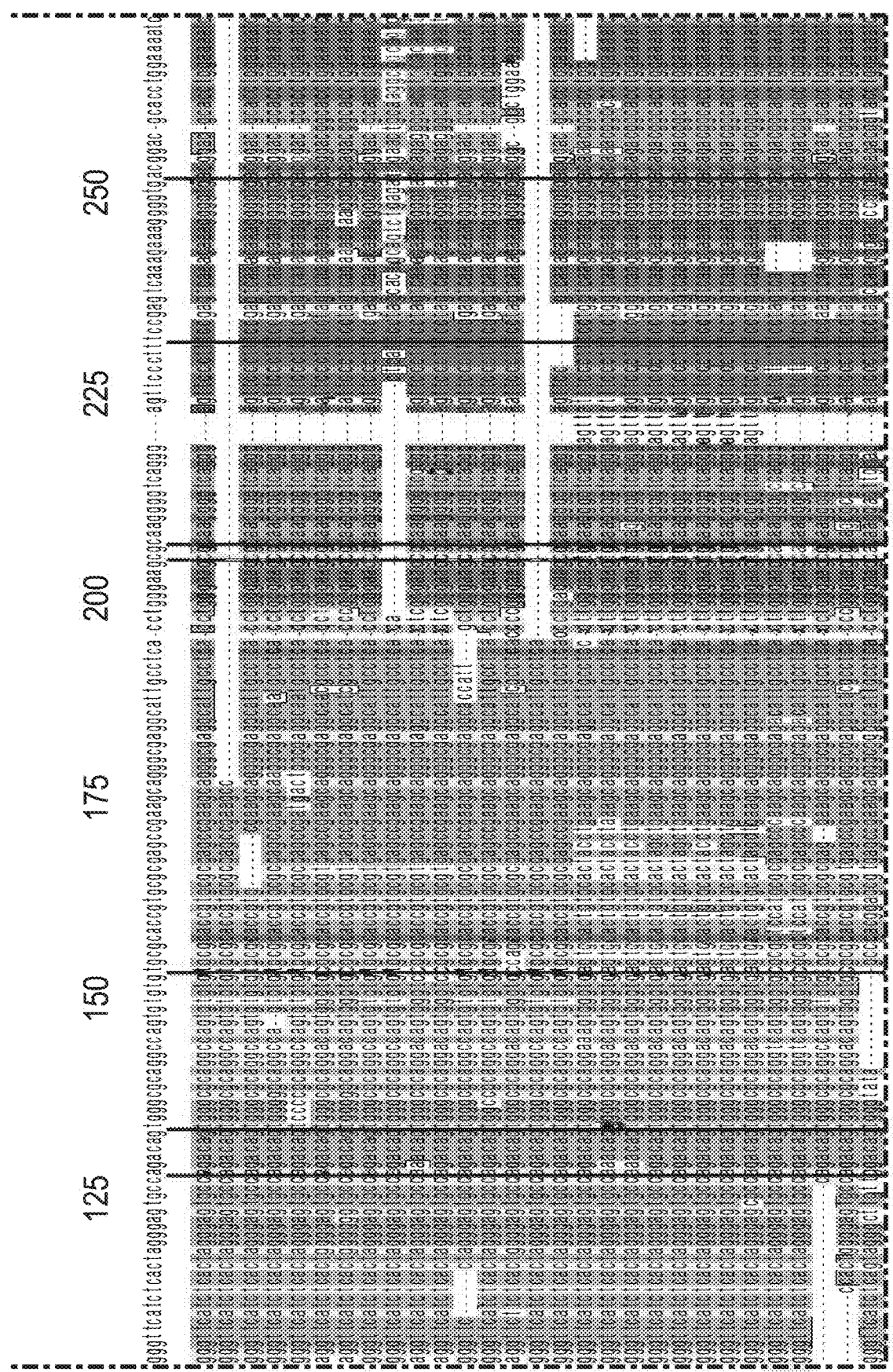
Figure 7A:
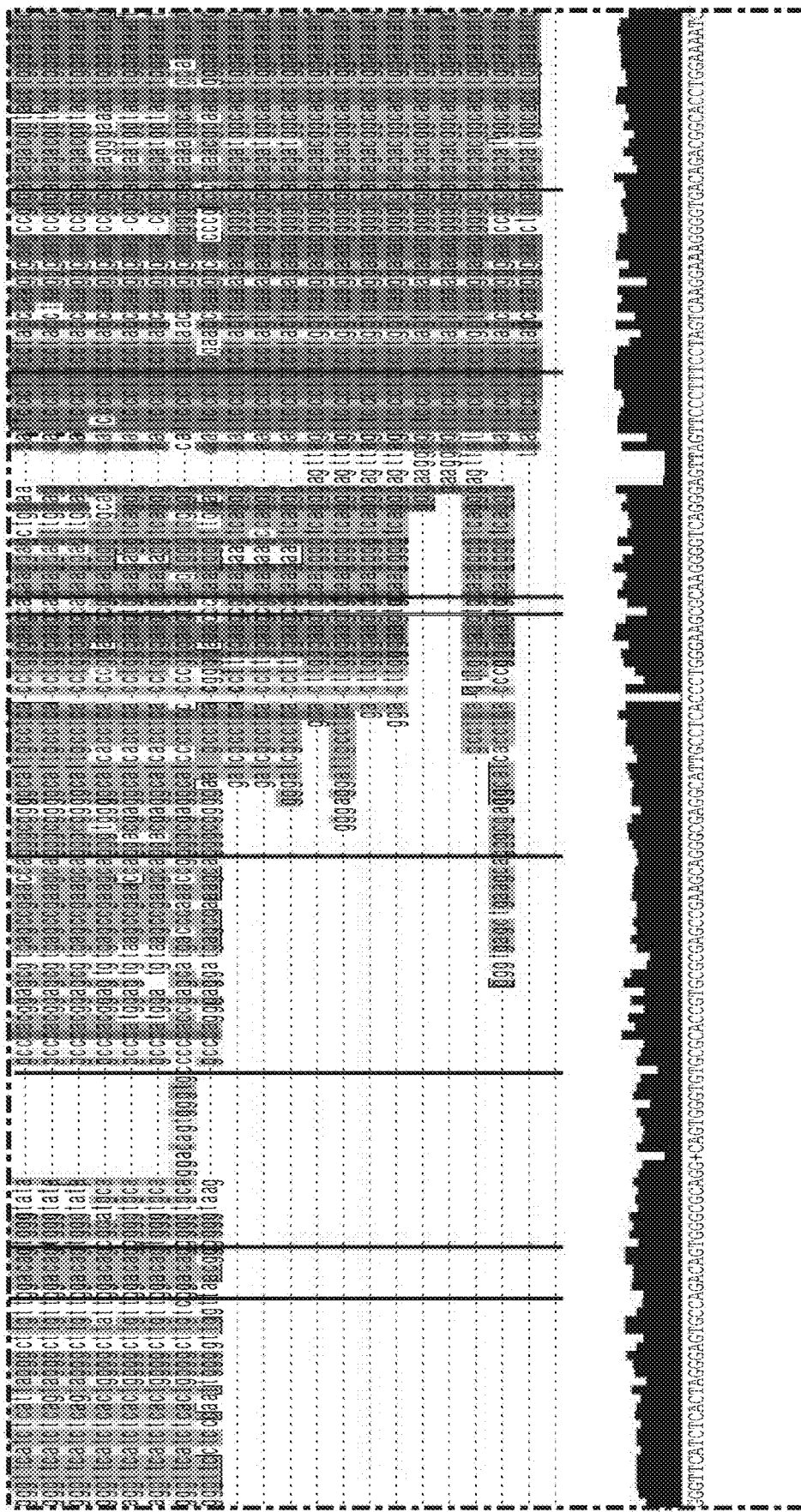
Figure 7A:

Total RNA from early passage, early and deep senescent cells (FIG. 6A) was extracted as described above. The total RNA was processed with the Illumina TruSeq Stranded Total RNA Ribo-Zero kit and subjected to Illumina HiSeq2500 2×125 bp paired end sequencing using v4 chemistry at Beckman Coulter Genomics Inc. Over 70 million reads were obtained for each sample. The RNA-seq experiment was performed in three biological replicates.

Raw RNA-sequencing reads were aligned to the GrCh38 build of the human genome using HiSat2.[73] Counts mapping to the genome were determined using featureCounts.[74] Counts were then normalized using the trimmed mean of M-values (TMM) method in EdgeR.[75] EdgeR was additionally used to derive differential expression from the normalized data set. Differential expression data were then ranked by log 2 fold change and input into the GenePattern interface for GSEA Preranked, using 1000 permutations, to determine enrichment for KEGG pathways, SASP, and the interferon response.[76,77] The outputs were then been corrected for multiple comparisons by adjusting the nominal p value using Benjamini-Hochberg method.[78] Data were displayed using GENE-E software.[79]

In Silico Analysis of Transcription Factors Binding to L1

Transcription factor profiles were created using ChIP-seq data from the ENCODE project (GEO accession numbers GSE2961 and GSE32465). Transcription factor ChIP-seq and input control reads were aligned to the consensus sequence of L1HS using bowtie1.[80] The $\log_2$ fold change enrichment was calculated per base pair of the L1HS consensus using the transcription factor ChIP-seq read coverage per million mapping reads (RPM) versus input control RPM values and smoothed by LOESS smoothing with a parameter $\alpha=0.1$. The total number of mapping reads used in RPM normalization was determined from a separate bowtie1 alignment to the human genome (hg19).

Construction of FOXA1 Reporters

L1 promoter reporter plasmids L1WT and L1 del (390-526) were obtained from Sergey Dmitriev, Institute of Bioorganic Chemistry, Moscow.[81,82] Both contain luciferase as the reporter cloned in the sense orientation. To determine antisense transcription from the same plasmid, EYFP was inserted in the inverse orientation upstream of the L1 5' UTR as follows. The EYFP sequence was excised from pEYFP-N1 (Clontech, Cat. #6006-1) with AgeI and NotI and blunt ended. Plasmids L1WT and L1del were digested with XbaI, blunted and treated with FastAP (Fermentas). Successful insertion of anti-sense EYFP was verified using PCR primers AAAGTTTCTTATGGCCGGGC (in EYFP) and GCTGAACTTGTGGCCGTTTA (in L1 promoter) and Sanger sequencing. Plasmid pcDNA3.1/LacZ was used as the co-transfection control. Luciferase and β-galactosidase assays were performed as described.[83] EYFP-N1 was used as a positive control for detecting the EYFP signal. Co-transfections were performed on early passage LF1 cells using Lipofectamine with Plus Reagent (Invitrogen) according to the manufacturer's instructions.

Lentiviral Vectors

Constructs were obtained from public depositories as indicated below. Virions were produced and target cells were infected as described.[84] shRNA sequences were obtained from The RNAi Consortium (TRC),[85] cloned into third generation pLKO.1 vectors and tested for efficacy. Four selectable markers were used to allow multiple drug selections: pLKO.1 puro (2 µg/ml) and pLKO.1 hygro (200 µg/ml) (Addgene plasmid #8453, 24150), pLKO.1 blast (5 µg/ml) (Addgene plasmid #26655), pLKO.1 neo (250 µg/ml) (Addgene plasmid 13425). pLKO-RB1-shRNA63 and pLKO-RB1-shRNA19 (Addgene plasmids #25641 and 25640).[86] For FOXA1 shRNAs TRCN0000014881 (a) and TRCN0000014882 (b) were used. For TREX1 shRNAs TRCN0000007902 (a) and TRCN0000011206 (b) were used. For knockdown of L1, nine shRNAs were designed and tested, of which two (shL1_11 to ORF1, AAGACACATGCACACGTATGT, and shL1_44 to ORF2 AAGACACATGCACACGTATGT) showed significant knockdown (FIG. 10G) and were chosen for further work. The remaining seven shRNAs produced no or minimal knockdown. For cGAS shRNAs TRCN0000128706 (a) and TRCN0000128310 (b) were used. For STING shRNAs TRCN0000161345 (a) and TRCN0000135555 (b) were used.

All ectopic expression experiments used constructs generated by the ORFeome Collaboration[87] in the lentivirus vector pLX304 (blasticidin resistant, Addgene plasmid 25890) and were obtained from the DNASU plasmid repository.[88] RB1 (ccsbBroad304_06846, HsCD00434323), TREX1 (ccsbBroad304_02667, HsCD00445909), FOXA1 (ccsbBroad304_06385, HsCD00441689).

All the interventions in senescent cells were initiated by infecting cells at 12 weeks of senescence (point D in FIG.

6A). Following appropriate drug selections, cells were incubated until 16 weeks of senescence (point E in FIG. 6A), when they were harvested for further analysis.

The 3× intervention was performed by infecting early passage LF1 cells sequentially with vectors pLKO.1 puro shRB, pLKO.1 hygro shTREX1 and pLX304 blast FOXA1 (FIG. 10C). After each infection, the arising drug resistant pool of cells was immediately infected with the next vector. After the third infection, the cells were harvested for further analysis 48 hours after the drug selection was complete. The infections were also performed in various combinations and in each case resulted in the activation of L1 expression, entry into senescence, and induction of an IFN-I response. The sequence above was chosen because it gave the most efficient selection of cells for further analysis. To allow an additional (fourth) intervention in 3× cells (shL1, shSTING, or shCGAS), hairpins targeting RB1 were re-cloned in pLKO.1 neo, thus freeing pLKO.1 puro for the fourth gene of interest. This allowed an efficient drug selection process and sample harvest 48 hrs after the last selection.

Retrotransposition Reporters

The two-vector dual luciferase reporter system reported by Xie et al. (2011)[89] was adapted for lentiviral delivery. The L1RP-Fluc reporters were recloned from plasmids pWA355 and pWA366 into the lentiviral backbone pLX304. pWA355 contained a functional, active $L1_{RP}$ element, whereas pWA366 contains L1RP(JM111), a mutated element carrying two missense mutations in ORF1 that is unable to retrotranspose. Early passage LF1 cells were infected with a puromycin resistant lentivirus expressing Rluc. Pooled drug resistant cells were then infected with high titer particles of pLX304-WA355 or pLX304-WA366 constructs. Immediately after infection cells were treated for four days with 3TC (at the indicated concentrations). Cells were then harvested and assayed for Rluc and Fluc luciferase activities. The native L1 retrotransposition reporter pLD143[90] was co-transfected with pLKO vectors (shLuc, shL1_11 and shL1_44) into HeLa cells using FuGene HD (Promega). Cell culture, transfection and retrotransposition assays were done as described above. Retrotransposition activity was normalized to the activity of $L1R_p$ co-transfected with shLuc. Three independent experiments were performed for each construct.

Identification of Expressed L1 Elements by Long-Range RT-PCR and 5'RACE

Total RNA was harvested from cells using the Trizol reagent (Invitrogen). The RNA was further purified using the Purelink RNA Mini kit (Invitrogen) with DNase I digestion. From the eluted total RNA, poly(A) RNA was isolated using the NEBNext Poly(A) mRNA Magnetic Isolation Module (New England Biolabs). The forward primer (MDL15UTRPRAF, primer set 1, Table 1) was used with either of two reverse primers (MDL15UTRPRCR, primer set 3, amplicon size 537 bp) or MDL15UTRPRDR, primer set 4, amplicon size 654 bp). A high-fidelity thermostable reverse transcriptase (PyroScript RT-PCR Master Mix Kit, Lucigen) was used with 10 ng of poly(A) mRNA per reaction and amplified for 10 cycles. No template and RNaseA-treated samples were used as negative controls. The generated amplicons were cloned into the TOPO-TA (Invitrogen) vector and the resulting plasmids were used to transform One Shot TOP10 chemically competent E. coli. Individual colonies were picked and subjected to Sanger sequencing using a T7 promoter sequencing primer at Beckman Coulter Genomics. 96 sequencing reactions (1 plate) were performed for each primer pair in four experiments for a total of 768 sequenced clones. Sequencing data were trimmed to remove the RT-PCR primers and BLASTed against the human genome (GRCh38) with a match/mismatch cost of +1, −4 and allowing species-specific repeats for Homo sapiens. Only perfect hits were scored and annotated for genomic coordinates. 658 clones could be mapped to the reference genome, 51 contained at least 1 mismatch and thus likely represent elements that are polymorphic in the cell line, and 58 were cloning artifacts. Whenever a clone presented multiple instances of perfect identity a fractional count was adopted, dividing the counts by the number of elements sharing the same sequence. Each mappable clone was further analyzed using L1Xplorer[91] to recover the classification features of the L1 element and whether it is intact.

Alternatively, poly(A) RNA isolated as above was subjected to Rapid Amplification of cDNA Ends (RACE). Each reaction contained 10 ng of poly(A) RNA and was processed using the 5'RACE System kit (Thermo Fisher, Cat. #18374-041). The two antisense gene-specific primers (GSP) used for 5'RACE were: for GSP1, MDL15UTRPRDR (primer set 4, Table 1), and for the nested GSP2, MDL15UTRPRCR (primer set 3, Table 1). Amplification products were cloned and sequenced as above, using a T7 promoter sequencing primer by Beckman Coulter Genomics. A total of 94 clones were sequenced; 26 contained mostly a polyG stretch generated by the tailing step in the RACE protocol and 18 could not be mapped to the human genome. The remaining 50 mappable clones contained L1 sequences and were aligned to the L1 HS consensus using a setting of >95% identity at positions 1-450.[92] The mappable clones were also assigned to individual L1 families using RepEnrich software.[93] Pairwise alignments to the consensus were performed with LALIGN.[94] Multiple sequence alignments were calculated using MAFFT (Multiple Alignment using Fast Fourier Transform) with the L-INS-i algorithm (accurate for alignments of <200 sequences).[95] Alignment visualization, %-identity coloring and consensus were generated by Jalview.[96]

Generation and Analysis of CRISPR-Cas9 Knockouts

Three distinct gRNA sequences for each chain of the IFNAR receptor (IFNAR1 and IFNAR2), listed in the GeCKO v2.0 resource (Feng Zhang Lab, MIT[97])[98], were tested and the following ones were chosen: IFNAR1 (HGLibA_29983) AACAGGAGCGATGAGTCTGTA; IFNAR2 (HGLibA_29985) GTGTATATCAGCCTCGTGTT. Cas9 and gRNAs were delivered using a single lentivirus vector (LentiCRISPR_v2, Feng Zhang Lab, MIT; Addgene plasmid #52961), carrying a puromycin resistance gene. The efficacy of the CRISPR-Cas9 mutagenesis, on the basis of which the above two gRNAs were chosen, was evaluated by treating the infected and drug-selected cells with interferon (universal type I interferon, PBL Assay Science, Cat. #11200-1) and monitoring nuclear translocation of phospho-STAT2 and IRF9 by immunofluorescence. The absence of translocation signifies lack of IFN-I responsiveness and hence loss of IFNAR function. Experimental procedures followed the protocols provided by the Zhang lab.[99,100] In the experiment shown in FIG. 3H (RS) and FIG. 10K, both IFNAR1 and IFNAR2 gRNAs were used to treat the same cells to further increase the efficacy of ablating the INF-I response. For early passage and senescent cells, co-infections of IFNAR1 and IFNAR2 vectors were performed followed by selection with puromycin. For senescent cells, high titer lentivirus particles were applied to senescent cells at 12 weeks in senescence (point D, FIG. 6A) and cells were assayed 4 weeks later (point E, FIG. 6A). For the experiment shown in FIG. 3H (SIPS), edited early passage cells were single-cell cloned. 24 single cells were isolated using the CellRaft technology (Cell Microsystems) and expanded. Genomic screening of the CRISPR cut site was performed by the CRISPR Sequencing Service (CCIB DNA Core, Massachusetts General Hospital).[101] The successful knock out of IFNAR1 and IFNAR2 was verified in four out of the 24 expanded clonal cell lines.

Immunoblotting

Cells were harvested in Laemmli sample buffer (60 mM Tris pH 6.8, 2% SDS, 10% glycerol, 100 mM DTT) and boiled for 5 min at 100° C. Whole cell extracts (60 μg protein) were separated by SDS-PAGE and transferred onto Immobilon-FL membranes (Millipore). Nonspecific binding was blocked by incubation in 4% bovine serum albumin (BSA; Thermo Fisher) and 0.1% Tween-20 in PBS for 1 hr at room temperature. Primary antibodies were diluted in the blocking solution and incubated overnight at 4° C. A list of all the primary antibodies is provided in Table 2. Secondary antibodies were diluted in blocking solution and incubated for 1 hour at room temperature. Signals were detected using the LI-COR Odyssey infrared imaging system (LI-COR Biosciences). For the quantification of signals all samples to be compared were run on the same gel. Loading standards were visualized on the same blot as the test samples using the LI-COR 2-color system. Bands were imaged and quantified using LI-COR software. All bands to be compared were quantified on the same image and were within the linear range of detection of the instrument.

Immunofluorescence Microscopy Performed on Cells in Culture

Cells were grown on glass cover slips and the samples were processed as previously described.[102] Primary antibodies are listed in Table 2. Staining of ssDNA was performed as described by Thomas et al.[103] Briefly, cells seeded on coverslips were fixed on ice with 4% paraformaldehyde (PFA) for 20 min and then incubated in 100% methanol at −20° C. overnight. The cells were then treated with 200 mg/mL RNase A at 37° C. for 4 hrs. Cells were blocked with 3% BSA and incubated overnight at 4° C. with primary antibodies diluted in 3% BSA. Images were acquired using a Zeiss LSM 710 confocal laser scanning microscope or a Nikon Ti-S inverted fluorescence microscope. All microscope settings were set to collect images below saturation and were kept constant for all images taken in one experiment, as previously described.[104] Image analysis was performed as described below for tissues.

PCR Arrays

Total RNA was harvested from cells as indicated above (Quantitative PCR) and analyzed using the Qiagen RT² Profiler™ Human Type I Interferon Response PCR Array (Cat. #PAHS-016ZE-4). Reverse transcription reactions were performed with the Qiagen RT² First Strand Kit (Cat. #330404) using 1 μg of total RNA as starting material. 102 μL of the completed reaction was combined with 650 μL of Qiagen RT² SYBR Green ROX qPCR Mastermix (Cat. #330521) and 548 μL of RNase-free molecular grade water and run in the 384-well block on a ViiA 7 Applied Biosystems instrument. All procedures followed the manufacturer's protocols. All conditions were run in triplicate. The results were analyzed using the Qiagen GeneGlobe Data Analysis Center.[105] Briefly, $C_t$ values were normalized to a panel of housekeeping genes (HKG). $\Delta C_t$ values ware calculated between a gene of interest (GOI) and the mean HKG value. Fold changes were then calculated using $2^{-\Delta\Delta C_T}$ formula. The lower limit of detection was set at $C_t$ of 35. For any GOI to be considered significant, the following filters were set: (i) >2-fold change in expression; and (ii) p-value >0.05. In addition, genes with an average $C_t$>32 in both control and test samples were also eliminated.

Enzyme Linked Immunosorbent Assay (ELISA)

Interferon β levels were quantified with the VeriKine-HS Human IFN Beta Serum ELISA Kit (PBL Assay Science, Cat. #41415). Cell culture media were conditioned for 48 hrs before harvest. To remove particles and debris, 1 mL aliquots were spun 5 min 5,000×g. All incubations were performed in a closed chamber at room temperature (22-25° C.) keeping the plate away from temperature fluctuations. 50 μL of sample buffer followed by 50 μL of diluted antibody solution were added to each well. Finally, 50 μL of test samples, standards or blanks were added per well. Plates were sealed and shaken at 450 rpm for 2 hrs. At the end of the incubation period the contents of the plate were removed, and the wells were washed three times with 300 μL of diluted wash solution. 100 μL of HRP solution was added to each well and incubated for 30 min under constant shaking. The wells were emptied and washed four times with wash solution. 100 μL of the TMB substrate solution was added to each well. Plates were incubated in the dark for 30 min Finally, 100 μL of stop solution was added to each well and within 5 min absorbance at 450 nm was recorded. The values recorded for the blank controls were subtracted from the standards as well as sample values to eliminate background. Optical densities (OD) units were plotted using a 4-parameter fit for the standard curve and were used to calculate the interferon titers in the samples.

Human Tissue Specimens

Human skin specimens were collected as part of the Leiden Longevity Study[106,107] and were provided by the Leiden University Medical Centre, Netherlands. Informed consent was obtained, and all protocols were approved by the ethical committee of the Leiden University Medical Centre. The samples were collected as 4 mm thickness full depth punch biopsies, embedded in optimal cutting compound (OCT), flash frozen, and stored at −80° C. The investigators were blinded to everything except the age and sex of the subjects. The OCT-embedded specimens were cryosectioned at 8 m thickness using a Leica CM3050S cryomicrotome. The slides were fixed with 4% PFA and 0.5% Triton X-100 in PBS (prewarmed to 37° C.) for 20 min at room temperature. No further permeabilization was performed. Antibody incubation was preceded by a blocking step with 4% bovine serum albumin (BSA; fraction V, Thermo Fisher), 2% donkey serum, 2% rabbit serum and 0.1% Triton X-100 in PBS for 1 hour at room temperature. Primary antibodies were diluted in the above blocking solution (1:200) and incubated overnight at 4° C. with rocking in a humidified chamber. The secondary antibodies (AlexaFluor 546 and AlexaFluor 647, Life Technologies) were also diluted in blocking solution and incubated for 2 hrs at room temperature. Three 15 min washing steps in PBS, containing 0.2% Triton X-100, followed each antibody incubation. Nuclei were counterstained with 2 μg/mL DAPI in PBS, containing 0.2% Triton X-100, for 15 min. Stained slides were mounted with ProLong Antifade Mountant without DAPI (Life Technologies) and imaged on a Zeiss LSM 710 Confocal Laser Scanning Microscope. A z-series encompassing the full thickness of the tissue was collected for each field. All microscope settings and exposure times were set to collect images below saturation and were kept constant for all images taken in one experiment. Image analysis was performed using either CellProfiler software,[108] or ImageJ open source software from the NIH.[109] Nuclei were defined using the DAPI channel. Cell outlines were defined by radially expanding the nuclear mask using the function Propagate until an intensity threshold in the AlexaFluor 546 and AlexaFluor 647 channels was reached. The fluorescence intensity within these regions was then recorded in both channels. For each sample a total of 200 nuclei were recorded in multiple fields. Mouse tissue sections were processed and analyzed in the same way as described above.

Mouse Tissue Specimens

Total RNA was extracted from 50 mg of visceral adipose, small intestine, skeletal muscle, brown adipose or liver tissue by mincing followed by homogenization in Trizol (Invitrogen) using a Power Gen 125 homogenizer (Fischer Scientific). After phase separation, the RNA in the aqueous layer was purified using the Purelink RNA Mini kit (Invitrogen) with DNase I digestion. To assess gene expression by RT-qPCR 1 µg of total RNA was reverse transcribed as described above. In each individual experiment, all samples were processed in parallel and no blinding was introduced.

Imaging of whole-mount white adipose tissue followed the method described by Martinez-Santibanez et al. (2014).[110] Briefly, white adipose tissue (visceral depot) were subdivided into 0.5-1 $cm^3$ sized pieces and incubated in 10 mL of fresh fixing buffer (1% PFA in PBS pH 7.4) for 30 min at room temperature with gentle rocking. After three washing steps with PBS, the tissue blocks were cut in six equal pieces. All subsequent incubations were performed in 2 mL cylindrical microcentrifuge tubes. Primary antibody incubation was preceded by a blocking step with 5% BSA, 0.1% Saponin in PBS for 30 min at room temperature. Primary antibodies were diluted in the above blocking solution (1:200) and incubated overnight at 4° C. with gentle rocking. The secondary antibodies (AlexaFluor 546, AlexaFluor 594 and AlexaFluor 647, Life Technologies) were also diluted in blocking solution and incubated for 2 hrs at room temperature. Three 10 min washing steps in PBS followed each antibody incubation. Antibody-independent staining of nuclei and lipids was performed after immuno-staining: DAPI and BODIPY (Thermo Fisher) were diluted in PBS with 5% BSA and incubated with tissue specimens for 20 min followed by three washing steps as above. Stained samples were carefully placed on confocal-imaging optimized #1.5 borosilicate glass chamber slides. A small drop of PBS prevented drying. Acquired images were analyzed as described above.

Co-staining of SA-β-Gal activity and ORF1 protein in liver sections was performed by staining for SA-β-Gal first as described.[1] Subsequently, samples underwent heat-induced epitope retrieval by steaming for 20 min in antigen retrieval buffer (10 mM Tris, 1 mM EDTA, 0.05% Tween 20, pH 9.0). Samples were then processed for immunofluorescence staining as above (Human tissue specimens).

Kidney tissue preserved in OCT was cryosectioned, treated for 10 min with 0.5% (w/v) periodic acid, then stained with periodic acid-Schiff's (PAS) reagent (Fisher Scientific, Cat. #SS32-500) for 10 min. Stained tissue sections were mounted with Shandon Aqua Mount (Fisher Scientific, Cat. #14-390-5) and then imaged under bright field illumination. Glomerulosclerosis was scored as described.[112] Briefly, 40 glomeruli per animal were assessed in a blinded fashion and assigned scores of 1-4: score of 1, <25% sclerosis; 2, 25-50% sclerosis; 3, 50-75% sclerosis; 4, >75% sclerosis. The feature used to assess sclerosis was the strength and pervasiveness of PAS-positive lesions within the glomeruli. As exemplified in FIG. 4E, a sclerotic glomerulus is more shrunken and stains more intensely with PAS.

Quadriceps muscles were embedded in OCT, sectioned at 12 µm thickness and mounted onto positively charged slides. Sections were stained with H&E (hematoxylin, 3 min followed by 30 eosin, sec). Mounted slides were imaged on a Zeiss Axiovert 200M microscope equipped with a Zeiss MRC5 color camera. To measure muscle fiber diameter, the shortest distance across ~100 muscle fibers per animal was measured using ImageJ software as described.[113] The Kolmogorov-Smirnov test was used to assess the statistical significance of the difference between the resulting distributions.

Statistical Treatments

Excel was used to perform general statistical analyses (means, s.d., t-tests, etc.). R software for statistical computing (64-bit version 3.3.2) was used for 1-way ANOVA and Tukey's multiple comparisons post-hoc test. For consistency of comparisons significance in all figures is denoted as follows: *P<0.05, **P<0.01. Sample sizes were based on previously published experiments and previous experience in which differences were observed. No statistical test was used to pre-determine sample size. No samples were excluded. All attempts at replication were successful. There were no findings that were not replicated or could not be reproduced. The nature and numbers of samples analyzed (defined as n) in each experiment are listed in the figure legends. The number of independent experiments is also listed in figure legends. The investigators were blinded when quantifying immunofluorescence results. Fields or sections of tissues for quantification were randomly selected and the scored, using methods as indicated for individual experiments. The investigators were also blinded when scoring glomerulosclerosis and muscle fiber diameter. For RNA-seq and PCR array experiments the statistical treatments are described under those sections (above).

Example 1 Activation of L1 and Interferon in Cellular Senescence

RTE activity can promote aberrant transcription, alternative splicing, insertional mutagenesis, DNA damage and genome instability.[114] RTE-derived sequences comprise up to two thirds of the human genome,[115] although the great majority were active millions of years ago and are no longer intact. The only human RTE capable of autonomous retrotransposition is the long-interspersed element-1 (LINE-1, or L1). However, germline activity of L1 is a major source of human structural polymorphisms.[116] Increasing evidence points to RTE activation in some cancers, in the adult brain, and during aging.[117,118,119,120] Cellular defenses include heterochromatinization of the elements, small RNA pathways that target the transcripts, and anti-viral innate immunity mechanisms.[121] Somatic activation of RTEs with age is conserved in yeast and *Drosophila* and reducing RTE activity has beneficial effects.[122]

As shown in FIG. 1A and FIGS. 6A-E, L1 transcription was activated exponentially during replicative senescence (RS) of human fibroblasts, increasing 4-5-fold by 16 weeks after cessation of proliferation, referred to as late senescence. Multiple RT-qPCR primers were designed to detect evolutionarily recent L1 elements (L1HS-L1 PA5; FIG. 1B, FIG. 6H). Levels of L1 polyA+ RNA increased 4-5-fold in late senescent cells (RS) in the sense but not antisense direction throughout the entire element (FIG. 1C). Long-range RT-PCR amplicons (FIG. 1B) were Sanger sequenced to identify 224 elements dispersed throughout the genome; one third (75, 33.5%) were L1 HS, of which 19 (25.3%, 8.5% of total) were intact (i.e., annotated to be free of ORF-inactivating mutations; FIGS. 6F, 6G). 5'RACE were also performed with the same primers and found that the majority of L1 transcripts upregulated in senescent cells initiated within or near the 5'UTR (FIG. 7).

L1 elements can stimulate an IFN-I response.[123] As shown in FIG. 1D and FIG. 6I, interferons IFN-α and IFN-β1 were induced to high levels in late senescent cells. Cellular senescence proceeds through an early DNA damage response phase followed by the SASP response.[124] Documented here by the present data, is a third and even later phase, characterized by the upregulation of L1 and an IFN-I response (FIG. 1E), which has not been previously noted, probably because most studies have focused on earlier times. Whole transcriptome RNA-seq analysis confirmed that the SASP and IFN-I responses are temporally distinct (FIG. 8). The late phase of L1 activation and IFN-I induction was also observed in oncogene-induced senescence (OIS) and stress-induced premature senescence (SIPS) (FIG. 1E).

Example 2 Mechanisms of L1 Activation

Figure 9G:
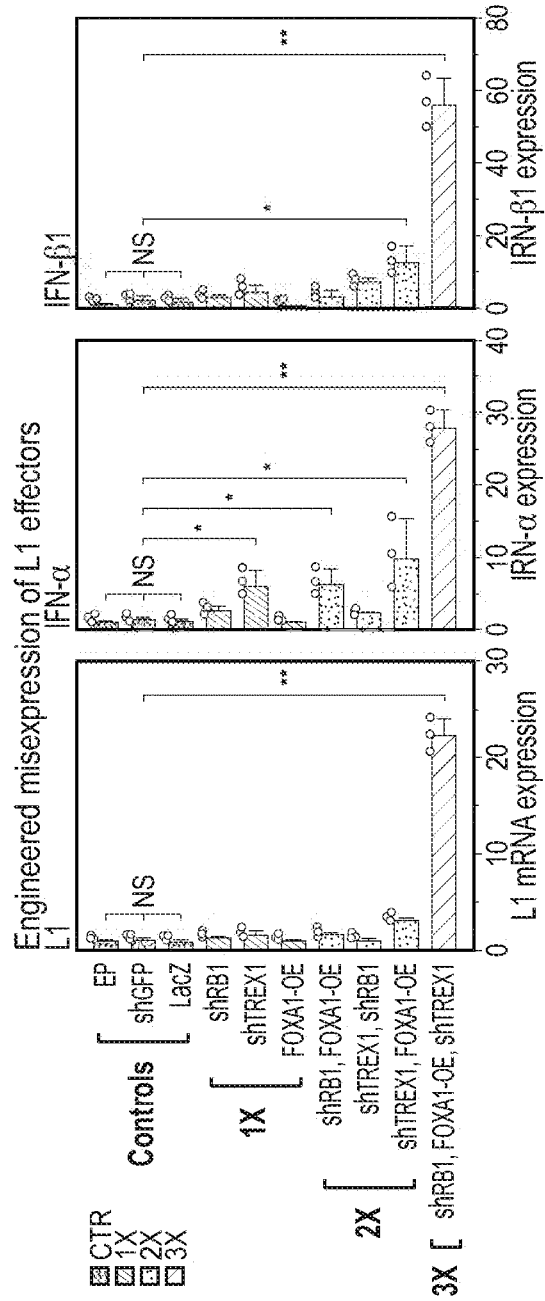
Figure 9H:
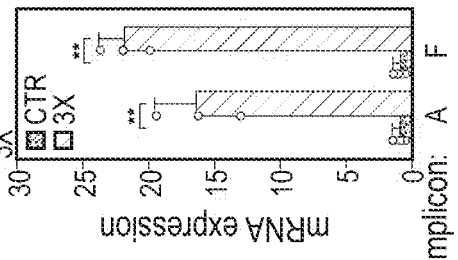
Figure 9I:
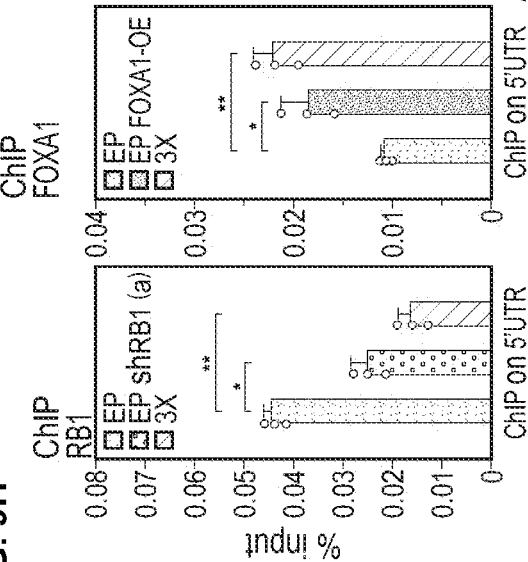

To explore how surveillance fails during senescence, three factors were examined: TREX1, RB1 and FOXA1. TREX1 is a 3' exonuclease that degrades foreign invading DNAs and its loss has been associated with the accumulation of cytoplasmic L1 cDNA.[125] As shown in FIG. 9A, the expression of TREX1 was significantly decreased in senescent cells. RB1 has been shown to bind to repetitive elements, including L1s, and promote their heterochromatinization.[126] As shown in FIG. 2A, the expression of RB1 declined strongly in senescent cells (RS) while that of other RB family members (RBL1, RBL2) did not change (FIG. 9B). RB1 enrichment in the 5'UTR of L1 elements was evident in proliferating cells, decreased in early senescence and became undetectable at later times (FIG. 2A). This coincided with a decrease of H3K9me3 and H3K27me3 marks in these regions (FIG. 9C).

To identify novel factors that interact with the L1 5'UTR, we examined the ENCODE ChIP-seq database and found that the pioneering transcription factor FOXA1 binds to this region in several cell lines (FIG. 9D). FOXA1 is upregulated in senescent cells.[127] As shown in FIG. 2B, FOXA1 bound to the central region of the L1 5'UTR. Using transcriptional reporters, we found that deletion of the FOXA1 binding site decreased both sense and antisense transcription from the L1 5' UTR[128] (FIG. 9e). Hence, the observed misregulation of these three factors in senescent cells could promote the activation of L1 by three additive mechanisms: loss of RB1 by relieving heterochromatin repression, gain of FOXA1 by activating the L1 promoter, and loss of TREX1 by compromising the removal of L1 cDNA.

Therefore, the effects of manipulating RB1, FOXA1 or TREX1 expression in fully senescent cells were tested using lentiviral vectors (FIGS. 10A, 10B). Ectopic expression of RB1 suppressed the elevated expression of L1, IFN-α and IFN-β1 in senescent cells, while its knockdown further enhanced their expression (FIG. 2B). RB1 overexpression also restored its occupancy of the L1 5'UTR (FIG. 2C). Conversely, knockdown of FOXA1 reduced its binding to the L1 5'UTR (FIG. 9F) and decreased the expression of L1, IFN-α and IFN-β1, while overexpression of FOXA1 increased L1, IFN-α and IFN-β1 levels (FIG. 2E). Congruent results were also obtained by manipulating TREX1 (FIG. 2G). Hence, each of these factors had a tangible effect on regulating L1 and the IFN-1 response in senescent cells.

Single or double interventions targeted at these factors elicited only modest changes in L1 and IFN-1 expression in growing early passage cells. While some of these effects were statistically significant, they were dwarfed by a triple intervention (3×) of RB1 and TREX1 knockdowns combined with FOXA1 overexpression, which resulted in a massive induction of L1 and IFN-I expression (FIGS. 2F, 9G-I, and 10C). Hence, in normal healthy cells, all three effectors have to be compromised to effectively unleash L1.

Example 3 Consequences of L1 Activation

To assess IFN-I activation by L1 in more detail, we examined the expression of 84 genes in this pathway using PCR arrays. We observed a widespread response, with the majority of the genes being upregulated (FIGS. 2H, 9J, 9K): 68% (57/84) were significantly upregulated in senescent cells, and 52% (44/84) were upregulated in 3× cells. These data verify and further extend the RNA-seq transcriptomic analysis (FIG. 8).

Some NRTIs developed against HIV have been found to also inhibit L1 RT activity.[129] We also developed shRNAs against L1, two of which reduced transcript levels by 40-50% and 70-90% in deeply senescent and 3× cells, respectively (FIG. 10G). ORF1 protein levels were correspondingly reduced in deeply senescent cells (FIG. 5H). Finally, the shRNAs also reduced the retrotransposition of recombinant L1 reporter constructs (FIG. 10K).

Cells devoid of TREX1 display cytoplasmic L1 DNA, accumulation of which can be inhibited with NRTIs.[130] While lack of BrdU incorporation is a canonical feature of senescent cells (FIG. 6B), longer term labeling revealed DNA that was predominantly cytoplasmic and highly enriched for L1 sequences (FIGS. 11A, 11B). The synthesis of cytoplasmic L1 DNA could be almost completely blocked with the NRTI lamivudine (3TC) or shRNA to L1 (FIGS. 3A, 3C). An antibody to DNA:RNA hybrids detected a cytoplasmic signal in senescent cells that largely colocalized with ORF1 protein and turned into a ssDNA signal following RNase digestion (FIG. 11C). Analysis of BrdU-labeled L1 sequences in senescent cells showed them to be localized throughout the L1 element (FIGS. 11D, 11E). A relative increase of L1 HS sequences in total cellular DNA can also be detected by a qPCR assay6,16.[131,132] 3TC in the range of 7.5-10 μM completely blocked this increase in senescent cells and also quenched the activity of a L1 retrotransposition reporter (FIGS. 10D, 10E).

L1 knockdown with shRNA or treatment of cells with 3TC significantly reduced interferon levels, as well as reducing the IFN-I response more broadly in both late senescent and 3× cells (FIGS. 3B, 12A). 3TC in the range of 7.5-10 μM optimally inhibited the IFN-I response, and was the most effective of 4 NRTIs tested (FIGS. 10F, 10J). The relative efficacies of the NRTIs are consistent with their ability to inhibit human L1 RT15. 3TC also antagonized the IFN-I response in other forms of senescence, OIS and SIPS (FIG. 3E).

Figure 11H:
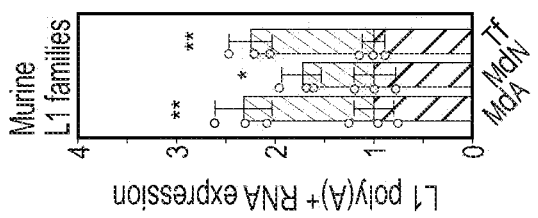
Figure 11G:
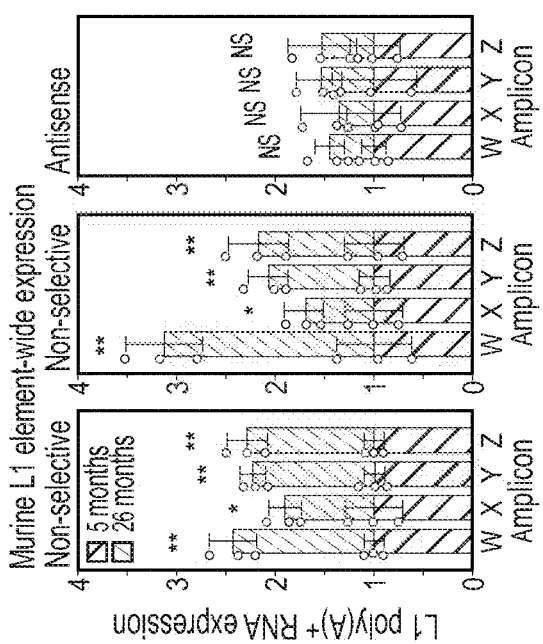
Figure 11F:
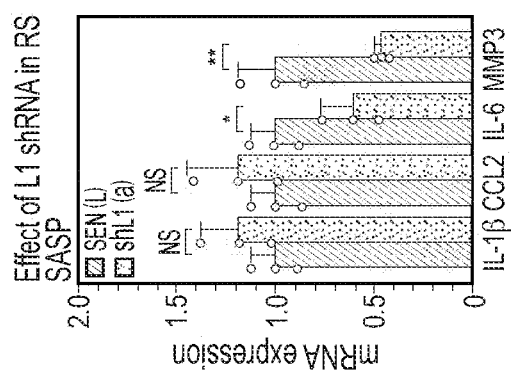
Figure 14A:
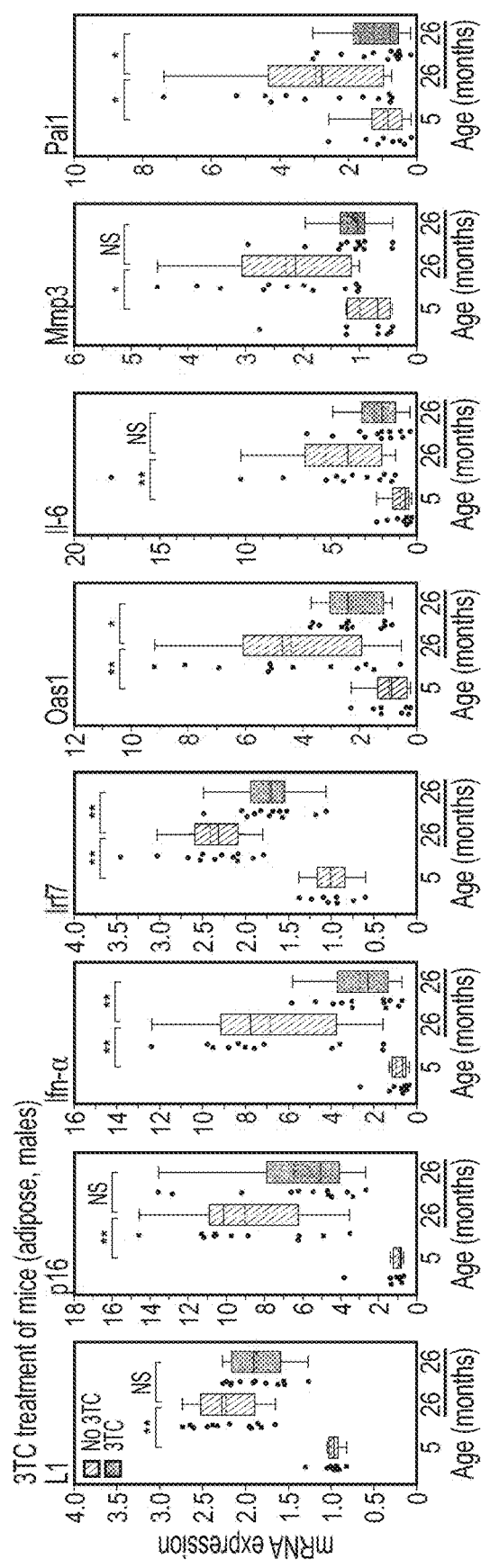
FIGS. 14A-D show the effects of 3TC or K-9 treatment on L1, p16, IFN-I and SASP gene expression in mouse tissues.
Figure 14B:
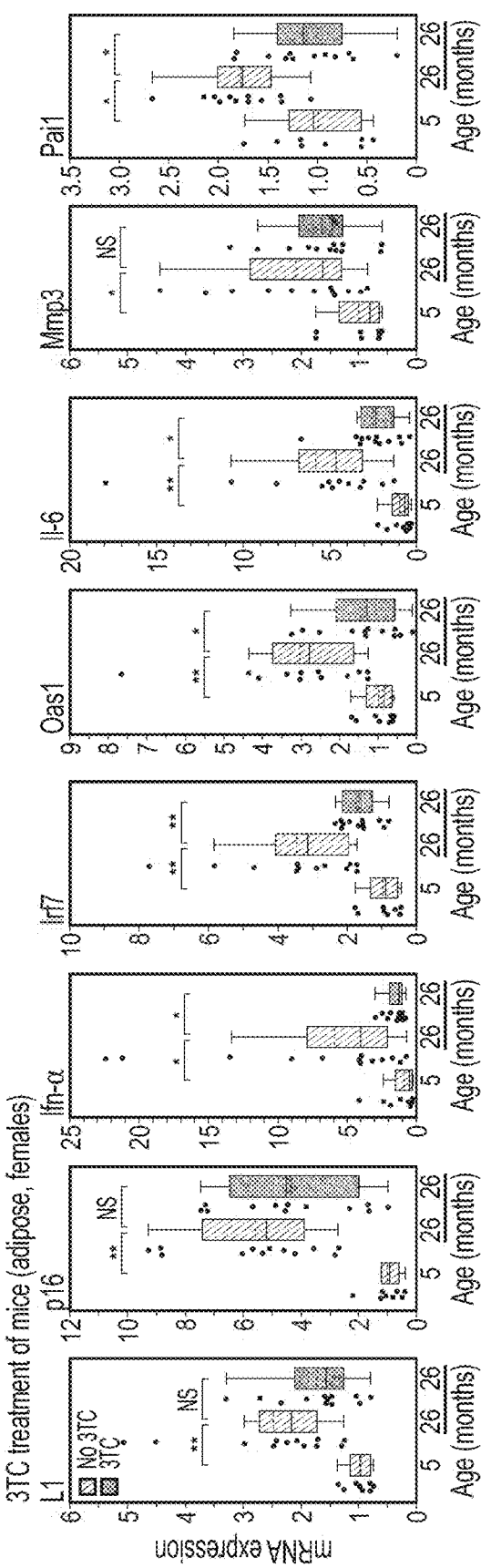
Figure 14C:
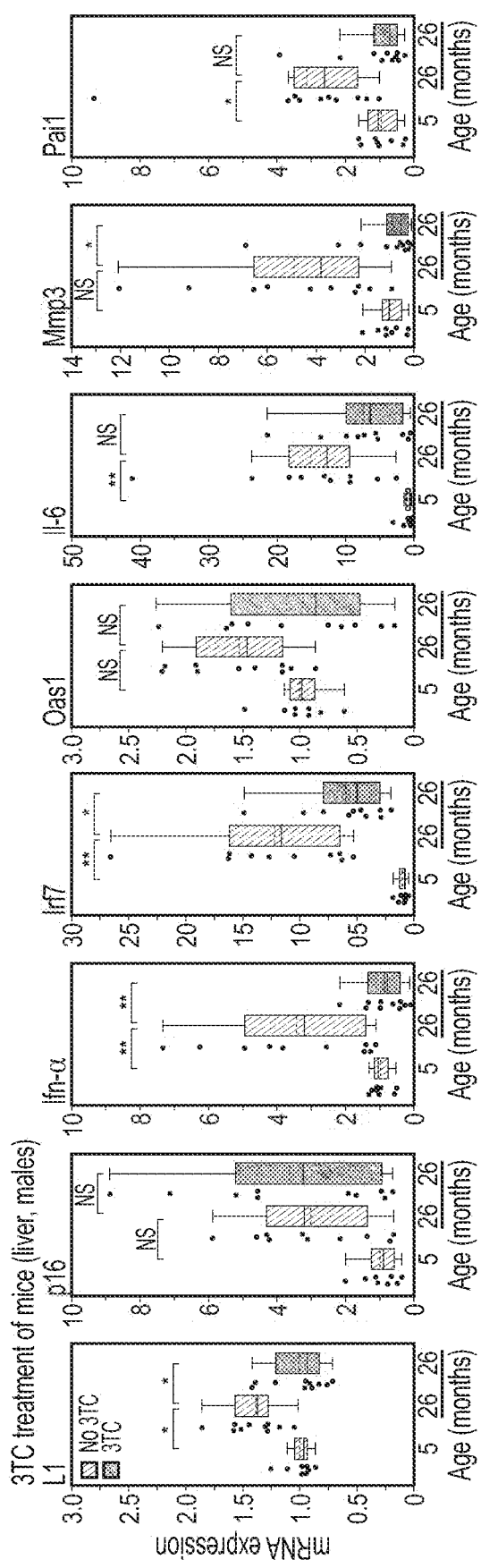
Figure 14D:
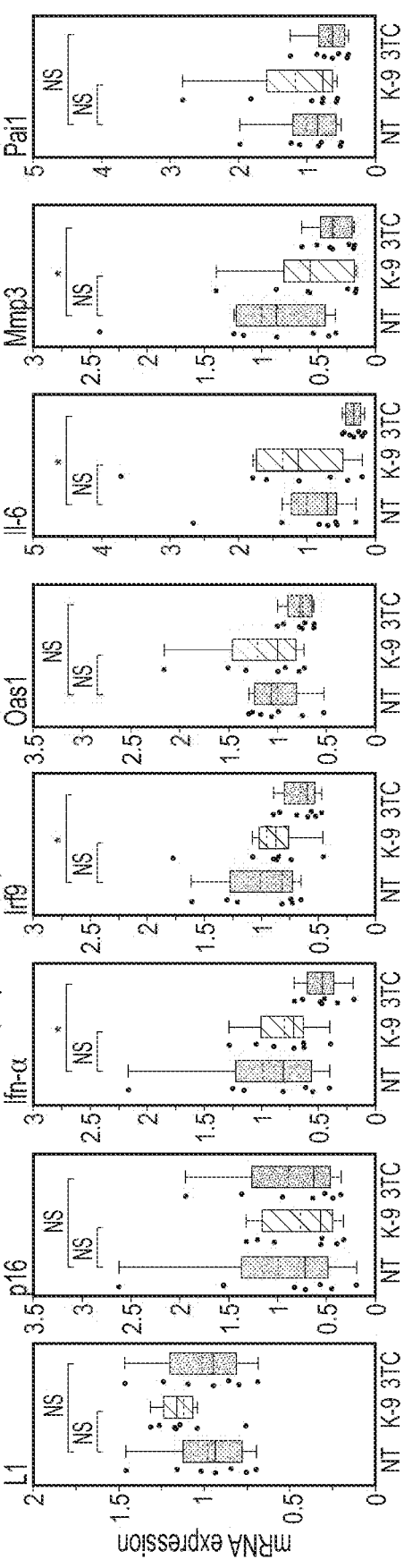
Figure 16A:
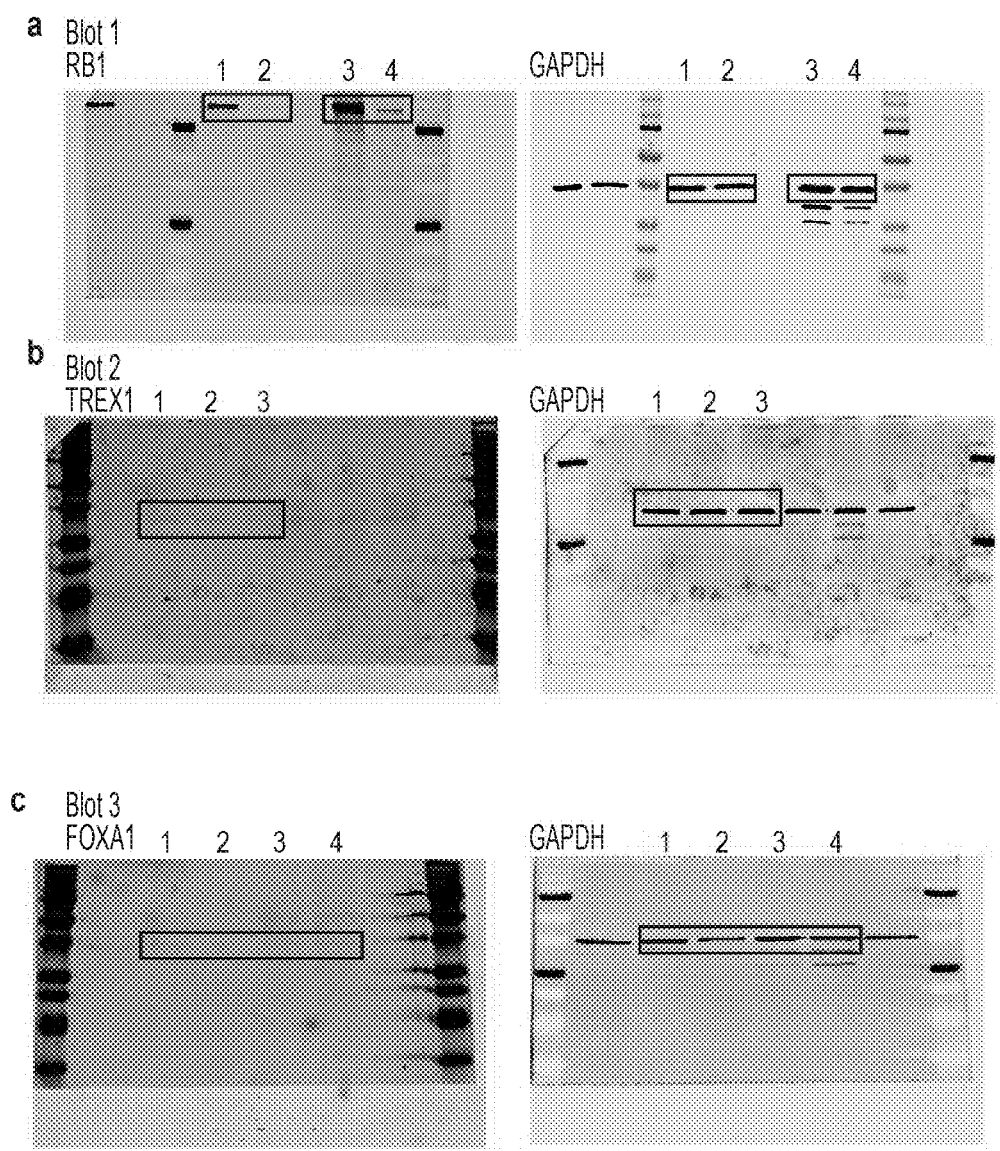
Figure 16B:
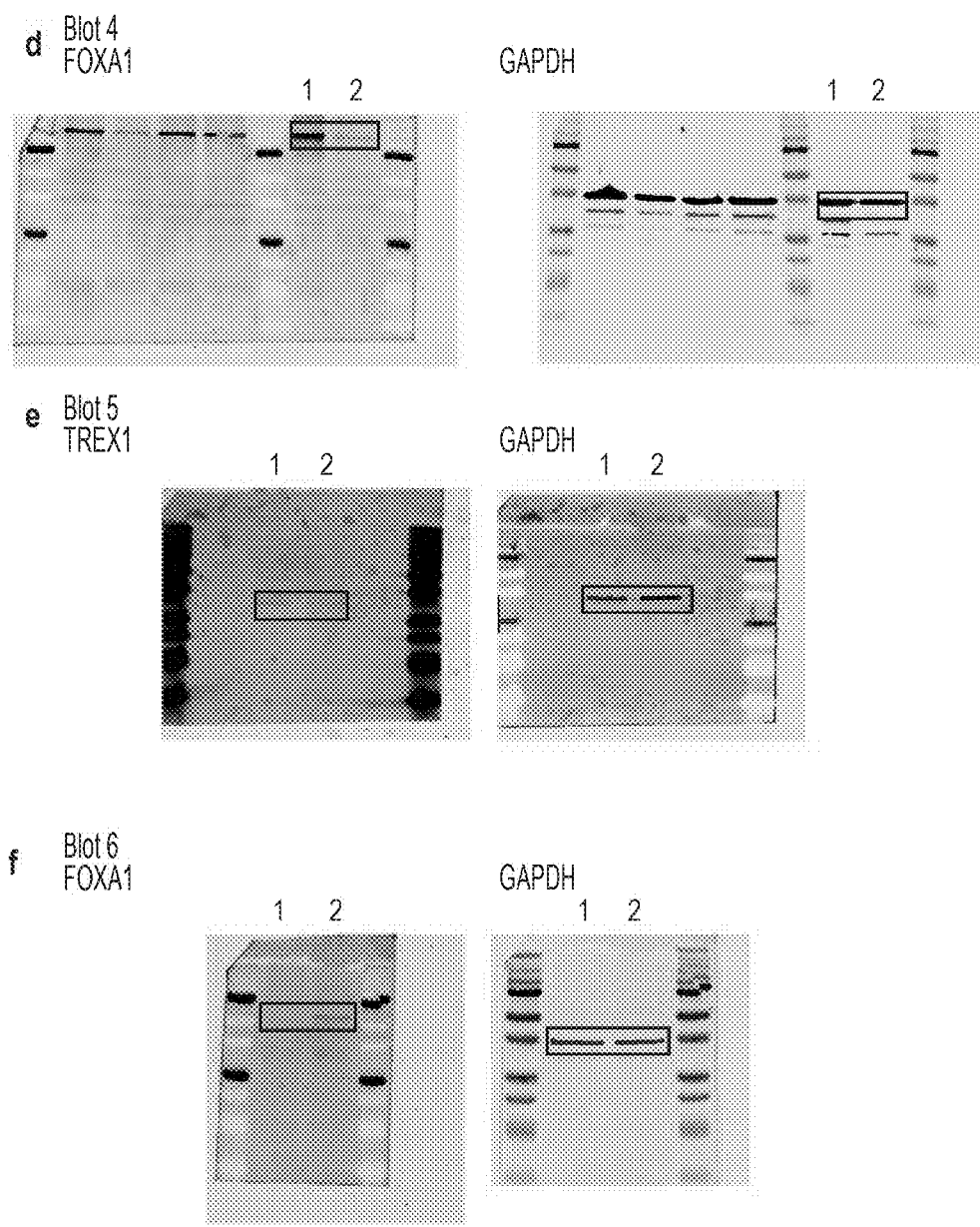
Figure 16C:
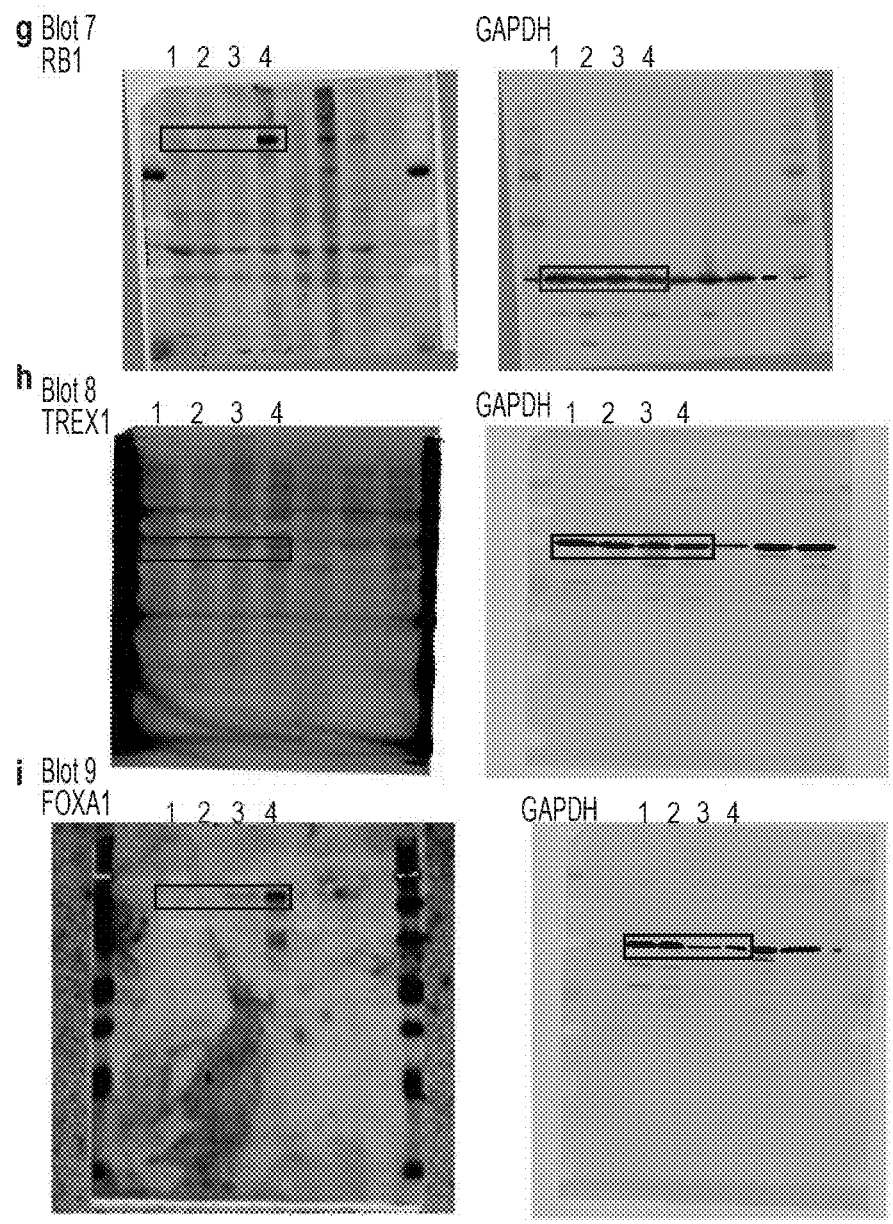
Figure 16D:
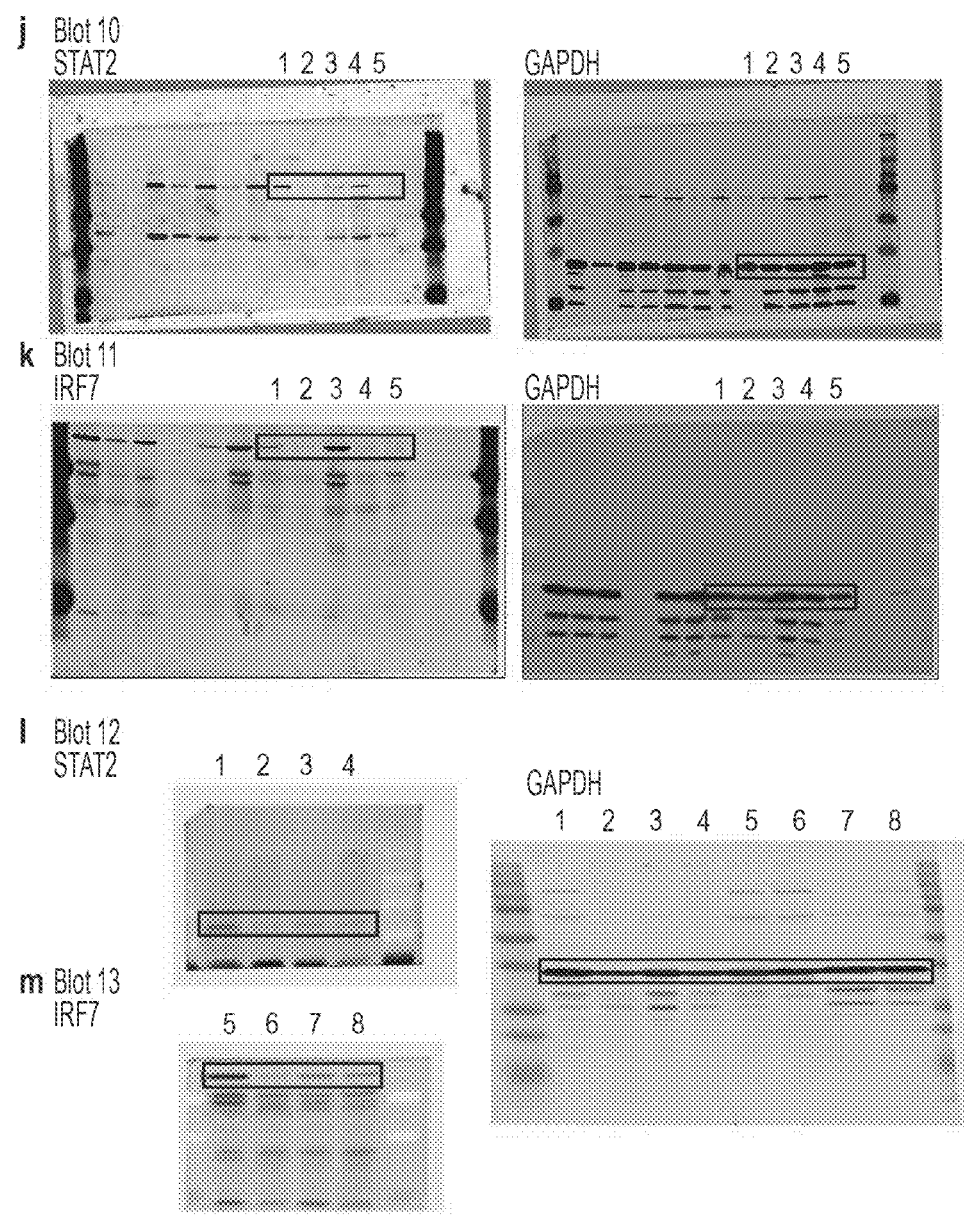

Cells were passaged in the continuous presence of 3TC from the proliferative phase into deep senescence. 3TC did not significantly affect the timing of entry into senescence, induction of p21 or p16, or the early SASP response, such as upregulation of IL-p (FIGS. 3F, 12B). However, the magnitude of the later SASP response (such as induction of CCL2, IL-6 and MMP3) was significantly dampened. Treatment with L1 shRNA also reduced the expression levels of IL-6 and MMP3 in late senescent cells (FIG. 11F). Hence, while L1 activation and the ensuing IFN-I response are relatively late in onset, they contribute importantly to the mature SASP and proinflammatory phenotype of senescent cells.

3TC did not affect L1 transcript levels (FIG. 10I), suggesting that the INF-I response is triggered by L1 cDNA. As this model would predict, knockdown of the cytosolic DNA sensing pathway components, cGAS or STING,[133] inhibited the IFN-I response in both late senescent and 3× cells (FIGS. 910L, 12C, 12D), and also downregulated the SASP response in late senescent cells (FIG. 12E).

NRTIs alkyl-modified at the 5' ribose position cannot be phosphorylated and hence do not inhibit RT enzymes. However, they possess intrinsic anti-inflammatory activity by inhibiting P2X7-mediated events that activate the NLRP3 inflammasome pathway.[134] Tri-methoxy-3TC (K-9), at 10 µM or 100 µM, did not inhibit the IFN-I response in either late senescent or 3× cells (FIG. 12F). Hence, the effect of 3TC on the IFN-I pathway requires RT inhibition. At high concentrations (100 µM), K-9 had some inhibitory activity on markers of inflammation (FIG. 12G).

To test the role of interferon signaling in SASP, the IFN-α/β receptors (IFNAR1 and 2) were inactivated using CRISPR/Cas9. Effective ablation of IFN-I signaling was achieved in both early passage and deep senescent cells (FIG. 10M). In both replicative and SIPS forms of senescence, loss of interferon signaling antagonized late (CCL2, IL-6, MMP3) but not early (IL-1p) SASP markers (FIG. 3D). This further demonstrates that IFN-I signaling contributes to the establishment of a full and mature SASP response in senescent cells.

Example 4 Activation of L1 in Human and Mouse Tissues

Figure 8A:
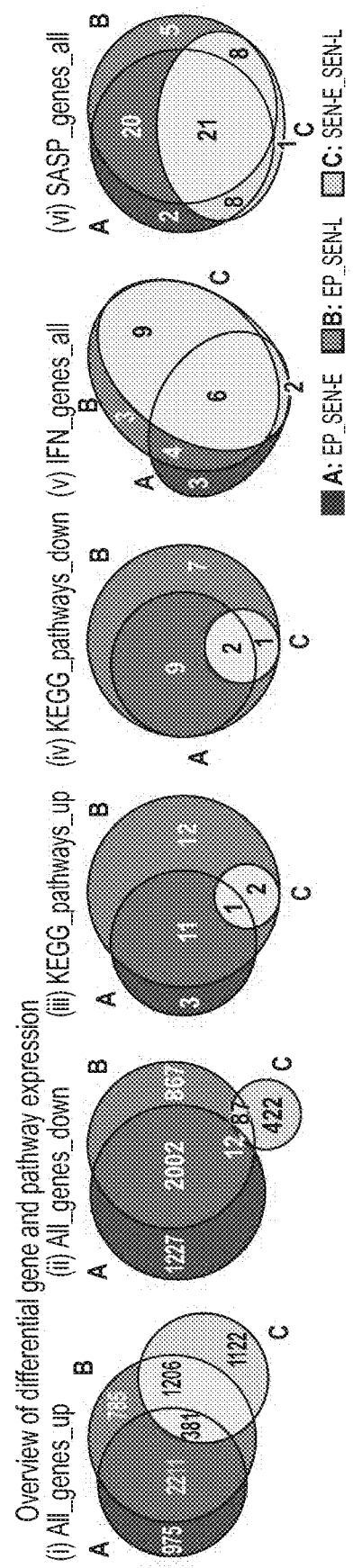
Figure 8B:
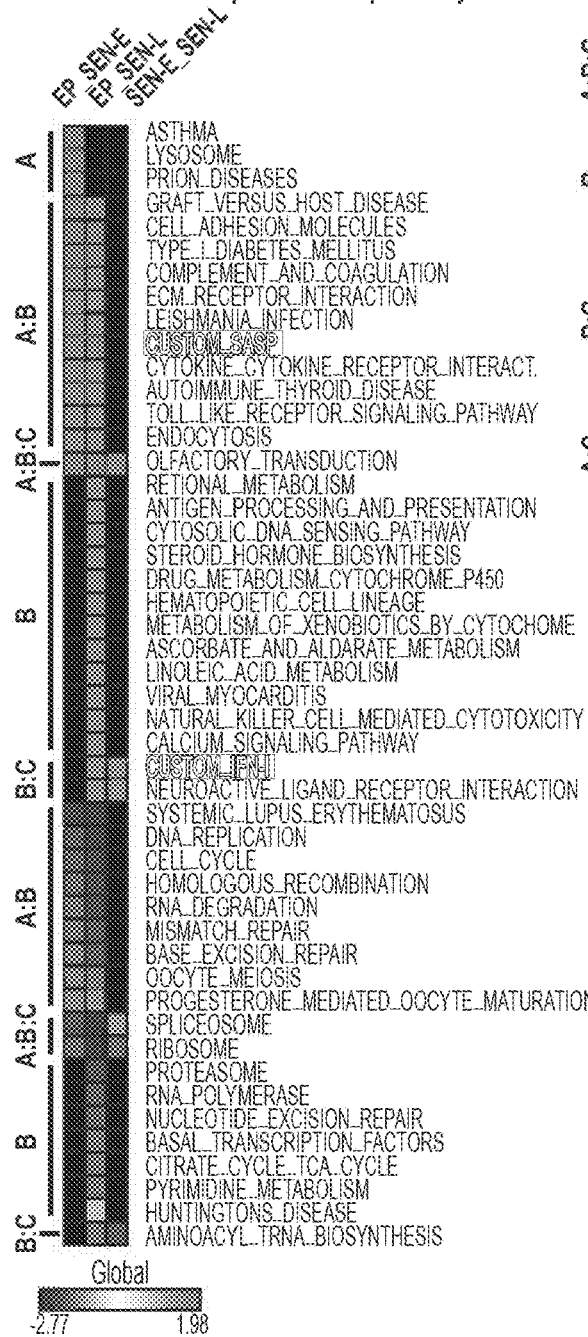
Figure 8D:
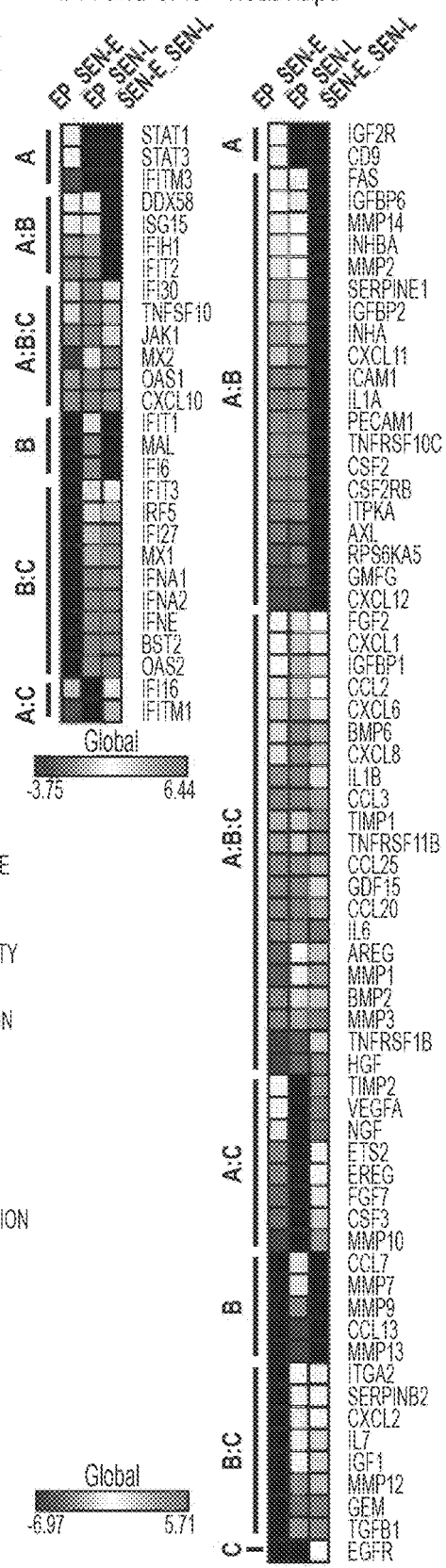
Figure 8F:
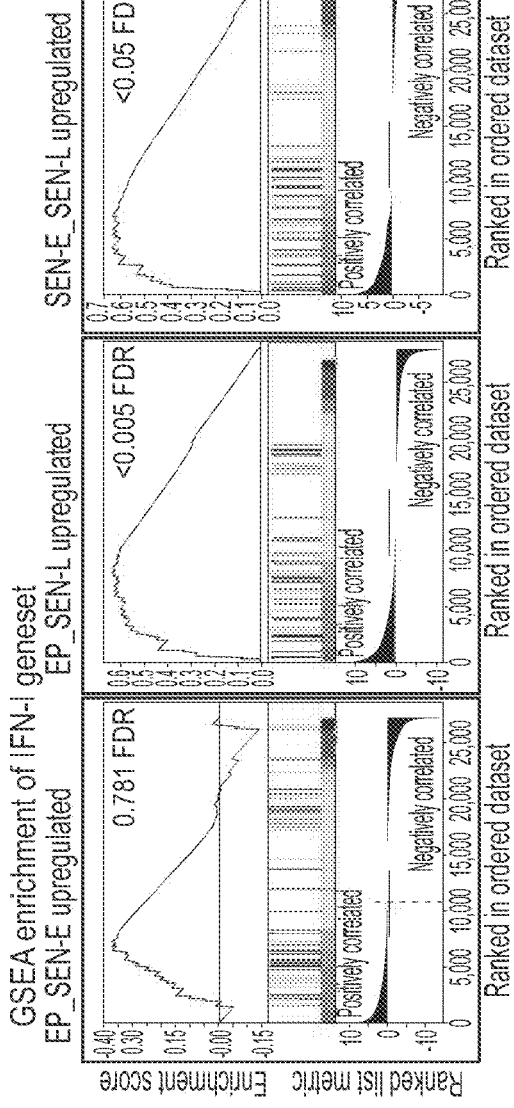
Figure 8G:
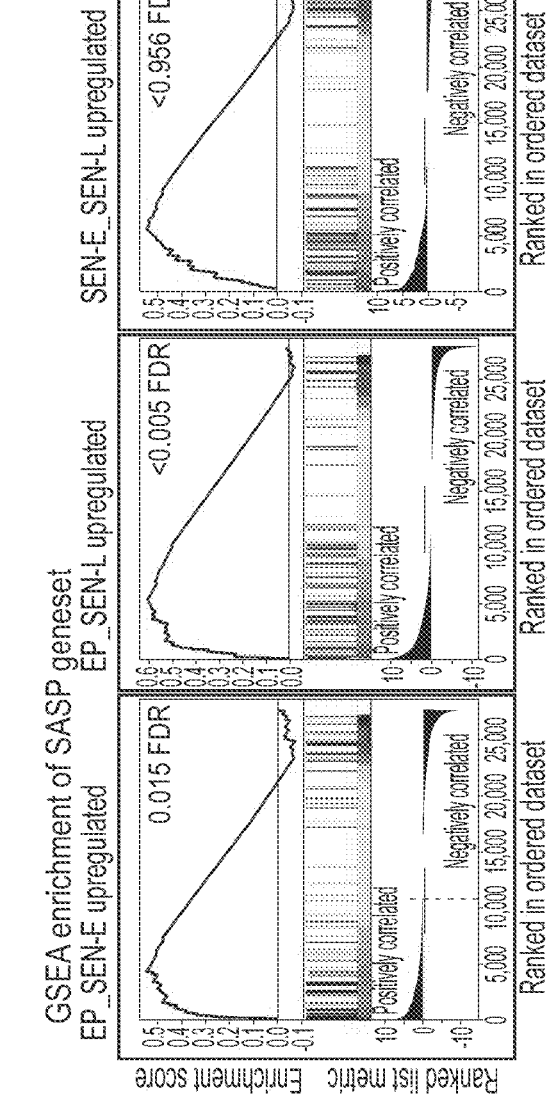
Figure 9J:
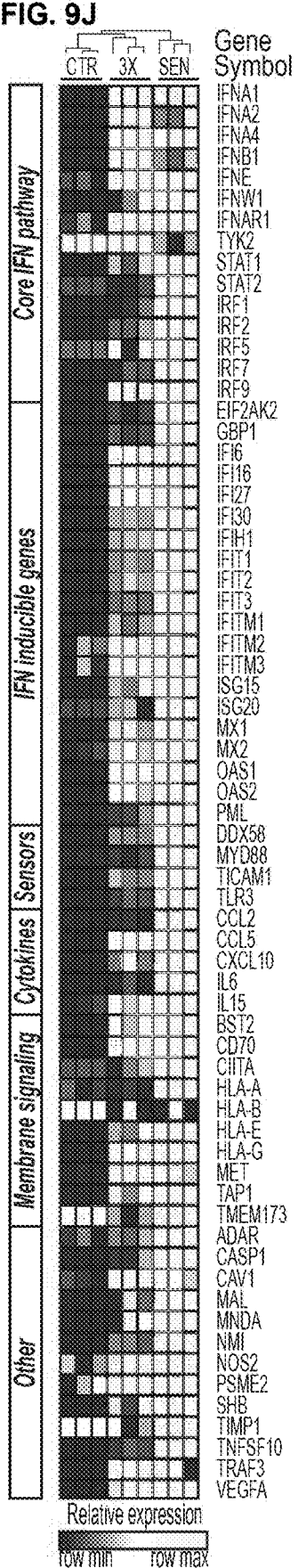
Figure 9K:
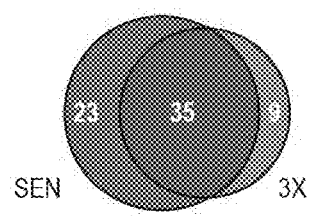

Activation of L1 expression in human cancers has been detected with an ORF1 antibody.[135] The same reagent showed widespread ORF1 expression in both senescent and 3× cells (FIGS. 8A, 8C, 8F). In skin biopsies of normal aged human individuals, we found that 10.7% of dermal fibroblasts were positive for the senescence marker p16, which is in the range documented in aging primates[136] (FIGS. 13B, 13D, 13F, 13H). Some of the p16 positive dermal fibroblasts were also positive for ORF1 (10.3%). Notably, we never observed ORF1 in the absence of p16 expression. We also detected, at the single cell level, the presence of phosphorylated STAT1, consistent with the presence of interferon signaling in the tissue microenvironment[137] (FIGS. 13B, 13E, 13G). Hence, a fraction of senescent cells in normal human individuals display activation of L1, consistent with these events accumulating during the progression of senescence.

We next examined mice and found that L1 mRNA was progressively upregulated with age in several tissues (FIG. 15G). The detected L1 RNA sequences were predominantly sense strand, represented throughout the element, and all three active L1 families were detectable (FIGS. 11G, 11H). At the protein level, the frequency of L1 Orf1 positive cells increased in tissues with age (FIG. 4A). Regions of Orf1 staining colocalized with senescence-associated β-galactosidase (SA-β-Gal) activity (FIG. 4B). Several IFN-1 response genes (Ifn-α, Irf7, Oas1), as well as pro-inflammatory and SASP markers (Il-6, Mmp3, Pai1, also known as Serpine1), were upregulated in tissues of old mice (FIGS. 4C, 14). An increase in L1 expression and IFN-1 response genes (Ifn-α, Oas1) were also observed in an experimentally-induced model of cellular senescence (young animals subjected to sublethal irradiation; FIG. 4D).

Figure 4E:
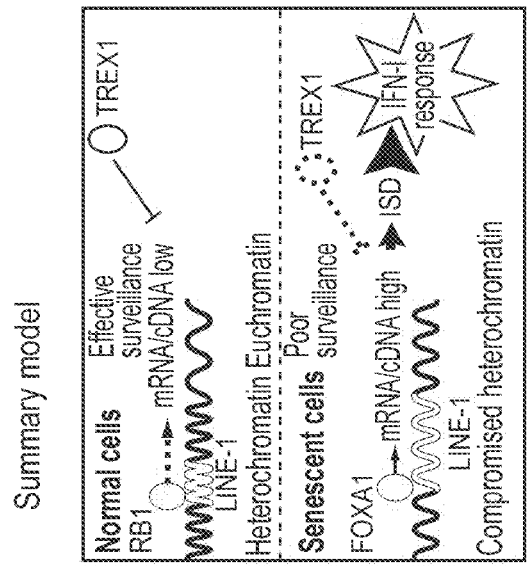
Figure 4F:
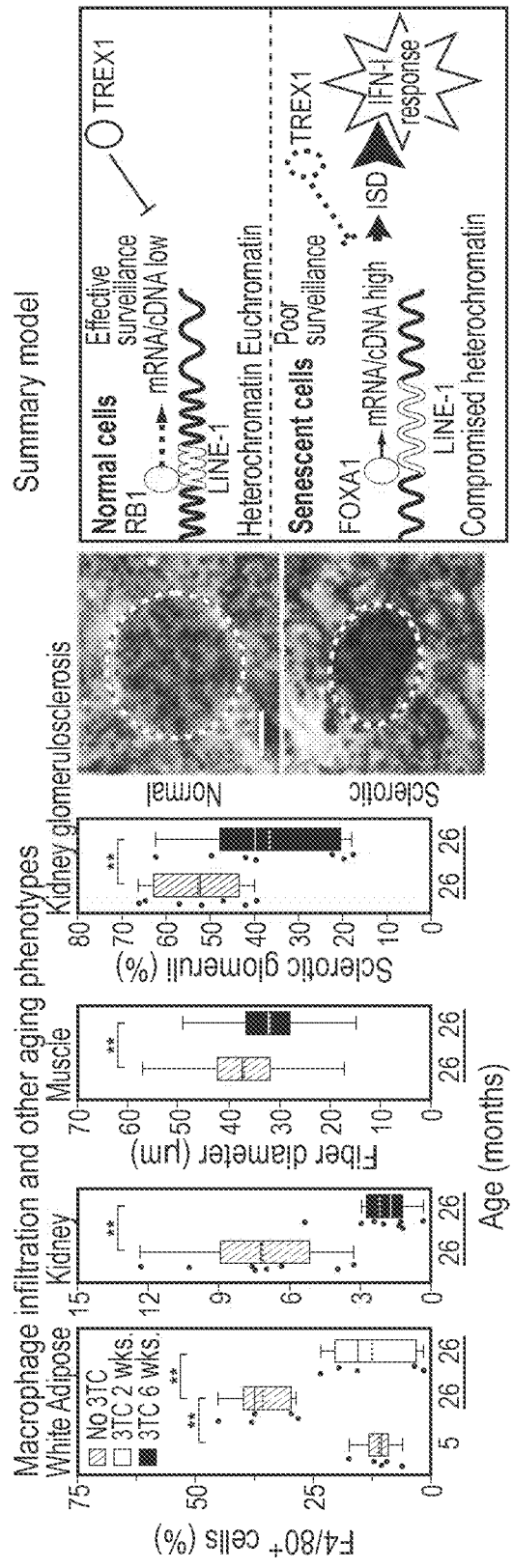

Old animals (26 months) were treated for two-weeks with 3TC (administered in water at human therapeutic doses). We found a broad and significant downregulation the IFN-1 response and alleviation of the SASP pro-inflammatory state (FIG. 4C; for the full dataset, see FIG. 14 and Table 7). Expression of L1 mRNA and p16 was weakly downregulated, but in most cases, did not reach statistical significance. K-9 did not affect either the IFN-1 or SASP responses. Immunofluorescence analysis of tissue sections confirmed that senescent cells expressed SASP, and Orf1-expressing cells activated IFN-1 signaling (FIGS. 15A-C). Treatment with 3TC significantly reduced both IFN-1 and SASP, but not L1 expression or the presence of senescent cells. Hence, NRTIs can be categorized as "senostatic" agents, to contrast them from "senolytic" treatments that remove senescent cells from tissues.[138,139] Decreased adipogenesis[140] and thermogenesis[141] are features of natural aging and both were increased in old animals by 2 weeks of 3TC treatment (FIGS. 15D-F). As shown in FIG. 4E, longer term treatments (from 20 to 26 months of age) were effective at opposing several known phenotypes of aging: (i) macrophage infiltration of tissues, a hallmark of chronic inflammation,[142,143] (ii) glomerulosclerosis of the kidney,[144] and (iii) skeletal muscle atrophy.[145] Macrophage infiltration of white adipose was especially responsive, returning to youthful (5 month) levels with only 2 weeks of 3TC.

The activation of endogenous L1 elements and the ensuing robust activation of an IFN-1 response is a novel phenotype of senescent cells, including naturally-occurring senescent cells in tissues. This phenotype evolves progressively during the senescence response and appears to be an important, but hitherto unappreciated component of SASP. We show that the expression of three regulators, RB1, FOXA1 and TREX1 changes during senescence, and that these changes are both sufficient and necessary to allow the transcriptional activation of L1s (FIG. 4G). Hence, multiple surveillance mechanisms need to be defeated to unleash L1, which underscores the importance of keeping these elements repressed in somatic cells.

The activation of innate immune signaling, in response to L1 activation during cellular senescence and aging, proceeds through the interferon-stimulatory DNA (ISD) pathway. Cytoplasmic DNA can originate from several sources, such as mtDNA released from stressed mitochondria[146] or cytoplasmic chromatin fragments (CCF) released from damaged nuclei.[147,148] The present results suggest that L1 cDNA is an important inducer of IFN-1 in senescent cells. Remarkably, NRTI treatment effectively antagonized not only the IFN-1 response but, also more broadly, reduced age-associated chronic inflammation in multiple tissues.

Sterile inflammation, also known as inflammaging, is a hallmark of aging and a contributing factor to many age-related diseases.[149,150] The present data indicates that activation of L1 elements (and possibly other RTEs) promotes inflammaging, and that the L1 RT is a relevant target for the treatment of age-associated inflammation and disorders.

Example 5 Effects of Adefovir and Lamivudine on Senescence-Induced Increases in L1 Sequence Abundance, Interferon Gene Expression, and SASP Gene Expression The effects of Adefovir and Lamivudine on senescence-induced increases in L1 sequence abundance, interferon gene expression, and SASP gene expression were assessed in human fibroblast cell lines.

L1 sequence abundance (copy number) were assessed in three different human fibroblast cell lines: LF1, IMR90, W138 using qPCR assays. Assays were normalized to 5S rDNA abundance. The control (CTRL) was non-treated, early passage, proliferating cells. Drugs were applied continuously, in medium, from a few passages before senescence, into senescence and then into late senescence. The "senescent" samples were harvested four months after onset of senescence. Both drugs were supplemented at 5 µM in the medium. Red bar in "senescent" conditions: cultures without drugs at 4 months in senescence. As shown in FIG. 17A, L1 copy number increased in senescence in all three cell lines, and both drugs significantly prevented this increase, with Adefovir being somewhat more effective than Lamivudine.

The effects of 5 µM Adefovir and Lamivudine on interferon gene expression were assessed in two cell lines (LF1 and IMR90) and two interferon genes (IFN-α and IFN-β1) as performed in FIG. 17A, except that the expression of the indicated genes was measured by RT-qPCR. As shown in FIG. 17B, the high interferon gene expression in senescent cells was significantly reduced in all cases by both drugs, and again Adefovir was somewhat more effective than Lamivudine. The red bars are cultures without drugs at 4 months in senescence.

The effects of 5 µM Adefovir and Lamivudine on SASP gene expression were assessed in one cell line (LF1) using two SASP genes (IL-6 and MMP3). CTRL was the expression in normal, pre-senescent, untreated cells. As shown in FIG. 17C, an increase in expression with senescence (red bars) was observed, and in both cases, SASP gene expression was significantly decreased with drug treatment, with Adefovir being somewhat more effective than Lamivudine.

Finally, the effects of high concentrations of Lamivudine and Emtricitabine (10 µM and 50 µM) on interferon gene expression (IFN-α and IFN-β1) were assessed in the LF1 cell line. These were done by passaging LF1 cells into senescence, keeping them in senescence for three months, adding the drugs, keeping the cells in the presence of the drugs for 1 month, then harvesting at 4 months. Interferon gene expression was assessed by RT-qPCR. The control (CTRL) was cells treated as above but without drugs. As shown in FIG. 17D, at 10 µM, Lamivudine decreased IFN-β induction, and was somewhat more effective than Emtricitabine. At 50 µM, Lamivudine actually induced an increase in the expression of interferons, even surpassing the levels seen in untreated cell. This increase is believed to be caused by the toxicity of the drug at these high levels. In contrast, Emtricitabine at 50 µM decreased the expression of interferons, even below the decrease observed with 10 µM.

Accordingly, at high doses, the toxicity of RTIs can impair their ability to halt or block the harmful effects of senescent cells and their ability to prevent or reverse age-related inflammation and disorders.

Example 6 Comparative Assessment of Several RTIs in a Dose-Response Assay of Inhibition of L1 Activity in Mouse and Human Cells Eight RTI compounds were assessed for their ability to inhibit LINE-1 (L1) activity in a mouse L1 retrotransposition assay: lamivudine (3TC); stavudine; emtricitabine; apricitabine; tenofovir disiproxil; censavudine; elvucitabine; and tenofovir. Three RTI compounds were assessed in a human L1 retrotransposition assay: lamivudine (3TC); censavudine; and elvucitabine.

Mouse LINE-1 Retrotransposition Assay

The dual luciferase-encoding plasmid pYX016 containing a mouse L1 element was described in Xie et al., 2011.[151] Lamivudine (3TC), stavudine (d4T), emtricitabine, apricitabine, tenofovir disoproxil and tenofovir were purchased from AK Science. Elvucitabine was obtained by custom synthesis. Censavudine was synthesized by Oncolys BioPharma. HeLa cervical cancer cells were cultivated at 37° C. in a humidified 5% CO2 incubator in Dulbecco's Modified Eagle's Medium (DMEM)—high glucose, with 4500 mg/L glucose, L-glutamine, sodium pyruvate and sodium bicarbonate (Sigma), supplemented with 10% of heat inactivated fetal bovine serum (Thermo Fisher).

Assays were performed as described in Xie et al., 2011[151] with several modifications. The reporter assay was performed in 96 well white Optical bottom plates. 6000 HeLa cells were seeded in each well 24 hours prior transfection and compound treatment. All compounds were resuspended in DMSO. Stock solution concentrations varied from 50 mM to 1.25 mM depending of the solubility of the compound. Serial dilutions (1:3) were prepared in DMSO. Ten different concentrations of each compound were tested in triplicate. Medium containing different concentrations of the compounds were prepared by adding 2 µL of the compound dilution to 1 mL of the culture medium. The final concentration of DMSO in the medium was 0.2%. FuGENE® HD transfection reagent (Promega) was used to transfect the plasmid pYX016 into the cells. The transfection mix was prepared in OpiMEM (Thermo Fisher) using a reagent to DNA ratio of 3.5:1 according to manufacturer's instructions. Culture medium was removed from the cells and discarded. The transfection mix (5 µL) was mixed with the compound containing medium (100 µL/well) and this was added onto the cells of each well. Cells were incubated for 48H at 37° C./5% $CO_2$.

Luciferase reporter activity was quantified with the Dual-Luciferase® Reporter Assay System (Promega) according to manufacturer's instructions for multiwell plates with the following modification: Cells were lysed directly on the multiwell plate with 30 µL of the passive lysis buffer (PLB) for 20 min at room temperature, with gentle shaking to ensure complete cell lysis (instead of 20 µL of PLB for 15 min). Firefly and *Renilla* luciferase signals were measured using a SpectraMax i3x Multi-Mode Microplate Reader. Integration times of 100 ms and 10 ms were used to measure the Firefly and *Renilla* signals respectively. Relative L1 activity was calculated as Firefly/*Renilla* *10,000. Dose response inhibition data were fit to a four-parameter logistic equation using non-linear regression (using Graphpad Prism 8), to determine $IC_{50}$ values for each inhibitor. The experiment was performed twice, independently.

Results

Figure 18A:
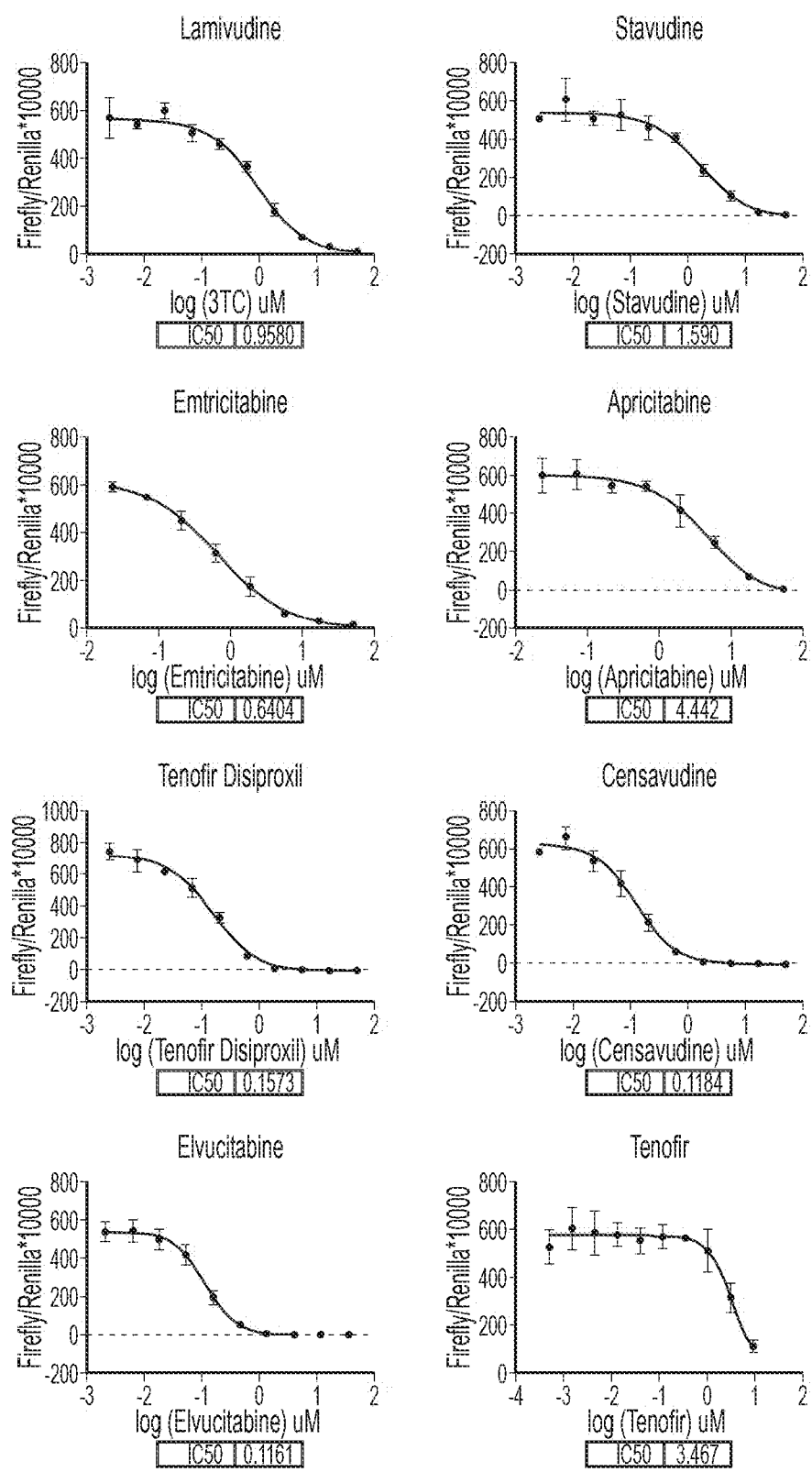
FIGS. 18A and 18B are each eight dose response curves showing the inhibition of mouse L1 activity with eight RTI compounds: Lamivudine (3TC); Stavudine; Emtricitabine; Apricitabine; Tenofovir Disiproxil; Censavudine; Elvucitabine; and Tenofovir. A dose-response was obtained on the retrotransposition activity of active mouse LINE-1 using HeLa cells in a first experiment (FIG. 18A) and in a second independent experiment (FIG. 18B).
Figure 18B:
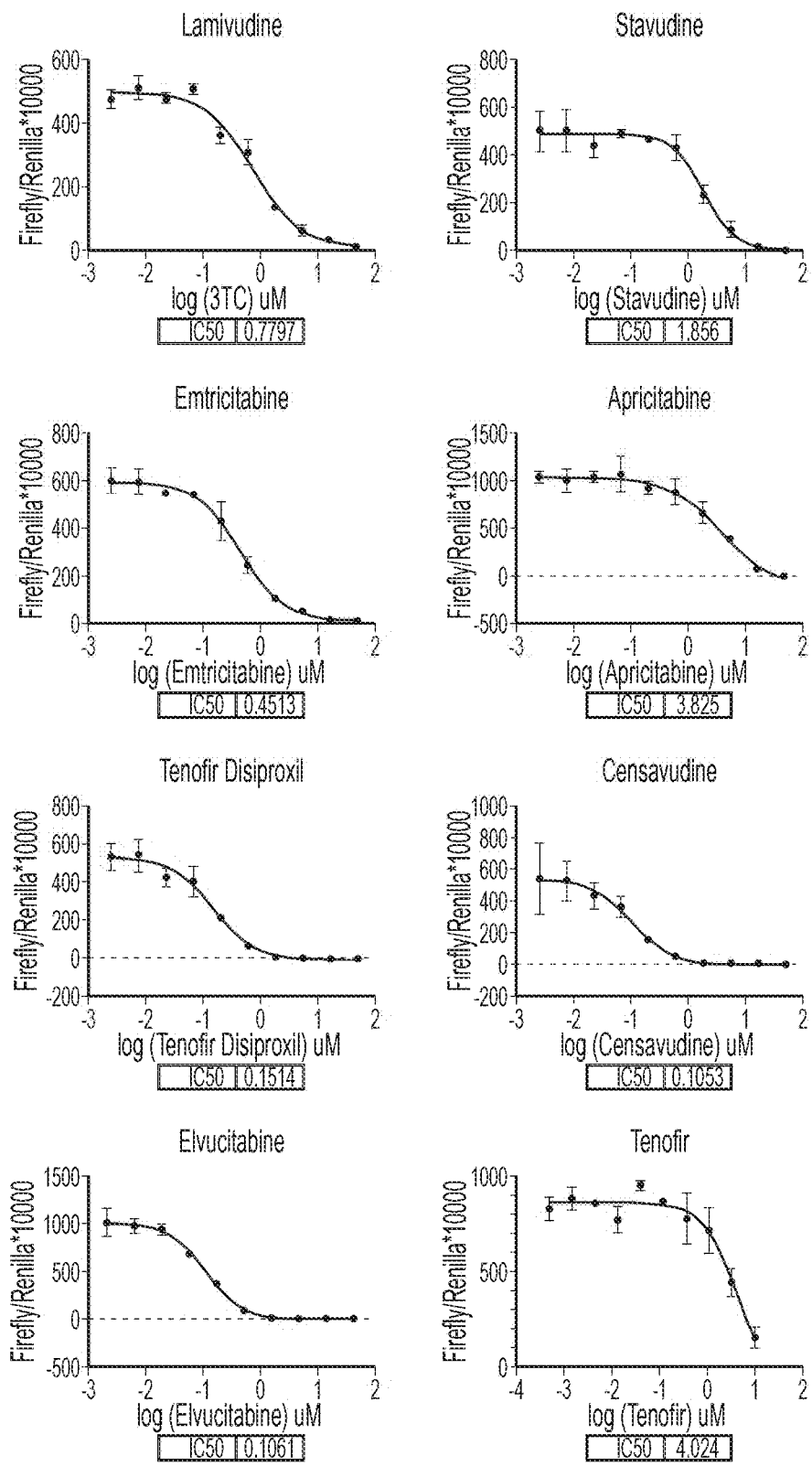

The inhibitory dose-response curves for the eight RTI compounds in the two independent experiments are provided in FIG. 18A and FIG. 18B, respectively. The $IC_{50}$ values are summarized in Table 10. Surprisingly, two RTI compounds, censavudine and elvucitabine, had much lower $IC_{50}$ values (about 100 nM) than the other RTI compounds, thus displaying unexpected mouse L1 inhibitory activity.

Human LINE-1 Retrotransposition Assay

Given their unexpected ability to inhibit mouse L1 activity, censavudine and elvucitabine were tested for their ability to inhibit human L1 activity. Lamivudine was also tested for comparison.

Assays for human L1 were performed in very similar manner to those for mouse. pYX017 encoding a human LINE-1 sequence[151] was used in place of pYX016. Because the human construct yields a lower signal, compounds were incubated with cells for 72 hours instead of 48 hours, and cells were seeded at a density of 2000/well instead of 6000/well. In addition, the transfection reagent to DNA ratio was 2:1 instead of 3.5:1.

Results

Figure 19A:
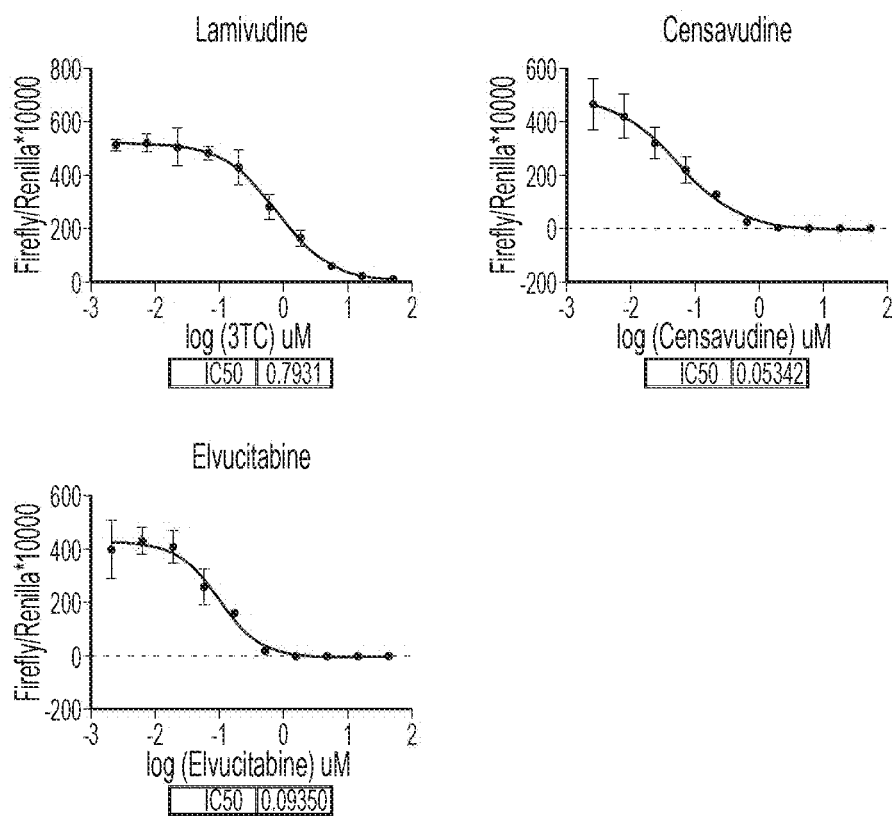
FIG. 19A is three dose response curves and FIG. 19B is two dose response curves showing the inhibition of human L1 activity with three RTI compounds: Lamivudine (3TC); Censavudine; and Elvucitabine. A dose-response was obtained on the retrotransposition activity of active human LINE-1 using HeLa cells in a first experiment using Lamivudine (3TC); Censavudine; and Elvucitabine (FIG. 19A); and in a second experiment using Lamivudine (3TC) and Elvucitabine (FIG. 19B).
Figure 19B:
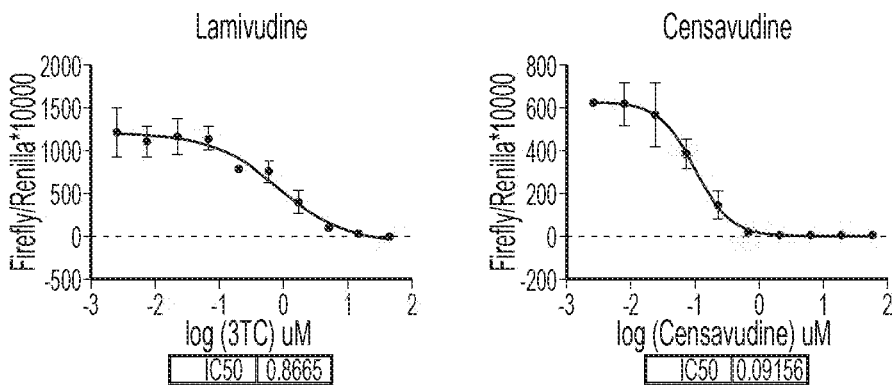

The inhibitory dose-response curves for the three RTI compounds are provided in FIG. 19A-B and the $IC_{50}$ values are summarized in Table 11. Again, censavudine and elvucitabine displayed surprising human L1 inhibitory activity ($IC_{50}$ about 100 nM) when compared to lamivudine ($IC_{50}$ over 800 nM).

Cell Viability Assay

As described above, the toxicity of RTIs could impair their ability to halt or block the harmful effects of senescent cells and their ability to prevent or reverse age-related inflammation and disorders. The potential toxicity of lamivudine (3TC); stavudine; emtricitabine; apricitabine; tenofovir disiproxil; censavudine; elvucitabine; and tenofovir was assessed in a cell viability assay at the doses used to generate the L1 inhibitory dose-response curves.

HeLa cells were treated with the different concentrations of the eight RTI compounds for 48 hours. Cell viability was measured with CellTiter-Glo® luminescent cell viability assay (Promega®) and presented as percentage of cell viability versus untreated cells. Staurosporine, known to induce cell death, was used as a control.

Results

Figure 20:
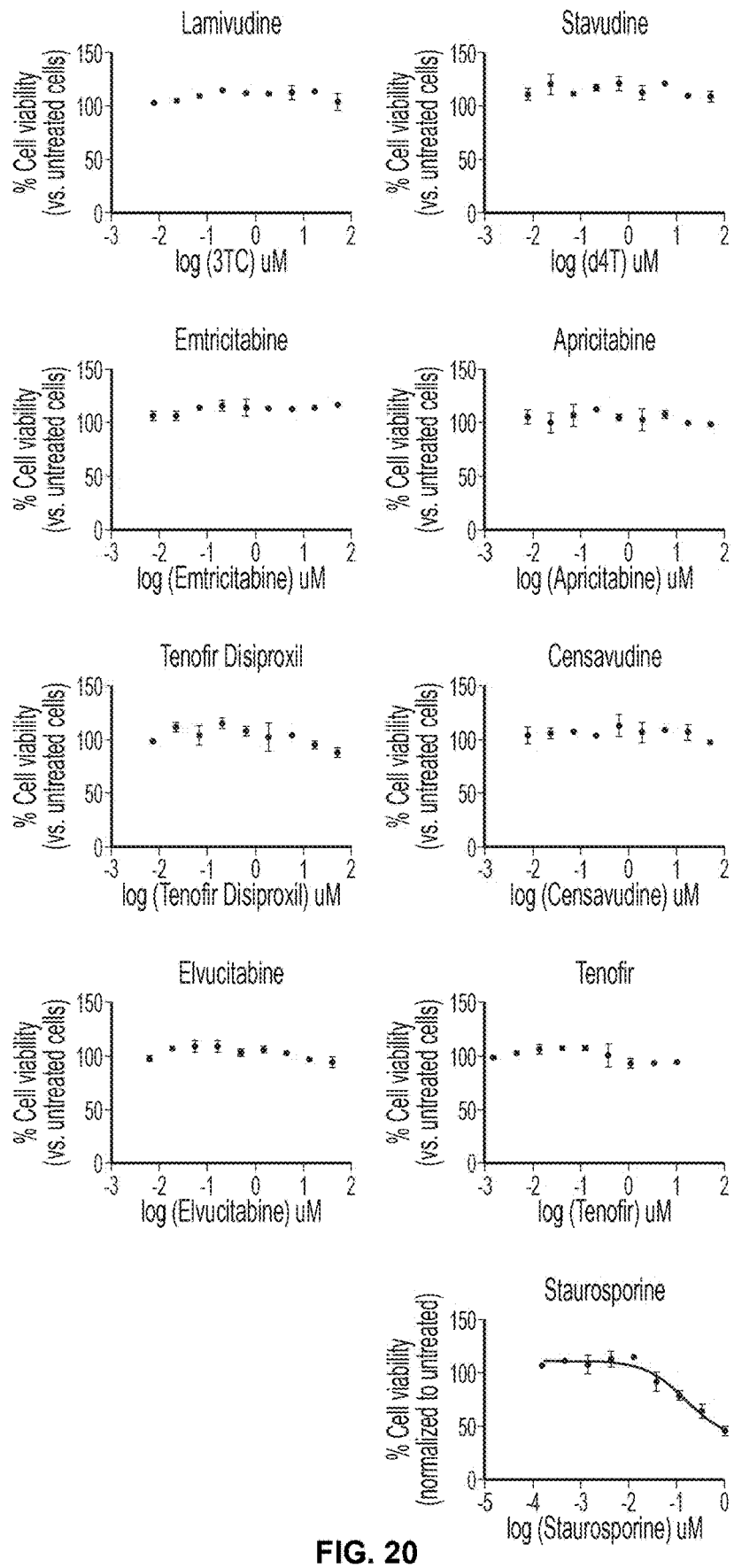
FIG. 20 is nine dose response curves showing the cell viability of HeLa cells following treatment with nine different RTI compounds: Lamivudine (3TC); Stavudine; Emtricitabine; Apricitabine; Tenofovir Disiproxil; Censavudine; Elvucitabine; Tenofovir; and Staurosporine.

As shown in FIG. 20, the eight RTI compounds did not induce any significant levels of cell death in contrast to the control, staurosporine.

In summary, censavudine and elvucitabine both displayed an unexpected ability to inhibit mouse and human L1 activity ($IC_{50}$ about 100 nM) without inducing toxicity in the cell viability assay at doses up to 2 μM.

In related experiments, islatravir and other compounds were tested for inhibition of retrotransposition activity of human LINE-1 in HeLa cells according to the following procedure.

HeLa cervical cancer cells were cultivated at 37° C. in a humidified 5% CO2 incubator in Dulbecco's Modified Eagle's Medium (DMEM)—high glucose, with 4500 mg/L glucose, L-glutamine, sodium pyruvate and sodium bicarbonate (Sigma), supplemented with 10% of heat inactivated fetal bovine serum (Thermo Fisher).

Assays were performed using reporter plasmid pYX017 as described (Xie, et al., 2011) with several modifications. The reporter assay was performed in 96-well white optical bottom plates. HeLa cells were seeded in wells 24 h prior to transfection and compound treatment so that cells were approximately 30% confluent on the day of transfection. Different cell plating densities were tested and a density of $2\times10^3$ cells was determined to be optimal.

Compounds were resuspended in DMSO. Serial dilutions (1:3) were prepared in DMSO. Medium containing different concentrations of the compounds were prepared by adding 2 μl of the compound dilution to 1 ml of the culture medium. The final concentration of DMSO in the medium was 0.2%.

FuGENE® HD transfection reagent (Promega, E2311, Lot 382574 and Lot 397842) was used to transfect the plasmids into the cells. The transfection reagent: DNA mixture was prepared in OpiMEM (Thermo Fisher) according to manufacturer's instructions. Different ratios of transfection reagent to DNA were tested and a ratio of 3:1 was determined to be optimal. Culture medium was removed from the cells and discarded. The transfection reagent: DNA mixture (5 μl) was mixed with the compound containing medium (100 μl/well) and this was added onto the cells of each well. Cells were incubated at 37° C./5% $CO_2$ for different incubation time. A 72 h incubation time was determined to be optimal.

Luciferase reporter activity was quantified with the Dual-Luciferase® Reporter Assay System (Promega) according to manufacturer's instructions for multiwell plates except that cells were lysed directly on the multiwell plate with 30 μl of the passive lysis buffer (PLB) for 20 min at room temperature, with gentle shaking to ensure complete cell lysis.

Firefly and *Renilla* luciferase signals were measured using a SpectraMax i3x Multi-Mode Microplate Reader. Integration times of 100 ms and 10 ms were used to measure the Firefly and *Renilla* signals respectively. Relative L1 activity is calculated as Firefly/*Renilla* *1000 or Firefly/*Renilla* *10,000. Dose response inhibition data were fit to a four parameter logistic equation using non-linear regression (using Graphpad Prism 8), to determine $IC_{50}$ values for each inhibitor.

The results are provided in Table 12 and Table 13. Islatravir exhibited unexpectedly better human LINE-1 inhibitor activity compared to the other reverse transcriptase inhibitory drugs tested. Also, islatravir penetrated the blood brain barrier (BBB) and demonstrated intracellular longevity following single oral doses in Rhesus macaque. See, Stoddard et al., Antimicrob. Agents Chemother. 59:4190-8 (2015). It was also found that intracellular half-life of the phosphorylated form of islatravir in PBMCs was greater than 72 h.

Example 7 Islatravir Inhibitory Quotient (IQ)

The in vitro $IC_{50}$ for human LINE-1 in cell-based assay is $1.29\times10^{-3}$ μM. See Table 12. The islatravir HIV WT $IC_{50}=0.2\times10^{-3}$ μM. Grobler et al, "MK-8591 POTENCY AND PK PROVIDE HIGH INHIBITORY QUOTIENTS AT LOW DOSES QD AND QW," Conference on Retroviruses and Opportunistic Infections, Abstract Number 481, March 2019.

The steady state PBMC EFdA-TP Inhibitory Quotient at $C_{avg}$ for HIV was modeled from single dose PK based on human PK parameters of EFdA (plasma) and EFdA-TP (intracellular). Levin, J., Conference Report, "Single Doses as Low as 0.5 mg of the Novel NRTTI MK-8591 Suppress HIV for At Least Seven Days," 9th IAS Conference on HIV Science; Paris, France; 23-26 Jul. 2017. The human plasma PK of EFdA (oral dose 0.5-30 mg) shows dose-proportional oral clearance (31-45 L/hr) and proportional increases in volume of distribution that contribute to longer T-half at doses >1 mg. Intracellular PK of EFdA-TP in human PBMC is dose proportional with a T-half of 78.5-128 h. The EFdA-TP $IC_{50}$ for HIV=49 nM. The Plasma-Brain $K_{app}$ (0.25) was determined in the non-human primate. Stoddart et al., Antimicrob Agents Chemother 59:4190-4198 (2015).

These data were used to estimate the IQ for human LINE-1 in PBMC and brain. Based upon steady-state the EFdA-TP intracellular concentrations, a daily dose of 2 mg of islatravir will have robust inhibitory activity for human LINE-1 in both PBMCs (IQ=51) and brain (IQ=13). See Table 14.

Tables described in the present disclosure are provided below.

TABLE 1

List of primers used in PCR analysis[1]

| Number | Designation | Sequence | Notes |
|---|---|---|---|
| Primer set 1 | MDL15UTRPRAF<br>MDL15UTRPRAR<br>Amplicon A,<br>FIG. 1b | GCCAAGATGGCCGAATAGGA<br>AAATCACCCGTCTTCTGCGT | LINE-1 5'UTR, positions 12-31, sense orientation[2].<br>LINE-1 5'UTR, positions 64-83, antisense orientation[2].<br>Used in RT-qPCR experiments to assess expression of L1Hs RNA. Also used in ChIP experiments. |
| Primer set 2 | MDL15UTRBF<br>MDL15UTRBR<br>Amplicon B,<br>FIG. 1b | CGAGATCAAACTGCAAGGCG<br>CCGGCCGCTTTGTTTACCTA | LINE-1 5'UTR, positions 402-421, sense orientation[2].<br>LINE-1 5'UTR, positions 454-473, antisense orientation[2].<br>Used in RT-qPCR experiments to assess expression of L1Hs RNA. Also used in ChIP experiments. |
| Primer set 3 | MDL15UTRCF<br>MDL15UTRCR<br>Amplicon C,<br>FIG. 1b | TAAACAAAGCGGCCGGGAA<br>AGAGGTGGAGCCTACAGAGG | LINE-1 5'UTR, positions 474-492, sense orientation[2].<br>LINE-1 5'UTR, positions 530-549, antisense orientation[2].<br>Used in RT-qPCR experiments to assess expression of L1Hs RNA. Also used in ChIP experiments. |
| Primer set 4 | MDL15UTRDF<br>MDL15UTRDR<br>Amplicon D,<br>FIG. 1b | AGAGAGCAGTGGTTCTCCCA<br>CAGTCTGCCCGTTCTCAGAT | LINE-1 5'UTR, positions 619-638, sense orientation[2].<br>LINE-1 5'UTR, positions 647-666, antisense orientation[2].<br>Used in RT-qPCR experiments to assess expression of L1Hs RNA. Also used in ChIP experiments. |
| Primer set 5 | MDL1ORF1F<br>MDL1ORF1R<br>Amplicon E,<br>FIG. 1b | ACCTGAAAGTGACGGGGAGA<br>CCTGCCTTGCTAGATTGGGG | LINE-1 ORF1, positions 1395-1414, sense orientation[2].<br>LINE-1 ORF1, positions 1508-1527, antisense orientation[2].<br>Used in RT-qPCR experiments to assess expression of L1Hs RNA. Also used in ChIP experiments. |
| Primer set 6 | ORF2F<br>ORF2R<br>ORF2 probe<br>Amplicon F,<br>FIG. 1b | CAAACACCGCATATTCTCACTCA<br>CTTCCTGTGTCCATGTGATCTCA<br>AGGTGGGAATTGAAC-VIC | LINE-1 ORF2, positions 5731-5753, sense orientation[2].<br>LINE-1 ORF2, positions 5772-5794, antisense orientation[2].<br>Probe for TaqMan experiments.<br>ORF2F and ORF2R were used in SYBR Green RT-qPCR experiments to assess expression of L1Hs RNA, and in conjunction with the ORF2 probe in TaqMan qPCR experiments on genomic DNA to determine relative copy numbers of L1Hs elements. Primers were developed and validated as described[3]. |
| Primer set 7 | 5SF<br>5SR<br>5S probe | CTCGTCTGATCTCGGAAGCTAAG<br>GCGGTCTCCCATCCAAGTAC<br>AGGGTCGGGCCTGG-6FAM | Ribosomal 5S RNA gene, sense orientation.<br>Ribosomal 5S RNA gene, antisense orientation.<br>Probe for TaqMan experiments.<br>Used for internal normalization, in conjunction with primer set 3, in TaqMan qPCR experiments on genomic DNA to determine relative copy numbers of L1Hs elements. Primers were developed and validated as described[3]. |
| Primer set 8 | GAPDHFW<br>GAPDHRV | TTGAGGTCAATGAAGGGGTC<br>GAAGGTGAAGGTCGGAGTCA | GAPDH, sense orientation.<br>GAPDH, antisense orientation.<br>Used for RT-qPCR of the mRNA of the GAPDH gene (NM_001256799). Primers span an intron. Used as the internal normalizer in gene expression experiments. |
| Primer set 9 | GAPDHINT4F<br>GAPDHINT4R | CCAGGAGTGAGTGGAAGACAG<br>CTAGTTGCCTCCCCAAAGCA | Intron 4 of GAPDH, sense orientation.<br>Intron 4 of GAPDH, antisense orientation.<br>Used as a negative control in ChIP experiments. |
| Primer set 10 | ACP1IFNAFW<br>ACP1IFNARV1<br>ACP1IFNARV2 | TTGATGGCAACCAGTTCCAG<br>TCATCCCAAGCAGCAGATGA<br>TGTTCCCAAGCAGCAGATGA | Interferon alpha consensus, sense orientation.<br>Interferon alpha consensus, antisense orientation.<br>Interferon alpha consensus, antisense orientation.<br>Used in RT-qPCR experiments to assess the collective expression of human interferon alpha genes. All 3 primers were used in a single reaction. |
| Primer set 11 | MDIFNB1FW<br>MDIFNB1RV | ACGCCGCATTGACCATCTAT<br>GTCTCATTCCAGCCAGTGCT | IFNB1, sense orientation.<br>IFNB1, antisense orientation.<br>Used for RT-qPCR of the mRNA of the IFNB1 gene (NM_002176). |
| Primer set 12 | MDHSRB1AF<br>MDHSRB1AR | ACTCTCACCTCCCATGTTGC<br>ATCCGTGCACTCCTGTTCTG | RB1, sense orientation.<br>RB1, antisense orientation.<br>Used for RT-qPCR of the mRNA of the RB1 gene (NM_000321). Primers span an intron. |
| Primer set 13 | MDHSP107AF<br>MDHSP107AR | CCAAGAAGCGCTCTGCTGTA<br>GCAGGGGATTCTGCATCACTA | RBL1, sense orientation.<br>RBL1, antisense orientation.<br>Used for RT-qPCR of the mRNA of the RBL1 gene (NM_0028955). Primers span an intron. |

TABLE 1 -continued

List of primers used in PCR analysis.

| Number | Designation | Sequence | Notes |
|---|---|---|---|
| Primer set 14 | MDHSP130F<br>MDHSP130R | AGTCGCCCACCCCTCAGAT<br>TTCCCTCCAGCGTGTAGCTT | RBL2, sense orientation.<br>RBL2, antisense orientation.<br>Used for RT-qPCR of the mRNA of the RBL2 gene (NM_005611). Primers span an intron. |
| Primer set 15 | MDTREX1CDSF<br>MDTREX1CDSR | TCCCCTTCGGATCTTAACAC<br>CGAAAAAGATGAGGGTCTGC | TREX1, sense orientation.<br>TREX1, antisense orientation.<br>Used for RT-qPCR of the mRNA of the TREX1 gene (NM_007248). Primers span an intron. |
| Primer set 16 | MDHSFOXA1F<br>MDHSFOXA1R | GGAAGACCGGCCAGCTAGAG<br>TGAAGGAGTAGTGGGGGTCC | FOXA1, sense orientation.<br>FOXA1, antisense orientation.<br>Used for RT-qPCR of the mRNA of the FOXA1 gene (NM_D04496). Primers span an intron. |
| Primer set 17 | JJMMP1FW<br>JJMMP1RV | AGCCTTCCAACTCTGGAG<br>TAATGT<br>CCGATGATCTCCCCTGACAA | MMP1, sense orientation.<br>MMP1, antisense orientation.<br>Used for RT-qPCR of the mRNA of the MMP1 gene (NM_001145938). Primers span an intron. |
| Primer set 18 | JJMMP3FW<br>JJMMP3RV | CCCACCTTACATACAGGATTGTG<br>A<br>CCCAGACTTTCAGAGCTTTCTCA | MMP3, sense orientation.<br>MMP3, antisense orientation.<br>Used for RT-qPCR of the mRNA of the MMP3 gene (NM_002422). Primers span an intron. |
| Primer set 19 | JJIL6FW<br>JJIL6RV | CACTGGCAGAAAACAACCTGAA<br>ACCAGGCAAGTCTCCTCATTGA | IL6, sense orientation.<br>IL6, antisense orientation.<br>Used for RT-qPCR of the mRNA of the IL6 gene (NM_000600). Primers span an intron. |
| Primer set 20 | JJIL8FW<br>JJIL8RV | GTTTTTGAAGAGGGCTGAGAATT<br>C<br>CCCTACAACAGACCCACACAATA<br>C | CXCL8 (IL8), sense orientation.<br>CXCL8 (IL8), antisense orientation.<br>Used for RT-qPCR of the mRNA of the CXCL8 gene (NM_000584). Primers span an intron. |
| Primer set 21 | JJCCL2FW<br>JJCCL2RV | AAGACCATTGTGGCCAAGGA<br>TTCGGAGTTTGGGTTTGCT | CCL2, sense orientation.<br>CCL2, antisense orientation.<br>Used for RT-qPCR of the mRNA of the CCL2 gene (NM_002982). Primers span an intron. |
| Primer set 22 | JJCXCL2FW<br>JJCXCL2RV | AGAATGGGCAGAAAGCTTGTCT<br>CCTTCTGGTCAGTTGGATTTGC | CXCL2, sense orientation.<br>CXCL2, antisense orientation.<br>Used for RT-qPCR of the mRNA of the CXCL2 gene (NM_002089). Primers span an intron. |
| Primer set 23 | IL1BETAFW<br>IL1BETARV | CGCCAGTGAAATGATGGCTTAT<br>CTGGAAGGAGCACTTCATCTGT | IL-1β, sense orientation.<br>IL-1β, antisense orientation.<br>Used for RT-qPCR of the mRNA of the IL1B gene (NM_000576). Primers span an intron |
| Primer set 24 | MDIRF9FW<br>MDIRF9RV | CAACTGAGGCCCCCTTTCAA<br>CGCCCGTTGTAGATGAAGGT | IRF9, sense orientation.<br>IRF9, antisense orientation.<br>Used for RT-qPCR of the mRNA of the IRF9 gene (NM_006084). Primers span an intron |
| Primer set 25 | MDIRF7FW<br>MDIRF7RV | GGCTGGAAAACCAACTTCCG<br>GTTATCCCGCAGCATCACGA | IRF7, sense orientation.<br>IRF7, antisense orientation.<br>Used for RT-qPCR of the mRNA of the IRF7 gene (NM_001572). Primers span an intron |
| Primer set 26 | MDHSOAS1AF<br>MDHSOAS1AR | TGGAGACCCAAAGGGTTGGA<br>AGGAAGCAGGAGGTCTCACC | OAS1, sense orientation.<br>OAS1, antisense orientation.<br>Used for RT-qPCR of the mRNA of the OAS1 gene (NM_016816). Primers span an intron |
| Primer set 27 | HSCGASFW<br>HSCGASRV | ACGTGCTGTGAAAACAAAGAAG<br>GTCCCACTGACTGTCTTGAGG | cGAS, sense orientation.<br>cGAS, antisense orientation.<br>Used for RT-qPCR of the mRNA of the MB21D1 gene (NM_138441). Primers span an intron |
| Primer set 28 | HSSTING1FW<br>HSSTING1RV | ATATCTGCGGCTGATCCTGC<br>GGTCTGCTGGGGCAGTTTAT | STING, sense orientation.<br>STING, antisense orientation.<br>Used for RT-qPCR of the mRNA of the TMEM173 gene (NM_198282). Primers span an intron |

TABLE 1-continued

List of primers used in PCR analysis,

| Number | Designation | Sequence | Notes |
|---|---|---|---|
| Primer set 29 | TICDKN1AFW<br>TICDKN1ARV | GAGACTCTCAGGGTCGAAAACG<br>TTCCTGTGGGCGGATTAGG | CDKN1A, sense orientation.<br>CDKN1A, antisense orientation.<br>Used for RT-qPCR of the mRNA of the CDKN1A gene (NM_000389). Primers span an intron |
| Primer set 30 | TICDKN2AFW<br>TICDKN2ARV | CGGAAGGTCCCTCAGACATC<br>CCCTGTAGGACCTTCGGTGA | CDKN2A (p16), sense orientation.<br>CDKN2A (p16), antisense orientation.<br>Used for RT-qPCR of the mRNA of the CDKN2A gene (NM_000077). Primers span an intron |
| Primer set 31 | MGAPDHF<br>MGAPDHR | CGGCCGCATCTTCTTGTG<br>GTGACCAGGCGCCCAATA | Gapdh, sense orientation.<br>Gapdh, antisense orientation.<br>Used for RT-qPCR of the mRNA of the Gapdh gene (NM_008084.3). Primers span an intron. Used as the internal normalizer in gene expression experiments. |
| Primer set 32 | MMHSP90AB1F<br>MMHSP90AB1R | CCACCACCCTGCTCTGTACTA<br>CCTCTCCATGGTGCACTTCC | Hsp90ab1, sense orientation.<br>Hsp90ab1, antisense orientation.<br>Used for RT-qPCR of the mRNA of the Hsp90ab1 gene (NM_008302). Primers span an intron. Used as secondary normalizer in gene expression experiments. |
| Primer set 33 | MMGUSBFW<br>MMGUSBRV | CGTGACCTTTGTGAGCAACG<br>CTGCTCCATACTCGCTCTGG | Gusb, sense orientation.<br>Gusb, antisense orientation.<br>Used for RT-qPCR of the mRNA of the Gusb gene (NM_010368). Primers span an intron. Used as secondary normalizer in gene expression experiments. |
| Primer set 34 | GBCONIFNAF<br>GBCONIFNAR | TCTGATGCAGCAGGTGGG<br>AGGGCTCTCCAGACTTCTGCTCTG | Interferon alpha consensus, sense orientation.<br>Interferon alpha consensus, antisense orientation.<br>Used in RT-qPCR experiments to assess the collective expression of murine interferon alpha genes. Primers were developed and validated as described[4]. |
| Primer set 35 | GBIRF7FW<br>GBIRF7RV | CTCCTGAGCGCAGCCTTG<br>GTTCTTACTGCTGGGGCCAT | Irf7, sense orientation.<br>Irf7, antisense orientation.<br>Used for RT-qPCR of the mRNA of the Irf7 gene (NM_016850). Primers span an intron. |
| Primer set 36 | MMOAS1BF<br>MMOAS1BR | TCTGCTTTATGGGGCTTCGG<br>TCGACTCCCATACTCCCAGG | Oas1, sense orientation.<br>Oas1, antisense orientation.<br>Used for RT-qPCR of the mRNA of the Irf9 gene (NM_001083925). Primers span an intron. |
| Primer set 37 | JKLINE1FW<br>JKLINE1RV<br>Amplicon W,<br>Ext. Data<br>FIG. 6f. | CTGCCTTGCAAGAAGAGAGC<br>AGTGCTGCGTTCTGATGATG | Murine LINE-1 5'UTR, positions 392-412, sense orientation.<br>Murine LINE-1 5'UTR, 596-616, antisense orientation.<br>Used in RT-qPCR experiments to assess expression of murine L1 RNA. |
| Primer set 38 | P16MouseF<br>P16MouseR | CCAGGGCCGTGTGCAT<br>TACGTGAACGTTGCCCATCA | Cdkn2a, sense orientation.<br>Cdkn2a, antisense orientation.<br>Used for RT-qPCR of the mRNA of the Cdkn2a gene (NM_009877). Primers span an intron. |
| Primer set 39 | GBMMP3FW<br>GBMMP3RV | GACTCAAGGGTGGATGCTGT<br>CCAACTGCGAAGATCCACTG | Mmp3, sense orientation.<br>Mmp3, antisense orientation.<br>Used for RT-qPCR of the mRNA of the Mmp3 gene (NM_0108209). Primers span an intron. |
| Primer set 40 | GBIL6FW<br>GBIL6RV | CGGAGAGGAGACTTCACAGAGGA<br>TTTCCACGATTTCCCAGAGAACA | Il-6, sense orientation.<br>Il-6, antisense orientation.<br>Used for RT-qPCR of the mRNA of the Il6 gene (NM_031168). Primers span an intron. |
| Primer set 41 | MMPAI1FW<br>MMPAI1RV | GGAAGGGCAACATGACCAGG<br>AGCTGCTCTTGGTCGGAAAG | Pai1, sense orientation.<br>Pai1, antisense orientation.<br>Used for RT-qPCR of the mRNA of the Pai1 gene (NM_008871). Primers span an intron. |
| Primer set 42 | APACACAF<br>APACACAR | CTGGCTGCATCCATTATGTCA<br>TGGTAGACTGCCCGTGTGAA | Acaca, sense orientation.<br>Acaca, antisense orientation.<br>Used for RT-qPCR of the mRNA of the Acaca gene (NM_133360). Primers span an intron. |

TABLE 1 -continued

List of primers used in PCR analysis₁

| Number | Designation | Sequence | Notes |
|---|---|---|---|
| Primer set 43 | APFASNF<br>APFASNR | CTGCGTGGCTATGATTATGG<br>AGGTTGCTGTCGTCTGTAGT | Fasn, sense orientation.<br>Fasn, antisense orientation.<br>Used for RT-qPCR of the mRNA of the Fasn gene (NM_007988). Primers span an intron. |
| Primer set 44 | APSREBF1F<br>APSREBF1R | ACTTTTCCTTAACGTGGGCCT<br>CATCTCGGCCAGTGTCTGTT | Srebf1, sense orientation.<br>Srebf1, antisense orientation.<br>Used for RT-qPCR of the mRNA of the Srebf1 gene (NM_Q11480). Primers span an intron. |
| Primer set 45 | APCEBPAF<br>APCEBPAR | TTCGGGTCGCTGGATCTCTA<br>TCAAGGAGAAACCACCACGG | C/EBPα, sense orientation.<br>C/EBPα, antisense orientation.<br>Used for RT-qPCR of the mRNA of the C/EBPα gene (NM_007678). |
| Primer set 46 | APACACBF<br>APACACBR | AGAAGCGAGCACTGCAAGGTTG<br>GGAAGATGGACTCCACCTGGTT | Acacb, sense orientation.<br>Acacb, antisense orientation.<br>Used for RT-qPCR of the mRNA of the Acacb gene (NM_133904). Primers span an intron. |
| Primer set 47 | APPPARGF<br>APPPARGR | TTCGCTGATGCACTGCCTAT<br>GGAATGCGAGTGGTCTTCCA | Pparg, sense orientation.<br>Pparg, antisense orientation.<br>Used for RT-qPCR of the mRNA of the Pparg gene (NM_011146). Primers span an intron. |
| Primer set 48 | MDMML1ORF1F<br>MDMML1ORF1R<br>Amplicon X,<br>Ext. Data<br>FIG. 6f. | ATCTGTCTCCCAGGTCTGCT<br>TCCTCCGTTTACCTTTCGCC | Murine LINE-1 ORF1, positions 1341-1360, sense orientation.<br>Murine LINE-1 ORF1, positions 1460-1441, antisense orientation.<br>Used in RT-qPCR experiments to assess expression of murine L1 RNA. |
| Primer set 49 | MDMML1ORF2F<br>MDMML1ORF2R<br>Amplicon Y,<br>Ext. Data<br>FIG. 6f. | GCTTCGGTGAAGTAGCTGGA<br>TTCGTTAGAGTCACGCCGAG | Murine LINE-1 ORF2, positions 4786-4805, sense orientation.<br>Murine LINE-1 ORF2, positions 4939-4920, antisense orientation.<br>Used in RT-qPCR experiments to assess expression of murine L1 RNA. |
| Primer set 50 | MDMML13UTRF<br>MDMML13UTRR<br>Amplicon Z,<br>Ext. Data<br>FIG. 6f. | AGCCAAATGGATGGACCTGG<br>AAGGAGGGGCATAGTGTCCA | Murine LINE-1 3'UTR, positions 6344-6363, sense orientation.<br>Murine LINE-1 3'UTR, positions 6538-6519, antisense orientation.<br>Used in RT-qPCR experiments to assess expression of murine L1 RNA. |
| Primer set 51 | MDMML1TFF<br>MDMML1TFR | ATCCGGACCAGAGGACAGG<br>ATGGCGACCGCTGCTG | Murine LINE-1 5'UTR sense orientation.<br>Murine LINE-1 5'UTR, antisense orientation.<br>Primers amplify one of the polymorphisms of L1Tf(I-III) families. |
| Primer set 52 | MDMML1MDNF<br>MDMML1MDNR | AGAGAACCGGACCCAATCCA<br>GCTTGTGCCCCTACTCAGAC | Murine LINE-1 5'UTR sense orientation.<br>Murine LINE-1 5'UTR, antisense orientation.<br>Primers amplify one of the polymorphisms of L1MdN(I) families. |
| Primer set 53 | MDMML1MDAF<br>MDMML1MDAF | TCCCCACGGGATCCTAAGAC<br>CTCTGCAGGCAAGCTCTCTT | Murine LINE-1 5'UTR sense orientation.<br>Murine LINE-1 5'UTR, antisense orientation.<br>Primers amplify one of the polymorphisms of L1MdA (IV-VII) families. |

₁1 All sequences are listed in the 5'->3' orientation. Primer sets 1-30 are specific for the listed human genes; primer sets 31-53 are murine-specific.

²2 All LINE-1 positions are relative to the L1Hs consensus sequence (Repbase, http://www.girinst.org/repbase/).

³ See Coufal, N.G. et al. L1 retrotransposition in human neural progenitor cells. Nature 460, 1127-31 (2009).

⁴4 See Gautier, G. et al. A type I interferon autocrine-paracrine loop is involved in Toll-like receptor-induced interleukin-12p70 secretion by dendritic cells. J. Exp. Med. 201,1435-46 (2005).

TABLE 2

List of antibodies

| Antibody | Antibody species | Vendor | Catalog Number | Application |
|---|---|---|---|---|
| GAPDH | Rabbit | Cell Signaling | 5174 | Loading control for immunoblotting |
| GAPDH | Mouse | Sigma | G8795 | Loading control for immunoblotting |
| p16 | Mouse | Santa Cruz | sc-756 | Immunoblotting |
| p16 | Mouse | Santa Cruz | sc-56330 (JC8) | Immunofluorescence |
| p21 | Rabbit | Santa Cruz | sc-397 | Immunoblotting |
| RB1 | Mouse | BD Biosciences | 554136 | Immunoblotting, ChIP |
| TREX1 | Rabbit | Cell Signaling | 12215 | Immunoblotting |
| FOXA1 | Rabbit | Abcam | ab170933 | Immunoblotting |
| FOXA1 | Goat | Abcam | ab5089 | ChIP |
| Phospho-STAT1 (Tyr701) | Mouse | Santa Cruz | sc-8394 | Immunofluorescence |
| Phospho-STAT2 (Tyr689) | Mouse | Millipore | 07-224 | Immunofluorescence |
| STAT2 | Rabbit | Cell Signaling | 4594S | Immunoblotting |
| IRF7 | Rabbit | Abcam | ab109255 | Immunoblotting |
| IRF9 | Rabbit | Novus Bio | NBP2-16991 | Immunofluorescence |
| BrdU | Mouse | BD Biosciences | 555627 | Immunofluorescence |
| γ-H2AX | Mouse | Millipore | 05-636 | Immunofluorescence |
| F4/80 | Rat | Abcam | ab6640 (CI:A3-1) | Immunofluorescence |
| ssDNA | Mouse | Enzo | MAb F7-26 | Immunofluorescence |
| DNA-RNA hybrids | Mouse | Kerafast | ENH001 (S9.6) | Immunofluorescence |
| LaminB1 | Goat | Santa Cruz | Sc-6216 (C-20) | Immunofluorescence |
| IL-6 | Rabbit | Cell Signaling | 12912 | Immunofluorescence |
| Human LINE-1 ORF1 | Rabbit | Gift of K. H. Burns, Johns Hopkins[1] | | Immunofluorescence |
| Mouse LINE-1 Orf1 | Rabbit | J. D. Boeke, abEA02 (RabMAb clone NYU-2-1_2 | | Immunofluorescence |

[1]See Rodic, N. et al. Long interspersed element-1 protein expression is a hallmark of many human cancers. Am. J. Pathol. 184, 1280-6 (2014).

TABLE 3

List of expressed L1 elements identified by long range RT-PCR

| ID | Chromosome | Coordinates (element length) | Family | Count | Intact |
|---|---|---|---|---|---|
| L1-07 | chr14 | 63,115,693-63,121,722 (6,029 bp) | L1HS | 16 | Yes |
| L1-09 | chrX | 11,934,270-11,940,496 (6,226 bp) | L1HS | 10 | Yes |
| L1-13 | chr17 | 66,596,080-66,602,096 (6,016 bp) | L1HS | 9 | Yes |
| L1-20 | chr14 | 70,546,288-70,552,339 (6,051 bp) | L1HS | 6 | Yes |
| L1-24 | chr7 | 49,679,257-49,685,289 (6,032 bp) | L1HS | 5 | Yes |
| L1-25 | chr4 | 21,158,389-21,164,420 (6,031 bp) | L1HS | 5 | Yes |
| L1-54 | chr17 | 9,614,984-9,621,024 (6,040 bp) | L1HS | 3 | Yes |
| L1-55 | chrX | 155,515,003-155,521,032 (6,029 bp) | L1HS | 2.125 | Yes |
| L1-58 | chrX | 47,782,657-47,788,686 (6,029 bp) | L1HS | 2.125 | Yes |
| L1-59 | chr1 | 118,851,349-118,857,375 (6,026 bp) | L1HS | 2.125 | Yes |
| L1-62 | chr16 | 9,583,477-9,589,517 (6,040 bp) | L1HS | 2.125 | Yes |
| L1-76 | chr2 | 166,987,450-166,993,486 (6,036 bp) | L1HS | 2 | Yes |
| L1-85 | chr8 | 128,451,975-128,458,006 (6,031 bp) | L1HS | 1.8 | Yes |
| L1-116 | chr5 | 104,517,585-104,523,614 (6,029 bp) | L1HS | 1 | Yes |
| L1-143 | chr1 | 180,865,798-180,871,853 (6,055 bp) | L1HS | 1 | Yes |
| L1-171 | chr10 | 98,781,926-98,787,958 (6,032 bp) | L1HS | 0.8 | Yes |
| L1-172 | chr6 | 2,416,758-2,422,787 (6,029 bp) | L1HS | 0.8 | Yes |
| L1-180 | chr3 | 159,094,350-159,100,395 (6,045 bp) | L1HS | 1 | Yes |
| L1-218 | chr15 | 70,728,652-70,734,159 (5,507 bp) | L1HS | 1 | Yes |
| Sum: L1HS intact Counts: 71.9 Individual elements: 19 | | | | | |
| L1-06 | chr7 | 70,193,829-70,199,858 (6,029 bp) | L1HS | 18 | |
| L1-08 | chr4 | 87,346,624-87,352,647 (6,023 bp) | L1HS | 11 | |
| L1-17 | chr4 | 78,346,978-78,353,011 (6,033 bp) | L1HS | 7 | |
| L1-23 | chr18 | 13,975,361-13,980,770 (5,409 bp) | L1HS | 5 | |
| L1-31 | chr9 | 110,787,598-110,793,630 (6,032 bp) | L1HS | 4 | |
| L1-35 | chr1 | 196,218,871-196,224,903 (6,032 bp) | L1HS | 4 | |
| L1-37 | chr3 | 103,555,522-103,561,554 (6,032 bp) | L1HS | 4 | |
| L1-38 | chr12 | 3,498,696-3,504,729 (6,033 bp) | L1HS | 4 | |
| L1-40 | chr16 | 65,686,512-65,692,528 (6,016 bp) | L1HS | 4 | |
| L1-41 | chrX | 50,018,977-50,025,006 (6,029 bp) | L1HS | 4 | |
| L1-45 | chr4 | 136,292,503-136,298,555 (6,052 bp) | L1HS | 4 | |
| L1-50 | chr3 | 26,397,518-26,403,541 (6,023 bp) | L1HS | 3 | |
| L1-56 | chr20 | 23,422,609-23,428,641 (6,032 bp) | L1HS | 2.125 | |
| L1-57 | chr1 | 125,119,462-125,125,488 (6,026 bp) | L1HS | 2.125 | |
| L1-60 | chr20 | 11,629,280-11,635,312 (6,032 bp) | L1HS | 2.125 | |
| L1-61 | chr13 | 76,612,324-76,618,354 (6,030 bp) | L1HS | 2.125 | |
| L1-64 | chr2 | 86,660,186-86,666,388 (6,202 bp) | L1HS | 2 | |
| L1-72 | chr3 | 132,945,507-132,951,535 (6,028 bp) | L1HS | 2 | |
| L1-80 | chr5 | 166,966,282-166,972,316 (6,034 bp) | L1HS | 2 | |
| L1-81 | chr4 | 19,077,399-19,083,430 (6,031 bp) | L1HS | 2 | |

TABLE 3-continued

List of expressed L1 elements identified by long range RT-PCR

| | | | | |
|---|---|---|---|---|
| L1-86 | chr7 | 96,846,151-96,852,181 (6,030 bp) | L1HS | 1.8 |
| L1-87 | chr2 | 230,336,570-230,342,014 (5,444 bp) | L1HS | 1.8 |
| L1-88 | chr4 | 135,177,641-135,183,248 (5,607 bp) | L1HS | 1.8 |
| L1-89 | chr4 | 52,534,972-52,540,999 (6,027 bp) | L1HS | 1.8 |
| L1-90 | chr5 | 81,612,591-81,618,619 (6,028 bp) | L1HS | 2 |
| L1-91 | chr8 | 128,890,989-128,897,136 (6,147 bp) | L1HS | 2 |
| L1-96 | chr11 | 87,339,532-87,345,562 (6,030 bp) | L1HS | 2 |
| L1-97 | chr5 | 177,771,244-177,777,273 (6,029 bp) | L1HS | 2 |
| L1-98 | chr5 | 166,140,692-166,146,724 (6,032 bp) | L1HS | 2 |
| L1-100 | chr4 | 62,726,449-62,732,470 (6,021 bp) | L1HS | 1 |
| L1-103 | chr1 | 80,942,648-80,948,701 (6,053 bp) | L1HS | 1 |
| L1-114 | chr10 | 105,775,021-105,781,052 (6,031 bp) | L1HS | 1 |
| L1-115 | chr5 | 34,144,346-34,150,370 (6,024 bp) | L1HS | 1 |
| L1-133 | chr7 | 113,530,583-113,536,613 (6,030 bp) | L1HS | 1 |
| L1-135 | chr1 | 180,330,072-180,336,104 (6,032 bp) | L1HS | 1 |
| L1-136 | chr1 | 118,634,254-118,640,283 (6,029 bp) | L1HS | 1 |
| L1-137 | chrX | 54,117,700-54,123,731 (6,031 bp) | L1HS | 1 |
| L1-138 | chrX | 147,650,235-147,656,268 (6,033 bp) | L1HS | 1 |
| L1-142 | chr1 | 187,217,153-187,223,183 (6,030 bp) | L1HS | 1 |
| L1-144 | chr12 | 69,772,911-69,778,942 (6,031 bp) | L1HS | 1 |
| L1-149 | chr1 | 239,622,999-239,629,024 (6,025 bp) | L1HS | 1 |
| L1-150 | chr1 | 146,716,693-146,722,719 (6,026 bp) | L1HS | 1 |
| L1-157 | chr3 | 19,495,494-19,501,518 (6,024 bp) | L1HS | 1 |
| L1-169 | chr5 | 58,383,173-58,389,205 (6,032 bp) | L1HS | 0.8 |
| L1-170 | chr6 | 19,761,393-19,767,419 (6,026 bp) | L1HS | 0.8 |
| L1-173 | chr2 | 36,112,007-36,118,038 (6,031 bp) | L1HS | 0.8 |
| L1-179 | chr6 | 112,700,246-112,706,279 (6,033 bp) | L1HS | 1 |
| L1-181 | chr3 | 108,745,901-108,751,932 (6,031 bp) | L1HS | 1 |
| L1-182 | chr4 | 15,838,047-15,844,384 (6,337 bp) | L1HS | 1 |
| L1-184 | chr8 | 135,872,363-135,878,417 (6,054 bp) | L1HS | 1 |
| L1-187 | chr13 | 58,673,408-58,679,295 (5,887 bp) | L1HS | 1 |
| L1-194 | chr1 | 85,745,020-85,749,612 (4,592 bp) | L1HS | 1 |
| L1-196 | chr15 | 82,882,394-82,888,420 (6,026 bp) | L1HS | 1 |
| L1-197 | chr15 | 51,416,717-51,422,747 (6,030 bp) | L1HS | 1 |
| L1-199 | chr2 | 4,730,230-4,736,261 (6,031 bp) | L1HS | 1 |
| L1-212 | chr3 | 54,393,823-54,400,093 (6,270 bp) | L1HS | 1 |
| Sum: L1HS non-intact Counts: 132.1 Individual elements: 56 | | | | |
| L1-05 | chr3 | 141,764,155-141,770,160 (6,005 bp) | L1PA2 | 24 |
| L1-10 | chr4 | 164,097,249-164,103,279 (6,030 bp) | L1PA2 | 9 |
| L1-12 | chr17 | 61,106,730-61,112,789 (6,059 bp) | L1PA2 | 9 |
| L1-18 | chr22 | 11,955,882-11,962,029 (6,147 bp) | L1PA2 | 6 |
| L1-22 | chr12 | 67,896,709-67,902,725 (6,016 bp) | L1PA2 | 5 |
| L1-27 | chr3 | 175,781,211-175,786,413 (5,202 bp) | L1PA2 | 5 |
| L1-30 | chr13 | 73,637,028-73,643,060 (6,032 bp) | L1PA2 | 5 |
| L1-33 | chr4 | 98,316,999-98,322,499 (5,500 bp) | L1PA2 | 4 |
| L1-34 | chr3 | 178,856,449-178,862,480 (6,031 bp) | L1PA2 | 4 |
| L1-39 | chr1 | 169,251,062-169,257,094 (6,032 bp) | L1PA2 | 4 |
| L1-42 | chr3 | 119,000,971-119,006,991 (6,020 bp) | L1PA2 | 4 |
| L1-53 | chr5 | 106,424,883-106,430,882 (5,999 bp) | L1PA2 | 3 |
| L1-66 | chr14 | 86,095,435-86,101,470 (6,035 bp) | L1PA2 | 2 |
| L1-73 | chr4 | 65,992,800-65,998,803 (6,003 bp) | L1PA2 | 2 |
| L1-74 | chr10 | 99,149,238-99,155,259 (6,021 bp) | L1PA2 | 2 |
| L1-75 | chr1 | 72,826,947-72,833,271 (6,324 bp) | L1PA2 | 2 |
| L1-77 | chr7 | 32,461,029-32,467,034 (6,005 bp) | L1PA2 | 2 |
| L1-83 | chr3 | 67,082,246-67,088,304 (6,058 bp) | L1PA2 | 2 |
| L1-101 | chr12 | 102,826,678-102,832,665 (5,987 bp) | L1PA2 | 1 |
| L1-105 | chr20 | 25,326,450-25,331,184 (4,734 bp) | L1PA2 | 1 |
| L1-107 | chr13 | 50,978,555-50,984,571 (6,016 bp) | L1PA2 | 1 |
| L1-108 | chr4 | 102,204,431-102,210,459 (6,028 bp) | L1PA2 | 1 |
| L1-111 | chrX | 113,084,049-113,090,072 (6,023 bp) | L1PA2 | 1 |
| L1-118 | chr21 | 9,333,222-9,339,374 (6,152 bp) | L1PA2 | 1 |
| L1-123 | chr2 | 129,037,643-129,043,675 (6,032 bp) | L1PA2 | 1 |
| L1-125 | chr5 | 85,454,310-85,460,328 (6,018 bp) | L1PA2 | 1 |
| L1-128 | chr5 | 4,611,929-4,617,955 (6,026 bp) | L1PA2 | 1 |
| L1-130 | chr16 | 48,768,072-48,774,104 (6,032 bp) | L1PA2 | 1 |
| L1-131 | chr6 | 162,989,238-162,995,263 (6,025 bp) | L1PA2 | 1 |
| L1-132 | chr8 | 68,358,979-68,364,479 (5,500 bp) | L1PA2 | 1 |
| L1-134 | chr5 | 65,160,518-65,166,549 (6,031 bp) | L1PA2 | 1 |
| L1-140 | chr4 | 119,273,614-119,279,671 (6,057 bp) | L1PA2 | 1 |
| L1-145 | chr3 | 24,088,959-24,094,992 (6,033 bp) | L1PA2 | 1 |
| L1-151 | chr12 | 108,993,448-108,999,474 (6,026 bp) | L1PA2 | 1 |
| L1-164 | chr17 | 41,200,368-41,206,401 (6,033 bp) | L1PA2 | 1 |
| L1-167 | chr3 | 118,910,744-118,916,772 (6,028 bp) | L1PA2 | 1 |
| L1-175 | chr2 | 197,687,033-197,693,062 (6,029 bp) | L1PA2 | 1 |
| L1-177 | chrX | 154,935,536-154,941,561 (6,025 bp) | L1PA2 | 1 |
| L1-186 | chr6 | 83,797,243-83,803,271 (6,028 bp) | L1PA2 | 1 |
| L1-188 | chr8 | 87,621,331-87,626,401 (5,070 bp) | L1PA2 | 1 |

TABLE 3-continued

List of expressed L1 elements identified by long range RT-PCR

| | | | | |
|---|---|---|---|---|
| L1-189 | chr11 | 100,649,611-100,655,672 (6,061 bp) | L1PA2 | 1 |
| L1-198 | chr15 | 54,904,988-54,911,051 (6,063 bp) | L1PA2 | 1 |
| L1-202 | chr2 | 153,781,069-153,787,086 (6,017 bp) | L1PA2 | 1 |
| L1-209 | chr1 | 85,923,568-85,927,951 (4,383 bp) | L1PA2 | 1 |
| L1-211 | chr2 | 156,251,019-156,257,086 (6,067 bp) | L1PA2 | 1 |
| L1-215 | chr4 | 132,940,946-132,946,970 (6,024 bp) | L1PA2 | 1 |
| L1-221 | chrX | 50,056,644-50,062,676 (6,032 bp) | L1PA2 | 1 |
| L1-223 | chrX | 113,337,323-113,343,354 (6,031 bp) | L1PA2 | 1 |
| | | Sum: L1PA2 Counts: 124 Individual elements: 48 | | |
| L1-03 | chr19 | 42,768,603-42,774,543 (5,940 bp) | L1PA3 | 31 |
| L1-04 | chr8 | 55,046,402-55,052,502 (6,100 bp) | L1PA3 | 28 |
| L1-11 | chr12 | 118,657,390-118,663,531 (6,141 bp) | L1PA3 | 9 |
| L1-15 | chr1 | 176,307,883-176,313,876 (5,993 bp) | L1PA3 | 7 |
| L1-19 | chr4 | 175,016,241-175,022,252 (6,011 bp) | L1PA3 | 6 |
| L1-26 | chr18 | 49,212,269-49,218,417 (6,148 bp) | L1PA3 | 5 |
| L1-29 | chr11 | 22,646,426-22,652,446 (6,020 bp) | L1PA3 | 5 |
| L1-36 | chr2 | 22,980,654-22,984,410 (3,756 bp) | L1PA3 | 4 |
| L1-44 | chr10 | 109,602,039-109,607,567 (5,528 bp) | L1PA3 | 4 |
| L1-46 | chr7 | 63,728,965-63,735,094 (6,129 bp) | L1PA3 | 4 |
| L1-48 | chr14 | 38,631,448-38,637,485 (6,037 bp) | L1PA3 | 4 |
| L1-49 | chr19 | 42,743,461-42,749,399 (5,938 bp) | L1PA3 | 4 |
| L1-52 | chr4 | 123,632,778-123,638,935 (6,157 bp) | L1PA3 | 3 |
| L1-65 | chr2 | 96,375,482-96,381,632 (6,150 bp) | L1PA3 | 2 |
| L1-69 | chr1 | 100,662,482-100,668,126 (5,644 bp) | L1PA3 | 2 |
| L1-70 | chr5 | 25,077,154-25,083,186 (6,032 bp) | L1PA3 | 2 |
| L1-78 | chr12 | 78,502,931-78,509,088 (6,157 bp) | L1PA3 | 2 |
| L1-82 | chr6 | 80,844,240-80,850,277 (6,037 bp) | L1PA3 | 2 |
| L1-84 | chr8 | 69,015,505-69,021,651 (6,146 bp) | L1PA3 | 2 |
| L1-94 | chr4 | 88,916,060-88,922,204 (6,144 bp) | L1PA3 | 2 |
| L1-104 | chr4 | 142,249,845-142,255,868 (6,023 bp) | L1PA3 | 1 |
| L1-110 | chr3 | 24,276,690-24,282,186 (5,496 bp) | L1PA3 | 1 |
| L1-113 | chr4 | 119,061,402-119,067,563 (6,161 bp) | L1PA3 | 1 |
| L1-117 | chr12 | 10,343,959-10,349,500 (5,541 bp) | L1PA3 | 1 |
| L1-121 | chr3 | 112,658,647-112,664,665 (6,018 bp) | L1PA3 | 1 |
| L1-124 | chr9 | 68,274,827-68,280,864 (6,037 bp) | L1PA3 | 1 |
| L1-126 | chr5 | 75,792,130-75,798,187 (6,057 bp) | L1PA3 | 1 |
| L1-139 | chr11 | 31,540,511-31,546,645 (6,134 bp) | L1PA3 | 1 |
| L1-141 | chr3 | 145,924,279-145,930,431 (6,152 bp) | L1PA3 | 1 |
| L1-147 | chr8 | 91,887,863-91,893,862 (5,999 bp) | L1PA3 | 1 |
| L1-148 | chrX | 94,858,876-94,864,901 (6,025 bp) | L1PA3 | 1 |
| L1-152 | chr18 | 55,886,913-55,892,940 (6,027 bp) | L1PA3 | 1 |
| L1-154 | chr9 | 125,006,549-125,012,715 (6,166 bp) | L1PA3 | 1 |
| L1-156 | chr6 | 71,826,216-71,832,235 (6,019 bp) | L1PA3 | 1 |
| L1-158 | chr8 | 91,191,345-91,197,369 (6,024 bp) | L1PA3 | 1 |
| L1-159 | chr12 | 55,586,438-55,592,480 (6,042 bp) | L1PA3 | 1 |
| L1-165 | chr2 | 97,521,921-97,528,067 (6,146 bp) | L1PA3 | 1 |
| L1-166 | chr6 | 126,670,052-126,676,070 (6,018 bp) | L1PA3 | 1 |
| L1-174 | chr12 | 80,143,556-80,149,577 (6,021 bp) | L1PA3 | 1 |
| L1-176 | chr12 | 51,562,132-51,568,340 (6,208 bp) | L1PA3 | 1 |
| L1-178 | chr9 | 17,536,062-17,542,081 (6,019 bp) | L1PA3 | 1 |
| L1-183 | chr12 | 80,074,170-80,080,329 (6,159 bp) | L1PA3 | 1 |
| L1-185 | chr6 | 48,733,849-48,740,059 (6,210 bp) | L1PA3 | 1 |
| L1-190 | chr4 | 82,171,911-82,177,138 (5,227 bp) | L1PA3 | 1 |
| L1-191 | chr15 | 32,045,176-32,051,279 (6,103 bp) | L1PA3 | 1 |
| L1-192 | chr17 | 71,351,460-71,357,401 (5,941 bp) | L1PA3 | 1 |
| L1-193 | chr5 | 99,339,116-99,345,270 (6,154 bp) | L1PA3 | 1 |
| L1-195 | chr5 | 122,509,114-122,515,140 (6,026 bp) | L1PA3 | 1 |
| L1-200 | chr10 | 35,855,169-35,861,196 (6,027 bp) | L1PA3 | 1 |
| L1-201 | chr12 | 31,159,575-31,165,595 (6,020 bp) | L1PA3 | 1 |
| L1-203 | chr14 | 37,766,297-37,772,332 (6,035 bp) | L1PA3 | 1 |
| L1-206 | chr14 | 56,013,511-56,019,543 (6,032 bp) | L1PA3 | 1 |
| L1-210 | chr2 | 95,866,030-95,872,191 (6,161 bp) | L1PA3 | 1 |
| L1-214 | chr4 | 94,835,259-94,841,286 (6,027 bp) | L1PA3 | 1 |
| L1-217 | chr7 | 84,049,212-84,055,231 (6,019 bp) | L1PA3 | 1 |
| L1-219 | chr16 | 12,069,684-12,075,804 (6,120 bp) | L1PA3 | 1 |
| L1-222 | chrX | 55,680,654-55,686,684 (6,030 bp) | L1PA3 | 1 |
| L1-224 | chrX | 149,432,338-149,438,331 (5,993 bp) | L1PA3 | 1 |
| | | Sum: L1PA3 Counts: 166 Individual elements: 58 | | |
| L1-01 | chr18 | 9,165,216-9,171,138 (5,922 bp) | L1PA4 | 46 |
| L1-14 | chr3 | 29,978,961-29,984,962 (6,001 bp) | L1PA4 | 7 |
| L1-16 | chr6 | 83,330,453-83,336,586 (6,133 bp) | L1PA4 | 7 |
| L1-21 | chr6 | 139,217,130-139,223,263 (6,133 bp) | L1PA4 | 6 |
| L1-28 | chr8 | 49,874,774-49,880,758 (5,984 bp) | L1PA4 | 5 |
| L1-32 | chr5 | 176,077,678-176,083,819 (6,141 bp) | L1PA4 | 4 |
| L1-43 | chr5 | 33,095,404-33,101,548 (6,144 bp) | L1PA4 | 4 |
| L1-47 | chr4 | 48,864,081-48,870,233 (6,152 bp) | L1PA4 | 4 |

TABLE 3-continued

List of expressed L1 elements identified by long range RT-PCR

| | | | | |
|---|---|---|---|---|
| L1-51 | chr5 | 130,779,991-130,786,158 (6,167 bp) | L1PA4 | 3 |
| L1-63 | chr6 | 7,942,696-7,948,800 (6,104 bp) | L1PA4 | 2 |
| L1-71 | chr7 | 56,505,920-56,512,049 (6,129 bp) | L1PA4 | 2 |
| L1-79 | chr10 | 93,517,474-93,523,652 (6,178 bp) | L1PA4 | 2 |
| L1-92 | chr21 | 9,182,589-9,188,720 (6,131 bp) | L1PA4 | 2 |
| L1-93 | chr4 | 173,772,935-173,779,072 (6,137 bp) | L1PA4 | 2 |
| L1-95 | chr1 | 125,011,752-125,017,885 (6,133 bp) | L1PA4 | 2 |
| L1-99 | chr9 | 90,682,773-90,689,210 (6,437 bp) | L1PA4 | 2 |
| L1-102 | chr10 | 64,014,843-64,021,048 (6,205 bp) | L1PA4 | 1 |
| L1-112 | chr15 | 76,776,415-76,782,548 (6,133 bp) | L1PA4 | 1 |
| L1-119 | chr12 | 11,373,698-11,379,329 (5,631 bp) | L1PA4 | 1 |
| L1-120 | chr19 | 24,012,879-24,018,978 (6,099 bp) | L1PA4 | 1 |
| L1-122 | chr3 | 99,031,289-99,037,430 (6,141 bp) | L1PA4 | 1 |
| L1-129 | chr10 | 15,664,019-15,669,631 (5,612 bp) | L1PA4 | 1 |
| L1-146 | chr4 | 90,478,877-90,483,706 (4,829 bp) | L1PA4 | 1 |
| L1-153 | chrX | 76,878,709-76,885,597 (6,888 bp) | L1PA4 | 1 |
| L1-155 | chr18 | 43,282,426-43,288,579 (6,153 bp) | L1PA4 | 1 |
| L1-160 | chr19 | 20,486,826-20,493,102 (6,276 bp) | L1PA4 | 1 |
| L1-161 | chr1 | 200,181,868-200,188,010 (6,142 bp) | L1PA4 | 1 |
| L1-162 | chr11 | 100,034,468-100,040,624 (6,156 bp) | L1PA4 | 1 |
| L1-163 | chr20 | 29,365,560-29,370,431 (4,871 bp) | L1PA4 | 1 |
| L1-168 | chr5 | 78,706,259-78,712,394 (6,135 bp) | L1PA4 | 1 |
| L1-204 | chr1 | 83,178,675-83,184,836 (6,161 bp) | L1PA4 | 1 |
| L1-205 | chr3 | 39,366,145-39,372,264 (6,119 bp) | L1PA4 | 1 |
| L1-208 | chr18 | 45,793,571-45,799,710 (6,139 bp) | L1PA4 | 1 |
| L1-216 | chr5 | 39,030,830-39,036,977 (6,147 bp) | L1PA4 | 1 |
| Sum: L1PA4 Counts: 118 Individual elements: 34 | | | | |
| L1-02 | chr5 | 80,840,410-80,845,999 (5,589 bp) | L1PA5 | 36 |
| L1-67 | chr12 | 370,113-376,219 (6,106 bp) | L1PA5 | 2 |
| L1-68 | chr11 | 95,811,406-95,816,742 (5,336 bp) | L1PA5 | 2 |
| L1-106 | chr10 | 109,822,318-109,828,350 (6,032 bp) | L1PA5 | 1 |
| L1-109 | chrX | 12,102,927-12,109,072 (6,145 bp) | L1PA5 | 1 |
| L1-127 | chr4 | 59,474,627-59,479,488 (4,861 bp) | L1PA5 | 1 |
| L1-207 | chr15 | 99,827,462-99,833,366 (5,904 bp) | L1PA5 | 1 |
| L1-213 | chr3 | 146,434,278-146,440,207 (5,929 bp) | L1PA5 | 1 |
| L1-220 | chr18 | 35,720,595-35,726,712 (6,117 bp) | L1PA5 | 1 |
| Sum: L1PA5 Counts: 46 Individual elements: 9 | | | | |

| Summary | Counts | % | Individual elements | % |
|---|---|---|---|---|
| L1HS intact | 71.9 | 10.9 | 19 | 8.5 |
| L1HS non-intact | 132.1 | 20.1 | 56 | 25.0 |
| L1PA2 | 124 | 18.8 | 48 | 21.4 |
| L1PA3 | 166 | 25.2 | 58 | 25.9 |
| L1 PA4 | 118 | 17.9 | 34 | 15.2 |
| L1PA5 | 46 | 7.0 | 9 | 4.0 |
| Sum: | 658 | 100.0 | 224 | 100.0 |

TABLE 4

Gene list used in GSEA for IFN-I (50 genes)

| Gene Symbol | Gene Name |
|---|---|
| ADAR | adenosine deaminase, RNA specific |
| BST2 | bone marrow stromal cell antigen 2 |
| CASP1 | caspase 1 |
| CAV1 | caveolin 1 |
| CXCL10 | C-X-C motif chemokine ligand 10 |
| DDX58 | DExD/H-box helicase 58 |
| EIF2AK2 | eukaryotic translation initiation factor 2 alpha kinase 2 |
| IFI16 | interferon gamma inducible protein 16 |
| IFI27 | interferon alpha inducible protein 27 |
| IFI30 | IFI30, lysosomal thiol reductase |
| IFI6 | interferon alpha inducible protein 6 |
| IFIH1 | interferon induced with helicase C domain 1 |
| IFIT1 | interferon induced protein with tetratricopeptide repeats 1 |
| IFIT2 | interferon induced protein with tetratricopeptide repeats 2 |
| IFIT3 | interferon induced protein with tetratricopeptide repeats 3 |
| IFITM1 | interferon induced transmembrane protein 1 |
| IFITM2 | interferon induced transmembrane protein 2 |
| IFITM3 | interferon induced transmembrane protein 3 |
| IFNA1 | interferon alpha 1 |
| IFNA2 | interferon alpha 2 |
| IFNA4 | interferon alpha 4 |
| IFNAR1 | interferon alpha and beta receptor subunit 1 |
| IFNAR2 | interferon alpha and beta receptor subunit 2 |
| IFNB1 | interferon beta 1 |
| IFNE | interferon epsilon |
| IFNW1 | interferon omega 1 |
| IRF1 | interferon regulatory factor 1 |
| IRF2 | interferon regulatory factor 2 |
| IRF3 | interferon regulatory factor 3 |
| IRF5 | interferon regulatory factor 5 |
| IRF7 | interferon regulatory factor 7 |
| IRF9 | interferon regulatory factor 9 |
| ISG15 | ISG15 ubiquitin-like modifier |
| ISG20 | interferon stimulated exonuclease gene 20 |
| JAK1 | Janus kinase 1 |
| JAK2 | Janus kinase 2 |

TABLE 4-continued

Gene list used in GSEA for IFN-I (50 genes)

| Gene Symbol | Gene Name |
|---|---|
| MAL | mal, T-cell differentiation protein |
| MET | MET proto-oncogene, receptor tyrosine kinase |
| MNDA | myeloid cell nuclear differentiation antigen |
| MX1 | MX dynamin like GTPase 1 |
| MX2 | MX dynamin like GTPase2 |
| MYD88 | myeloid differentiation primary response 88 |
| NOS2 | nitric oxide synthase 2 |
| OAS1 | 2'-5'-oligoadenylate synthetase 1 |
| OAS2 | 2'-5'-oligoadenylate synthetase 2 |
| STAT1 | signal transducer and activator of transcription 1 |
| STAT2 | signal transducer and activator of transcription 2 |
| STAT3 | signal transducer and activator of transcription 3 |
| TMEM173 | transmembrane protein 173 |
| TNFSF10 | tumor necrosis factor superfamily member 10 |

TABLE 5

GSEA analysis of KEGG pathways comparing early passage with early senescence
UPREGULATED FROM EARLY PASSAGE (EP) TO EARLY SENESCENCE (SEN-E)

| PATHWAY NAME | SIZE | ES | NES | NOM p-val | FDR p-val |
|---|---|---|---|---|---|
| KEGG_ASTHMA | 28 | 0.7237 | 1.7864 | <1.00E−03 | <1.00E−02 |
| KEGG_GRAFT_VERSUS_HOST_DISEASE | 35 | 0.6852 | 1.7654 | <1.00E−03 | <1.00E−02 |
| KEGG_CELL_ADHESION_MOLECULES_CAMS | 127 | 0.5578 | 1.7538 | <1.00E−03 | <1.00E−02 |
| KEGG_OLFACTORY_TRANSDUCTION | 367 | 0.4965 | 1.7468 | <1.00E−03 | <1.00E−02 |
| KEGG_TYPE_I_DIABETES_MELLITUS | 41 | 0.6457 | 1.7140 | <1.00E−03 | <1.00E−02 |
| KEGG_LYSOSOME | 119 | 0.5388 | 1.6878 | <1.00E−03 | <1.00E−02 |
| KEGG_COMPLEMENT_AND_COAGULATION_CASCADES | 67 | 0.5786 | 1.6854 | <1.00E−03 | <1.00E−02 |
| KEGG_ECM_RECEPTOR_INTERACTION | 84 | 0.5123 | 1.5487 | <1.00E−03 | <1.00E−02 |
| KEGG_LEISHMANIA_INFECTION | 68 | 0.5688 | 1.6559 | 1.79E−03 | 1.51E−02 |
| CUSTOM_SASP | 85 | 0.5471 | 1.6517 | 1.80E−03 | 1.51E−02 |
| KEGG_PRION_DISEASES | 34 | 0.6326 | 1.6397 | 1.84E−03 | 1.51E−02 |
| KEGG_CYTOKINE_CYTOKINE_RECEPTOR_INTERACTION | 254 | 0.4561 | 1.5705 | 1.62E−03 | 1.51E−02 |
| KEGG_TOLL_LIKE_RECEPTOR_SIGNALING_PATHWAY | 99 | 0.4868 | 1.4920 | 1.73E−03 | 1.51E−02 |
| KEGG_AUTOIMMUNE_THYROID_DISEASE | 48 | 0.5605 | 1.5336 | 3.77E−03 | 2.66E−02 |
| KEGG_ENDOCYTOSIS | 174 | 0.4365 | 1.4427 | 5.21E−03 | 3.49E−02 |
| KEGG_VIRAL_MYOCARDITIS | 68 | 0.5313 | 1.5277 | 8.68E−03 | 5.47E−02 |
| KEGG_RIG_I_LIKE_RECEPTOR_SIGNALING_PATHWAY | 67 | 0.5169 | 1.4977 | 9.06E−03 | 5.47E−02 |
| KEGG_INTESTINALIMMUNE_NETWORK_FOR_IGA_PRODUCTION | 45 | 0.5848 | 1.5670 | 1.08E−02 | 6.11E−02 |
| KEGG_HYPERTROPHIC_CARDIOMYOPATHY_HCM | 83 | 0.4814 | 1.4387 | 1.08E−02 | 6.11E−02 |
| KEGG_NEUROACTIVE_LIGAND_RECEPTOR_INTERACTION | 270 | 0.3779 | 1.2928 | 1.12E−02 | 6.14E−02 |
| KEGG_ANTIGEN_PROCESSING_AND_PRESENTATION | 73 | 0.5096 | 1.4914 | 1.28E−02 | 6.81E−02 |
| KEGG_EPITHELIAL_CELL_SIGNALING_IN_HELICOBACTER_PYLORI_INFECTION | 67 | 0.5106 | 1.5038 | 1.64E−02 | 8.00E−02 |
| KEGG_STARCH_AND_SUCROSE_METABOLISM | 45 | 0.5382 | 1.4727 | 1.68E−02 | 8.00E−02 |
| KEGG_MAPK_SIGNALING_PATHWAY | 263 | 0.3751 | 1.2821 | 1.64E−02 | 8.00E−02 |
| KEGG_ASCORBATE_AND_ALDARATE_METABOLISM | 21 | 0.6766 | 1.5631 | 2.06E−02 | 9.32E−02 |
| KEGG_NOD_LIKE_RECEPTOR_SIGNALING_PATHWAY | 60 | 0.5046 | 1.4370 | 2.16E−02 | 9.54E−02 |
| KEGG_ABC_TRANSPORTERS | 44 | 0.5440 | 1.4685 | 2.51E−02 | 1.08E−01 |
| KEGG_CYTOSOLIC_DNA_SENSING_PATHWAY | 52 | 0.5357 | 1.4752 | 2.64E−02 | 1.11E−01 |
| KEGG_NATURAL_KILLER_CELL_MEDIATED_CYTOTOXICITY | 123 | 0.4218 | 1.3254 | 2.83E−02 | 1.16E−01 |
| KEGG_OTHER_GLYCAN_DEGRADATION | 16 | 0.6967 | 1.5277 | 3.13E−02 | 1.24E−01 |
| KEGG_ALANINE_ASPARTATE_AND_GLUTAMATE_METABOLISM | 32 | 0.5745 | 1.4414 | 3.22E−02 | 1.24E−01 |
| KEGG_HEMATOPOIETIC_CELL_LINEAGE | 85 | 0.4547 | 1.3563 | 3.42E−02 | 1.27E−01 |
| KEGG_GLYCOSAMINOGLYCAN_BIOSYNTHESIS_CHONDROITIN_SULFATE | 22 | 0.6172 | 1.4675 | 3.59E−02 | 1.27E−01 |
| KEGG_ARRHYTHMOGENIC_RIGHT_VENTRICULAR_CARDIOMYOPATHY_ARVC | 74 | 0.4733 | 1.3664 | 3.54E−02 | 1.27E−01 |
| KEGG_DILATED_CARDIOMYOPATHY | 90 | 0.4453 | 1.3480 | 3.55E−02 | 1.27E−01 |
| KEGG_ALLOGRAFT_REJECTION | 35 | 0.5607 | 1.4452 | 3.92E−02 | 1.36E−01 |
| KEGG_CALCIUM_SIGNALING_PATHWAY | 173 | 0.3956 | 1.2886 | 4.46E−02 | 1.52E−01 |
| KEGG_REGULATION_OF_ACTIN_CYTOSKELETON | 210 | 0.3708 | 1.2426 | 4.93E−02 | 1.62E−01 |
| KEGG_STEROID_HORMONE_BIOSYNTHESIS | 49 | 0.4982 | 1.3661 | 5.14E−02 | 1.66E−01 |
| KEGG_LINOLEIC_ACID_METABOLISM | 29 | 0.5664 | 1.3972 | 5.98E−02 | 1.90E−01 |
| KEGG_FOCAL_ADHESION | 197 | 0.3646 | 1.2184 | 6.69E−02 | 2.09E−01 |
| KEGG_LEUKOCYTE_TRANSENDOTHELIAL_MIGRATION | 115 | 0.4016 | 1.2474 | 7.64E−02 | 2.34E−01 |
| KEGG_RETINOL_METABOLISM | 56 | 0.4497 | 1.2695 | 9.09E−02 | 2.70E−01 |
| KEGG_CHEMOKINE_SIGNALING_PATHWAY | 183 | 0.3602 | 1.1945 | 9.02E−02 | 2.70E−01 |
| KEGG_VASCULAR_SMOOTH_MUSCLE_CONTRACTION | 112 | 0.3902 | 1.2155 | 9.52E−02 | 2.78E−01 |
| KEGG_PATHOGENIC_ESCHERICHIA_COLI_INFECTION | 53 | 0.4475 | 1.2529 | 1.16E−01 | 3.33E−01 |
| KEGG_GLYCOSPHINGOLIPID_BIOSYNTHESIS_GANGLIO_SERIES | 15 | 0.5941 | 1.2772 | 1.73E−01 | 4.70E−01 |
| KEGG_SPHINGOLIPID_METABOLISM | 36 | 0.4710 | 1.2155 | 1.79E−01 | 4.70E−01 |
| KEGG_REGULATION_OF_AUTOPHAGY | 32 | 0.4748 | 1.2109 | 1.75E−01 | 4.70E−01 |
| KEGG_ARACHIDONIC_ACID_METABOLISM | 58 | 0.4212 | 1.1842 | 1.78E−01 | 4.70E−01 |
| KEGG_MELANOMA | 71 | 0.4044 | 1.1820 | 1.76E−01 | 4.70E−01 |
| KEGG_METABOLISM_OF_XENOBIOTICS_BY_CYTOCHROME_P450 | 62 | 0.4067 | 1.1816 | 1.88E−01 | 4.86E−01 |
| KEGG_AXON_GUIDANCE | 127 | 0.3540 | 1.1188 | 2.01E−01 | 5.12E−01 |
| KEGG_SNARE_INTERACTIONS_IN_VESICULAR_TRANSPORT | 38 | 0.4560 | 1.1899 | 2.08E−01 | 5.23E−01 |
| KEGG_NICOTINATE_AND_NICOTINAMIDE_METABOLISM | 22 | 0.5028 | 1.1791 | 2.20E−01 | 5.31E−01 |
| KEGG_TASTE_TRANSDUCTION | 50 | 0.4249 | 1.1650 | 2.19E−01 | 5.31E−01 |
| KEGG_NITROGEN_METABOLISM | 23 | 0.5036 | 1.1769 | 2.24E−01 | 5.33E−01 |
| KEGG_PPAR_SIGNALING_PATHWAY | 69 | 0.3797 | 1.1045 | 2.63E−01 | 5.77E−01 |

TABLE 5-continued

GSEA analysis of KEGG pathways comparing early passage with early senescence
UPREGULATED FROM EARLY PASSAGE (EP) TO EARLY SENESCENCE (SEN-E)

| PATHWAY NAME | SIZE | ES | NES | NOM p-val | FDR p-val |
| --- | --- | --- | --- | --- | --- |
| KEGG_JAK_STAT_SIGNALING_PATHWAY | 148 | 0.3340 | 1.0743 | 2.65E−01 | 5.77E−01 |
| KEGG_APOPTOSIS | 86 | 0.3669 | 1.0996 | 2.67E−01 | 5.77E−01 |
| KEGG_DRUG_METABOLISM_OTHER_ENZYMES | 44 | 0.4154 | 1.1191 | 2.81E−01 | 5.98E−01 |
| KEGG_DRUG_METABOLISM_CYTOCHROME_P450 | 63 | 0.3754 | 1.0737 | 2.93E−01 | 6.17E−01 |
| KEGG_INOSITOL_PHOSPHATE_METABOLISM | 54 | 0.3887 | 1.0905 | 3.04E−01 | 6.32E−01 |
| KEGG_PHOSPHATIDYLINOSITOL_SIGNALING_SYSTEM | 73 | 0.3662 | 1.0598 | 3.33E−01 | 6.77E−01 |
| KEGG_GLYCOSPHINGOLIPID_BIOSYNTHESIS_LACTO_AND_NEOLACTO_SERIES | 25 | 0.4434 | 1.0764 | 3.41E−01 | 6.86E−01 |
| KEGG_ALZHEIMERS_DISEASE | 153 | 0.3226 | 1.0359 | 3.57E−01 | 7.10E−01 |
| CUSTOM_IFN-I | 50 | 0.3781 | 1.0455 | 3.69E−01 | 7.18E−01 |
| KEGG_FRUCTOSE_AND_MANNOSE_METABOLISM | 34 | 0.3971 | 1.0438 | 3.81E−01 | 7.24E−01 |
| KEGG_GLYCOSAMINOGLYCAN_BIOSYNTHESIS_HEPARAN_SULFATE | 26 | 0.4256 | 1.0321 | 3.84E−01 | 7.24E−01 |
| KEGG_PANTOTHENATE_AND_COA_BIOSYNTHESIS | 16 | 0.4687 | 1.0325 | 4.21E−01 | 7.67E−01 |
| KEGG_N_GLYCAN_BIOSYNTHESIS | 46 | 0.3798 | 1.0231 | 4.32E−01 | 7.67E−01 |
| KEGG_GALACTOSE_METABOLISM | 26 | 0.4132 | 1.0123 | 4.50E−01 | 7.83E−01 |
| KEGG_GLYCEROLIPID_METABOLISM | 43 | 0.3679 | 0.9942 | 4.71E−01 | 8.12E−01 |
| KEGG_LONG_TERM_POTENTIATION | 66 | 0.3408 | 0.9796 | 4.99E−01 | 8.36E−01 |
| KEGG_RENIN_ANGIOTENSIN_SYSTEM | 17 | 0.4406 | 0.9772 | 4.95E−01 | 8.36E−01 |
| KEGG_MATURITY_ONSET_DIABETES_OF_THE_YOUNG | 25 | 0.4094 | 0.9773 | 5.17E−01 | 8.41E−01 |
| KEGG_WNT_SIGNALING_PATHWAY | 149 | 0.3005 | 0.9739 | 5.21E−01 | 8.41E−01 |
| KEGG_FC_GAMMA_R_MEDIATED_PHAGOCYTOSIS | 92 | 0.3151 | 0.9621 | 5.27E−01 | 8.41E−01 |
| KEGG_TGF_BETA_SIGNALING_PATHWAY | 85 | 0.3190 | 0.9616 | 5.47E−01 | 8.41E−01 |
| KEGG_BETA_ALANINE_METABOLISM | 22 | 0.4046 | 0.9468 | 5.33E−01 | 8.41E−01 |
| KEGG_ERBB_SIGNALING_PATHWAY | 86 | 0.3133 | 0.9462 | 5.80E−01 | 8.41E−01 |
| KEGG_BLADDER_CANCER | 40 | 0.3590 | 0.9449 | 5.46E−01 | 8.41E−01 |
| KEGG_TRYPTOPHAN_METABOLISM | 39 | 0.3580 | 0.9438 | 5.65E−01 | 8.41E−01 |
| KEGG_GLYCOSYLPHOSPHATIDYLINOSITOL_GPI_ANCHOR_BIOSYNTHESIS | 25 | 0.3874 | 0.9353 | 5.43E−01 | 8.41E−01 |
| KEGG_GLYCINE_SERINE_AND_THREONINE_METABOLISM | 30 | 0.3770 | 0.9349 | 5.68E−01 | 8.41E−01 |
| KEGG_PENTOSE_AND_GLUCURONATE_INTERCONVERSIONS | 23 | 0.3978 | 0.9310 | 5.80E−01 | 8.41E−01 |
| KEGG_STEROID_BIOSYNTHESIS | 16 | 0.4313 | 0.9285 | 5.80E−01 | 8.41E−01 |
| KEGG_GLYCOSAMINOGLYCAN_DEGRADATION | 21 | 0.3990 | 0.9236 | 5.81E−01 | 8.41E−01 |
| KEGG_PATHWAYS_IN_CANCER | 321 | 0.2739 | 0.9494 | 6.20E−01 | 8.70E−01 |
| KEGG_FC_EPSILON_RI_SIGNALING_PATHWAY | 79 | 0.3108 | 0.9249 | 6.15E−01 | 8.70E−01 |
| KEGG_CARDIAC_MUSCLE_CONTRACTION | 73 | 0.3058 | 0.8963 | 6.30E−01 | 8.77E−01 |
| KEGG_CYSTEINE_AND_METHIONINE_METABOLISM | 33 | 0.3410 | 0.8707 | 6.63E−01 | 9.16E−01 |
| KEGG_T_CELL_RECEPTOR_SIGNALING_PATHWAY | 106 | 0.2915 | 0.8919 | 7.09E−01 | 9.26E−01 |
| KEGG_GLIOMA | 62 | 0.3116 | 0.8857 | 6.93E−01 | 9.26E−01 |
| KEGG_ADHERENS_JUNCTION | 68 | 0.3059 | 0.8855 | 6.97E−01 | 9.26E−01 |
| KEGG_FATTY_ACID_METABOLISM | 42 | 0.3279 | 0.8719 | 6.83E−01 | 9.26E−01 |
| KEGG_BASAL_CELL_CARCINOMA | 55 | 0.3100 | 0.8612 | 7.21E−01 | 9.26E−01 |
| KEGG_PENTOSE_PHOSPHATE_PATHWAY | 26 | 0.3492 | 0.8408 | 7.11E−01 | 9.26E−01 |
| KEGG_BIOSYNTHESIS_OF_UNSATURATED_FATTY_ACIDS | 20 | 0.3583 | 0.8338 | 7.01E−01 | 9.26E−01 |
| KEGG_RIBOFLAVIN_METABOLISM | 16 | 0.3816 | 0.8159 | 7.21E−01 | 9.26E−01 |
| KEGG_ADIPOCYTOKINE_SIGNALING_PATHWAY | 67 | 0.3025 | 0.8755 | 7.38E−01 | 9.41E−01 |
| KEGG_GAP_JUNCTION | 87 | 0.2863 | 0.8629 | 7.78E−01 | 9.58E−01 |
| KEGG_TYPE_II_DIABETES_MELLITUS | 46 | 0.3026 | 0.8226 | 7.91E−01 | 9.67E−01 |
| KEGG_GLYCEROPHOSPHOLIPID_METABOLISM | 71 | 0.2827 | 0.8316 | 8.21E−01 | 9.91E−01 |
| KEGG_VASOPRESSIN_REGULATED_WATER_REABSORPTION | 44 | 0.2918 | 0.8032 | 8.31E−01 | 9.96E−01 |
| KEGG_TIGHT_JUNCTION | 128 | 0.2691 | 0.8537 | 8.45E−01 | 1.00E+00 |
| KEGG_GNRH_SIGNALING_PATHWAY | 98 | 0.2748 | 0.8397 | 8.54E−01 | 1.00E+00 |
| KEGG_MELANOGENESIS | 98 | 0.2604 | 0.7985 | 9.00E−01 | 1.00E+00 |
| KEGG_THYROID_CANCER | 29 | 0.3078 | 0.7626 | 8.66E−01 | 1.00E+00 |
| KEGG_DORSO_VENTRAL_AXIS_FORMATION | 24 | 0.3171 | 0.7609 | 8.57E−01 | 1.00E+00 |
| KEGG_INSULIN_SIGNALING_PATHWAY | 134 | 0.2351 | 0.7496 | 9.91E−01 | 1.00E+00 |
| KEGG_ENDOMETRIAL_CANCER | 52 | 0.2653 | 0.7338 | 9.37E−01 | 1.00E+00 |
| KEGG_PEROXISOME | 78 | 0.2441 | 0.7164 | 9.85E−01 | 1.00E+00 |
| KEGG_RENAL_CELL_CARCINOMA | 66 | 0.2430 | 0.7008 | 9.72E−01 | 1.00E+00 |
| KEGG_NEUROTROPHIN_SIGNALING_PATHWAY | 122 | 0.2183 | 0.6909 | 9.96E−01 | 1.00E+00 |
| KEGG_B_CELL_RECEPTOR_SIGNALING_PATHWAY | 74 | 0.2309 | 0.6826 | 9.98E−01 | 1.00E+00 |
| KEGG_NOTCH_SIGNALING_PATHWAY | 47 | 0.2500 | 0.6804 | 9.61E−01 | 1.00E+00 |
| KEGG_AMINO_SUGAR_AND_NUCLEOTIDE_SUGAR_METABOLISM | 44 | 0.2466 | 0.6598 | 9.87E−01 | 1.00E+00 |
| KEGG_VALINE_LEUCINE_AND_ISOLEUCINE_DEGRADATION | 44 | 0.2416 | 0.6441 | 9.89E−01 | 1.00E+00 |
| KEGG_MTOR_SIGNALING_PATHWAY | 51 | 0.2221 | 0.6199 | 9.98E−01 | 1.00E+00 |
| KEGG_PROPANOATE_METABOLISM | 32 | 0.2372 | 0.5923 | 9.89E−01 | 1.00E+00 |
| KEGG_HUNTINGTONS_DISEASE | 170 | 0.1817 | 0.5895 | 1.00E+00 | 1.00E+00 |
| KEGG_PYRUVATE_METABOLISM | 39 | 0.2174 | 0.5683 | 9.96E−01 | 1.00E+00 |
| KEGG_SYSTEMIC_LUPUS_ERYTHEMATOSUS | 123 | −0.7308 | −2.3625 | <1.00E−03 | <1.00E−02 |
| KEGG_SPLICEOSOME | 120 | −0.6589 | −2.1285 | <1.00E−03 | <1.00E−02 |
| KEGG_DNA_REPLICATION | 36 | −0.7853 | −2.0793 | <1.00E−03 | <1.00E−02 |
| KEGG_CELL_CYCLE | 124 | −0.6132 | −1.9829 | <1.00E−03 | <1.00E−02 |
| KEGG_HOMOLOGOUS_RECOMBINATION | 26 | −0.7502 | −1.8667 | <1.00E−03 | <1.00E−02 |
| KEGG_RIBOSOME | 87 | −0.6122 | −1.8588 | <1.00E−03 | <1.00E−02 |
| KEGG_RNA_DEGRADATION | 56 | −0.6176 | −1.7888 | <1.00E−03 | <1.00E−02 |
| KEGG_OOCYTE_MEIOSIS | 107 | −0.5171 | −1.6434 | <1.00E−03 | <1.00E−02 |
| KEGG_PROGESTERONE_MEDIATED_OOCYTE_MATURATION | 85 | −0.5121 | −1.6010 | <1.00E−03 | <1.00E−02 |
| KEGG_BASE_EXCISION_REPAIR | 33 | −0.6575 | −1.7074 | 2.19E−03 | 1.39E−02 |

TABLE 5-continued

GSEA analysis of KEGG pathways comparing early passage with early senescence
UPREGULATED FROM EARLY PASSAGE (EP) TO EARLY SENESCENCE (SEN-E)

| PATHWAY NAME | SIZE | ES | NES | NOM p-val | FDR p-val |
| --- | --- | --- | --- | --- | --- |
| KEGG_MISMATCH_REPAIR | 23 | −0.7278 | −1.7707 | 2.36E−03 | 1.39E−02 |
| KEGG_PROTEASOME | 43 | −0.5630 | −1.5802 | 8.83E−03 | 5.32E−02 |
| KEGG_NUCLEOTIDE_EXCISION_REPAIR | 44 | −0.5541 | −1.5345 | 1.53E−02 | 7.76E−02 |
| KEGG_PYRIMIDINE_METABOLISM | 94 | −0.4476 | −1.3925 | 2.03E−02 | 8.83E−02 |
| KEGG_BASAL_TRANSCRIPTION_FACTORS | 35 | −0.5618 | −1.4699 | 3.23E−02 | 1.21E−01 |
| KEGG_RNA_POLYMERASE | 27 | −0.5679 | −1.4123 | 4.53E−02 | 1.51E−01 |
| KEGG_COLORECTAL_CANCER | 62 | −0.4119 | −1.1964 | 1.75E−01 | 4.72E−01 |
| KEGG_PRIMARY_IMMUNODEFICIENCY | 34 | −0.4517 | −1.1747 | 2.13E−01 | 5.24E−01 |
| KEGG_PRIMARY_BILE_ACID_BIOSYNTHESIS | 16 | −0.5303 | −1.1852 | 2.27E−01 | 5.34E−01 |
| KEGG_CITRATE_CYCLE_TCA_CYCLE | 30 | −0.4512 | −1.1431 | 2.36E−01 | 5.48E−01 |
| KEGG_SMALL_CELL_LUNG_CANCER | 84 | −0.3558 | −1.1053 | 2.44E−01 | 5.59E−01 |
| KEGG_PROXIMAL_TUBULE_BICARBONATE_RECLAMATION | 23 | −0.4753 | −1.1566 | 2.56E−01 | 5.74E−01 |
| KEGG_PURINE_METABOLISM | 152 | −0.3191 | −1.0691 | 2.68E−01 | 5.82E−01 |
| KEGG_HISTIDINE_METABOLISM | 27 | −0.4347 | −1.0768 | 3.10E−01 | 6.38E−01 |
| KEGG_PHENYLALANINE_METABOLISM | 18 | −0.4584 | −1.0618 | 3.65E−01 | 7.16E−01 |
| KEGG_ALDOSTERONE_REGULATED_SODIUM_REABSORPTION | 42 | −0.3858 | −1.0507 | 3.77E−01 | 7.16E−01 |
| KEGG_ETHER_LIPID_METABOLISM | 30 | −0.4050 | −1.0352 | 4.00E−01 | 7.46E−01 |
| KEGG_GLYOXYLATE_AND_DICARBOXYLATE_METABOLISM | 16 | −0.4608 | −1.0148 | 4.14E−01 | 7.63E−01 |
| KEGG_PROSTATE_CANCER | 89 | −0.3204 | −0.9982 | 4.27E−01 | 7.63E−01 |
| KEGG_HEDGEHOG_SIGNALING_PATHWAY | 56 | −0.3540 | −1.0074 | 4.30E−01 | 7.63E−01 |
| KEGG_P53_SIGNALING_PATHWAY | 66 | −0.3441 | −1.0082 | 4.49E−01 | 7.83E−01 |
| KEGG_ONE_CARBON_POOL_BY_FOLATE | 17 | −0.4277 | −0.9850 | 4.88E−01 | 8.33E−01 |
| KEGG_GLUTATHIONE_METABOLISM | 48 | −0.3354 | −0.9456 | 5.51E−01 | 8.40E−01 |
| KEGG_TYROSINE_METABOLISM | 41 | −0.3461 | −0.9432 | 5.59E−01 | 8.40E−01 |
| KEGG_TERPENOID_BACKBONE_BIOSYNTHESIS | 15 | −0.4210 | −0.9251 | 5.66E−01 | 8.40E−01 |
| KEGG_NON_SMALL_CELL_LUNG_CANCER | 54 | −0.3267 | −0.9320 | 5.75E−01 | 8.40E−01 |
| KEGG_SELENOAMINO_ACID_METABOLISM | 24 | −0.3674 | −0.9087 | 5.94E−01 | 8.52E−01 |
| KEGG_VIBRIO_CHOLERAE_INFECTION | 53 | −0.3177 | −0.9225 | 5.98E−01 | 8.52E−01 |
| KEGG_ALPHA_LINOLENIC_ACID_METABOLISM | 19 | −0.3620 | −0.8293 | 7.19E−01 | 9.24E−01 |
| KEGG_LONG_TERM_DEPRESSION | 70 | −0.2922 | −0.8691 | 7.45E−01 | 9.43E−01 |
| KEGG_ACUTE_MYELOID_LEUKEMIA | 57 | −0.2957 | −0.8524 | 7.58E−01 | 9.53E−01 |
| KEGG_CHRONIC_MYELOID_LEUKEMIA | 73 | −0.2905 | −0.8710 | 7.70E−01 | 9.60E−01 |
| KEGG_PANCREATIC_CANCER | 69 | −0.2928 | −0.8606 | 7.77E−01 | 9.60E−01 |
| KEGG_AMYOTROPHIC_LATERAL_SCLEROSIS_ALS | 52 | −0.2946 | −0.8457 | 8.00E−01 | 9.72E−01 |
| KEGG_O_GLYCAN_BIOSYNTHEIS | 27 | −0.2958 | −0.7509 | 8.78E−01 | 1.00E+00 |
| KEGG_UBIQUITIN_MEDIATED_PROTEOLYSIS | 131 | −0.2490 | −0.8209 | 9.31E−01 | 1.00E+00 |
| KEGG_ARGININE_AND_PROLINE_METABOLISM | 48 | −0.2670 | −0.7389 | 9.36E−01 | 1.00E+00 |
| KEGG_BUTANOATE_METABOLISM | 34 | −0.2643 | −0.6990 | 9.55E−01 | 1.00E+00 |
| KEGG_PROTEIN_EXPORT | 22 | −0.2643 | −0.6293 | 9.74E−01 | 1.00E+00 |
| KEGG_PARKINSONS_DISEASE | 112 | −0.2391 | −0.7645 | 9.74E−01 | 1.00E+00 |
| KEGG_VEGF_SIGNALING_PATHWAY | 75 | −0.2379 | −0.7151 | 9.77E−01 | 1.00E+00 |
| KEGG_LYSINE_DEGRADATION | 39 | −0.2282 | −0.6218 | 9.89E−01 | 1.00E+00 |
| KEGG_AMINOACYL_TRNA_BIOSYNTHESIS | 41 | −0.2402 | −0.6572 | 9.90E−01 | 1.00E+00 |
| KEGG_GLYCOLYSIS_GLUCONEOGENESIS | 61 | −0.2270 | −0.6631 | 9.93E−01 | 1.00E+00 |
| KEGG_PORPHYRIN_AND_CHLOROPHYLL_METABOLISM | 37 | −0.2269 | −0.6034 | 9.96E−01 | 1.00E+00 |
| KEGG_OXIDATIVE_PHOSPHORYLATION | 116 | −0.1799 | −0.5790 | 1.00E+00 | 1.00E+00 |

TABLE 6

Summary of Qiagen PCR array analysis

|  | SEN (L) cells | | 3X cells | |
|---|---|---|---|---|
|  | Number of genes | Percent[1] | Number of genes | Percent[1] |
| Total genes | 84 | 100% | 84 | 100% |
| Upregulated genes | 77 | 92% | 80 | 95% |
| Downregulated genes | 7 | 8% | 4 | 5% |
| Changing genes passing filters[2] | 58 | 69% | 44 | 52% |
| Passing genes upregulated | 57 | 68% | 44 | 52% |
| Passing genes downregulated | 1 | 1% | 0 | 0% |
| Changing genes failing filters | 26 | 31% | 40 | 48% |
| Genes passing filters, unique[3] | 23 | 27% | 9 | 11% |
| Genes passing filters, overlap[4] | 35 | 42% | 35 | 42% |
| Genes passing filters, total[5] | 67 | 80% | 67 | 80% |

[1]All percentages are calculated with respect to the total number of genes (84) found on the array. Data for all 84 genes displayed as scatter plots are shown in FIG. 2h.
[2]The sum of upregulated and downregulated genes that pass a set of significance filters, see Methods for definitions of filters.
[3]Changing genes that pass the significance filters that are unique to either SEN (L) or 3X cells.
[4]Changing genes that pass the significance filters that are common to (found in both) SEN (L) and 3X cells.
[5]Changing genes that pass the significance filters that are found in SEN (L) and/or 3X cells. The heatmap representation for this set of genes (67) is shown in Extended FIG. 4j, k.

TABLE 7

| Age-group Foldchanges | L1 | p16 | IFNA | IRF7 | OAS1 | IL6 | MMP3 | PAI |
|---|---|---|---|---|---|---|---|---|
| 05 mo-WT | 1.000 | 1.000 | 1.000 | 1.000 | 1.000 | 1.000 | 1.000 | 1.000 |
| 05 mo-3TC | 1.420 | 0.868 | 1.489 | 0.922 | 2.229 | 2.046 | 0.993 | 1.265 |
| 26 mo-WT | 6.265 | 2.917 | 13.219 | 1.560 | 1.898 | 8.775 | 3.078 | 6.603 |
| 26 mo-3TC | 3.947 | 2.213 | 6.579 | 1.076 | 1.681 | 2.355 | 1.762 | 2.839 |

| T-TEST | | | | | | | | |
|---|---|---|---|---|---|---|---|---|
| 05 VS 3TC | 0.152 | 0.819 | 0.304 | 0.542 | 0.125 | 0.123 | 0.981 | 0.547 |
| 05 VS 26 | 0.001 | 0.001 | 0.000 | 0.001 | 0.207 | 0.001 | 0.022 | 0.110 |
| 26 VS 3TC | 0.068 | 0.129 | 0.016 | 0.070 | 0.786 | 0.001 | 0.090 | 0.194 |

| Individual Foldchanges | L1 | p16 | IFNA | IRF7 | OAS1 | IL6 | MMP3 | PAI |
|---|---|---|---|---|---|---|---|---|
| 05 mo-WT | 1.013 | 0.372 | 0.874 | 1.062 | 0.684 | 0.953 | 0.488 | 0.645 |
|  | 1.249 | 0.342 | 0.982 | 0.868 | 0.769 | 1.059 | 1.011 | 0.916 |
|  | 0.884 | 0.412 | 0.394 | 0.835 | 1.441 | 1.003 | 0.663 | 0.695 |
|  | 1.343 | 3.419 | 1.540 | 0.953 | 0.791 | 0.848 | 1.660 | 1.291 |
|  | 1.085 | 1.107 | 1.037 | 1.079 | 0.355 | 0.881 | 0.755 | 2.511 |
|  | 0.755 | 0.552 | 1.886 | 1.397 | 1.799 | 1.352 | 1.971 | 0.314 |
|  | 0.979 | 1.408 | 0.557 | 0.679 | 0.977 | 1.112 | 0.913 | 0.596 |
|  | 0.692 | 0.388 | 0.729 | 1.127 | 1.183 | 0.792 | 0.539 | 1.033 |
| 05 mo-3TC | 1.458 | 2.881 | 1.821 | 1.040 | 2.867 | 1.455 | 1.587 | 2.291 |
|  | 1.464 | 0.457 | 2.748 | 1.153 | 1.521 | 0.924 | 0.601 | 0.842 |
|  | 0.484 | 0.957 | 2.909 | 1.132 | 6.031 | 5.604 | 1.946 | 2.212 |
|  | 1.829 | 0.270 | 0.645 | 0.684 | 1.317 | 1.622 | 0.711 | 1.683 |
|  | 2.537 | 0.104 | 0.465 | 0.565 | 0.037 | 1.920 | 0.635 | 0.180 |
|  | 0.747 | 0.541 | 0.346 | 0.960 | 1.603 | 0.751 | 0.476 | 0.380 |
| 26 mo-WT | 10.645 | 2.563 | 17.947 | 1.801 | 5.442 | 17.058 | 6.449 | 0.979 |
|  | 3.930 | 1.799 | 1.336 | 1.478 | 0.423 | 3.264 | 1.275 | 1.842 |
|  | 1.688 | 4.441 | 8.010 | 1.439 | 0.531 | 3.254 | 2.541 | 3.243 |
|  | 10.959 | 2.315 | 22.657 | 1.891 | 0.516 | 19.464 | 5.831 | 32.301 |
|  | 13.251 | 4.668 | 24.009 | 1.007 | 4.476 | 10.752 | 6.948 | 5.159 |
|  | 2.413 | 4.457 | 17.239 | 2.233 | 0.231 | 4.028 | 1.564 | 0.306 |
|  | 4.278 | 1.361 | 12.879 | 1.461 | 1.699 | 4.075 | 0.764 | 9.405 |
|  | 2.796 | 2.689 | 0.531 | 1.971 | 4.666 | 7.083 | 1.161 | 16.692 |
|  | 6.245 | 3.037 | 13.076 | 1.660 | 2.248 | 8.622 | 3.317 | 1.188 |
|  | 4.788 | 1.777 | 10.981 | 1.422 | 0.963 | 3.754 | 1.551 | 1.605 |
|  | 6.397 | 2.575 | 13.747 | 1.240 | 0.598 | 14.603 | 0.982 | 4.307 |
|  | 7.793 | 3.327 | 16.220 | 1.120 | 0.986 | 9.347 | 4.554 | 2.206 |
| 26 mo-3TC | 2.819 | 2.290 | 10.115 | 0.540 | 1.658 | 1.116 | 1.044 | 1.034 |
|  | 2.160 | 3.653 | 2.941 | 0.506 | 0.643 | 1.553 | 0.972 | 1.056 |
|  | 2.053 | 1.731 | 4.156 | 0.498 | 0.055 | 2.194 | 1.618 | 2.696 |
|  | 1.491 | 1.168 | 1.283 | 0.424 | 0.482 | 0.686 | 1.650 | 0.493 |
|  | 6.524 | 0.844 | 1.601 | 0.954 | 1.094 | 1.395 | 1.033 | 1.562 |
|  | 2.863 | 1.243 | 8.335 | 0.831 | 0.695 | 1.291 | 1.166 | 1.675 |
|  | 7.191 | 3.690 | 19.836 | 0.891 | 7.091 | 8.067 | 4.484 | 2.347 |
|  | 5.433 | 2.458 | 3.982 | 3.302 | 3.841 | 0.654 | 0.374 | 0.529 |
|  | 3.817 | 2.135 | 6.531 | 0.993 | 1.945 | 2.119 | 1.543 | 0.747 |
|  | 4.409 | 4.053 | 8.332 | 1.155 | 0.636 | 3.177 | 3.656 | 8.508 |
|  | 5.864 | 1.969 | 5.514 | 0.950 | 0.565 | 1.148 | 1.964 | 6.112 |
|  | 2.745 | 1.326 | 6.321 | 1.866 | 1.469 | 4.866 | 1.637 | 7.313 |

TABLE 8

NRTIs Approved as Anti-HIV Therapies

| Trade Name | Generic Name | Formulation | Std Adult Dose |
|---|---|---|---|
| Nucleoside/nucleotide reverse transcriptase inhibitors (NRTIs) | | | |
| ZIAGEN ™ | Abacavir | 300 mg tablet | 300 mg twice a day or 600 mg once a day |
| EMTRIVA ™ | Emtricitabine | 200 mg capsule | 200 mg once a day |
| EPIVIlR ™ | Lamivudine | 150 and 300 mg tablets | 150 mg twice a day or 300 mg once a day |
| RETROVIR ™ | Zidovudine | 100 and 250 mg capsules | 100 mg 5 times a day or 250 mg twice a day |
| VIREAD ™ | Tenofovir disoproxil | 245 mg tablet | 245 mg once a day |
| NRTI fixed-dose combinations | | | |
| KIVEXA ™ | Abacavir/lamivudine | Tablet comprising: 600 mg abacavir and 300 mg lamivudine | One tablet once a day |
| TRIZIVIR ™ | Abacavir/lamivudine/zidovudine | Tablet comprising: 300 mg abacavir, 150 mg lamivudine and 300 mg zidovudine | One tablet once a day |
| TRUVADA ® | Emtricitabine/tenofovir disoproxil | Tablet comprising: 200 mg emtricitabine and 245 mg tenofovir disoproxil | One tablet once a day |
| DESCOVY ® | Emtricitabine/tenofovir alafenamide | Tablet comprising: 200 mg emtricitabine and 10 or 25 mg tenofovir alafenamide | One tablet once a day |
| COMBIVIR ™ | Lamivudine/zidovudine | Tablet comprising: 150 mg lamivudine and 300 mg zidovudine | One tablet once a day |
| ATRIPLA ® | Efavirenz/emtricitabine/tenofovir disoproxil | Tablet comprising: 600 mg efavirenz, 200 mg emtricitabine, and 245 mg tenofovir disoproxil | One tablet once a day |
| EVIPLERA ™ | Rilpivirine/emtricitabine/tenofovir disoproxil | Tablet comprising: 25 mg rilpivirine, 200 mg emtricitabine, and 245 mg tenofovir disoproxil | One tablet once a day |
| ODEFSEY ® | Rilpivirine/tenofovir alafenamide/emtricitabine | Tablet comprising: 25 mg rilpivirine, 25 mg tenofovir alafenamide, and 200 mg emtricitabine | One tablet once a day |
| GENVOYA ® | Elvitegravir/cobicistat/emtricitabine/tenofovir alafenamide | Tablet comprising: 150 mg elvitegravir, 150 mg cobicistat, 200 mg emtricitabine, 10 mg tenofovir alafenamide | One tablet once a day |
| STRIBILD ® | Elvitegravir/cobicistat/emtricitabine/tenofovir disoproxil | Tablet comprising: 150 mg elvitegravir, 150 mg cobicistat, 200 mg emtricitabine, and 245 mg tenofovir disoproxil | One tablet once a day |
| TRIUMEQ ® | Dolutegravir/abacavir/lamivudine | Tablet comprising: 50 mg dolutegravir, 600 mg abacavir, and 300 mg lamivudine | One tablet once a day |

TABLE 9

Lower dosage (50%) of NRTIs

| Trade Name | Generic Name | Formulation | Std Adult Dose |
|---|---|---|---|
| Nucleoside/nucleotide reverse transcriptase inhibitors (NRTIs) | | | |
| ZIAGEN ™ | Abacavir | 150 mg tablet | 150 mg twice a day or 300 mg once a day |
| EMTRIVA ™ | Emtricitabine | 100 mg capsule | 100 mg once a day |
| EPIVIR ™ | Lamivudine | 75 and 150 mg tablets | 75 mg twice a day or 150 mg once a day |
| RETROVIR ™ | Zidovudine | 50 and 125 mg capsules | 50 mg 5 times a day or 125 mg twice a day |
| VIREAD ™ | Tenofovir disoproxil | 120 mg tablet | 120 mg once a day |
| NRTI fixed-dose combinations | | | |
| KIVEXA ™ | Abacavir/lamivudine | Tablet comprising: 300 mg abacavir and 150 mg lamivudine | One tablet once a day |
| TRIZIVIR ™ | Abacavir/lamivudine/zidovudine | Tablet comprising: 150 mg abacavir, 75 mg lamivudine and 150 mg zidovudine | One tablet once a day |
| TRUVADA ® | Emtricitabine/tenofovir disoproxil | Tablet comprising: 100 mg emtricitabine and 120 mg tenofovir disoproxil | One tablet once a day |
| DESCOVY ® | Emtricitabine/tenofovir alafenamide | Tablet comprising: 100 mg emtricitabine and 5 or 12 mg tenofovir alafenamide | One tablet once a day |
| COMBIVIR ™ | Lamivudine/zidovudine | Tablet comprising: 75 mg lamivudine and 150 mg zidovudine | One tablet once a day |
| ATRIPLA ® | Efavirenz/emtricitabine/tenofovir disoproxil | Tablet comprising: 300 mg efavirenz, 100 mg emtricitabine, and 120 mg tenofovir disoproxil | One tablet once a day |

TABLE 9-continued

Lower dosage (50%) of NRTIs

| Trade Name | Generic Name | Formulation | Std Adult Dose |
|---|---|---|---|
| EVIPLERA ™ | Rilpivirine/emtricitabine/tenofovir disoproxil | Tablet comprising: 12 mg rilpivirine, 100 mg emtricitabine, and 120 mg tenofovir disoproxil | One tablet once a day |
| ODEFSEY ® | Rilpivirine/tenofovir alafenamide/emtricitabine | Tablet comprising: 12 mg rilpivirine, 12 mg tenofovir alafenamide, and 100 mg emtricitabine | One tablet once a day |
| GENVOYA ® | Elvitegravir/cobicistat/emtricitabine/tenofovir alafenamide | Tablet comprising: 75 mg elvitegravir, 75 mg cobicistat, 100 mg emtricitabine, 10 mg tenofovir alafenamide | One tablet once a day |
| STRIBILD ® | Elvitegravir/cobicistat/emtricitabine/tenofovir disoproxil | Tablet comprising: 75 mg elvitegravir, 75 mg cobicistat, 100 mg emtricitabine, and 120 mg tenofovir disoproxil | One tablet once a day |
| TRIUMEQ ® | Dolutegravir/abacavir/lamivudine | Tablet comprising: 25 mg dolutegravir, 300 mg abacavir, and 150 mg lamivudine | One tablet once a day |

TABLE 10

Mouse L1 activity inhibition

| | $IC_{50}$ (µM), n = 2 | | |
|---|---|---|---|
| Compounds | Exp. 1 | Exp. 2 | Average |
| Lamivudine | 0.958 | 0.780 | 0.869 |
| Stavudine | 1.590 | 1.856 | 1.723 |
| Empricitabine | 0.640 | 0.451 | 0.546 |
| Apricitabine | 4.442 | 3.825 | 4.134 |
| Tenofovir Disiproxil | 0.157 | 0.151 | 0.154 |
| Tenofovir | 3.467 | 4.024 | 3.746 |
| Censavudine | 0.118 | 0.105 | 0.112 |
| Elvucitabine | 0.116 | 0.106 | 0.111 |

$IC_{50}$ determination for nine compounds to inhibit the retrotransposition activity of active mouse LINE-1 in HeLa cells. Retrotransposition activity was determined with the dual luciferase pYX016 reporter. Cells were treated with different concentrations of each compounds and transfected with pYX016 at the same time. Luminescence was measured at 48 H post-transfection. The experiment was performed two times independently.

TABLE 11

Human L1 activity inhibition

| | $IC_{50}$ (µM), n = 2 | | |
|---|---|---|---|
| Compounds | Exp. 1 | Exp. 2 | Average |
| Lamivudine | 0.793 | 0.867 | 0.830 |
| Censavudine | 0.053 | 0.092 | 0.072 |
| Elvucitabine | 0.094 | n/a | n/a |

$IC_{50}$ determination for three compounds to inhibit the retrotransposition activity of active human LINE-1 in HeLa cells. Retrotransposition activity was determined with the dual luciferase pYX017 reporter. Cells were treated with different concentrations of each compounds and transfected with pYX017 at the same time. Luminescence was measured at 72 H post-transfection. The experiment was performed two times independently.

TABLE 12

Human L1 activity inhibition

| Compounds | Human LINE-1 IC50 (μM), n = 3 | | | |
|---|---|---|---|---|
| | Exp.1 | Exp.2 | Exp. 3 | Average |
| Lamivudine | 0.90 | 0.70 | N/A | 0.80 |
| Censavudine | 0.13 | 0.12 | 0.05 | 0.10 |
| Bictegravir* | 12.41 | >50 | N/A | >12.41 |
| Efavirenz | >50 | >0.25 | N/A | >0.25 |
| Nevirapine | >50 | >50 | N/A | >50 |
| Rilpivirine* | >50 | 15.08 | 45.49 | >15.08 |
| Zidovudine | 0.41 | 0.34 | 1.68 | 0.81 |
| Islatravir | N/A | 1.18E−03 | 1.40E−03 | 1.29E−03 |
| Raltegravir potassium | 9.86 | >50 | 49.28 | >9.86 |
| Dolutegravir sodium | 9.38 | N/A | >20 | >9.38 |

TABLE 13

Comparative Studies

| | | Lamivudine (3TC) | Emtricitabine (FTC) | Tenofovir (TFV) | Tenofovir disoproxil (TDF) | Stavudine (d4T) | Islatravir | Abacavir (ABC) |
|---|---|---|---|---|---|---|---|---|
| Human Line-1 | $IC_{50}$ (uM) | 0.64 | 1.34 | 2.77 | 0.20 | 0.75 | 0.005 | 17.1 |
| Human Line-1 | Intracellular drug conc. (% of IC-50 conc.) | 9% | 67% | 0.66% | N/A | 63% | TBD | 106% |
| | huCSF/Plasma | 0.42 | 0.35 | 0.02 | N/A | 0.2 | 0.25 | 0.67 |

TABLE 14

Human LINE-1 Inhibitory Quotient (IQ)

| | Human LINE-1 Inhibitory Quotient (IQ) | | | |
|---|---|---|---|---|
| | PBMC (EFdA-TP EC50 = 316 nM) | | Brain (assume Br./plasma = 0.25) | |
| Dose (mg) | single dose IQ $C_{168\ hr}$ | q.d. IQ $C_{avg\ (ss)}$ | single dose IQ $C_{168\ hr}$ | q.d. IQ $C_{avg\ (ss)}$ |
| 0.5 | 1.84 | 23.41 | 0.46 | 5.85 |
| 1 | 2.61 | 39.79 | 0.66 | 9.95 |
| 2 | 3.00 | 50.54 | 0.75 | 12.64 |
| 10 | 15.64 | 295.15 | 3.92 | 73.79 |
| 30 | 76.88 | 915.31 | 19.22 | 228.83 |

REFERENCES

[1] Engel, P. (2014). These Staggering Maps Show How Much The World's Population Is Aging. Business Insider, May 16, 2014.

[2] Chung H Y, et al., (2009). Molecular inflammation: underpinnings of aging and age-related diseases. Ageing Res. Rev. 8(1): 18-30

[3]

[4] Pawelec G, et al., (2014). Inflammation, ageing and chronic disease. Current Opinion in Immunology. 29: 23-28.

[5] Jurk, D. et al. (2014). Chronic inflammation induces telomere dysfunction and accelerates ageing in mice. Nature Communications, Vol 5, Article: 4172.

[6] Singh, T. & Newman, A. B. (2011). Inflammatory markers in population studies of aging. Ageing Res Rev. 10(3): 319-329.

[7] Diagnostic and Statistical Manual of Mental Disorders, Fifth Edition, pp. 602-614, American Psychiatric Association Publishing, Washington, DC (2013).

[8] Schorl, C. & Sedivy, J. M. (2007). Analysis of cell cycle phases and progression in cultured mammalian cells. Methods 41, 143-50.

[9] Itahana, K., Campisi, J. & Dimri, G. P. (2007). Methods to detect biomarkers of cellular senescence: the senescence-associated beta-galactosidase assay. Methods Mol. Biol. 371, 21-31.

[10] Herbig, U. et al. (2004). Telomere shortening triggers senescence of human cells through a pathway involving ATM, p53, and p21(CIP1), but not p16(INK4a). Mol. Cell 14, 501-513.

[11] Rangwala, S. H., et al. (2009). Many LINE1 elements contribute to the transcriptome of human somatic cells. Genome Biol 10, R100.

[12] Criscione, S. W., et al. (2014). Transcriptional landscape of repetitive elements in normal and cancer human cells. BMC Genomics 15, 583.

[13] Athanikar, J. N., et al. (2004). A YY1-binding site is required for accurate human LINE-1 transcription initiation. Nucleic Acids Res. 32, 3846-55.

[14] Xie, Y., et al. (2011). Characterization of L1 retrotransposition with high-throughput dual-luciferase assays. Nucleic Acids Res 39, e16.

[15] An, W., et al. (2011). Characterization of a synthetic human LINE-1 retrotransposon ORFeus-Hs. Mob DNA 2, 2.

[16] Schoenmaker, M., et al. (2006). Evidence of genetic enrichment for exceptional survival using a family approach: the Leiden Longevity Study. Eur. J. Hum. Genet. 14, 79-84.

[17] Herbig, U., et al. (2004). Telomere shortening triggers senescence of human cells through a pathway involving ATM, p53, and p21(CIP1), but not p16(INK4a). Mol. Cell 14, 501-13.

[18] See, e.g., Isselbacher et al. (1996) *Harrison's Principles of Internal Medicine* 13 ed., 1814-1882.

[19] De Cecco, M., et al. (2013). Genomes of replicatively senescent cells undergo global epigenetic changes leading to gene silencing and activation of transposable elements. Aging Cell 12, 247-256.

[20] De Cecco, M., et al. (2013). Transposable elements become active and mobile in the genomes of aging mammalian somatic tissues. Aging (Albany NY).

[21] Li, Q., et al. (2013) FOXA1 mediates p16(INK4a) activation during cellular senescence. EMBO J 32, 858-873.

[22] Sun, X., et al. (2018). Transcription factor profiling reveals molecular choreography and key regulators of human retrotransposon expression. Proc Natl Acad Sci USA 115, E5526-E5535.

[23] Montoya-Durango, D. E., et al. (2009). Epigenetic control of mammalian LINE-1 retrotransposon by retinoblastoma proteins. Mutat Res 665, 20-28.

[24] Stetson, D. B., et al. (2008). Trex1 prevents cell-intrinsic initiation of autoimmunity. Cell 134, 587-598.

[25] West, A. P., et al. (2015). Mitochondrial DNA stress primes the antiviral innate immune response. Nature 520, 553-557.

[26] Ivanov, A., et al. (2013). Lysosome-mediated processing of chromatin in senescence. J Cell Biol 202, 129-143.

[27] Dou, Z., et al. (2017). Cytoplasmic chromatin triggers inflammation in senescence and cancer. Nature 550, 402-406.

[28] Takahashi, A., et al. (2018). Downregulation of cytoplasmic DNases is implicated in cytoplasmic DNA accumulation and SASP in senescent cells. Nat Commun 9, 1249.

[29] Stetson, D. B., et al. (2008). Trex1 prevents cell-intrinsic initiation of autoimmunity. Cell 134, 587-598.

[30] Thomas, C. A., et al. (2017). Modeling of TREX1-dependent autoimmune disease using human stem cells highlights L1 accumulation as a source of neuroinflammation. Cell Stem Cell 21, 319-331 e318.

[31] Dou, Z., et al. (2017). Cytoplasmic chromatin triggers inflammation in senescence and cancer. Nature 550, 402-406.

[32] Takahashi, A., et al. (2018). Downregulation of cytoplasmic DNases is implicated in cytoplasmic DNA accumulation and SASP in senescent cells. Nat Commun 9, 1249.

[33] Dou, Z., et al. (2017). Cytoplasmic chromatin triggers inflammation in senescence and cancer. Nature 550, 402-406.

[34] Takahashi, A., et al. (2018). Downregulation of cytoplasmic DNases is implicated in cytoplasmic DNA accumulation and SASP in senescent cells. Nat Commun 9, 1249.

[35] Lopez-Otin, C., et al. (2013). The hallmarks of aging. Cell 153, 1194-1217.

[36] https:Hen.wikipedia.org/wiki/Senotherapy

[37] Franceschi, C. & Campisi, J. (2014). Chronic inflammation (inflammaging) and its potential contribution to age-associated diseases. J. Gerontol. A Biol. Sci. Med. Sci. 69 Suppl. 1, S4-9.

[38] Lopez-Otin, C. et al. (2013). The hallmarks of aging. Cell 153, 1194-217.

[39] Safrin, S., (2012). Antiviral Agents (Chapter 49). In: *Basic and Clinical Pharmacology.* 12e. Katzung BG, Masters SB, Trevor AJ (Editors). McGraw-Hill/Lange. (AccessMedicine).

[40] Lopez-Otin, C., et al. (2013). The hallmarks of aging. Cell 153, 1194-1217.

[41] Bussian, T. J., et al. (2018). Clearance of senescent glial cells prevents tau-dependent pathology and cognitive decline. Nature 562, 578-582.

[42] Childs, B. G., et al. (2016). Senescent intimal foam cells are deleterious at all stages of atherosclerosis. Science 354, 472-477.

[43] Baker, D. J., et al. (2016). Naturally occurring p16(Ink4a)-positive cells shorten healthy lifespan. Nature 530, 184-189.

[44] Demaria, M., et al. (2017). Cellular Senescence Promotes Adverse Effects of Chemotherapy and Cancer Relapse. Cancer Discov 7, 165-176.

[45] Chang, J., et al. (2016). Clearance of senescent cells by ABT263 rejuvenates aged hematopoietic stem cells in mice. Nat Med 22, 78-83.

[46] Schafer, M. J., et al. (2017). Cellular senescence mediates fibrotic pulmonary disease. Nat Commun 8, 14532.

[47] Farr, J. N., et al. (2017). Targeting cellular senescence prevents age-related bone loss in mice. Nat Med 23, 1072-1079.

[48] Chinta, S. J., et al. (2018). Cellular Senescence Is Induced by the Environmental Neurotoxin Paraquat and Contributes to Neuropathology Linked to Parkinson's Disease. Cell Rep 22, 930-940.

[49] Xu, M., et al. (2018). Senolytics improve physical function and increase lifespan in old age. Nat Med 24, 1246-1256.

[50] Schafer, M. J., et al. (2017). Cellular senescence mediates fibrotic pulmonary disease. Nat Commun 8, 14532.

[51] Demaria, M., et al. (2014). An essential role for senescent cells in optimal wound healing through secretion of PDGF-AA. Dev Cell 31, 722-733.

[52] See, U. S. Published Patent Application 2018/0050000.

[53] See, U. S. Published Patent Application 2018/0050000.

[54] Caira M., et al. (2004). Preparation and crystal characterization of a polymorph, a monohydrate, and an ethyl acetate solvate of the antifungal fluconazole. J. Pharmaceut. Sci., 93(3):601-611.

[55] Van Tonder E. C., et al. (2004). Preparation and Physicochemical Characterization of 5 Niclosamide Solvates and 1 Hemisolvate. AAPS Pharm. Sci. Tech., 5(1): Article 12.

[56] Bingham A. L., et al. (2001). Over one hundred solvates of sulfathiazole: solvates and adducts of sulfathiazole. Chem. Commun. 7: 603-604.

[57] Remington's Pharmaceutical Sciences, Mack Publishing Co., Easton, PA, 19th ed. 1995.

[58] Brown, J. P., et al., (1997). Bypass of senescence after disruption of p21CIP1/WAF1 gene in normal diploid human fibroblasts. Science 277, 831-834.

[59] Herbig, U. et al., (2004). Telomere shortening triggers senescence of human cells through a pathway involving ATM, p53, and p21(CIP1), but not p16(INK4a). Mol. Cell 14, 501-513.

[60] Fumagalli, M., et al., (2014). Stable cellular senescence is associated with persistent DDR activation. PLoS One 9, el 10969.

[61] www.nia.nih.gov/research/dab/aged-rodent-colonies-handbook

[62] Else, L. J. et al. (2012). Pharmacokinetics of lamivudine and lamivudine-triphosphate after administration of 300 milligrams and 150 milligrams once daily to healthy volunteers: results of the ENCORE 2 study. Antimicrob. Agents Chemother. 56, 1427-1433.

[63] Le, O. N. et al. (2010). Ionizing radiation-induced long-term expression of senescence markers in mice is independent of p53 and immune status. Aging Cell 9, 398-409.

[64] Coufal, N. G. et al. (2009). L1 retrotransposition in human neural progenitor cells. Nature 460, 1127-1131.

[65] http://www.girinst.org/repbase/update/browse.php

[66] http://www.ebi.ac.uk/Tools/msa/clustalo/

[67] Li, W. et al. (2015). The EMBL-EBI bioinformatics web and programmatic tools framework. Nucleic Acids Res. 43, W580-584.

[68] http://www.ncbi.nlm.nih.gov/primer-blast/

[69] Ye, J. et al. (2012). Primer-BLAST: a tool to design target-specific primers for polymerase chain reaction. BMC Bioinf. 13, 134.

[70] https://genome.ucsc.edu/cgi-bin/hgPcr

[71] Gautier, G. et al. (2005). A type I interferon autocrine-paracrine loop is involved in Toll-like receptor-induced interleukin-12p70 secretion by dendritic cells. J. Exp. Med. 201, 1435-1446.

[72] Coufal, N. G. et al. (2009). L1 retrotransposition in human neural progenitor cells. Nature 460, 1127-1131.

73. Kim, D., et al. (2015). HISAT: a fast spliced aligner with low memory requirements. Nat Methods 12, 357-360.
74. Liao, Y., et al. (2014). featureCounts: an efficient general purpose program for assigning sequence reads to genomic features. Bioinformatics 30, 923-930.
75. Robinson, M. D., et al. (2010). edgeR: a Bioconductor package for differential expression analysis of digital gene expression data. Bioinformatics 26, 139-140.
76. Reich, M. et al. (2006). GenePattern 2.0. Nat Genet 38, 500-501.
77. Subramanian, A. et al. (2005). Gene set enrichment analysis: a knowledge-based approach for interpreting genome-wide expression profiles. Proc Natl Acad Sci USA 102, 15545-15550.
78. Benjamini, Y. & Hochberg, Y. (1995). Controlling the false discovery rate: a practical and powerful approach to multiple testing. J Roy Stat Soc B 57, 289-300.
79. http://www.broadinstitute.org/cancer/software/GENE-E
80. Langmead, B. (2010). Aligning short sequencing reads with Bowtie. Curr. Protoc. Bioinformatics Chapter 11, Unit 11.7.
81. Alexandrova, E. A. et al. (2012). Sense transcripts originated from an internal part of the human retrotransposon LINE-1 5' UTR. Gene 511, 46-53.
82. Olovnikov, I. A. et al. (2007). A key role of the internal region of the 5-untranslated region in the human L1 retrotransposon transcription activity. Mol. Biol. (Mosk) 41, 508-514.
83. Alexandrova, E. A. et al. (2012). Sense transcripts originated from an internal part of the human retrotransposon LINE-1 5' UTR. Gene 511, 46-53.
84. https://www.addgene.org/tools/protocols/plko/
85. http://www.broad.mit.edu/genome_bio/trc/rnai.html
86. Michaud, K. et al. (2010). Pharmacologic inhibition of cyclin-dependent kinases 4 and 6 arrests the growth of glioblastoma multiforme intracranial xenografts. Cancer Res. 70, 3228-3238.
87. http://www.orfeomecollaboration.org/
88. https://dnasu.org/DNASU/Home.do
89. Xie, Y. et al. (2011). Characterization of L1 retrotransposition with high-throughput dual-luciferase assays. Nucleic Acids Res 39, e16.
90. An, W., et al. (2011). Characterization of a synthetic human LINE-1 retrotransposon ORFeus-Hs. Mob DNA 2, 2.
91. Penzkofer, T., et al. (2005). L1Base: from functional annotation to prediction of active LINE-1 elements. Nucleic Acids Res 33, D498-500.
92. http://www.girinst.org/repbase/update/browse.php
93. Criscione, S. W., et al. (2014). Transcriptional landscape of repetitive elements in normal and cancer human cells. BMC Genomics 15, 583.
94. Childs, B. G., et al. (2015). Cellular senescence in aging and age-related disease: from mechanisms to therapy. Nat. Med. 21, 1424-1435.
95. Katoh, K. & Standley, D. M. (2013). MAFFT multiple sequence alignment software version 7: improvements in performance and usability. Mol Biol Evol 30, 772-780.
96. Waterhouse, A. M. et al. (2009). Jalview Version 2—a multiple sequence alignment editor and analysis workbench. Bioinformatics 25, 1189-1191.
97. http://genome-engineering.org/gecko/?page_id=15
98. Sanjana, N. E., et al. (2014). Improved vectors and genome-wide libraries for CRISPR screening. Nat. Methods 11, 783-784.
99. http://genome-engineering.org/gecko/wp-content/uploads/2013/12/lentiCRISPRv2-and-lentiGuide-oligo-cloning-protocol.pdf
100. Shalem, O. et al. (2014). Genome-scale CRISPR-Cas9 knockout screening in human cells. Science 343, 84-87.
101. https://dnacore.mgh.harvard.edu/
102. Kreiling, J. A. et al. (2011). Age-associated increase in heterochromatic marks in murine and primate tissues. Aging Cell 10, 292-304.
103. Thomas, C. A. et al. (2017). Modeling of TREX1-dependent autoimmune disease using human stem cells highlights L1 accumulation as a source of neuroinflammation. Cell Stem Cell 21, 319-331 e8.
104. Kreiling, J. A. et al. (2011). Age-associated increase in heterochromatic marks in murine and primate tissues. Aging Cell 10, 292-304.
105. http://www.qiagen.com/us/shop/genes-and-pathways/data-analysis-center-overview-page/
106. Schoenmaker, M. et al. (2006). Evidence of genetic enrichment for exceptional survival using a family approach: the Leiden Longevity Study. Eur. J. Hum. Genet. 14, 79-84.
107. Waaijer, M. E. et al. (2012). The number of p16INK4a positive cells in human skin reflects biological age. Aging Cell 11, 722-725.
108. Kamentsky, L., et al. (2011). Improved structure, function and compatibility for CellProfiler: modular high-throughput image analysis software. Bioinformatics 27, 1179-1180.
109. http://rsbweb.nih.gov/ij/
110. Martinez-Santibanez, G., et al. (2014). Imaging white adipose tissue with confocal microscopy. Methods Enzymol 537, 17-30.
111. Itahana, K., Campisi, J. & Dimri, G. P. Methods to detect biomarkers of cellular senescence: the senescence-associated beta-galactosidase assay. Methods Mol. Biol. 371, 21-31 (2007).
112. Baker, D. J., et al. (2016). Naturally occurring p16 (Ink4a)-positive cells shorten healthy lifespan. Nature 530, 184-189.
113. Baker, D. J., et al. (2011). Clearance of p16Ink4a-positive senescent cells delays ageing-associated disorders. Nature 479, 232-236.
114. Huang, C. R., et al. (2012). Active transposition in genomes. Annu. Rev. Genet. 46, 651-675.
115. de Koning, A. P., et al. (2011). Repetitive elements may comprise over two-thirds of the human genome. PLoS Genet. 7, e1002384.
116. Hancks, D. C. & Kazazian Jr, H. H. (2012). Active human retrotransposons: variation and disease. Curr. Opin. Genet. Dev. 22, 191-203.
117. Rodic, N., et al. (2014). Long interspersed element-1 protein expression is a hallmark of many human cancers. Am. J. Pathol. 184, 1280-1286.
118. Erwin, J. A., et al. (2014). Mobile DNA elements in the generation of diversity and complexity in the brain. Nat. Rev. Neurosci. 15, 497-506.
119. De Cecco, M., et al. (2013). Genomes of replicatively senescent cells undergo global epigenetic changes leading to gene silencing and activation of transposable elements. Aging Cell 12, 247-256.
120. Van Meter, M., et al. (2014). SIRT6 represses LINE1 retrotransposons by ribosylating KAP1 but this repression fails with stress and age. Nat Commun 5, 5011.

[121] Kreiling, J. A., et al. Contribution of retrotransposable elements to aging. in *Human Retrotransposons in Health and Disease* (ed. Cristofari, G.) 297-321 (Springer International, 2017).

[122] Id.

[123] Volkman, H. E. & Stetson, D. B. (2014). The enemy within: endogenous retroelements and autoimmune disease. Nat. Immunol. 15, 415-422.

[124] Salama, R., et al. (2014). Cellular senescence and its effector programs. Genes Dev 28, 99-114.

[125] Thomas, C. A., et al. (2017). Modeling of TREX1-dependent autoimmune disease using human stem cells highlights L1 accumulation as a source of neuroinflammation. Cell Stem Cell 21, 319-331 e8.

[126] Ishak, C. A. et al. (2016). An RB-EZH2 complex mediates silencing of repetitive DNA sequences. Mol Cell 64, 1074-1087.

[127] Li, Q., et al. (2013). FOXA1 mediates p16(INK4a) activation during cellular senescence. EMBO J. 32, 858-873.

[128] Denli, A. M., et al. (2015). Primate-specific ORF0 contributes to retrotransposon-mediated diversity. Cell 163, 583-593.

[129] Dai, L., et al. (2011). Effect of reverse transcriptase inhibitors on LINE-1 and Ty1 reverse transcriptase activities and on LINE-1 retrotransposition. BMC Biochem. 12, 18.

[130] Thomas, C. A., et al. (2017). Modeling of TREX1-dependent autoimmune disease using human stem cells highlights L1 accumulation as a source of neuroinflammation. Cell Stem Cell 21, 319-331 e8.

[131] De Cecco, M., et al. (2013). Genomes of replicatively senescent cells undergo global epigenetic changes leading to gene silencing and activation of transposable elements. Aging Cell 12, 247-256.

[132] Coufal, N. G., et al. (2009). L1 retrotransposition in human neural progenitor cells. Nature 460, 1127-1131.

[133] Dhanwani, R., et al. (2017). Cytosolic sensing of immuno-stimulatory DNA, the enemy within. Curr Opin Immunol 50, 82-87.

[134] Fowler, B. J., et al. (2014). Nucleoside reverse transcriptase inhibitors possess intrinsic anti-inflammatory activity. Science 346, 1000-1003.

[135] Rodic, N., et al. (2014). Long interspersed element-1 protein expression is a hallmark of many human cancers. Am. J. Pathol. 184, 1280-1286.

[136] Herbig, U., et al. (2006). Cellular senescence in aging primates. Science 311, 1257.

[137] Coppe, J. P., et al. (2010). The senescence-associated secretory phenotype: the dark side of tumor suppression. Annu. Rev. Pathol. 5, 99-118.

[138] Chang, J., et al. (2016). Clearance of senescent cells by ABT263 rejuvenates aged hematopoietic stem cells in mice. Nat Med 22, 78-83.

[139] Zhu, Y., et al. The Achilles' heel of senescent cells: from transcriptome to senolytic drugs. Aging Cell 14, 644-58 (2015).

[140] Tchkonia, T., et al. (2010). Fat tissue, aging, and cellular senescence. Aging Cell 9, 667-684.

[141] Mattson, M. P. (2010). Perspective: Does brown fat protect against diseases of aging?Ageing Res Rev 9, 69-76.

[142] Tchkonia, T., et al. (2010). Fat tissue, aging, and cellular senescence. Aging Cell 9, 667-684.

[143] Frasca, D. & Blomberg, B. B. (2016). Inflammaging decreases adaptive and innate immune responses in mice and humans. Biogerontology 17, 7-19.

[144] Baker, D. J., et al. (2016). Naturally occurring p16 (Ink4a)-positive cells shorten healthy lifespan. Nature 530, 184-189.

[145] Baker, D. J., et al. (2011). Clearance of p16Ink4a-positive senescent cells delays ageing-associated disorders. Nature 479, 232-236.

[146] West, A. P. & Shadel, G. S. (2017). Mitochondrial DNA in innate immune responses and inflammatory pathology. Nat Rev Immunol 17, 363-375.

[147] Dou, Z., et al. (2017). Cytoplasmic chromatin triggers inflammation in senescence and cancer. Nature 550, 402-406.

[148] Takahashi, A., et al. (2018). Downregulation of cytoplasmic DNases is implicated in cytoplasmic DNA accumulation and SASP in senescent cells. Nat Commun 9, 1249.

[149] Franceschi, C., & Campisi, J. (2014). Chronic inflammation (inflammaging) and its potential contribution to age-associated diseases. J. Gerontol. A Biol. Sci. Med. Sci. 69 Suppl 1, S4-9.

[150] Lopez-Otin, C., et al. (2013). The hallmarks of aging. Cell 153, 1194-1217.

[151] Xie Y., Rosser J. M., Thompson T. L., Boeke J. D. (2011). An W. Characterization of L1 retrotransposition with high-throughput dual-luciferase assays. Nucleic Acids Res. 39: e16.

All patents, patent application, and publications cited herein are fully incorporated by reference herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

What is claimed is:

1. A method for slowing down the progression of and/or lessening the symptoms of Alzheimer's disease, amyotrophic lateral sclerosis, autism spectrum disorder, dementia with Lewy Bodies, frontotemporal dementia, mild cognitive impairment, Parkinson's disease, progressive supra nuclear palsy, Rett Syndrome, or Aicardi-Goutieres syndrome in a patient in need thereof, the method comprising administering a therapeutically effective amount of censavudine to the patient.

2. The method of claim 1 comprising administering about 1 µg/kg to about 100 mg/kg of censavudine to the patient per day.

3. The method of claim 2 comprising administering about 1 mg/kg to about 50 mg/kg of censavudine to the patient per day.

4. The method of claim 3 comprising administering about 5 mg/kg of censavudine to the patient per day.

5. The method of claim 3 comprising administering about 10 mg/kg of censavudine to the patient per day.

6. The method of claim 3 comprising administering about 15 mg/kg of censavudine to the patient per day.

7. The method of claim 3 comprising administering about 20 mg/kg of censavudine to the patient per day.

8. The method of claim 1 comprising administering 1 mg to 500 mg of censavudine to the patient once a day, twice a day, or three times a day.

9. The method of claim 8 comprising administering 10 mg, 20 mg, 30 mg, 40 mg, 50 mg, 60 mg, 70 mg, 80 mg, 90 mg, 100 mg, 110 mg, 120 mg, 130 mg, 140 mg, or 150 mg of censavudine to the patient once a day, twice a day, or three times a day.

10. The method of claim 1, wherein the censavudine is orally administered to the patient in the form of a tablet, capsule, or suspension.

11. The method of claim 1 slowing down the progression of and/or lessening the symptoms of Alzheimer's disease.

12. The method of claim 1 slowing down the progression of and/or lessening the symptoms of amyotrophic lateral sclerosis.

13. The method of claim 1 slowing down the progression of and/or lessening the symptoms of autism spectrum disorder.

14. The method of claim 1 slowing down the progression of and/or lessening the symptoms of dementia with Lewy Bodies.

15. The method of claim 1 for curing, slowing down the progression of and/or lessening the symptoms of frontotemporal dementia.

16. The method of claim 1 slowing down the progression of and/or lessening the symptoms of mild cognitive impairment.

17. The method of claim 1 slowing down the progression of and/or lessening the symptoms of Parkinson's disease.

18. The method of claim 1 slowing down the progression of and/or lessening the symptoms of progressive supra nuclear palsy.

19. The method of claim 1 slowing down the progression of and/or lessening the symptoms of Rett Syndrome.

20. The method of claim 1 slowing down the progression of and/or lessening the symptoms of Aicardi-Goutieres syndrome.

* * * * *

UNITED STATES PATENT AND TRADEMARK OFFICE
CERTIFICATE OF CORRECTION

PATENT NO. : 12,246,022 B2
APPLICATION NO. : 18/470182
DATED : March 11, 2025
INVENTOR(S) : John M. Sedivy et al.

It is certified that error appears in the above-identified patent and that said Letters Patent is hereby corrected as shown below:

In the Claims

In Column 128, Claim 11, Line 15, after "The method of claim 1" insert -- for --.

In Column 128, Claim 12, Line 17, after "The method of claim 1" insert -- for --.

In Column 128, Claim 13, Line 20, after "The method of claim 1" insert -- for --.

In Column 128, Claim 14, Line 23, after "The method of claim 1" insert -- for --.

In Column 128, Claim 15, Line 26, delete "curing,".

In Column 128, Claim 16, Line 29, after "The method of claim 1" insert -- for --.

In Column 128, Claim 17, Line 32, after "The method of claim 1" insert -- for --.

In Column 128, Claim 18, Line 34, after "The method of claim 1" insert -- for --.

In Column 128, Claim 19, Line 37, after "The method of claim 1" insert -- for --.

In Column 128, Claim 20, Line 39, after "The method of claim 1" insert -- for --.

Signed and Sealed this
Fifth Day of August, 2025

Coke Morgan Stewart
*Acting Director of the United States Patent and Trademark Office*